United States Patent
Watts

(10) Patent No.: US 11,866,745 B2
(45) Date of Patent: Jan. 9, 2024

(54) VARIANTS OF CAS12A NUCLEASES AND METHODS OF MAKING AND USE THEREOF

(71) Applicant: Pairwise Plants Services, Inc., Durham, NC (US)

(72) Inventor: Joseph Matthew Watts, Cary, NC (US)

(73) Assignee: Pairwise Plants Services, Inc., Durham, NC (US)

(*) Notice: Subject to any disclaimer, the term of this patent is extended or adjusted under 35 U.S.C. 154(b) by 202 days.

(21) Appl. No.: 17/071,095

(22) Filed: Oct. 15, 2020

(65) Prior Publication Data

US 2021/0115421 A1 Apr. 22, 2021

Related U.S. Application Data

(60) Provisional application No. 62/916,392, filed on Oct. 17, 2019.

(51) Int. Cl.
| | | |
|---|---|---|
| *C12N 9/22* | (2006.01) | |
| *C07K 14/20* | (2006.01) | |
| *C12N 15/10* | (2006.01) | |
| *C12N 15/113* | (2010.01) | |

(52) U.S. Cl.
CPC ............... *C12N 9/22* (2013.01); *C07K 14/20* (2013.01); *C12N 15/102* (2013.01); *C12N 15/113* (2013.01); *C07K 2319/70* (2013.01); *C12N 2310/20* (2017.05)

(58) Field of Classification Search
CPC ...... C12N 9/22; C12N 15/102; C12N 15/113; C12N 2310/20; C12N 9/78; C12N 15/1093; C07K 14/20; C07K 2319/70; C07K 2319/00; C12Y 305/04004; C12Y 305/04005
See application file for complete search history.

(56) References Cited

U.S. PATENT DOCUMENTS

| | | | |
|---|---|---|---|
| 2018/0155716 A1 | 6/2018 | Zhang et al. | |
| 2019/0010441 A1 | 1/2019 | Kindaichi | |
| 2019/0010481 A1* | 1/2019 | Joung | ............... C12N 9/22 |

FOREIGN PATENT DOCUMENTS

| | | |
|---|---|---|
| WO | 2017184768 A1 | 10/2017 |
| WO | 2018213708 A1 | 11/2018 |
| WO | 2018213726 A1 | 11/2018 |
| WO | 2019138052 A1 | 7/2019 |

OTHER PUBLICATIONS

Gaj et al. (Genome-Editing Technologies: Principles and Applications. Cold Spring Harbor Perspectives in Biology, vol. 8, issue 12, Dec. 2012) (Year: 2012).*
Written Opinion corresponding to PCT/US2019/055659; dated Mar. 9, 2021 (12 pages).
Gao, Linyi, et al., "Engineered Cpf1 variants with altered PAM specificities", Nat Biotechnol 35(8), 2017, 789-792.
Hu, Jonny H., et al., "Evolved Cas9 variants with broad PAM compatibility and high DNA specificity", Nature 556, 2018, 57-63.
Kleinstiver, Benjamin P., et al., "Broadening the targeting range of *Staphylococcus aureus* CRISPR-Cas9 by modifying PAM recognition", Nat Biotechnol 33(12), 2015a, 1293-1298.
Kleinstiver, Benjamin P., et al., "Engineered CRISPR-Cas12a variants with increased activities and improved targeting ranges for gene, epigenetic and base editing", Nat Biotechnol 37, 2019, 276-282.
Kleinstiver, Benjamin P., et al., "Engineered CRISPR-Cas9 nucleases with altered PAM specificities", Nature 523, 2015b, 481-485.
Nishimasu, Hiroshi, et al., "Engineered CRISPR-Cas9 nuclease with expanded targeting space", Science 361 (6408), 2018, 1259-1262.
Tang, Xu, et al., "A CRISPR-Cpf1 system for efficient genome editing and transcriptional repression in plants", Nat Plants 3, Article No. 17018, 2017.
Yamano, Takashi, et al., "Structural Basis for the Canonical and Non-canonical PAM Recognition by CRISPR-Cpf1", Mol Cell 67(4), 2017, 633-645.e3.
Jinek, Martin, et al., "A Programmable Dual-RNA-Guided DNA Endonuclease in Adaptive Bacterial Immunity", Science. vol. 337, pp. 816-821 (2012).
Leenay, Ryan T., et al., "Identifying and Visualizing Functional PAM Diversity across CRISPR-Cas Systems", Molecular Cell. vol. 62, pp. 137-147 (2016).
Zetsche, Bernd, et al., "Cpf1 is a single RNA-guided endonuclease of a Class 2 CRISPR-Cas system", Cell. vol. 163(3), pp. 759-771 (2015).

* cited by examiner

*Primary Examiner* — Kara D Johnson
*Assistant Examiner* — Matasha Dhar
(74) *Attorney, Agent, or Firm* — Myers Bigel, P.A.

(57) ABSTRACT

This invention relates to variants of Cas12a nucleases having altered protospacer adjacent motif recognition specificity. The invention further relates to methods of making CRISPR-CAS nuclease variants and methods of modifying nucleic acids using the variants.

29 Claims, 20 Drawing Sheets

Specification includes a Sequence Listing.

Fig. 3
A
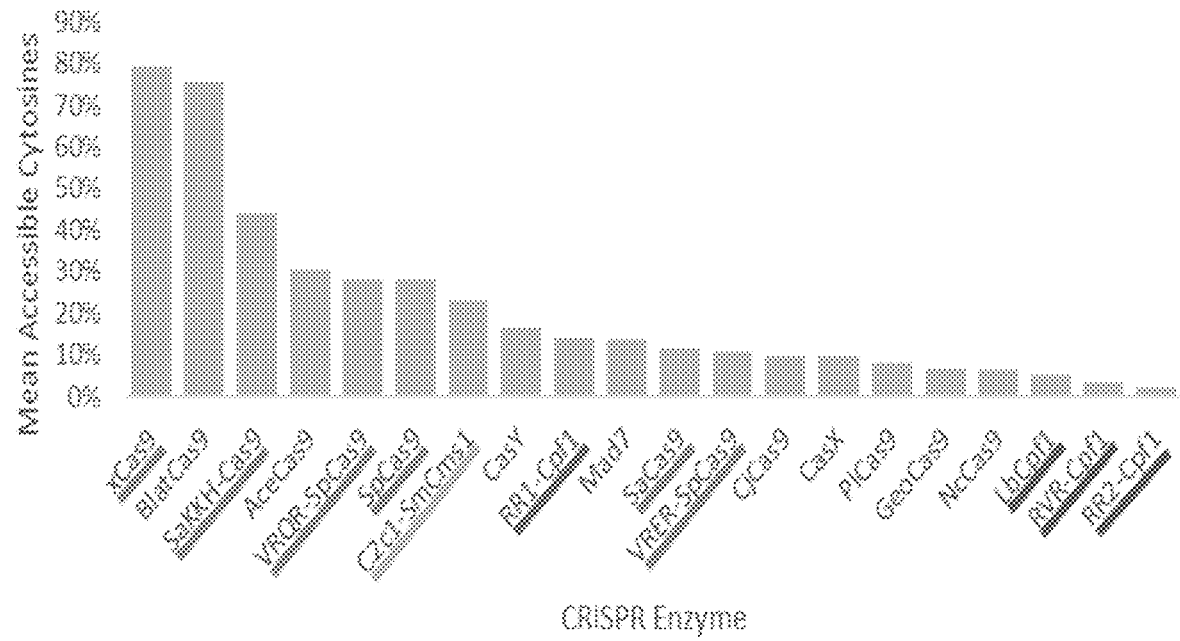
B
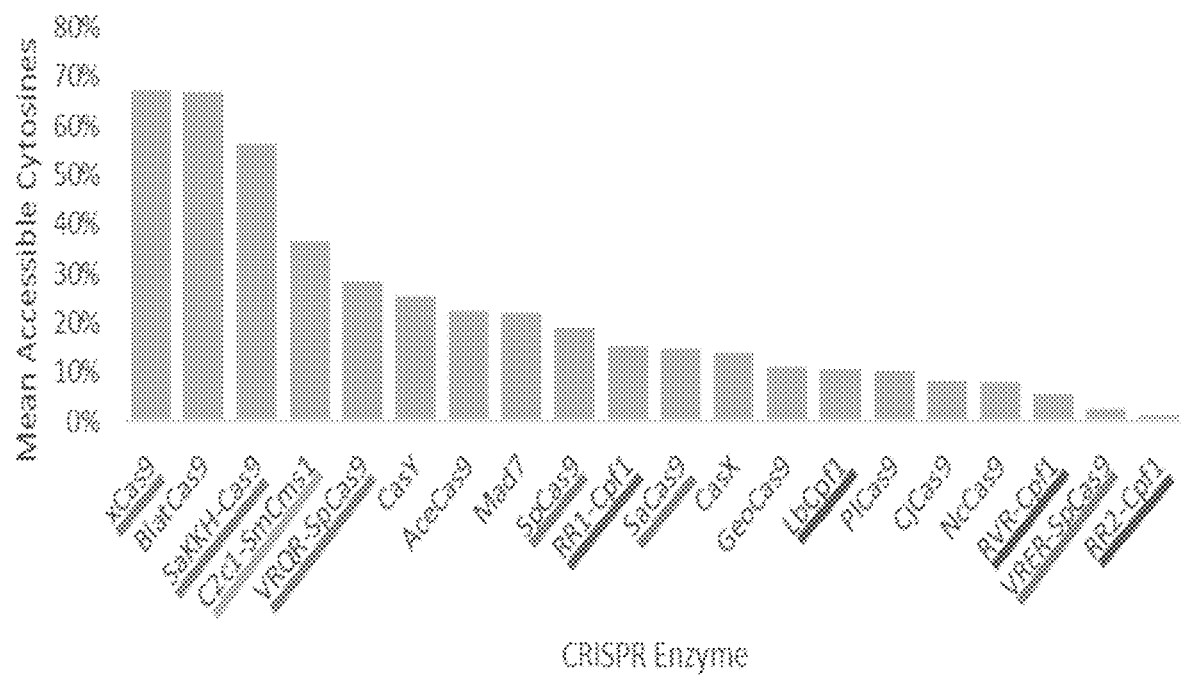

Fig. 3 (con't)
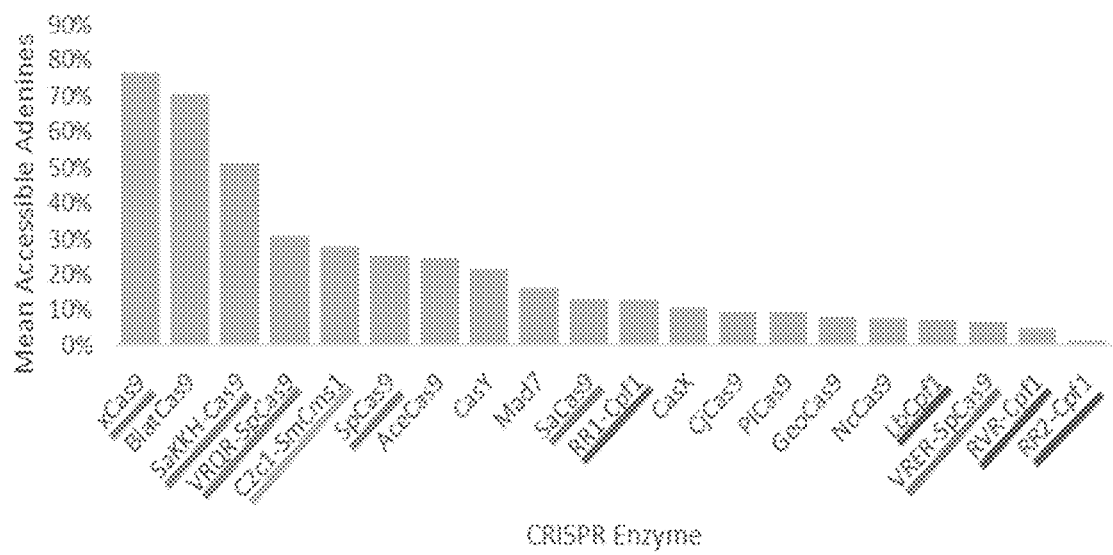
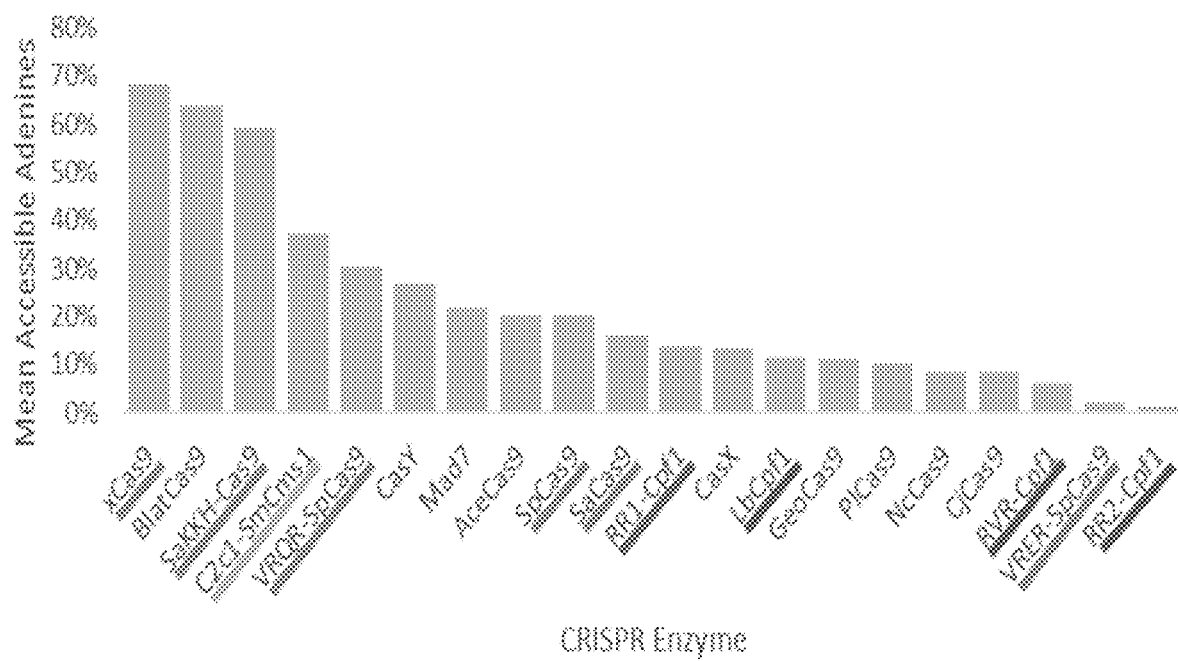

Fig. 15

| PAM | K538W | K595Y | K538W+K595Y |
|---|---|---|---|
| AATG | ✓ | | |
| ACCC | | ✓ | ✓ |
| ACGC | | ✓ | |
| AGCT | ✓ | | |
| ATTA | | | ✓ |
| ATTC | | | ✓ |
| ATTG | | | ✓ |
| CCCA | | | ✓ |
| CCCC | | ✓ | ✓ |
| CCCG | | | ✓ |
| CCGC | | ✓ | |
| CTCC | | | ✓ |
| CTTA | ✓ | | |
| CTTC | ✓ | | |
| CTTG | | | ✓ |
| GCCA | | | ✓ |
| GCCC | | ✓ | ✓ |
| GCCG | | | ✓ |
| GCGC | | ✓ | |
| GCTA | | | ✓ |
| GTCC | | | ✓ |
| GTTA | | | ✓ |
| GTTC | | | ✓ |
| GTTG | | | ✓ |
| TCCA | | ✓ | ✓ |
| TCCC | | ✓ | ✓ |
| TCCG | | | ✓ |
| TCGC | | ✓ | |
| TCGG | | ✓ | |
| TCTA | | | ✓ |
| TCTC | | | ✓ |
| TCTG | | | ✓ |
| TTCA | | ✓ | |
| TTCC | | ✓ | |
| TTCG | | ✓ | |
| TTGC | | ✓ | |
| TTGG | | | ✓ |
| TTTA | | | ✓ |
| TTTC | ✓ | | ✓ |
| TTTG | | | ✓ |

Fig. 16

| PAM | T152R | K538W | K595Y | T152R+K538W | K538W+K595Y | T152R+K538W+K595Y |
|---|---|---|---|---|---|---|
| AACC |  |  |  |  |  | ■ |
| AAGC |  |  |  |  |  | ■ |
| AATG |  | ■ |  |  |  | ■ |
| ACCA |  |  |  |  |  |  |
| ACCC |  |  | ■ | ■ | ■ | ■ |
| ACCG |  |  |  |  |  | ■ |
| ACGC |  |  | ■ |  | ■ | ■ |
| AGAG | ■ |  |  |  |  |  |
| AGCA |  |  |  |  |  |  |
| AGCC |  |  |  |  |  | ■ |
| AGCT |  | ■ |  |  |  |  |
| AGGC |  |  |  |  |  | ■ |
| ATTA |  |  |  | ■ |  |  |
| ATTC |  |  |  | ■ | ■ |  |
| ATTG |  |  |  | ■ | ■ |  |
| CAGC |  |  |  |  |  | ■ |
| CCCA |  |  | ■ | ■ | ■ |  |
| CCCC |  |  | ■ | ■ | ■ | ■ |
| CCCG |  |  |  | ■ | ■ |  |
| CCGC |  |  | ■ |  |  |  |
| CGGC |  |  |  |  |  | ■ |
| CTCC |  |  |  | ■ |  |  |
| CTGC |  |  |  |  |  | ■ |
| CTTA | ■ | ■ |  |  |  |  |
| CTTC |  | ■ |  |  |  |  |
| CTTG | ■ |  |  |  |  |  |
| GACA |  |  |  |  |  |  |
| GACC |  |  |  |  |  |  |
| GCCA | ■ |  |  |  |  |  |
| GCCC |  |  |  |  |  |  |
| GCCG |  |  |  |  |  |  |
| GCGC |  |  | ■ |  | ■ |  |
| GCTA |  |  |  |  |  |  |
| GGCA |  |  |  |  |  |  |
| GGCC |  |  |  |  |  |  |
| GGGC |  |  |  |  |  |  |
| GGGG |  |  |  |  |  |  |
| GTCA |  |  |  | ■ |  |  |
| GTCC |  |  |  |  |  |  |
| GTTA | ■ |  |  |  |  |  |
| GTTC |  |  |  | ■ |  |  |
| GTTG |  |  |  | ■ |  |  |
| TACA |  |  |  |  |  | ■ |
| TACC |  |  |  |  |  |  |
| TACG |  |  |  |  |  |  |
| TAGC |  |  |  |  |  |  |
| TCCA | ■ |  | ■ |  | ■ |  |
| TCCC |  |  |  |  |  |  |
| TCCG |  |  |  |  |  |  |
| TCGC |  |  |  | ■ |  |  |
| TCGG |  |  |  | ■ |  |  |
| TCTA | ■ |  |  |  |  |  |
| TCTC |  |  |  | ■ |  |  |
| TCTG |  |  |  | ■ |  |  |
| TGCA |  |  |  |  |  | ■ |
| TGCC |  |  |  |  |  |  |
| TGGC |  |  |  |  |  |  |
| TTCA |  |  |  | ■ |  |  |
| TTCC |  |  |  |  |  |  |
| TTCG |  |  |  | ■ |  |  |
| TTGC |  |  |  | ■ |  |  |
| TTGG |  |  |  |  |  |  |
| TTTA | ■ |  |  | ■ |  |  |
| TTTC | ■ | ■ |  |  |  |  |
| TTTG | ■ |  |  |  |  |  |
| TTTT | ■ |  |  | ■ |  |  |

| PAM | K595Y | PAM Depletion Score |
|---|---|---|
| ACCC |  | 18.7 |
| ACGC |  | 13.8 |
| CCCA |  | 11.5 |
| CCGC |  | 16.7 |
| GCGC |  | 17.5 |
| TCCA |  | 16.9 |
| TCCC |  | 18.6 |
| TCCG |  | 16.2 |
| TCGC |  | 13.3 |
| TCGG |  | 14.7 |
| TTCC |  | 11.3 |
| TTCG |  | 17.8 |
| TTGC |  | 11.5 |

| PAM | T152R | PAM Depletion Score |
|---|---|---|
| AGAG |  |  |
| ATTG |  | 10.8 |
| CTTA |  | 10.9 |
| CTTC |  | 16.1 |
| CTTG |  | 9.5 |
| GCCA |  | 10.4 |
| GTTA |  | 10.3 |
| GTTC |  | 9.9 |
| GTTG |  | 12.7 |
| TCCA |  | 10.7 |
| TCTA |  | 10.4 |
| TTTT |  | 10.4 |

SEQUENCE LISTING

<160> NUMBER OF SEQ ID NOS: 62

<210> SEQ ID NO 1
<211> LENGTH: 1228

```
<212> TYPE: PRT
<213> ORGANISM: Unknown
<220> FEATURE:
<223> OTHER INFORMATION: Lachnospiraceae bacterium

<400> SEQUENCE: 1

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
                100                 105                 110

Glu Gly Tyr Lys Ser Leu Phe Lys Lys Asp Ile Ile Thr Ile Leu
            115                 120                 125

Pro Glu Phe Leu Asp Asp Lys Asp Glu Ile Ala Leu Val Asn Ser Phe
        130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380
```

```
Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
            405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
            485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
            565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
            645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
            725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
            770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
```

```
                    805                 810                 815
Arg Val Leu Leu Lys His Asp Asp Asn Pro Tyr Val Ile Gly Ile Asp
            820                 825                 830
Arg Gly Glu Arg Asn Leu Leu Tyr Ile Val Val Asp Gly Lys Gly
            835                 840                 845
Asn Ile Val Glu Gln Tyr Ser Leu Asn Glu Ile Ile Asn Asn Phe Asn
    850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
            915                 920                 925
Ser Gly Phe Lys Asn Ser Arg Val Lys Val Glu Lys Gln Val Tyr Gln
    930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Gln Asn Gly Phe
            980                 985                 990
Ile Phe Tyr Ile Pro Ala Trp Leu Thr Ser Lys Ile Asp Pro Ser Thr
            995                 1000                1005
Gly Phe Val Asn Leu Leu Lys Thr Lys Tyr Thr Ser Ile Ala Asp
    1010                1015                1020
Ser Lys Lys Phe Ile Ser Ser Phe Asp Arg Ile Met Tyr Val Pro
    1025                1030                1035
Glu Glu Asp Leu Phe Glu Phe Ala Leu Asp Tyr Lys Asn Phe Ser
    1040                1045                1050
Arg Thr Asp Ala Asp Tyr Ile Lys Lys Trp Lys Leu Tyr Ser Tyr
    1055                1060                1065
Gly Asn Arg Ile Arg Ile Phe Arg Asn Pro Lys Lys Asn Asn Val
    1070                1075                1080
Phe Asp Trp Glu Glu Val Cys Leu Thr Ser Ala Tyr Lys Glu Leu
    1085                1090                1095
Phe Asn Lys Tyr Gly Ile Asn Tyr Gln Gln Gly Asp Ile Arg Ala
    1100                1105                1110
Leu Leu Cys Glu Gln Ser Asp Lys Ala Phe Tyr Ser Ser Phe Met
    1115                1120                1125
Ala Leu Met Ser Leu Met Leu Gln Met Arg Asn Ser Ile Thr Gly
    1130                1135                1140
Arg Thr Asp Val Asp Phe Leu Ile Ser Pro Val Lys Asn Ser Asp
    1145                1150                1155
Gly Ile Phe Tyr Asp Ser Arg Asn Tyr Glu Ala Gln Glu Asn Ala
    1160                1165                1170
Ile Leu Pro Lys Asn Ala Asp Ala Asn Gly Ala Tyr Asn Ile Ala
    1175                1180                1185
Arg Lys Val Leu Trp Ala Ile Gly Gln Phe Lys Lys Ala Glu Asp
    1190                1195                1200
Glu Lys Leu Asp Lys Val Lys Ile Ala Ile Ser Asn Lys Glu Trp
    1205                1210                1215
```

```
Leu Glu  Tyr Ala Gln Thr Ser  Val Lys His
    1220            1225

<210> SEQ ID NO 2
<211> LENGTH: 1307
<212> TYPE: PRT
<213> ORGANISM: Acidaminococcus sp.

<400> SEQUENCE: 2

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
```

-continued

```
              355                 360                 365
Lys Lys Leu Glu Thr Ile Ser Ser Ala Leu Cys Asp His Trp Asp Thr
370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
                    405                 410                 415
Asp Ile Asn Leu Gln Glu Ile Ser Ala Ala Gly Lys Glu Leu Ser
            420                 425                 430
Glu Ala Phe Lys Gln Lys Thr Ser Glu Ile Leu Ser His Ala His Ala
            435                 440                 445
Ala Leu Asp Gln Pro Leu Pro Thr Leu Lys Lys Gln Glu Glu Lys
        450                 455                 460
Glu Ile Leu Lys Ser Gln Leu Asp Ser Leu Leu Gly Leu Tyr His Leu
465                 470                 475                 480
Leu Asp Trp Phe Ala Val Asp Glu Ser Asn Glu Val Asp Pro Glu Phe
                    485                 490                 495
Ser Ala Arg Leu Thr Gly Ile Lys Leu Glu Met Glu Pro Ser Leu Ser
            500                 505                 510
Phe Tyr Asn Lys Ala Arg Asn Tyr Ala Thr Lys Lys Pro Tyr Ser Val
            515                 520                 525
Glu Lys Phe Lys Leu Asn Phe Gln Met Pro Thr Leu Ala Ser Gly Trp
            530                 535                 540
Asp Val Asn Lys Glu Lys Asn Asn Gly Ala Ile Leu Phe Val Lys Asn
545                 550                 555                 560
Gly Leu Tyr Tyr Leu Gly Ile Met Pro Lys Gln Lys Gly Arg Tyr Lys
                    565                 570                 575
Ala Leu Ser Phe Glu Pro Thr Glu Lys Thr Ser Glu Gly Phe Asp Lys
            580                 585                 590
Met Tyr Tyr Asp Tyr Phe Pro Asp Ala Ala Lys Met Ile Pro Lys Cys
            595                 600                 605
Ser Thr Gln Leu Lys Ala Val Thr Ala His Phe Gln Thr His Thr
610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Glu Lys Glu Pro Lys Lys Phe Gln
                    645                 650                 655
Thr Ala Tyr Ala Lys Lys Thr Gly Asp Gln Lys Gly Tyr Arg Glu Ala
                    660                 665                 670
Leu Cys Lys Trp Ile Asp Phe Thr Arg Asp Phe Leu Ser Lys Tyr Thr
            675                 680                 685
Lys Thr Thr Ser Ile Asp Leu Ser Ser Leu Arg Pro Ser Ser Gln Tyr
            690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                    725                 730                 735
Thr Gly Lys Leu Tyr Leu Phe Gln Ile Tyr Asn Lys Asp Phe Ala Lys
                    740                 745                 750
Gly His His Gly Lys Pro Asn Leu His Thr Leu Tyr Trp Thr Gly Leu
            755                 760                 765
Phe Ser Pro Glu Asn Leu Ala Lys Thr Ser Ile Lys Leu Asn Gly Gln
770                 775                 780
```

```
Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
            805                 810                 815

Pro Ile Pro Asp Thr Leu Tyr Gln Glu Leu Tyr Asp Tyr Val Asn His
        820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
                900                 905                 910

Asn Leu Ile Tyr Ile Thr Val Ile Asp Ser Thr Gly Lys Ile Leu Glu
            915                 920                 925

Gln Arg Ser Leu Asn Thr Ile Gln Gln Phe Asp Tyr Gln Lys Lys Leu
        930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
                980                 985                 990

Glu Asn Leu Asn Phe Gly Phe Lys  Ser Lys Arg Thr Gly  Ile Ala Glu
            995                 1000                1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185
```

-continued

```
Lys Gly Ile Val Phe Arg Asp Gly Ser Asn Ile Leu Pro Lys Leu
    1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
    1220                1225                1230

Glu Asp Tyr Ile Asn Ser Pro Val Arg Asp Leu Asn Gly Val Cys
    1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
    1265                1270                1275

Asn His Leu Lys Glu Ser Lys Asp Leu Lys Leu Gln Asn Gly Ile
    1280                1285                1290

Ser Asn Gln Asp Trp Leu Ala Tyr Ile Gln Glu Leu Arg Asn
    1295                1300                1305

<210> SEQ ID NO 3
<211> LENGTH: 1241
<212> TYPE: PRT
<213> ORGANISM: utyrivibrio proteoclasticus

<400> SEQUENCE: 3

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30

Glu Leu Asn Leu Leu Glu Gln Asp Lys Ala Ile Tyr Ala Leu Leu Glu
        35                  40                  45

Arg Leu Lys Pro Val Ile Asp Glu Gly Ile Lys Asp Ile Ala Arg Asp
    50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110

Lys Ile Ser Glu Ile Asn Ser Ala Lys Tyr Leu Asn Gly Val Leu Tyr
        115                 120                 125

Asp Phe Ile Asp Lys Thr His Lys Asp Ser Glu Glu Lys Gln Asn Ile
    130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
        195                 200                 205

Ile Cys Ser Val Asp Tyr Tyr Asn Gln Ile Leu Ser Gln Glu Asp Ile
    210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255
```

```
Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
            275                 280                 285

Ile Asp Ser Asp Glu Glu Val Val Gln Val Thr Lys Glu Ala Phe Glu
        290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
        355                 360                 365

Arg Arg Thr Lys Ser Glu Asp Ala Arg Tyr Asp Lys Phe Val Asn Ala
370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
        435                 440                 445

Glu Ser Leu Val Ser Phe Tyr Asp Glu Leu Thr Lys Phe Arg Ser Ala
450                 455                 460

Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                485                 490                 495

Ala Glu Asn Leu Cys Arg Asn Tyr Val Thr Lys Ser Pro Ala Asp Asp
            500                 505                 510

Ala Arg Ile Met Ala Ser Cys Leu Gly Thr Pro Ala Arg Leu Arg Thr
        515                 520                 525

His Trp Trp Asn Gly Glu Glu Asn Phe Ala Ile Asn Asp Val Ala Met
530                 535                 540

Ile Arg Arg Gly Asp Glu Tyr Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
            580                 585                 590

Phe Lys Cys Ile Leu Glu Pro Tyr Phe Glu Ser Pro Glu His Lys Asn
        595                 600                 605

Asp Lys Asn Cys Val Ile Glu Glu Tyr Val Ser Lys Pro Leu Thr Ile
610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
            660                 665                 670
```

```
Tyr Ser Cys Phe Asn Met Ser Gly Leu Lys Arg Ala Asp Glu Tyr Asn
        675                 680                 685

Asp Ile Gly Glu Phe Phe Ser Asp Val Asp Thr Arg Leu Cys Thr Met
690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
            740                 745                 750

Asn Met Glu His Thr Ser Met Leu Leu Asn Ser Arg Ala Met Ile Gln
        755                 760                 765

Tyr Arg Ala Ala Ser Leu Pro Arg Arg Val Thr His Lys Lys Gly Ser
    770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
            820                 825                 830

Ile Lys Lys Ala Asn Glu Asp Ile Ile Arg Asn Arg Arg Tyr Thr Glu
        835                 840                 845

Asp Lys Phe Phe Leu Ser Leu Ser Tyr Thr Lys Asn Ala Asp Ile Ser
    850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
    930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Glu Ser
                965                 970                 975

Met Ser Ser Thr Phe Lys Asp Lys Phe Ser Phe Leu Ser Glu Gln Ile
            980                 985                 990

Phe Lys Ala Phe Glu Ala Arg Leu Cys Ala Arg Met Ser Asp Leu Ser
        995                 1000                1005

Phe Asn Thr Ile Lys Glu Gly Glu Ala Gly Ser Ile Ser Asn Pro
        1010                1015                1020

Ile Gln Val Ser Asn Asn Gly Asn Ser Tyr Gln Asp Gly Val
        1025                1030                1035

Ile Tyr Phe Leu Asn Asn Ala Tyr Thr Arg Thr Leu Cys Pro Asp
        1040                1045                1050

Thr Gly Phe Val Asp Val Phe Asp Lys Thr Arg Leu Ile Thr Met
        1055                1060                1065

Gln Ser Lys Arg Gln Phe Phe Ala Lys Met Lys Asp Ile Arg Ile
        1070                1075                1080

Asp Asp Gly Glu Met Leu Phe Thr Phe Asn Leu Glu Glu Tyr Pro
```

```
                1085                1090                1095
Thr Lys Arg Leu Leu Asp Arg Lys Glu Trp Thr Val Lys Ile Ala
    1100                1105                1110

Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val
    1235                1240

<210> SEQ ID NO 4
<211> LENGTH: 1238
<212> TYPE: PRT
<213> ORGANISM: Candidatus Methanoplasma termitum

<400> SEQUENCE: 4

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
                20                  25                  30

Thr Phe Asn Phe Phe Glu Glu Asp Arg Asp Arg Ala Glu Lys Tyr Lys
            35                  40                  45

Ile Leu Lys Glu Ala Ile Asp Glu Tyr His Lys Lys Phe Ile Asp Glu
        50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
                100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
        130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
                180                 185                 190

Lys Tyr Gln Glu Ala Arg Lys Lys Tyr Pro Glu Trp Ile Ile Lys Ala
            195                 200                 205
```

```
Glu Ser Ala Leu Val Ala His Asn Ile Lys Met Asp Ile Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Glu Lys Ser Ser
                260                 265                 270

Lys Gly Arg Ile His Met Thr Pro Leu Phe Lys Gln Ile Leu Ser Glu
                275                 280                 285

Lys Glu Ser Phe Ser Tyr Ile Pro Asp Val Phe Thr Glu Asp Ser Gln
                290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
                340                 345                 350

Val Ser Asn Val Ile Phe Gly Glu Trp Gly Thr Leu Gly Gly Leu Met
                355                 360                 365

Arg Glu Tyr Lys Ala Asp Ser Ile Asn Asp Ile Asn Leu Glu Arg Thr
                370                 375                 380

Cys Lys Lys Val Asp Lys Trp Leu Asp Ser Lys Glu Phe Ala Leu Ser
385                 390                 395                 400

Asp Val Leu Glu Ala Ile Asp Arg Thr Gly Asn Asn Asp Ala Phe Asn
                405                 410                 415

Glu Tyr Ile Ser Lys Met Arg Thr Ala Arg Glu Lys Ile Asp Ala Ala
                420                 425                 430

Arg Lys Glu Met Lys Phe Ile Ser Glu Lys Ile Ser Gly Asp Glu Glu
                435                 440                 445

Ser Ile His Ile Ile Lys Thr Leu Leu Asp Ser Val Gln Gln Phe Leu
                450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
                500                 505                 510

Asn Thr Lys Lys Ile Lys Leu Asn Phe Lys Asn Pro Thr Leu Ala Asn
                515                 520                 525

Gly Trp Asp Gln Asn Lys Val Tyr Asp Tyr Ala Ser Leu Ile Phe Leu
                530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Arg Pro Val
                580                 585                 590

Phe Leu Thr Ser Thr Lys Gly Lys Lys Glu Tyr Lys Pro Ser Lys Glu
                595                 600                 605

Ile Ile Glu Gly Tyr Glu Ala Asp Lys His Ile Arg Gly Asp Lys Phe
610                 615                 620

Asp Leu Asp Phe Cys His Lys Leu Ile Asp Phe Phe Lys Glu Ser Ile
```

-continued

```
            625                 630                 635                 640
Glu Lys His Lys Asp Trp Ser Lys Phe Asn Phe Tyr Phe Ser Pro Thr
                    645                 650                 655
Glu Ser Tyr Gly Asp Ile Ser Glu Phe Tyr Leu Asp Val Glu Lys Gln
                660                 665                 670
Gly Tyr Arg Met His Phe Glu Asn Ile Ser Ala Glu Thr Ile Asp Glu
                675                 680                 685
Tyr Val Glu Lys Gly Asp Leu Phe Leu Phe Gln Ile Tyr Asn Lys Asp
    690                 695                 700
Phe Val Lys Ala Ala Thr Gly Lys Lys Asp Met His Thr Ile Tyr Trp
705                 710                 715                 720
Asn Ala Ala Phe Ser Pro Glu Asn Leu Gln Asp Val Val Lys Leu
                    725                 730                 735
Asn Gly Glu Ala Glu Leu Phe Tyr Arg Asp Lys Ser Asp Ile Lys Glu
                740                 745                 750
Ile Val His Arg Glu Gly Glu Ile Leu Val Asn Arg Thr Tyr Asn Gly
                755                 760                 765
Arg Thr Pro Val Pro Asp Lys Ile His Lys Lys Leu Thr Asp Tyr His
    770                 775                 780
Asn Gly Arg Thr Lys Asp Leu Gly Glu Ala Lys Glu Tyr Leu Asp Lys
785                 790                 795                 800
Val Arg Tyr Phe Lys Ala His Tyr Asp Ile Thr Lys Asp Arg Arg Tyr
                805                 810                 815
Leu Asn Asp Lys Ile Tyr Phe His Val Pro Leu Thr Leu Asn Phe Lys
                820                 825                 830
Ala Asn Gly Lys Lys Asn Leu Asn Lys Met Val Ile Glu Lys Phe Leu
                835                 840                 845
Ser Asp Glu Lys Ala His Ile Ile Gly Ile Asp Arg Gly Glu Arg Asn
    850                 855                 860
Leu Leu Tyr Tyr Ser Ile Ile Asp Arg Ser Gly Lys Ile Ile Asp Gln
865                 870                 875                 880
Gln Ser Leu Asn Val Ile Asp Gly Phe Asp Tyr Arg Glu Lys Leu Asn
                885                 890                 895
Gln Arg Glu Ile Glu Met Lys Asp Ala Arg Gln Ser Trp Asn Ala Ile
                900                 905                 910
Gly Lys Ile Lys Asp Leu Lys Glu Gly Tyr Leu Ser Lys Ala Val His
                915                 920                 925
Glu Ile Thr Lys Met Ala Ile Gln Tyr Asn Ala Ile Val Val Met Glu
    930                 935                 940
Glu Leu Asn Tyr Gly Phe Lys Arg Gly Arg Phe Lys Val Glu Lys Gln
945                 950                 955                 960
Ile Tyr Gln Lys Phe Glu Asn Met Leu Ile Asp Lys Met Asn Tyr Leu
                965                 970                 975
Val Phe Lys Asp Ala Pro Asp Glu Ser Pro Gly Gly Val Leu Asn Ala
                980                 985                 990
Tyr Gln Leu Thr Asn Pro Leu Glu Ser Phe Ala Lys Leu Gly Lys Gln
                995                 1000                1005
Thr Gly Ile Leu Phe Tyr Val Pro Ala Ala Tyr Thr Ser Lys Ile
    1010                1015                1020
Asp Pro Thr Thr Gly Phe Val Asn Leu Phe Asn Thr Ser Ser Lys
    1025                1030                1035
Thr Asn Ala Gln Glu Arg Lys Glu Phe Leu Gln Lys Phe Glu Ser
    1040                1045                1050
```

-continued

```
Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp
    1235

<210> SEQ ID NO 5
<211> LENGTH: 1281
<212> TYPE: PRT
<213> ORGANISM: Eubacterium eligens

<400> SEQUENCE: 5

Met Asn Gly Asn Arg Ser Ile Val Tyr Arg Glu Phe Val Gly Ile
1               5                   10                  15

Pro Val Ala Lys Thr Leu Arg Asn Glu Leu Arg Pro Val Gly His Thr
                20                  25                  30

Gln Glu His Ile Ile Gln Asn Gly Leu Ile Gln Glu Asp Glu Leu Arg
                35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
                100                 105                 110

Cys Thr His Leu Gln Ser Asp Ser Asn Tyr Lys Asn Ile Phe Asn Ala
            115                 120                 125

Lys Leu Leu Lys Glu Ile Leu Pro Asp Phe Ile Lys Asn Tyr Asn Gln
        130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
```

```
            165                 170                 175
Val Phe Thr Lys Glu Ala Val Ser Thr Ser Ile Ala Tyr Arg Ile Val
                180                 185                 190

His Glu Asn Ser Leu Ile Phe Leu Ala Asn Met Thr Ser Tyr Lys Lys
                195                 200                 205

Ile Ser Glu Lys Ala Leu Asp Glu Ile Glu Val Ile Glu Lys Asn Asn
            210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
                260                 265                 270

Lys Asn Asn Tyr Asn Leu Phe Lys Met Arg Lys Leu His Lys Gln Ile
            275                 280                 285

Leu Ala Tyr Thr Ser Thr Ser Phe Glu Val Pro Lys Met Phe Glu Asp
            290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
                340                 345                 350

Leu Ser Cys Phe Met Ser Gly Asn Trp Asn Leu Ile Thr Gly Cys Val
            355                 360                 365

Glu Asn Phe Tyr Asp Glu Asn Ile His Ala Lys Gly Lys Ser Lys Glu
            370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
                420                 425                 430

Ile Ile Thr Asp Thr Glu Thr Ala His Leu Glu Tyr Asp Asp His Ile
            435                 440                 445

Ser Leu Ile Glu Ser Glu Glu Lys Ala Asp Glu Met Lys Lys Arg Leu
            450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
            515                 520                 525

Gln Ser Pro Thr Leu Ala Asn Gly Trp Ser Gln Ser Lys Glu Phe Asp
            530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
                565                 570                 575

Asp Lys Lys Asn Asp Asn Asp Tyr Lys Lys Met Val Tyr Asn Leu Leu
                580                 585                 590
```

```
Pro Gly Ala Asn Lys Met Leu Pro Lys Val Phe Leu Ser Lys Lys Gly
        595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
                645                 650                 655

Arg Lys Tyr Glu Phe Lys Phe Ser Ala Thr Asp Ser Tyr Ser Asp Ile
                660                 665                 670

Ser Glu Phe Tyr Arg Glu Val Glu Met Gln Gly Tyr Arg Ile Asp Trp
                675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
                725                 730                 735

Glu Asn Leu Asp Lys Ile Ile Lys Leu Asn Gly Gln Ala Glu Leu Phe
                740                 745                 750

Tyr Arg Arg Ala Ser Val Lys Asn Pro Val Lys His Lys Lys Asp Ser
    755                 760                 765

Val Leu Val Asn Lys Thr Tyr Lys Asn Gln Leu Asp Asn Gly Asp Val
    770                 775                 780

Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
                820                 825                 830

Asp Tyr Arg Tyr Thr Val Asp Lys Tyr Phe Ile His Thr Pro Ile Thr
                835                 840                 845

Ile Asn Tyr Lys Val Thr Ala Arg Asn Asn Val Asn Asp Met Val Val
    850                 855                 860

Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
                900                 905                 910

Lys Lys Leu Val Glu Lys Glu Lys Thr Arg Glu Tyr Ala Arg Lys Asn
                915                 920                 925

Trp Lys Ser Ile Gly Asn Ile Lys Glu Leu Lys Glu Gly Tyr Ile Ser
    930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
                980                 985                 990

Leu Asn Tyr Phe Ala Ser Lys Glu Lys Ser Val Asp Glu Pro Gly Gly
                995                 1000                1005
```

Leu Leu Lys Gly Tyr Gln Leu Thr Tyr Val Pro Asp Asn Ile Lys
    1010                1015                1020

Asn Leu Gly Lys Gln Cys Gly Val Ile Phe Tyr Val Pro Ala Ala
    1025                1030                1035

Phe Thr Ser Lys Ile Asp Pro Ser Thr Gly Phe Ile Ser Ala Phe
    1040                1045                1050

Asn Phe Lys Ser Ile Ser Thr Asn Ala Ser Arg Lys Gln Phe Phe
    1055                1060                1065

Met Gln Phe Asp Glu Ile Arg Tyr Cys Ala Glu Lys Asp Met Phe
    1070                1075                1080

Ser Phe Gly Phe Asp Tyr Asn Asn Phe Asp Thr Tyr Asn Ile Thr
    1085                1090                1095

Met Gly Lys Thr Gln Trp Thr Val Tyr Thr Asn Gly Glu Arg Leu
    1100                1105                1110

Gln Ser Glu Phe Asn Asn Ala Arg Arg Thr Gly Lys Thr Lys Ser
    1115                1120                1125

Ile Asn Leu Thr Glu Thr Ile Lys Leu Leu Leu Glu Asp Asn Glu
    1130                1135                1140

Ile Asn Tyr Ala Asp Gly His Asp Ile Arg Ile Asp Met Glu Lys
    1145                1150                1155

Met Asp Glu Asp Lys Lys Ser Glu Phe Phe Ala Gln Leu Leu Ser
    1160                1165                1170

Leu Tyr Lys Leu Thr Val Gln Met Arg Asn Ser Tyr Thr Glu Ala
    1175                1180                1185

Glu Glu Gln Glu Asn Gly Ile Ser Tyr Asp Lys Ile Ile Ser Pro
    1190                1195                1200

Val Ile Asn Asp Glu Gly Glu Phe Phe Asp Ser Asp Asn Tyr Lys
    1205                1210                1215

Glu Ser Asp Asp Lys Glu Cys Lys Met Pro Lys Asp Ala Asp Ala
    1220                1225                1230

Asn Gly Ala Tyr Cys Ile Ala Leu Lys Gly Leu Tyr Glu Val Leu
    1235                1240                1245

Lys Ile Lys Ser Glu Trp Thr Glu Asp Gly Phe Asp Arg Asn Cys
    1250                1255                1260

Leu Lys Leu Pro His Ala Glu Trp Leu Asp Phe Ile Gln Asn Lys
    1265                1270                1275

Arg Tyr Glu
    1280

<210> SEQ ID NO 6
<211> LENGTH: 1300
<212> TYPE: PRT
<213> ORGANISM: Francisella novicida

<400> SEQUENCE: 6

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
35 40 45

Lys Ala Lys Gln Ile Ile Asp Lys Tyr His Gln Phe Phe Ile Glu Glu
50 55 60

Ile Leu Ser Ser Val Cys Ile Ser Glu Asp Leu Leu Gln Asn Tyr Ser
65 70 75 80

```
Asp Val Tyr Phe Lys Leu Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495
```

```
Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
        610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
        690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
        770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815

Leu Gln Asp Val Val Tyr Lys Leu Asn Gly Glu Ala Glu Leu Phe Tyr
        820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
```

-continued

```
            915                 920                925
Val Asp Gly Lys Gly Asn Ile Ile Lys Gln Asp Thr Phe Asn Ile Ile
    930                 935                940

Gly Asn Asp Arg Met Lys Thr Asn Tyr His Asp Lys Leu Ala Ala Ile
945                 950                955                960

Glu Lys Asp Arg Asp Ser Ala Arg Lys Asp Trp Lys Lys Ile Asn Asn
                965                970                975

Ile Lys Glu Met Lys Glu Gly Tyr Leu Ser Gln Val Val His Glu Ile
            980                 985                990

Ala Lys Leu Val Ile Glu Tyr Asn Ala Ile Val Val Phe Glu Asp Leu
            995                 1000               1005

Asn Phe Gly Phe Lys Arg Gly Arg Phe Lys Val Glu Lys Gln Val
    1010                1015               1020

Tyr Gln Lys Leu Glu Lys Met Leu Ile Glu Lys Leu Asn Tyr Leu
    1025                1030               1035

Val Phe Lys Asp Asn Glu Phe Asp Lys Thr Gly Gly Val Leu Arg
    1040                1045               1050

Ala Tyr Gln Leu Thr Ala Pro Phe Glu Thr Phe Lys Lys Met Gly
    1055                1060               1065

Lys Gln Thr Gly Ile Ile Tyr Tyr Val Pro Ala Gly Phe Thr Ser
    1070                1075               1080

Lys Ile Cys Pro Val Thr Gly Phe Val Asn Gln Leu Tyr Pro Lys
    1085                1090               1095

Tyr Glu Ser Val Ser Lys Ser Gln Glu Phe Phe Ser Lys Phe Asp
    1100                1105               1110

Lys Ile Cys Tyr Asn Leu Asp Lys Gly Tyr Phe Glu Phe Ser Phe
    1115                1120               1125

Asp Tyr Lys Asn Phe Gly Asp Lys Ala Ala Lys Gly Lys Trp Thr
    1130                1135               1140

Ile Ala Ser Phe Gly Ser Arg Leu Ile Asn Phe Arg Asn Ser Asp
    1145                1150               1155

Lys Asn His Asn Trp Asp Thr Arg Glu Val Tyr Pro Thr Lys Glu
    1160                1165               1170

Leu Glu Lys Leu Leu Lys Asp Tyr Ser Ile Glu Tyr Gly His Gly
    1175                1180               1185

Glu Cys Ile Lys Ala Ala Ile Cys Gly Glu Ser Asp Lys Lys Phe
    1190                1195               1200

Phe Ala Lys Leu Thr Ser Val Leu Asn Thr Ile Leu Gln Met Arg
    1205                1210               1215

Asn Ser Lys Thr Gly Thr Glu Leu Asp Tyr Leu Ile Ser Pro Val
    1220                1225               1230

Ala Asp Val Asn Gly Asn Phe Phe Asp Ser Arg Gln Ala Pro Lys
    1235                1240               1245

Asn Met Pro Gln Asp Ala Asp Ala Asn Gly Ala Tyr His Ile Gly
    1250                1255               1260

Leu Lys Gly Leu Met Leu Leu Gly Arg Ile Lys Asn Asn Gln Glu
    1265                1270               1275

Gly Lys Lys Leu Asn Leu Val Ile Lys Asn Glu Glu Tyr Phe Glu
    1280                1285               1290

Phe Val Gln Asn Arg Asn Asn
    1295                1300
```

<210> SEQ ID NO 7

```
<211> LENGTH: 1206
<212> TYPE: PRT
<213> ORGANISM: Unknown
<220> FEATURE:
<223> OTHER INFORMATION: Lachnospiraceae bacterium

<400> SEQUENCE: 7
```

| | | | | | | | | | | | | | | |
|---|---|---|---|---|---|---|---|---|---|---|---|---|---|---|
| Met | Tyr | Tyr | Glu | Ser | Leu | Thr | Lys | Gln | Tyr | Pro | Val | Ser | Lys | Thr | Ile |
| 1 | | | | 5 | | | | | 10 | | | | | 15 | |

| Arg | Asn | Glu | Leu | Ile | Pro | Ile | Gly | Lys | Thr | Leu | Asp | Asn | Ile | Arg | Gln |
|---|---|---|---|---|---|---|---|---|---|---|---|---|---|---|---|
| | | | 20 | | | | | 25 | | | | | 30 | | |

| Asn | Asn | Ile | Leu | Glu | Ser | Asp | Val | Lys | Arg | Lys | Gln | Asn | Tyr | Glu | His |
|---|---|---|---|---|---|---|---|---|---|---|---|---|---|---|---|
| | | | | 35 | | | | | 40 | | | | | 45 | |

| Val | Lys | Gly | Ile | Leu | Asp | Glu | Tyr | His | Lys | Gln | Leu | Ile | Asn | Glu | Ala |
|---|---|---|---|---|---|---|---|---|---|---|---|---|---|---|---|
| | 50 | | | | | 55 | | | | | 60 | | | | |

| Leu | Asp | Asn | Cys | Thr | Leu | Pro | Ser | Leu | Lys | Ile | Ala | Ala | Glu | Ile | Tyr |
|---|---|---|---|---|---|---|---|---|---|---|---|---|---|---|---|
| 65 | | | | | 70 | | | | | 75 | | | | | 80 |

| Leu | Lys | Asn | Gln | Lys | Glu | Val | Ser | Asp | Arg | Glu | Asp | Phe | Asn | Lys | Thr |
|---|---|---|---|---|---|---|---|---|---|---|---|---|---|---|---|
| | | | | 85 | | | | | 90 | | | | | 95 | |

| Gln | Asp | Leu | Leu | Arg | Lys | Glu | Val | Val | Glu | Lys | Leu | Lys | Ala | His | Glu |
|---|---|---|---|---|---|---|---|---|---|---|---|---|---|---|---|
| | | | 100 | | | | | 105 | | | | | 110 | | |

| Asn | Phe | Thr | Lys | Ile | Gly | Lys | Lys | Asp | Ile | Leu | Asp | Leu | Leu | Glu | Lys |
|---|---|---|---|---|---|---|---|---|---|---|---|---|---|---|---|
| | | | | 115 | | | | | 120 | | | | | 125 | |

| Leu | Pro | Ser | Ile | Ser | Glu | Asp | Asp | Tyr | Asn | Ala | Leu | Glu | Ser | Phe | Arg |
|---|---|---|---|---|---|---|---|---|---|---|---|---|---|---|---|
| | 130 | | | | | 135 | | | | | 140 | | | | |

| Asn | Phe | Tyr | Thr | Tyr | Phe | Thr | Ser | Tyr | Asn | Lys | Val | Arg | Glu | Asn | Leu |
|---|---|---|---|---|---|---|---|---|---|---|---|---|---|---|---|
| 145 | | | | | 150 | | | | | 155 | | | | | 160 |

| Tyr | Ser | Asp | Lys | Glu | Lys | Ser | Ser | Thr | Val | Ala | Tyr | Arg | Leu | Ile | Asn |
|---|---|---|---|---|---|---|---|---|---|---|---|---|---|---|---|
| | | | | 165 | | | | | 170 | | | | | 175 | |

| Glu | Asn | Phe | Pro | Lys | Phe | Leu | Asp | Asn | Val | Lys | Ser | Tyr | Arg | Phe | Val |
|---|---|---|---|---|---|---|---|---|---|---|---|---|---|---|---|
| | | | 180 | | | | | 185 | | | | | 190 | | |

| Lys | Thr | Ala | Gly | Ile | Leu | Ala | Asp | Gly | Leu | Gly | Glu | Glu | Gly | Gln | Asp |
|---|---|---|---|---|---|---|---|---|---|---|---|---|---|---|---|
| | | | 195 | | | | | 200 | | | | | 205 | | |

| Ser | Leu | Phe | Ile | Val | Glu | Thr | Phe | Asn | Lys | Thr | Leu | Thr | Gln | Asp | Gly |
|---|---|---|---|---|---|---|---|---|---|---|---|---|---|---|---|
| | 210 | | | | | 215 | | | | | 220 | | | | |

| Ile | Asp | Thr | Tyr | Asn | Ser | Gln | Val | Gly | Lys | Ile | Asn | Ser | Ser | Ile | Asn |
|---|---|---|---|---|---|---|---|---|---|---|---|---|---|---|---|
| 225 | | | | | 230 | | | | | 235 | | | | | 240 |

| Leu | Tyr | Asn | Gln | Lys | Asn | Gln | Lys | Ala | Asn | Gly | Phe | Arg | Lys | Ile | Pro |
|---|---|---|---|---|---|---|---|---|---|---|---|---|---|---|---|
| | | | | 245 | | | | | 250 | | | | | 255 | |

| Lys | Met | Lys | Met | Leu | Tyr | Lys | Gln | Ile | Leu | Ser | Asp | Arg | Glu | Glu | Ser |
|---|---|---|---|---|---|---|---|---|---|---|---|---|---|---|---|
| | | | 260 | | | | | 265 | | | | | 270 | | |

| Phe | Ile | Asp | Glu | Phe | Gln | Ser | Asp | Glu | Val | Leu | Ile | Asp | Asn | Val | Glu |
|---|---|---|---|---|---|---|---|---|---|---|---|---|---|---|---|
| | | 275 | | | | | 280 | | | | | 285 | | | |

| Ser | Tyr | Gly | Ser | Val | Leu | Ile | Glu | Ser | Leu | Lys | Ser | Ser | Lys | Val | Ser |
|---|---|---|---|---|---|---|---|---|---|---|---|---|---|---|---|
| | 290 | | | | | 295 | | | | | 300 | | | | |

| Ala | Phe | Phe | Asp | Ala | Leu | Arg | Glu | Ser | Lys | Gly | Lys | Asn | Val | Tyr | Val |
|---|---|---|---|---|---|---|---|---|---|---|---|---|---|---|---|
| 305 | | | | | 310 | | | | | 315 | | | | | 320 |

| Lys | Asn | Asp | Leu | Ala | Lys | Thr | Ala | Met | Ser | Val | Ile | Val | Phe | Glu | Asn |
|---|---|---|---|---|---|---|---|---|---|---|---|---|---|---|---|
| | | | | 325 | | | | | 330 | | | | | 335 | |

| Trp | Arg | Thr | Phe | Asp | Asp | Leu | Leu | Asn | Gln | Glu | Tyr | Asp | Leu | Ala | Asn |
|---|---|---|---|---|---|---|---|---|---|---|---|---|---|---|---|
| | | | 340 | | | | | 345 | | | | | 350 | | |

| Glu | Asn | Lys | Lys | Lys | Asp | Asp | Lys | Tyr | Phe | Glu | Lys | Arg | Gln | Lys | Glu |
|---|---|---|---|---|---|---|---|---|---|---|---|---|---|---|---|
| | | | 355 | | | | | 360 | | | | | 365 | | |

| Leu | Lys | Lys | Asn | Lys | Ser | Tyr | Ser | Leu | Glu | His | Leu | Cys | Asn | Leu | Ser |
|---|---|---|---|---|---|---|---|---|---|---|---|---|---|---|---|
| | | 370 | | | | | 375 | | | | | 380 | | | |

```
Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
        405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
    450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
        675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
    770                 775                 780

Met Asn Phe Gly Val Asp Glu Val Lys Arg Phe Asn Asp Ala Val Asn
785                 790                 795                 800
```

```
Ser Ala Ile Arg Ile Asp Glu Asn Val Asn Val Gly Ile Asp Arg
            805                 810                 815

Gly Glu Arg Asn Leu Leu Tyr Val Val Ile Asp Ser Lys Gly Asn
            820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Ala Lys Leu Val
            885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
            930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
            965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr Met Lys Cys Glu Asn Val Glu Lys
            995                 1000                1005

Ser Lys Arg Phe Phe Asp Gly Phe Asp Phe Ile Arg Phe Asn Ala
            1010                1015                1020

Leu Glu Asn Val Phe Glu Phe Gly Phe Asp Tyr Arg Ser Phe Thr
            1025                1030                1035

Gln Arg Ala Cys Gly Ile Asn Ser Lys Trp Thr Val Cys Thr Asn
            1040                1045                1050

Gly Glu Arg Ile Ile Lys Tyr Arg Asn Pro Asp Lys Asn Asn Met
            1055                1060                1065

Phe Asp Glu Lys Val Val Val Thr Asp Glu Met Lys Asn Leu
            1070                1075                1080

Phe Glu Gln Tyr Lys Ile Pro Tyr Glu Asp Gly Arg Asn Val Lys
            1085                1090                1095

Asp Met Ile Ile Ser Asn Glu Ala Glu Phe Tyr Arg Arg Leu
            1100                1105                1110

Tyr Arg Leu Leu Gln Gln Thr Leu Gln Met Arg Asn Ser Thr Ser
            1115                1120                1125

Asp Gly Thr Arg Asp Tyr Ile Ile Ser Pro Val Lys Asn Lys Arg
            1130                1135                1140

Glu Ala Tyr Phe Asn Ser Glu Leu Ser Asp Gly Ser Val Pro Lys
            1145                1150                1155

Asp Ala Asp Ala Asn Gly Ala Tyr Asn Ile Ala Arg Lys Gly Leu
            1160                1165                1170

Trp Val Leu Glu Gln Ile Arg Gln Lys Ser Glu Gly Glu Lys Ile
            1175                1180                1185

Asn Leu Ala Met Thr Asn Ala Glu Trp Leu Glu Tyr Ala Gln Thr
            1190                1195                1200

His Leu Leu
```

-continued

1205

<210> SEQ ID NO 8
<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 8

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu

-continued

```
                355                 360                 365
Arg Lys Glu Ser Lys Lys Arg Leu Glu Gly Leu Glu His Ile Arg
        370                 375                 380
Lys Ser Thr Tyr Thr Phe Asp Glu Leu Asn Arg Tyr Ala Glu Lys Asn
385                 390                 395                 400
Val Met Ala Ala Tyr Ile Ala Ala Val Glu Ser Cys Ala Glu Ile
                405                 410                 415
Met Arg Lys Glu Lys Asp Leu Arg Thr Leu Leu Ser Lys Glu Asp Val
        420                 425                 430
Lys Ile Arg Gly Asn Arg His Asn Thr Leu Ile Val Lys Asn Tyr Phe
        435                 440                 445
Asn Ala Trp Thr Val Phe Arg Asn Leu Ile Arg Ile Leu Arg Arg Lys
        450                 455                 460
Ser Glu Ala Glu Ile Asp Ser Asp Phe Tyr Asp Val Leu Asp Ser
465                 470                 475                 480
Val Glu Val Leu Ser Leu Thr Tyr Lys Gly Glu Asn Leu Cys Arg Ser
                485                 490                 495
Tyr Ile Thr Lys Lys Ile Gly Ser Asp Leu Lys Pro Glu Ile Ala Thr
                500                 505                 510
Tyr Gly Ser Ala Leu Arg Pro Asn Ser Arg Trp Trp Ser Pro Gly Glu
        515                 520                 525
Lys Phe Asn Val Lys Phe His Thr Ile Val Arg Arg Asp Gly Arg Leu
        530                 535                 540
Tyr Tyr Phe Ile Leu Pro Lys Gly Ala Lys Pro Val Glu Leu Glu Asp
545                 550                 555                 560
Met Asp Gly Asp Ile Glu Cys Leu Gln Met Arg Lys Ile Pro Asn Pro
                565                 570                 575
Thr Ile Phe Leu Pro Lys Leu Val Phe Lys Asp Pro Glu Ala Phe Phe
        580                 585                 590
Arg Asp Asn Pro Glu Ala Asp Glu Phe Val Phe Leu Ser Gly Met Lys
        595                 600                 605
Ala Pro Val Thr Ile Thr Arg Glu Thr Tyr Glu Ala Tyr Arg Tyr Lys
        610                 615                 620
Leu Tyr Thr Val Gly Lys Leu Arg Asp Gly Glu Val Ser Glu Glu Glu
625                 630                 635                 640
Tyr Lys Arg Ala Leu Leu Gln Val Leu Thr Ala Tyr Lys Glu Phe Leu
                645                 650                 655
Glu Asn Arg Met Ile Tyr Ala Asp Leu Asn Phe Gly Phe Lys Asp Leu
                660                 665                 670
Glu Glu Tyr Lys Asp Ser Ser Glu Phe Ile Lys Gln Val Glu Thr His
        675                 680                 685
Asn Thr Phe Met Cys Trp Ala Lys Val Ser Ser Gln Leu Asp Asp
        690                 695                 700
Leu Val Lys Ser Gly Asn Gly Leu Leu Phe Glu Ile Trp Ser Glu Arg
705                 710                 715                 720
Leu Glu Ser Tyr Tyr Lys Tyr Gly Asn Glu Lys Val Leu Arg Gly Tyr
                725                 730                 735
Glu Gly Val Leu Leu Ser Ile Leu Lys Asp Glu Asn Leu Val Ser Met
                740                 745                 750
Arg Thr Leu Leu Asn Ser Arg Pro Met Leu Val Tyr Arg Pro Lys Glu
        755                 760                 765
Ser Ser Lys Pro Met Val Val His Arg Asp Gly Ser Arg Val Val Asp
        770                 775                 780
```

```
Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
            805                 810                 815

Lys Ala Arg Lys Ile Leu Asp Asn Lys Val Lys Val Lys Val Leu
        820                 825                 830

Glu Ser Glu Arg Val Lys Trp Ser Lys Phe Tyr Asp Glu Gln Phe Ala
        835                 840                 845

Val Thr Phe Ser Val Lys Lys Asn Ala Asp Cys Leu Asp Thr Thr Lys
        850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Lys Leu Ala Lys Leu Ser Asp Leu His Phe Arg Gly
            995                 1000                1005

Ile Lys Asp Gly Glu Pro Cys  Ser Phe Thr Asn Pro  Leu Gln Leu
    1010                1015                 1020

Cys Gln Asn Asp Ser Asn Lys  Ile Leu Gln Asp Gly  Val Ile Phe
    1025                1030                 1035

Met Val Pro Asn Ser Met Thr  Arg Ser Leu Asp Pro  Asp Thr Gly
    1040                1045                 1050

Phe Ile Phe Ala Ile Asn Asp His Asn Ile Arg Thr  Lys Lys Ala
    1055                1060                 1065

Lys Leu Asn Phe Leu Ser Lys  Phe Asp Gln Leu Lys  Val Ser Ser
    1070                1075                 1080

Glu Gly Cys Leu Ile Met Lys  Tyr Ser Gly Asp Ser  Leu Pro Thr
    1085                1090                 1095

His Asn Thr Asp Asn Arg Val  Trp Asn Cys Cys Cys  Asn His Pro
    1100                1105                 1110

Ile Thr Asn Tyr Asp Arg Glu  Thr Lys Lys Val Glu  Phe Ile Glu
    1115                1120                 1125

Glu Pro Val Glu Glu Leu Ser  Arg Val Leu Glu Glu  Asn Gly Ile
    1130                1135                 1140

Glu Thr Asp Thr Glu Leu Asn  Lys Leu Asn Glu Arg  Glu Asn Val
    1145                1150                 1155

Pro Gly Lys Val Val Asp Ala  Ile Tyr Ser Leu Val  Leu Asn Tyr
    1160                1165                 1170

Leu Arg Gly Thr Val Ser Gly  Val Ala Gly Gln Arg  Ala Val Tyr
    1175                1180                 1185
```

```
Tyr Ser Pro Val Thr Gly Lys Lys Tyr Asp Ile Ser Phe Ile Gln
    1190            1195                1200

Ala Met Asn Leu Asn Arg Lys Cys Asp Tyr Tyr Arg Ile Gly Ser
    1205            1210                1215

Lys Glu Arg Gly Glu Trp Thr Asp Phe Val Ala Gln Leu Ile Asn
    1220            1225                1230

<210> SEQ ID NO 9
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 9

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
50                  55                  60

Val Leu His Ser Ile Lys Leu Lys Asn Leu Asn Asn Tyr Ile Ser Leu
65              70                  75                  80

Phe Arg Lys Lys Thr Arg Thr Glu Lys Glu Asn Lys Glu Leu Glu Asn
            85                  90                  95

Leu Glu Ile Asn Leu Arg Lys Glu Ile Ala Lys Ala Phe Lys Gly Asn
        100                 105                 110

Glu Gly Tyr Lys Ser Leu Phe Lys Lys Asp Ile Ile Glu Thr Ile Leu
    115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145             150                 155                 160

Met Phe Ser Glu Glu Ala Lys Ser Thr Ser Ile Ala Phe Arg Cys Ile
            165                 170                 175

Asn Glu Asn Leu Thr Arg Tyr Ile Ser Asn Met Asp Ile Phe Glu Lys
        180                 185                 190

Val Asp Ala Ile Phe Asp Lys His Glu Val Gln Glu Ile Lys Glu Lys
    195                 200                 205

Ile Leu Asn Ser Asp Tyr Asp Val Glu Asp Phe Phe Glu Gly Glu Phe
210                 215                 220

Phe Asn Phe Val Leu Thr Gln Glu Gly Ile Asp Val Tyr Asn Ala Ile
225             230                 235                 240

Ile Gly Gly Phe Val Thr Glu Ser Gly Glu Lys Ile Lys Gly Leu Asn
            245                 250                 255

Glu Tyr Ile Asn Leu Tyr Asn Gln Lys Thr Lys Gln Lys Leu Pro Lys
        260                 265                 270

Phe Lys Pro Leu Tyr Lys Gln Val Leu Ser Asp Arg Glu Ser Leu Ser
    275                 280                 285

Phe Tyr Gly Glu Gly Tyr Thr Ser Asp Glu Glu Val Leu Glu Val Phe
290                 295                 300

Arg Asn Thr Leu Asn Lys Asn Ser Glu Ile Phe Ser Ser Ile Lys Lys
305             310                 315                 320
```

```
Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
                340                 345                 350

Gly Glu Trp Asn Val Ile Arg Asp Lys Trp Asn Ala Glu Tyr Asp Asp
                355                 360                 365

Ile His Leu Lys Lys Lys Ala Val Val Thr Glu Lys Tyr Glu Asp Asp
                370                 375             380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
                420                 425                 430

Glu Lys Leu Phe Asp Ala Asp Phe Val Leu Glu Lys Ser Leu Lys Lys
                435                 440                 445

Asn Asp Ala Val Val Ala Ile Met Lys Asp Leu Leu Asp Ser Val Lys
                450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
                515                 520                 525

Gln Phe Met Gly Gly Trp Asp Lys Asp Lys Glu Thr Asp Tyr Arg Ala
                530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
                595                 600                 605

Ser Glu Asp Ile Gln Lys Ile Tyr Lys Asn Gly Thr Phe Lys Lys Gly
                610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
                690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
```

```
                740             745             750
Lys Glu Glu Leu Val Val His Pro Ala Asn Ser Pro Ile Ala Asn Lys
            755             760             765
Asn Pro Asp Asn Pro Lys Lys Thr Thr Thr Leu Ser Tyr Asp Val Tyr
            770             775             780
Lys Asp Lys Arg Phe Ser Glu Asp Gln Tyr Glu Leu His Ile Pro Ile
785             790             795             800
Ala Asn Ile Asn Lys Cys Pro Lys Asn Ile Phe Lys Ile Asn Thr Glu
            805             810             815
Val Arg Val Leu Leu Lys His Asp Asp Asn Pro Tyr Val Ile Gly Ile
            820             825             830
Asp Arg Gly Glu Arg Asn Leu Leu Tyr Ile Val Val Asp Gly Lys
            835             840             845
Gly Asn Ile Val Glu Gln Tyr Ser Leu Asn Glu Ile Ile Asn Asn Phe
            850             855             860
Asn Gly Ile Arg Ile Lys Thr Asp Tyr His Ser Leu Leu Asp Lys Lys
865             870             875             880
Glu Lys Glu Arg Phe Glu Ala Arg Gln Asn Trp Thr Ser Ile Glu Asn
            885             890             895
Ile Lys Glu Leu Lys Ala Gly Tyr Ile Ser Gln Val Val His Lys Ile
            900             905             910
Cys Glu Leu Val Glu Lys Tyr Asp Ala Val Ile Ala Leu Glu Asp Leu
            915             920             925
Asn Ser Gly Phe Lys Asn Ser Arg Val Lys Val Glu Lys Gln Val Tyr
            930             935             940
Gln Lys Phe Glu Lys Met Leu Ile Asp Lys Leu Asn Tyr Met Val Asp
945             950             955             960
Lys Lys Ser Asn Pro Cys Ala Thr Gly Gly Ala Leu Lys Gly Tyr Gln
            965             970             975
Ile Thr Asn Lys Phe Glu Ser Phe Lys Ser Met Ser Thr Gln Asn Gly
            980             985             990
Phe Ile Phe Tyr Ile Pro Ala Trp Leu Thr Ser Lys Ile Asp Pro Ser
            995             1000            1005
Thr Gly Phe Val Asn Leu Leu Lys Thr Lys Tyr Thr Ser Ile Ala
            1010            1015            1020
Asp Lys Lys Phe Ile Ser Ser Phe Asp Arg Ile Met Tyr Val Pro
            1025            1030            1035
Glu Glu Asp Leu Phe Glu Phe Ala Leu Asp Tyr Lys Asn Phe Ser
            1040            1045            1050
Arg Thr Asp Ala Asp Tyr Ile Lys Lys Trp Lys Leu Tyr Ser Tyr
            1055            1060            1065
Gly Asn Arg Ile Arg Ile Phe Arg Asn Pro Lys Lys Asn Asn Val
            1070            1075            1080
Phe Asp Trp Glu Glu Val Cys Leu Thr Ser Ala Tyr Lys Glu Leu
            1085            1090            1095
Phe Asn Lys Tyr Gly Ile Asn Tyr Gln Gln Gly Asp Ile Arg Ala
            1100            1105            1110
Leu Leu Cys Glu Gln Ser Asp Lys Ala Phe Tyr Ser Ser Phe Met
            1115            1120            1125
Ala Leu Met Ser Leu Met Leu Gln Met Arg Asn Ser Ile Thr Gly
            1130            1135            1140
Arg Thr Asp Val Asp Phe Leu Ile Ser Pro Val Lys Asn Ser Asp
            1145            1150            1155
```

```
Gly Ile Phe Tyr Asp Ser Arg Asn Tyr Glu Ala Gln Glu Asn Ala
            1160                1165                1170

Ile Leu Pro Lys Asn Ala Asp Ala Asn Gly Ala Tyr Asn Ile Ala
            1175                1180                1185

Arg Lys Val Leu Trp Ala Ile Gly Gln Phe Lys Lys Ala Glu Asp
            1190                1195                1200

Glu Lys Leu Asp Lys Val Lys Ile Ala Ser Asn Lys Glu Trp Leu
            1205                1210                1215

Glu Tyr Ala Gln Thr Ser Val Lys His
            1220                1225

<210> SEQ ID NO 10
<211> LENGTH: 1264
<212> TYPE: PRT
<213> ORGANISM: Leptospira inadai

<400> SEQUENCE: 10

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
            35                  40                  45

Ala Val Lys Lys Ile Ile Asp Lys Tyr His Arg Ala Tyr Ile Glu Glu
            50                  55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Glu Leu Tyr
            85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
            115                 120                 125

Ser Glu Glu Val Ala Gly Lys Tyr Asn Lys Asn Leu Phe Ser Lys Glu
            130                 135                 140

Leu Ile Arg Asn Glu Ile Glu Lys Phe Cys Glu Thr Asp Glu Glu Arg
145                 150                 155                 160

Lys Gln Val Ser Asn Phe Lys Ser Phe Thr Thr Tyr Phe Thr Gly Phe
            165                 170                 175

His Ser Asn Arg Gln Asn Ile Tyr Ser Asp Glu Lys Lys Ser Thr Ala
            180                 185                 190

Ile Gly Tyr Arg Ile Ile His Gln Asn Leu Pro Lys Phe Leu Asp Asn
            195                 200                 205

Leu Lys Ile Ile Glu Ser Ile Gln Arg Arg Phe Lys Asp Phe Pro Trp
            210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
            245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
            275                 280                 285

Lys Asn Asn Ile Asp Arg Lys Asn Pro Leu Asn Val Lys Ile Leu Phe
```

```
            290                 295                 300
Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ile Ala Glu Leu Lys
            340                 345                 350

Lys Phe Leu Ser Ser Phe Asn Arg Tyr Glu Leu Asp Gly Ile Tyr Leu
            355                 360                 365

Ala Asn Asp Asn Ser Leu Ala Ser Ile Ser Thr Phe Leu Phe Asp Asp
            370                 375                 380

Trp Ser Phe Ile Lys Lys Ser Val Ser Phe Lys Tyr Asp Glu Ser Val
385                 390                 395                 400

Gly Asp Pro Lys Lys Ile Lys Ser Pro Leu Lys Tyr Glu Lys Glu
            405                 410                 415

Lys Glu Lys Trp Leu Lys Gln Lys Tyr Tyr Thr Ile Ser Phe Leu Asn
            420                 425                 430

Asp Ala Ile Glu Ser Tyr Ser Lys Ser Gln Asp Glu Lys Arg Val Lys
            435                 440                 445

Ile Arg Leu Glu Ala Tyr Phe Ala Glu Phe Lys Ser Lys Asp Asp Ala
            450                 455                 460

Lys Lys Gln Phe Asp Leu Leu Glu Arg Ile Glu Glu Ala Tyr Ala Ile
465                 470                 475                 480

Val Glu Pro Leu Leu Gly Ala Glu Tyr Pro Arg Asp Arg Asn Leu Lys
                485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
            515                 520                 525

Asp Glu Lys Asp Leu Gly Phe Tyr Asn Gln Leu Glu Gly Tyr Tyr Glu
            530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
                565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
            595                 600                 605

Lys Glu Asn Asn Thr Ile Leu Ser Asp Ile Pro Lys Val Lys Pro Asn
610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
                645                 650                 655

Asn Pro Ser Lys Ser Ile Leu Lys Ile Arg Glu Ala Lys Ser Phe Lys
            660                 665                 670

Glu Gly Lys Asn Phe Lys Leu Lys Asp Cys His Lys Phe Ile Asp Phe
            675                 680                 685

Tyr Lys Glu Ser Ile Ser Lys Asn Glu Asp Trp Ser Arg Phe Asp Phe
            690                 695                 700

Lys Phe Ser Lys Thr Ser Ser Tyr Glu Asn Ile Ser Glu Phe Tyr Arg
705                 710                 715                 720
```

-continued

```
Glu Val Glu Arg Gln Gly Tyr Asn Leu Asp Phe Lys Val Ser Lys
                725                 730                 735
Phe Tyr Ile Asp Ser Leu Val Glu Asp Gly Lys Leu Tyr Leu Phe Gln
                740                 745                 750
Ile Tyr Asn Lys Asp Phe Ser Ile Phe Ser Lys Gly Lys Pro Asn Leu
                755                 760                 765
His Thr Ile Tyr Phe Arg Ser Leu Phe Ser Lys Glu Asn Leu Lys Asp
            770                 775                 780
Val Cys Leu Lys Leu Asn Gly Glu Ala Glu Met Phe Phe Arg Lys Lys
785                 790                 795                 800
Ser Ile Asn Tyr Asp Glu Lys Lys Arg Glu Gly His His Pro Glu
                805                 810                 815
Leu Phe Glu Lys Leu Lys Tyr Pro Ile Leu Lys Asp Lys Arg Tyr Ser
                820                 825                 830
Glu Asp Lys Phe Gln Phe His Leu Pro Ile Ser Leu Asn Phe Lys Ser
                835                 840                 845
Lys Glu Arg Leu Asn Phe Asn Leu Lys Val Asn Glu Phe Leu Lys Arg
                850                 855                 860
Asn Lys Asp Ile Asn Ile Gly Ile Asp Arg Gly Glu Arg Asn Leu
865                 870                 875                 880
Leu Tyr Leu Val Met Ile Asn Gln Lys Gly Glu Ile Leu Lys Gln Thr
                885                 890                 895
Leu Leu Asp Ser Met Gln Ser Gly Lys Gly Arg Pro Glu Ile Asn Tyr
                900                 905                 910
Lys Glu Lys Leu Gln Glu Lys Glu Ile Glu Arg Asp Lys Ala Arg Lys
                915                 920                 925
Ser Trp Gly Thr Val Glu Asn Ile Lys Glu Leu Lys Glu Gly Tyr Leu
                930                 935                 940
Ser Ile Val Ile His Gln Ile Ser Lys Leu Met Val Glu Asn Asn Ala
945                 950                 955                 960
Ile Val Val Leu Glu Asp Leu Asn Ile Gly Phe Lys Arg Gly Arg Gln
                965                 970                 975
Lys Val Glu Arg Gln Val Tyr Gln Lys Phe Glu Lys Met Leu Ile Asp
                980                 985                 990
Lys Leu Asn Phe Leu Val Phe Lys Glu Asn Lys Pro Thr Glu Pro Gly
                995                 1000                1005
Gly Val Leu Lys Ala Tyr Gln Leu Thr Asp Glu Phe Gln Ser Phe
                1010                1015                1020
Glu Lys Leu Ser Lys Gln Thr Gly Phe Leu Phe Tyr Val Pro Ser
                1025                1030                1035
Trp Asn Thr Ser Lys Ile Asp Pro Arg Thr Gly Phe Ile Asp Phe
                1040                1045                1050
Leu His Pro Ala Tyr Glu Asn Ile Glu Lys Ala Lys Gln Trp Ile
                1055                1060                1065
Asn Lys Phe Asp Ser Ile Arg Phe Asn Ser Lys Met Asp Trp Phe
                1070                1075                1080
Glu Phe Thr Ala Asp Thr Arg Lys Phe Ser Glu Asn Leu Met Leu
                1085                1090                1095
Gly Lys Asn Arg Val Trp Val Ile Cys Thr Thr Asn Val Glu Arg
                1100                1105                1110
Tyr Phe Thr Ser Lys Thr Ala Asn Ser Ser Ile Gln Tyr Asn Ser
                1115                1120                1125
```

-continued

```
Ile Gln Ile Thr Glu Lys Leu Lys Glu Leu Phe Val Asp Ile Pro
    1130                1135                1140

Phe Ser Asn Gly Gln Asp Leu Lys Pro Glu Ile Leu Arg Lys Asn
    1145                1150                1155

Asp Ala Val Phe Phe Lys Ser Leu Leu Phe Tyr Ile Lys Thr Thr
    1160                1165                1170

Leu Ser Leu Arg Gln Asn Asn Gly Lys Lys Gly Glu Glu Lys
    1175                1180                1185

Asp Phe Ile Leu Ser Pro Val Val Asp Ser Lys Gly Arg Phe Phe
    1190                1195                1200

Asn Ser Leu Glu Ala Ser Asp Glu Pro Lys Asp Ala Asp Ala
    1205                1210                1215

Asn Gly Ala Tyr His Ile Ala Leu Lys Gly Leu Met Asn Leu Leu
    1220                1225                1230

Val Leu Asn Glu Thr Lys Glu Glu Asn Leu Ser Arg Pro Lys Trp
    1235                1240                1245

Lys Ile Lys Asn Lys Asp Trp Leu Glu Phe Val Trp Glu Arg Asn
    1250                1255                1260

Arg

<210> SEQ ID NO 11
<211> LENGTH: 1373
<212> TYPE: PRT
<213> ORGANISM: Moraxella bovoculi

<400> SEQUENCE: 11

Met Leu Phe Gln Asp Phe Thr His Leu Tyr Pro Leu Ser Lys Thr Val
1               5                   10                  15

Arg Phe Glu Leu Phe Ile Asp Arg Thr Leu Glu His Ile His Ala Lys
            20                  25                  30

Asn Phe Leu Ser Gln Asp Glu Thr Met Ala Asp Met His Gln Lys Val
        35                  40                  45

Lys Val Ile Leu Asp Asp Tyr His Arg Asp Phe Ile Ala Asp Met Met
    50                  55                  60

Gly Glu Val Lys Leu Thr Lys Leu Ala Glu Phe Tyr Asp Val Tyr Leu
65                  70                  75                  80

Lys Phe Arg Lys Asn Pro Lys Asp Asp Glu Leu Gln Lys Ala Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
    210                 215                 220
```

```
Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
            245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
            275                 280                 285

Ile Ala Lys Leu Arg Pro Leu His Lys Gln Ile Leu Ser Asp Gly Met
290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
            325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
            355                 360                 365

Asp Phe Ala Leu Leu Gly Arg Val Leu Asp Gly Tyr Tyr Val Asp Val
370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
            405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
            450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
            485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
            530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
            565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
```

```
                      645                 650                 655
Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
            690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
            755                 760                 765

Glu Asn Phe Tyr Asn Asn His Pro Lys Phe Lys Lys Asp Leu Val Arg
            770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830

Phe Cys Asn Ile Asn Ala Asp Tyr Ile Asp Glu Leu Val Glu Gln Gly
            835                 840                 845

Gln Leu Tyr Leu Phe Gln Ile Tyr Asn Lys Asp Phe Ser Pro Lys Ala
850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
            915                 920                 925

Arg Gln Phe Val Tyr Asp Ile Ile Lys Asp Lys Arg Tyr Thr Gln Lys
            930                 935                 940

Asp Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser Lys Gly Glu Ile Leu Glu Gln Cys
            995                1000                1005

Ser Leu Asn Asp Ile Thr Thr Ala Ser Ala Asn Gly Thr Gln Met
    1010                1015                1020

Thr Thr Pro Tyr His Lys Ile Leu Asp Lys Arg Glu Ile Glu Arg
    1025                1030                1035

Leu Asn Ala Arg Val Gly Trp Gly Glu Ile Glu Thr Ile Lys Glu
    1040                1045                1050

Leu Lys Ser Gly Tyr Leu Ser His Val Val His Gln Ile Ser Gln
    1055                1060                1065
```

```
Leu Met Leu Lys Tyr Asn Ala Ile Val Val Leu Glu Asp Leu Asn
    1070            1075                1080

Phe Gly Phe Lys Arg Gly Arg Phe Lys Val Glu Lys Gln Ile Tyr
    1085            1090                1095

Gln Asn Phe Glu Asn Ala Leu Ile Lys Lys Leu Asn His Leu Val
    1100            1105                1110

Leu Lys Asp Lys Ala Asp Asp Glu Ile Gly Ser Tyr Lys Asn Ala
    1115            1120                1125

Leu Gln Leu Thr Asn Asn Phe Thr Asp Leu Lys Ser Ile Gly Lys
    1130            1135                1140

Gln Thr Gly Phe Leu Phe Tyr Val Pro Ala Trp Asn Thr Ser Lys
    1145            1150                1155

Ile Asp Pro Glu Thr Gly Phe Val Asp Leu Leu Lys Pro Arg Tyr
    1160            1165                1170

Glu Asn Ile Gln Ala Ser Gln Ala Phe Phe Gly Lys Phe Asp Lys
    1175            1180                1185

Ile Cys Tyr Asn Ala Asp Lys Asp Tyr Phe Glu Phe His Ile Asp
    1190            1195                1200

Tyr Ala Lys Phe Thr Asp Lys Ala Lys Asn Ser Arg Gln Ile Trp
    1205            1210                1215

Thr Ile Cys Ser His Gly Asp Lys Arg Tyr Val Tyr Asp Lys Thr
    1220            1225                1230

Ala Asn Gln Asn Lys Gly Ala Ala Lys Gly Ile Asn Val Asn Asp
    1235            1240                1245

Ile Leu Lys Ser Leu Phe Ala Arg His His Ile Asn Glu Lys Gln
    1250            1255                1260

Pro Asn Leu Val Met Asp Ile Cys Gln Asn Asn Asp Lys Glu Phe
    1265            1270                1275

His Lys Ser Leu Met Tyr Leu Leu Lys Thr Leu Leu Ala Leu Arg
    1280            1285                1290

Tyr Ser Asn Ala Ser Ser Asp Glu Asp Phe Ile Leu Ser Pro Val
    1295            1300                1305

Ala Asn Asp Glu Gly Val Phe Phe Asn Ser Ala Leu Ala Asp Asp
    1310            1315                1320

Thr Gln Pro Gln Asn Ala Asp Ala Asn Gly Ala Tyr His Ile Ala
    1325            1330                1335

Leu Lys Gly Leu Trp Leu Leu Asn Glu Leu Lys Asn Ser Asp Asp
    1340            1345                1350

Leu Asn Lys Val Lys Leu Ala Ile Asp Asn Gln Thr Trp Leu Asn
    1355            1360                1365

Phe Ala Gln Asn Arg
    1370

<210> SEQ ID NO 12
<211> LENGTH: 1352
<212> TYPE: PRT
<213> ORGANISM: Unknown
<220> FEATURE:
<223> OTHER INFORMATION: Parcubacteria bacterium

<400> SEQUENCE: 12

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30
```

```
Lys Ile Asn Lys Val Phe Glu Lys Asp Gln Thr Ile Asp Asp Ser Tyr
             35                  40                  45

Asn Gln Ala Lys Phe Tyr Phe Asp Ser Leu His Gln Lys Phe Ile Asp
 50                  55                  60

Ala Ala Leu Ala Ser Asp Lys Thr Ser Glu Leu Ser Phe Gln Asn Phe
 65                  70                  75                  80

Ala Asp Val Leu Glu Lys Gln Asn Lys Ile Ile Leu Asp Lys Lys Arg
                 85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
             115                 120                 125

Lys Glu Lys Ile Tyr Lys Asp Val Arg Thr Leu Phe Asp Asn Glu Ala
130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
                180                 185                 190

Lys Glu Lys Glu Phe Gln Ala Lys Asn Gln Pro Ser Leu Phe Val Glu
            195                 200                 205

Glu Lys Glu Asn Pro Gly Gln Lys Arg Tyr Ile Phe Asp Ser Phe Asp
210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
                260                 265                 270

Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
                340                 345                 350

Val Glu Lys Glu Lys Gln Leu Ile Glu Lys Thr Arg Glu Lys Thr Glu
            355                 360                 365

Glu Asp Val Leu Ile Glu Arg Phe Lys Glu Phe Ile Glu Asn Asn Glu
370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
                420                 425                 430

Lys Leu Pro Gln Gln Lys Ser Lys Asn Lys Ser Glu Lys Asn Glu Pro
            435                 440                 445
```

-continued

```
Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                    485                 490                 495

Tyr Glu Phe Glu Tyr Leu Phe Arg Asp Ile Glu Arg Glu Asn Gly Glu
                500                 505                 510

Lys Leu Leu Gly Tyr Asp Ser Cys Leu Lys Ile Ala Lys Gln Leu Gly
                515                 520                 525

Ile Phe Pro Gln Glu Lys Glu Ala Arg Glu Lys Ala Thr Ala Val Ile
530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Lys Asp Phe Glu Phe
                580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
                660                 665                 670

Gln Lys Met Ile Tyr Lys Gln Ile Ala Asp Ala Ser Lys Asp Val Pro
            675                 680                 685

Arg Leu Leu Leu Thr Ser Lys Lys Ala Met Glu Lys Phe Lys Pro Ser
    690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
                740                 745                 750

Gln Asp Thr Gly Lys Tyr Gln Asn Ile Lys Glu Phe Thr Asp Val
            755                 760                 765

Gln Lys Tyr Gly Tyr Lys Ile Ser Phe Arg Asp Ile Asp Asp Glu Tyr
770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
                820                 825                 830

Phe Lys Leu Ser Gly Met Ala Glu Ile Phe Gln Arg Gln Pro Ser Val
                835                 840                 845

Asn Glu Arg Glu Lys Ile Thr Thr Gln Lys Asn Gln Cys Ile Leu Asp
850                 855                 860

Lys Gly Asp Arg Ala Tyr Lys Tyr Arg Arg Tyr Thr Glu Lys Lys Ile
```

```
                865                 870                 875                 880
Met Phe His Met Ser Leu Val Leu Asn Thr Gly Lys Gly Glu Ile Lys
                        885                 890                 895
Gln Val Gln Phe Asn Lys Ile Ile Asn Gln Arg Ile Ser Ser Ser Asp
                        900                 905                 910
Asn Glu Met Arg Val Asn Val Gly Ile Asp Arg Gly Glu Lys Asn
                        915                 920                 925
Leu Leu Tyr Tyr Ser Val Val Lys Gln Asn Gly Glu Ile Ile Glu Gln
                        930                 935                 940
Ala Ser Leu Asn Glu Ile Asn Gly Val Asn Tyr Arg Asp Lys Leu Ile
945                         950                 955                 960
Glu Arg Glu Lys Glu Arg Leu Lys Asn Arg Gln Ser Trp Lys Pro Val
                        965                 970                 975
Val Lys Ile Lys Asp Leu Lys Lys Gly Tyr Ile Ser His Val Ile His
                        980                 985                 990
Lys Ile Cys Gln Leu Ile Glu Lys Tyr Ser Ala Ile Val Val Leu Glu
                        995                 1000                1005
Asp Leu Asn Met Arg Phe Lys Gln Ile Arg Gly Gly Ile Glu Arg
            1010                1015                1020
Ser Val Tyr Gln Gln Phe Glu Lys Ala Leu Ile Asp Lys Leu Gly
            1025                1030                1035
Tyr Leu Val Phe Lys Asp Asn Arg Asp Leu Arg Ala Pro Gly Gly
            1040                1045                1050
Val Leu Asn Gly Tyr Gln Leu Ser Ala Pro Phe Val Ser Phe Glu
            1055                1060                1065
Lys Met Arg Lys Gln Thr Gly Ile Leu Phe Tyr Thr Gln Ala Glu
            1070                1075                1080
Tyr Thr Ser Lys Thr Asp Pro Ile Thr Gly Phe Arg Lys Asn Val
            1085                1090                1095
Tyr Ile Ser Asn Ser Ala Ser Leu Asp Lys Ile Lys Glu Ala Val
            1100                1105                1110
Lys Lys Phe Asp Ala Ile Gly Trp Asp Gly Lys Glu Gln Ser Tyr
            1115                1120                1125
Phe Phe Lys Tyr Asn Pro Tyr Asn Leu Ala Asp Glu Lys Tyr Lys
            1130                1135                1140
Asn Ser Thr Val Ser Lys Glu Trp Ala Ile Phe Ala Ser Ala Pro
            1145                1150                1155
Arg Ile Arg Arg Gln Lys Gly Glu Asp Gly Tyr Trp Lys Tyr Asp
            1160                1165                1170
Arg Val Lys Val Asn Glu Glu Phe Glu Lys Leu Leu Lys Val Trp
            1175                1180                1185
Asn Phe Val Asn Pro Lys Ala Thr Asp Ile Lys Gln Glu Ile Ile
            1190                1195                1200
Lys Lys Ile Lys Ala Gly Asp Leu Gln Gly Glu Lys Glu Leu Asp
            1205                1210                1215
Gly Arg Leu Arg Asn Phe Trp His Ser Phe Ile Tyr Leu Phe Asn
            1220                1225                1230
Leu Val Leu Glu Leu Arg Asn Ser Phe Ser Leu Gln Ile Lys Ile
            1235                1240                1245
Lys Ala Gly Glu Val Ile Ala Val Asp Glu Gly Val Asp Phe Ile
            1250                1255                1260
Ala Ser Pro Val Lys Pro Phe Phe Thr Thr Pro Asn Pro Tyr Ile
            1265                1270                1275
```

```
Pro Ser Asn Leu Cys Trp Leu Ala Val Glu Asn Ala Asp Ala Asn
    1280            1285                1290

Gly Ala Tyr Asn Ile Ala Arg Lys Gly Val Met Ile Leu Lys Lys
    1295            1300                1305

Ile Arg Glu His Ala Lys Lys Asp Pro Glu Phe Lys Lys Leu Pro
    1310            1315                1320

Asn Leu Phe Ile Ser Asn Ala Glu Trp Asp Glu Ala Ala Arg Asp
    1325            1330                1335

Trp Gly Lys Tyr Ala Gly Thr Thr Ala Leu Asn Leu Asp His
    1340            1345                1350

<210> SEQ ID NO 13
<211> LENGTH: 1260
<212> TYPE: PRT
<213> ORGANISM: Porphyromonas crevioricanis

<400> SEQUENCE: 13

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
                20                  25                  30

Lys Ala Gly Ile Leu Lys Glu Asp Glu His Arg Ala Glu Ser Tyr Arg
            35                  40                  45

Arg Val Lys Lys Ile Ile Asp Thr Tyr His Lys Val Phe Ile Asp Ser
        50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
```

-continued

```
               290                 295                 300
Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
                340                 345                 350

Thr Gln Gln Leu Met Thr Ser Ile Ser Glu Tyr Asp Leu Ser Arg Ile
                355                 360                 365

Tyr Val Arg Asn Asp Ser Gln Leu Thr Asp Ile Ser Lys Lys Met Leu
370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
                420                 425                 430

Cys Ile Ala Phe Leu Asp Asn Val Arg Asp Cys Arg Val Asp Thr Tyr
                435                 440                 445

Leu Ser Thr Leu Gly Gln Lys Glu Gly Pro His Gly Leu Ser Asn Leu
450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
                500                 505                 510

Leu Lys Pro Leu Trp Gly Met Gly Asp Glu Pro Asp Lys Asp Glu Arg
                515                 520                 525

Phe Tyr Gly Glu Tyr Asn Tyr Ile Arg Gly Ala Leu Asp Gln Val Ile
                530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575

Trp Asp Arg Asn Lys Glu Lys Asp Asn Ser Cys Val Ile Leu Arg Lys
                580                 585                 590

Gly Gln Asn Phe Tyr Leu Ala Ile Met Asn Asn Arg His Lys Arg Ser
                595                 600                 605

Phe Glu Asn Lys Met Leu Pro Glu Tyr Lys Glu Gly Glu Pro Tyr Phe
610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
                660                 665                 670

Phe Ser Met Asp Asp Leu His Glu Leu Ile Asp Phe Phe Lys His Ser
                675                 680                 685

Ile Glu Ala His Glu Asp Trp Lys Gln Phe Gly Phe Lys Phe Ser Asp
                690                 695                 700

Thr Ala Thr Tyr Glu Asn Val Ser Ser Phe Tyr Arg Glu Val Glu Asp
705                 710                 715                 720
```

-continued

```
Gln Gly Tyr Lys Leu Ser Phe Arg Lys Val Ser Glu Ser Tyr Val Tyr
            725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
            755                 760                 765

Trp Arg Met Leu Phe Asp Glu Arg Asn Leu Ala Asp Val Ile Tyr Lys
            770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Ser Arg
                805                 810                 815

Gln Lys Lys Gly Glu Glu Ser Leu Phe Glu Tyr Asp Leu Val Lys Asp
                820                 825                 830

Arg Arg Tyr Thr Met Asp Lys Phe Gln Phe His Val Pro Ile Thr Met
                835                 840                 845

Asn Phe Lys Cys Ser Ala Gly Ser Lys Val Asn Asp Met Val Asn Ala
850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
                900                 905                 910

Leu Leu Glu Ser Arg Asp Lys Asp Arg Gln Gln Glu His Arg Asn Trp
                915                 920                 925

Gln Thr Ile Glu Gly Ile Lys Glu Leu Lys Gln Gly Tyr Leu Ser Gln
                930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
                980                 985                 990

Asn Tyr Leu Val Asp Lys Lys Lys Arg Pro Glu Asp Ile Gly Gly Leu
                995                 1000                1005

Leu Arg Ala Tyr Gln Phe Thr Ala Pro Phe Lys Ser Phe Lys Glu
        1010                1015                1020

Met Gly Lys Gln Asn Gly Phe Leu Phe Tyr Ile Pro Ala Trp Asn
        1025                1030                1035

Thr Ser Asn Ile Asp Pro Thr Gly Phe Val Asn Leu Phe His
        1040                1045                1050

Val Gln Tyr Glu Asn Val Asp Lys Ala Lys Ser Phe Phe Gln Lys
        1055                1060                1065

Phe Asp Ser Ile Ser Tyr Asn Pro Lys Lys Asp Trp Phe Glu Phe
        1070                1075                1080

Ala Phe Asp Tyr Lys Asn Phe Thr Lys Lys Ala Glu Gly Ser Arg
        1085                1090                1095

Ser Met Trp Ile Leu Cys Thr His Gly Ser Arg Ile Lys Asn Phe
        1100                1105                1110

Arg Asn Ser Gln Lys Asn Gly Gln Trp Asp Ser Glu Glu Phe Ala
        1115                1120                1125
```

```
Leu Thr Glu Ala Phe Lys Ser Leu Phe Val Arg Tyr Glu Ile Asp
    1130                1135                1140

Tyr Thr Ala Asp Leu Lys Thr Ala Ile Val Asp Glu Lys Gln Lys
1145                1150                1155

Asp Phe Phe Val Asp Leu Leu Lys Leu Phe Lys Leu Thr Val Gln
    1160                1165                1170

Met Arg Asn Ser Trp Lys Glu Lys Asp Leu Asp Tyr Leu Ile Ser
    1175                1180                1185

Pro Val Ala Gly Ala Asp Gly Arg Phe Phe Asp Thr Arg Glu Gly
    1190                1195                1200

Asn Lys Ser Leu Pro Lys Asp Ala Asp Ala Asn Gly Ala Tyr Asn
    1205                1210                1215

Ile Ala Leu Lys Gly Leu Trp Ala Leu Arg Gln Ile Arg Gln Thr
    1220                1225                1230

Ser Glu Gly Gly Lys Leu Lys Leu Ala Ile Ser Asn Lys Glu Trp
    1235                1240                1245

Leu Gln Phe Val Gln Glu Arg Ser Tyr Glu Lys Asp
    1250                1255                1260

<210> SEQ ID NO 14
<211> LENGTH: 1324
<212> TYPE: PRT
<213> ORGANISM: Prevotella disiens

<400> SEQUENCE: 14

Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
        115                 120                 125

Ala Phe Leu Lys Ser Pro Gln Lys Lys Leu Leu Ala Ile Lys Asn Leu
    130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240
```

```
Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
                260                 265                 270

Glu His Ile Asn Leu Tyr Asn Gln Lys His Lys Asp Arg Arg Leu Pro
            275                 280                 285

Phe Phe Ile Ser Leu Lys Lys Gln Ile Leu Ser Asp Arg Glu Ala Leu
        290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
                340                 345                 350

Ile Phe Ile Arg Asn Asn Glu Ala Leu Ser Ser Leu Ser Gln Asn Val
            355                 360                 365

Tyr Arg Asn Phe Ser Ile Asp Glu Ala Ile Asp Ala Gln Asn Ala Glu
        370                 375                 380

Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
                405                 410                 415

Glu Glu Tyr Ile Asp Lys Lys Val Lys Ala Ile Asp Ser Leu Ser Ile
                420                 425                 430

Gln Glu Ile Asn Glu Leu Val Glu Asn Tyr Val Ser Glu Phe Asn Ser
            435                 440                 445

Asn Ser Gly Asn Met Pro Arg Lys Val Glu Asp Tyr Phe Ser Leu Met
        450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
                500                 505                 510

Leu Leu Asp Ala Thr Lys Gln Phe Gln His Phe Ile Lys Pro Leu Leu
            515                 520                 525

Gly Thr Gly Glu Glu Ala Asp Arg Asp Leu Val Phe Tyr Gly Asp Phe
        530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
                580                 585                 590

Thr Glu Lys Ser Asp Asn Gly Thr Gln Tyr Gly Gly Tyr Leu Phe Arg
            595                 600                 605

Lys Lys Asn Glu Ile Gly Glu Tyr Asp Tyr Phe Leu Gly Ile Ser Ser
        610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655
```

```
Tyr Glu Gly Glu Asn Ser Tyr Lys Glu Asp Lys Lys Arg Leu Asn Lys
            660                 665                 670

Val Ile Ile Ala Tyr Ile Glu Gln Ile Lys Gln Thr Asn Ile Lys Lys
675                 680                 685

Ser Ile Ile Glu Ser Ile Ser Lys Tyr Pro Asn Ile Ser Asp Asp Asp
            690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
755                 760                 765

Glu Val Gln Ala Val Ile Asp Glu Ile Cys Lys Gln Lys Thr Phe Ile
            770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
                805                 810                 815

Ala Lys Thr Phe Ser Ala Asn Leu Arg Lys Lys Arg Gly Ala Glu Asn
            820                 825                 830

Leu His Thr Met Leu Phe Lys Ala Leu Met Glu Gly Asn Gln Asp Asn
                835                 840                 845

Leu Asp Leu Gly Ser Gly Ala Ile Phe Tyr Arg Ala Lys Ser Leu Asp
850                 855                 860

Gly Asn Lys Pro Thr His Pro Ala Asn Glu Ala Ile Lys Cys Arg Asn
865                 870                 875                 880

Val Ala Asn Lys Asp Lys Val Ser Leu Phe Thr Tyr Asp Ile Tyr Lys
                885                 890                 895

Asn Arg Arg Tyr Met Glu Asn Lys Phe Leu Phe His Leu Ser Ile Val
            900                 905                 910

Gln Asn Tyr Lys Ala Ala Asn Asp Ser Ala Gln Leu Asn Ser Ser Ala
            915                 920                 925

Thr Glu Tyr Ile Arg Lys Ala Asp Asp Leu His Ile Ile Gly Ile Asp
930                 935                 940

Arg Gly Glu Arg Asn Leu Leu Tyr Tyr Ser Val Ile Asp Met Lys Gly
945                 950                 955                 960

Asn Ile Val Glu Gln Asp Ser Leu Asn Ile Ile Arg Asn Asn Asp Leu
                965                 970                 975

Glu Thr Asp Tyr His Asp Leu Leu Asp Lys Arg Glu Lys Glu Arg Lys
                980                 985                 990

Ala Asn Arg Gln Asn Trp Glu Ala Val Glu Gly Ile Lys Asp Leu Lys
            995                 1000                1005

Lys Gly Tyr Leu Ser Gln Ala Val His Gln Ile Ala Gln Leu Met
            1010                1015                1020

Leu Lys Tyr Asn Ala Ile Ile Ala Leu Glu Asp Leu Gly Gln Met
            1025                1030                1035

Phe Val Thr Arg Gly Gln Lys Ile Glu Lys Ala Val Tyr Gln Gln
            1040                1045                1050

Phe Glu Lys Ser Leu Val Asp Lys Leu Ser Tyr Leu Val Asp Lys
            1055                1060                1065

Lys Arg Pro Tyr Asn Glu Leu Gly Gly Ile Leu Lys Ala Tyr Gln
```

-continued

```
            1070                1075                1080

Leu Ala Ser Ser Ile Thr Lys Asn Asn Ser Asp Lys Gln Asn Gly
        1085                1090                1095

Phe Leu Phe Tyr Val Pro Ala Trp Asn Thr Ser Lys Ile Asp Pro
    1100                1105                1110

Val Thr Gly Phe Thr Asp Leu Leu Arg Pro Lys Ala Met Thr Ile
    1115                1120                1125

Lys Glu Ala Gln Asp Phe Phe Gly Ala Phe Asp Asn Ile Ser Tyr
    1130                1135                1140

Asn Asp Lys Gly Tyr Phe Glu Phe Glu Thr Asn Tyr Asp Lys Phe
    1145                1150                1155

Lys Ile Arg Met Lys Ser Ala Gln Thr Arg Trp Thr Ile Cys Thr
    1160                1165                1170

Phe Gly Asn Arg Ile Lys Arg Lys Lys Asp Lys Asn Tyr Trp Asn
    1175                1180                1185

Tyr Glu Glu Val Glu Leu Thr Glu Glu Phe Lys Lys Leu Phe Lys
    1190                1195                1200

Asp Ser Asn Ile Asp Tyr Glu Asn Cys Asn Leu Lys Glu Glu Ile
    1205                1210                1215

Gln Asn Lys Asp Asn Arg Lys Phe Phe Asp Asp Leu Ile Lys Leu
    1220                1225                1230

Leu Gln Leu Thr Leu Gln Met Arg Asn Ser Asp Asp Lys Gly Asn
    1235                1240                1245

Asp Tyr Ile Ile Ser Pro Val Ala Asn Ala Glu Gly Gln Phe Phe
    1250                1255                1260

Asp Ser Arg Asn Gly Asp Lys Lys Leu Pro Leu Asp Ala Asp Ala
    1265                1270                1275

Asn Gly Ala Tyr Asn Ile Ala Arg Lys Gly Leu Trp Asn Ile Arg
    1280                1285                1290

Gln Ile Lys Gln Thr Lys Asn Lys Asp Asp Leu Asn Leu Ser Ile
    1295                1300                1305

Ser Ser Thr Glu Trp Leu Asp Phe Val Arg Glu Lys Pro Tyr Leu
    1310                1315                1320

Lys

<210> SEQ ID NO 15
<211> LENGTH: 1484
<212> TYPE: PRT
<213> ORGANISM: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 15

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
                20                  25                  30

Lys Asp His Leu Glu Tyr Asp Glu Lys Leu Gln Thr Phe Leu Lys Asp
            35                  40                  45

Gln Asn Ile Asp Asp Ala Tyr Gln Ala Leu Lys Pro Gln Phe Asp Glu
        50                  55                  60

Ile His Glu Glu Phe Ile Thr Asp Ser Leu Glu Ser Lys Lys Ala Lys
65                  70                  75                  80
```

-continued

```
Glu Ile Asp Phe Ser Glu Tyr Leu Asp Leu Phe Gln Glu Lys Lys Glu
            85                  90                  95
Leu Asn Asp Ser Glu Lys Lys Leu Arg Asn Lys Ile Gly Glu Thr Phe
            100                 105                 110
Asn Lys Ala Gly Glu Lys Trp Lys Lys Glu Lys Tyr Pro Gln Tyr Glu
            115                 120                 125
Trp Lys Lys Gly Ser Lys Ile Ala Asn Gly Ala Asp Ile Leu Ser Cys
            130                 135                 140
Gln Asp Met Leu Gln Phe Ile Lys Tyr Lys Asn Pro Glu Asp Glu Lys
145                 150                 155                 160
Ile Lys Asn Tyr Ile Asp Asp Thr Leu Lys Gly Phe Phe Thr Tyr Phe
            165                 170                 175
Gly Gly Phe Asn Gln Asn Arg Ala Asn Tyr Tyr Glu Thr Lys Lys Glu
            180                 185                 190
Ala Ser Thr Ala Val Ala Thr Arg Ile Val His Glu Asn Leu Pro Lys
            195                 200                 205
Phe Cys Asp Asn Val Ile Gln Phe Lys His Ile Ile Lys Arg Lys Lys
            210                 215                 220
Asp Gly Thr Val Glu Lys Thr Glu Arg Lys Thr Glu Tyr Leu Asn Ala
225                 230                 235                 240
Tyr Gln Tyr Leu Lys Asn Asn Asn Lys Ile Thr Gln Ile Lys Asp Ala
            245                 250                 255
Glu Thr Glu Lys Met Ile Glu Ser Thr Pro Ile Ala Glu Lys Ile Phe
            260                 265                 270
Asp Val Tyr Tyr Phe Ser Ser Cys Leu Ser Gln Lys Gln Ile Glu Glu
            275                 280                 285
Tyr Asn Arg Ile Ile Gly His Tyr Asn Leu Leu Ile Asn Leu Tyr Asn
            290                 295                 300
Gln Ala Lys Arg Ser Glu Gly Lys His Leu Ser Ala Asn Glu Lys Lys
305                 310                 315                 320
Tyr Lys Asp Leu Pro Lys Phe Lys Thr Leu Tyr Lys Gln Ile Gly Cys
            325                 330                 335
Gly Lys Lys Lys Asp Leu Phe Tyr Thr Ile Lys Cys Asp Thr Glu Glu
            340                 345                 350
Glu Ala Asn Lys Ser Arg Asn Glu Gly Lys Glu Ser His Ser Val Glu
            355                 360                 365
Glu Ile Ile Asn Lys Ala Gln Glu Ala Ile Asn Lys Tyr Phe Lys Ser
            370                 375                 380
Asn Asn Asp Cys Glu Asn Ile Asn Thr Val Pro Asp Phe Ile Asn Tyr
385                 390                 395                 400
Ile Leu Thr Lys Glu Asn Tyr Glu Gly Val Tyr Trp Ser Lys Ala Ala
            405                 410                 415
Met Asn Thr Ile Ser Asp Lys Tyr Phe Ala Asn Tyr His Asp Leu Gln
            420                 425                 430
Asp Arg Leu Lys Glu Ala Lys Val Phe Gln Lys Ala Asp Lys Lys Ser
            435                 440                 445
Glu Asp Asp Ile Lys Ile Pro Glu Ala Ile Glu Leu Ser Gly Leu Phe
            450                 455                 460
Gly Val Leu Asp Ser Leu Ala Asp Trp Gln Thr Thr Leu Phe Lys Ser
465                 470                 475                 480
Ser Ile Leu Ser Asn Glu Lys Leu Lys Ile Ile Thr Asp Ser Gln Thr
            485                 490                 495
Pro Ser Glu Ala Leu Leu Lys Met Ile Phe Asn Asp Ile Glu Lys Asn
```

```
                500             505             510
Met Glu Ser Phe Leu Lys Glu Thr Asn Asp Ile Ile Thr Leu Lys Lys
            515             520             525

Tyr Lys Gly Asn Lys Glu Gly Thr Glu Lys Ile Lys Gln Trp Phe Asp
            530             535             540

Tyr Thr Leu Ala Ile Asn Arg Met Leu Lys Tyr Phe Leu Val Lys Glu
545             550             555             560

Asn Lys Ile Lys Gly Asn Ser Leu Asp Thr Asn Ile Ser Glu Ala Leu
            565             570             575

Lys Thr Leu Ile Tyr Ser Asp Ala Glu Trp Phe Lys Trp Tyr Asp
            580             585             590

Ala Leu Arg Asn Tyr Leu Thr Gln Lys Pro Gln Asp Glu Ala Lys Glu
            595             600             605

Asn Lys Leu Lys Leu Asn Phe Asp Asn Pro Ser Leu Ala Gly Gly Trp
            610             615             620

Asp Val Asn Lys Glu Cys Ser Asn Phe Cys Val Ile Leu Lys Asp Lys
625             630             635             640

Asn Glu Lys Lys Tyr Leu Ala Met Ile Lys Lys Gly Glu Asn Thr Leu
            645             650             655

Phe Gln Lys Glu Trp Thr Glu Gly Arg Gly Lys Asn Leu Thr Lys Lys
            660             665             670

Ser Asn Pro Leu Phe Glu Ile Asn Asn Cys Glu Ile Leu Ser Lys Met
            675             680             685

Glu Tyr Asp Phe Trp Ala Asp Val Ser Lys Met Ile Pro Lys Cys Ser
            690             695             700

Thr Gln Leu Lys Ala Val Val Asn His Phe Lys Gln Ser Asp Asn Glu
705             710             715             720

Phe Ile Phe Pro Ile Gly Tyr Lys Val Thr Ser Gly Glu Lys Phe Arg
            725             730             735

Glu Glu Cys Lys Ile Ser Lys Gln Asp Phe Glu Leu Asn Asn Lys Val
            740             745             750

Phe Asn Lys Asn Glu Leu Ser Val Thr Ala Met Arg Tyr Asp Leu Ser
            755             760             765

Ser Thr Gln Glu Lys Gln Tyr Ile Lys Ala Phe Gln Lys Glu Tyr Trp
            770             775             780

Glu Leu Leu Phe Lys Gln Glu Lys Arg Asp Thr Lys Leu Thr Asn Asn
785             790             795             800

Glu Ile Phe Asn Glu Trp Ile Asn Phe Cys Asn Lys Lys Tyr Ser Glu
            805             810             815

Leu Leu Ser Trp Glu Arg Lys Tyr Lys Asp Ala Leu Thr Asn Trp Ile
            820             825             830

Asn Phe Cys Lys Tyr Phe Leu Ser Lys Tyr Pro Lys Thr Thr Leu Phe
            835             840             845

Asn Tyr Ser Phe Lys Glu Ser Glu Asn Tyr Asn Ser Leu Asp Glu Phe
            850             855             860

Tyr Arg Asp Val Asp Ile Cys Ser Tyr Lys Leu Asn Ile Asn Thr Thr
865             870             875             880

Ile Asn Lys Ser Ile Leu Asp Arg Leu Val Glu Glu Gly Lys Leu Tyr
            885             890             895

Leu Phe Glu Ile Lys Asn Gln Asp Ser Asn Asp Gly Lys Ser Ile Gly
            900             905             910

His Lys Asn Asn Leu His Thr Ile Tyr Trp Asn Ala Ile Phe Glu Asn
            915             920             925
```

-continued

```
Phe Asp Asn Arg Pro Lys Leu Asn Gly Glu Ala Glu Ile Phe Tyr Arg
    930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
                980                 985                 990

Tyr Val Asn Asp Ile Val Asn Thr Lys Phe Tyr Asn Phe Ser Asn Leu
        995                 1000                1005

His Phe Leu Gly Ile Asp Arg Gly Glu Lys His Leu Ala Tyr Tyr
    1010                1015                1020

Ser Leu Val Asn Lys Asn Gly Glu Ile Val Asp Gln Gly Thr Leu
    1025                1030                1035

Asn Leu Pro Phe Thr Asp Lys Asp Gly Asn Gln Arg Ser Ile Lys
    1040                1045                1050

Lys Glu Lys Tyr Phe Tyr Asn Lys Gln Glu Asp Lys Trp Glu Ala
    1055                1060                1065

Lys Glu Val Asp Xaa Trp Asn Tyr Asn Asp Leu Leu Asp Ala Met
    1070                1075                1080

Ala Ser Asn Arg Asp Met Ala Arg Lys Asn Trp Gln Arg Ile Gly
    1085                1090                1095

Thr Ile Lys Glu Ala Lys Asn Gly Tyr Val Ser Leu Val Ile Arg
    1100                1105                1110

Lys Ile Ala Asp Leu Ala Val Asn Asn Glu Arg Pro Ala Phe Ile
    1115                1120                1125

Val Leu Glu Asp Leu Asn Thr Gly Phe Lys Arg Ser Arg Gln Lys
    1130                1135                1140

Ile Asp Lys Ser Val Tyr Gln Lys Phe Glu Leu Ala Leu Ala Lys
    1145                1150                1155

Lys Leu Asn Phe Leu Val Asp Lys Asn Ala Lys Arg Asp Glu Ile
    1160                1165                1170

Gly Ser Pro Thr Lys Ala Leu Gln Leu Thr Pro Pro Val Asn Asn
    1175                1180                1185

Tyr Gly Asp Ile Glu Asn Lys Lys Gln Ala Gly Ile Met Leu Tyr
    1190                1195                1200

Thr Arg Ala Asn Tyr Thr Ser Gln Thr Asp Pro Ala Thr Gly Trp
    1205                1210                1215

Arg Lys Thr Ile Tyr Leu Lys Ala Gly Pro Glu Glu Thr Thr Tyr
    1220                1225                1230

Lys Lys Asp Gly Lys Ile Lys Asn Lys Ser Val Lys Asp Gln Ile
    1235                1240                1245

Ile Glu Thr Phe Thr Asp Ile Gly Phe Asp Gly Lys Asp Tyr Tyr
    1250                1255                1260

Phe Glu Tyr Asp Lys Gly Glu Phe Val Asp Glu Lys Thr Gly Glu
    1265                1270                1275

Ile Lys Pro Lys Lys Trp Arg Leu Tyr Ser Gly Glu Asn Gly Lys
    1280                1285                1290

Ser Leu Asp Arg Phe Arg Gly Glu Arg Glu Lys Asp Lys Tyr Glu
    1295                1300                1305

Trp Lys Ile Asp Lys Ile Asp Ile Val Lys Ile Leu Asp Asp Leu
    1310                1315                1320
```

-continued

```
Phe Val Asn Phe Asp Lys Asn Ile Ser Leu Leu Lys Gln Leu Lys
    1325                1330                1335

Glu Gly Val Glu Leu Thr Arg Asn Asn Glu His Gly Thr Gly Glu
    1340                1345                1350

Ser Leu Arg Phe Ala Ile Asn Leu Ile Gln Gln Ile Arg Asn Thr
    1355                1360                1365

Gly Asn Asn Glu Arg Asp Asn Asp Phe Ile Leu Ser Pro Val Arg
    1370                1375                1380

Asp Glu Asn Gly Lys His Phe Asp Ser Arg Glu Tyr Trp Asp Lys
    1385                1390                1395

Glu Thr Lys Gly Glu Lys Ile Ser Met Pro Ser Ser Gly Asp Ala
    1400                1405                1410

Asn Gly Ala Phe Asn Ile Ala Arg Lys Gly Ile Ile Met Asn Ala
    1415                1420                1425

His Ile Leu Ala Asn Ser Asp Ser Lys Asp Leu Ser Leu Phe Val
    1430                1435                1440

Ser Asp Glu Glu Trp Asp Leu His Leu Asn Asn Lys Thr Glu Trp
    1445                1450                1455

Lys Lys Gln Leu Asn Ile Phe Ser Ser Arg Lys Ala Met Ala Lys
    1460                1465                1470

Arg Lys Lys Lys Arg Pro Ala Ala Thr Lys Lys
    1475                1480

<210> SEQ ID NO 16
<211> LENGTH: 1245
<212> TYPE: PRT
<213> ORGANISM: Porphyromonas macacae

<400> SEQUENCE: 16

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45

Asp Tyr Glu Lys Leu Lys Lys Val Ile Asp Glu Tyr His Glu Asp Phe
        50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
                100                 105                 110

Tyr Lys Ser Ile Phe Lys Lys Glu Leu Val Lys Lys Asp Ile Pro Val
            115                 120                 125

Trp Cys Pro Ala Tyr Lys Ser Leu Cys Lys Lys Phe Asp Asn Phe Thr
        130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
                180                 185                 190

Met Gly Ala Asp Leu Tyr Leu Glu Met Met Glu Asn Leu Arg Asn Val
            195                 200                 205
```

-continued

Trp Pro Ser Phe Val Lys Thr Pro Asp Asp Leu Cys Asn Leu Lys Thr
        210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
        260                 265                 270

Gly Leu Val Phe Leu His Lys Gln Ile Leu Ala Lys Val Asp Ser Ser
                275                 280                 285

Ser Phe Ile Ser Asp Thr Leu Glu Asn Asp Asp Gln Val Phe Cys Val
290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
                340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Lys Glu Ser Val Glu Arg Tyr
        370                 375                 380

Ala Glu Lys Ile Ser Lys Gln Ile Lys Lys Arg Gln Ser Tyr Ser Leu
385                 390                 395                 400

Ala Glu Leu Asp Asp Leu Leu Ala His Tyr Ser Glu Glu Ser Leu Pro
                405                 410                 415

Ala Gly Phe Ser Leu Leu Ser Tyr Phe Thr Ser Leu Gly Gly Gln Lys
                420                 425                 430

Tyr Leu Val Ser Asp Gly Glu Val Ile Leu Tyr Glu Glu Gly Ser Asn
                435                 440                 445

Ile Trp Asp Glu Val Leu Ile Ala Phe Arg Asp Leu Gln Val Ile Leu
        450                 455                 460

Asp Lys Asp Phe Thr Glu Lys Lys Leu Gly Lys Asp Glu Glu Ala Val
465                 470                 475                 480

Ser Val Ile Lys Lys Ala Leu Asp Ser Ala Leu Arg Leu Arg Lys Phe
                485                 490                 495

Phe Asp Leu Leu Ser Gly Thr Gly Ala Glu Ile Arg Arg Asp Ser Ser
                500                 505                 510

Phe Tyr Ala Leu Tyr Thr Asp Arg Met Asp Lys Leu Lys Gly Leu Leu
        515                 520                 525

Lys Met Tyr Asp Lys Val Arg Asn Tyr Leu Thr Lys Lys Pro Tyr Ser
530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
                580                 585                 590

Phe Lys Thr Leu Pro Lys Leu Gly Ala Glu Glu Met Phe Tyr Glu Lys
        595                 600                 605

Met Glu Tyr Lys Gln Ile Ala Glu Pro Met Leu Met Leu Pro Lys Val
610                 615                 620

```
Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
            645                 650                 655

Asn Lys Lys Asp Leu Tyr Arg Leu Ile Asp Phe Tyr Lys Glu Ala Leu
        660                 665                 670

Thr Val His Glu Trp Lys Leu Phe Asn Phe Ser Phe Ser Pro Thr Glu
    675                 680                 685

Gln Tyr Arg Asn Ile Gly Glu Phe Phe Asp Glu Val Arg Glu Gln Ala
690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
        755                 760                 765

Gly Gly Glu Leu Phe Tyr Arg Lys Ala Ser Leu His Met Gln Asp Thr
770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln His Gly Ile Asp Arg Gly Glu Arg Asn
850                 855                 860

Leu Leu Tyr Ile Ser Arg Ile Asp Thr Arg Gly Asn Leu Leu Glu Gln
865                 870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
            900                 905                 910

Gln Glu Trp Lys Ser Ile Glu Ser Ile Lys Asp Leu Lys Asp Gly Tyr
        915                 920                 925

Met Ser Gln Val Val His Lys Ile Cys Asn Met Val Val Glu His Lys
930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
            980                 985                 990

Pro Gly Gly Leu Tyr Ala Ala Tyr Gln Leu Thr Asn Pro Leu Phe Ser
                995                 1000                1005

Phe Glu Glu Leu His Arg Tyr Pro Gln Ser Gly Ile Leu Phe Phe
        1010                1015                1020

Val Asp Pro Trp Asn Thr Ser Leu Thr Asp Pro Ser Thr Gly Phe
        1025                1030                1035

Val Asn Leu Leu Gly Arg Ile Asn Tyr Thr Asn Val Gly Asp Ala
```

```
               1040                1045                1050
Arg Lys Phe Phe Asp Arg Phe Asn Ala Ile Arg Tyr Asp Gly Lys
            1055                1060                1065

Gly Asn Ile Leu Phe Asp Leu Asp Leu Ser Arg Phe Asp Val Arg
        1070                1075                1080

Val Glu Thr Gln Arg Lys Leu Trp Thr Leu Thr Thr Phe Gly Ser
    1085                1090                1095

Arg Ile Ala Lys Ser Lys Lys Ser Gly Lys Trp Met Val Glu Arg
1100                1105                1110

Ile Glu Asn Leu Ser Leu Cys Phe Leu Glu Leu Phe Glu Gln Phe
    1115                1120                1125

Asn Ile Gly Tyr Arg Val Glu Lys Asp Leu Lys Lys Ala Ile Leu
        1130                1135                1140

Ser Gln Asp Arg Lys Glu Phe Tyr Val Arg Leu Ile Tyr Leu Phe
            1145                1150                1155

Asn Leu Met Met Gln Ile Arg Asn Ser Asp Gly Glu Glu Asp Tyr
                1160                1165                1170

Ile Leu Ser Pro Ala Leu Asn Glu Lys Asn Leu Gln Phe Asp Ser
            1175                1180                1185

Arg Leu Ile Glu Ala Lys Asp Leu Pro Val Asp Ala Asp Ala Asn
        1190                1195                1200

Gly Ala Tyr Asn Val Ala Arg Lys Gly Leu Met Val Val Gln Arg
    1205                1210                1215

Ile Lys Arg Gly Asp His Glu Ser Ile His Arg Ile Gly Arg Ala
1220                1225                1230

Gln Trp Leu Arg Tyr Val Gln Glu Gly Ile Val Glu
    1235                1240                1245

<210> SEQ ID NO 17
<211> LENGTH: 1250
<212> TYPE: PRT
<213> ORGANISM: Smithella sp.

<400> SEQUENCE: 17

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160
```

```
Met Tyr Val Ala Asp Glu Lys Arg Thr Ala Ile Ala Ser Arg Leu Ile
                165                 170                 175
His Glu Asn Leu Pro Lys Phe Ile Asp Asn Ile Lys Ile Phe Glu Lys
            180                 185                 190
Met Lys Lys Glu Ala Pro Glu Leu Leu Ser Pro Phe Asn Gln Thr Leu
        195                 200                 205
Lys Asp Met Lys Asp Val Ile Lys Gly Thr Thr Leu Glu Glu Ile Phe
    210                 215                 220
Ser Leu Asp Tyr Phe Asn Lys Thr Leu Thr Gln Ser Gly Ile Asp Ile
225                 230                 235                 240
Tyr Asn Ser Val Ile Gly Gly Arg Thr Pro Glu Glu Gly Lys Thr Lys
                245                 250                 255
Ile Lys Gly Leu Asn Glu Tyr Ile Asn Thr Asp Phe Asn Gln Lys Gln
            260                 265                 270
Thr Asp Lys Lys Lys Arg Gln Pro Lys Phe Lys Gln Leu Tyr Lys Gln
        275                 280                 285
Ile Leu Ser Asp Arg Gln Ser Leu Ser Phe Ile Ala Glu Ala Phe Lys
    290                 295                 300
Asn Asp Thr Glu Ile Leu Glu Ala Ile Glu Lys Phe Tyr Val Asn Glu
305                 310                 315                 320
Leu Leu His Phe Ser Asn Glu Gly Lys Ser Thr Asn Val Leu Asp Ala
                325                 330                 335
Ile Lys Asn Ala Val Ser Asn Leu Glu Ser Phe Asn Leu Thr Lys Met
            340                 345                 350
Tyr Phe Arg Ser Gly Ala Ser Leu Thr Asp Val Ser Arg Lys Val Phe
        355                 360                 365
Gly Glu Trp Ser Ile Ile Asn Arg Ala Leu Asp Asn Tyr Tyr Ala Thr
    370                 375                 380
Thr Tyr Pro Ile Lys Pro Arg Glu Lys Ser Glu Lys Tyr Glu Glu Arg
385                 390                 395                 400
Lys Glu Lys Trp Leu Lys Gln Asp Phe Asn Val Ser Leu Ile Gln Thr
                405                 410                 415
Ala Ile Asp Glu Tyr Asp Asn Glu Thr Val Lys Gly Lys Asn Ser Gly
            420                 425                 430
Lys Val Ile Ala Asp Tyr Phe Ala Lys Phe Cys Asp Asp Lys Glu Thr
        435                 440                 445
Asp Leu Ile Gln Lys Val Asn Glu Gly Tyr Ile Ala Val Lys Asp Leu
    450                 455                 460
Leu Asn Thr Pro Cys Pro Glu Asn Glu Lys Leu Gly Ser Asn Lys Asp
465                 470                 475                 480
Gln Val Lys Gln Ile Lys Ala Phe Met Asp Ser Ile Met Asp Ile Met
                485                 490                 495
His Phe Val Arg Pro Leu Ser Leu Lys Asp Thr Asp Lys Glu Lys Asp
            500                 505                 510
Glu Thr Phe Tyr Ser Leu Phe Thr Pro Leu Tyr Asp His Leu Thr Gln
        515                 520                 525
Thr Ile Ala Leu Tyr Asn Lys Val Arg Asn Tyr Leu Thr Gln Lys Pro
    530                 535                 540
Tyr Ser Thr Glu Lys Ile Lys Leu Asn Phe Glu Asn Ser Thr Leu Leu
545                 550                 555                 560
Gly Gly Trp Asp Leu Asn Lys Glu Thr Asp Asn Thr Ala Ile Ile Leu
                565                 570                 575
Arg Lys Asp Asn Leu Tyr Tyr Leu Gly Ile Met Asp Lys Arg His Asn
```

```
                580             585             590
Arg Ile Phe Arg Asn Val Pro Lys Ala Asp Lys Lys Asp Phe Cys Tyr
            595             600             605

Glu Lys Met Val Tyr Lys Leu Leu Pro Gly Ala Asn Lys Met Leu Pro
    610             615             620

Lys Val Phe Phe Ser Gln Ser Arg Ile Gln Glu Phe Thr Pro Ser Ala
625             630             635             640

Lys Leu Leu Glu Asn Tyr Ala Asn Glu Thr His Lys Lys Gly Asp Asn
                645             650             655

Phe Asn Leu Asn His Cys His Lys Leu Ile Asp Phe Lys Asp Ser
                660             665             670

Ile Asn Lys His Glu Asp Trp Lys Asn Phe Asp Phe Arg Phe Ser Ala
            675             680             685

Thr Ser Thr Tyr Ala Asp Leu Ser Gly Phe Tyr His Glu Val Glu His
    690             695             700

Gln Gly Tyr Lys Ile Ser Phe Gln Ser Val Ala Asp Ser Phe Ile Asp
705             710             715             720

Asp Leu Val Asn Glu Gly Lys Leu Tyr Leu Phe Gln Ile Tyr Asn Lys
                725             730             735

Asp Phe Ser Pro Phe Ser Lys Gly Lys Pro Asn Leu His Thr Leu Tyr
                740             745             750

Trp Lys Met Leu Phe Asp Glu Asn Asn Leu Lys Asp Val Val Tyr Lys
            755             760             765

Leu Asn Gly Glu Ala Glu Val Phe Tyr Arg Lys Lys Ser Ile Ala Glu
    770             775             780

Lys Asn Thr Thr Ile His Lys Ala Asn Glu Ser Ile Ile Asn Lys Asn
785             790             795             800

Pro Asp Asn Pro Lys Ala Thr Ser Thr Phe Asn Tyr Asp Ile Val Lys
                805             810             815

Asp Lys Arg Tyr Thr Ile Asp Lys Phe Gln Phe His Ile Pro Ile Thr
                820             825             830

Met Asn Phe Lys Ala Glu Gly Ile Phe Asn Met Asn Gln Arg Val Asn
            835             840             845

Gln Phe Leu Lys Ala Asn Pro Asp Ile Asn Ile Ile Gly Ile Asp Arg
    850             855             860

Gly Glu Arg His Leu Leu Tyr Tyr Ala Leu Ile Asn Gln Lys Gly Lys
865             870             875             880

Ile Leu Lys Gln Asp Thr Leu Asn Val Ile Ala Asn Glu Lys Gln Lys
                885             890             895

Val Asp Tyr His Asn Leu Leu Asp Lys Lys Glu Gly Asp Arg Ala Thr
                900             905             910

Ala Arg Gln Glu Trp Gly Val Ile Glu Thr Ile Lys Glu Leu Lys Glu
            915             920             925

Gly Tyr Leu Ser Gln Val Ile His Lys Leu Thr Asp Leu Met Ile Glu
    930             935             940

Asn Asn Ala Ile Ile Val Met Glu Asp Leu Asn Phe Gly Phe Lys Arg
945             950             955             960

Gly Arg Gln Lys Val Glu Lys Gln Val Tyr Gln Lys Phe Glu Lys Met
                965             970             975

Leu Ile Asp Lys Leu Asn Tyr Leu Val Asp Lys Asn Lys Lys Ala Asn
                980             985             990

Glu Leu Gly Gly Leu Leu Asn Ala  Phe Gln Leu Ala Asn  Lys Phe Glu
            995             1000            1005
```

```
Ser Phe Gln Lys Met Gly Lys Gln Asn Gly Phe Ile Phe Tyr Val
    1010                1015                1020

Pro Ala Trp Asn Thr Ser Lys Thr Asp Pro Ala Thr Gly Phe Ile
    1025                1030                1035

Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Gln Trp Asn Arg Ala Leu Asn Asn Arg Gly Ser Gln
    1100                1105                1110

Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly
    1250

<210> SEQ ID NO 18
<211> LENGTH: 166
<212> TYPE: PRT
<213> ORGANISM: Escherichia coli

<400> SEQUENCE: 18

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
                35                  40                  45

Gly Arg His Asp Pro Thr Ala His Ala Glu Ile Met Ala Leu Arg Gln
            50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
```

-continued

```
            100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
        130                 135                 140

Ser Asp Phe Phe Arg Met Arg Arg Gln Glu Ile Lys Ala Gln Lys Lys
145                 150                 155                 160

Ala Gln Ser Ser Thr Asp
                165
```

<210> SEQ ID NO 19
<211> LENGTH: 166
<212> TYPE: PRT
<213> ORGANISM: Artificial
<220> FEATURE:
<223> OTHER INFORMATION: adenosine deaminase

<400> SEQUENCE: 19

```
Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
        130                 135                 140

Cys Tyr Phe Phe Arg Met Pro Arg Gln Val Phe Asn Ala Gln Lys Lys
145                 150                 155                 160

Ala Gln Ser Ser Thr Asp
                165
```

<210> SEQ ID NO 20
<211> LENGTH: 166
<212> TYPE: PRT
<213> ORGANISM: Artificial
<220> FEATURE:
<223> OTHER INFORMATION: adenosine deaminase

<400> SEQUENCE: 20

```
Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val Leu Asn Asn Arg Val Ile Gly Glu Gly Trp Asn Arg Ser Ile
        35                  40                  45

Gly Leu His Asp Pro Thr Ala His Ala Glu Ile Met Ala Leu Arg Gln
    50                  55                  60
```

```
Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 21
<211> LENGTH: 166
<212> TYPE: PRT
<213> ORGANISM: Artificial
<220> FEATURE:
<223> OTHER INFORMATION: adenosine deaminase

<400> SEQUENCE: 21

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 22
<211> LENGTH: 166
<212> TYPE: PRT
<213> ORGANISM: Artificial
<220> FEATURE:
<223> OTHER INFORMATION: adenosine deaminase

<400> SEQUENCE: 22

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30
```

```
Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Asn Ala Leu Leu
        130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 23
<211> LENGTH: 228
<212> TYPE: PRT
<213> ORGANISM: Rattus norvegicus

<400> SEQUENCE: 23

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
        50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
                100                 105                 110

Ile Tyr Ile Ala Arg Leu Tyr His His Ala Asp Pro Arg Asn Arg Gln
            115                 120                 125

Gly Leu Arg Asp Leu Ile Ser Ser Gly Val Thr Ile Gln Ile Met Thr
        130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Pro Gln Leu Thr Phe Phe Thr Ile Ala
            195                 200                 205

Leu Gln Ser Cys His Tyr Gln Arg Leu Pro Pro His Ile Leu Trp Ala
210                 215                 220

Thr Gly Leu Lys
```

<210> SEQ ID NO 24
<211> LENGTH: 199
<212> TYPE: PRT
<213> ORGANISM: Homo sapiens

<400> SEQUENCE: 24

```
Met Glu Ala Ser Pro Ala Ser Gly Pro Arg His Leu Met Asp Pro His
1               5                   10                  15
Ile Phe Thr Ser Asn Phe Asn Asn Gly Ile Gly Arg His Lys Thr Tyr
            20                  25                  30
Leu Cys Tyr Glu Val Glu Arg Leu Asp Asn Gly Thr Ser Val Lys Met
        35                  40                  45
Asp Gln His Arg Gly Phe Leu His Asn Gln Ala Lys Asn Leu Leu Cys
    50                  55                  60
Gly Phe Tyr Gly Arg His Ala Glu Leu Arg Phe Leu Asp Leu Val Pro
65                  70                  75                  80
Ser Leu Gln Leu Asp Pro Ala Gln Ile Tyr Arg Val Thr Trp Phe Ile
                85                  90                  95
Ser Trp Ser Pro Cys Phe Ser Trp Gly Cys Ala Gly Glu Val Arg Ala
            100                 105                 110
Phe Leu Gln Glu Asn Thr His Val Arg Leu Arg Ile Phe Ala Ala Arg
        115                 120                 125
Ile Tyr Asp Tyr Asp Pro Leu Tyr Lys Glu Ala Leu Gln Met Leu Arg
    130                 135                 140
Asp Ala Gly Ala Gln Val Ser Ile Met Thr Tyr Asp Glu Phe Lys His
145                 150                 155                 160
Cys Trp Asp Thr Phe Val Asp His Gln Gly Cys Pro Phe Gln Pro Trp
                165                 170                 175
Asp Gly Leu Asp Glu His Ser Gln Ala Leu Ser Gly Arg Leu Arg Ala
            180                 185                 190
Ile Leu Gln Asn Gln Gly Asn
        195
```

<210> SEQ ID NO 25
<211> LENGTH: 621
<212> TYPE: DNA
<213> ORGANISM: Petromyzon marinus

<400> SEQUENCE: 25

```
acagatgcag agtatgtgag aattcacgaa aagctggaca tctatacctt caagaagcag     60
ttctttaaca ataagaagtc tgtgagccat aggtgctacg tgctgttcga gctgaagaga    120
agggtgaaa gaagggcatg tttttggggg tatgctgtga acaagcccca gtctggaact    180
gagagaggca ttcacgccga aattttcagc atcagaaagg tggaggaata cctgagggat    240
aaccctggac agtttacaat taattggtat tctagctggt ctccatgcgc tgactgtgcc    300
gagaagatcc tggaatggta caaccaggag ctgagaggaa atggccatac cctgaagatt    360
tgggcctgca agctgtacta tgaaaagaac gcaagaaatc agatcggact gtggaacctg    420
agggataatg tgtggggct gaacgtgatg gtgtccgagc actatcagtg ctgtagaaag    480
attttcattc agtcctcaca taatcagctg aacgagaata gatggctgga aagactctg    540
aagagggctg agaagagaag gtccgaactg tcaattatga tccaggtgaa gatcctgcac    600
accactaagt cacctgccgt g                                               621
```

<210> SEQ ID NO 26
<211> LENGTH: 83
<212> TYPE: PRT
<213> ORGANISM: Bacillus phage

<400> SEQUENCE: 26

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 27
<211> LENGTH: 19
<212> TYPE: RNA
<213> ORGANISM: Artificial
<220> FEATURE:
<223> OTHER INFORMATION: polynucleotide
<220> FEATURE:
<221> NAME/KEY: misc_feature
<222> LOCATION: (1)..(19)
<223> OTHER INFORMATION: wherein n is A, C, T or G

<400> SEQUENCE: 27
nnnnnnnnnn nnnnnnnnn                                            19

<210> SEQ ID NO 28
<211> LENGTH: 22
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (4)..(22)
<223> OTHER INFORMATION: wherein n is A, C, T or G

<400> SEQUENCE: 28
aaannnnnnn nnnnnnnnnn nn                                        22

<210> SEQ ID NO 29
<211> LENGTH: 22
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (4)..(22)
<223> OTHER INFORMATION: wherein n is A, C, T or G

<400> SEQUENCE: 29
tttnnnnnnn nnnnnnnnnn nn                                        22

<210> SEQ ID NO 30
<211> LENGTH: 23
<212> TYPE: DNA
<213> ORGANISM: Artificial
<220> FEATURE:

```
<223> OTHER INFORMATION: polynucleotide

<400> SEQUENCE: 30
ggaatccctt ctgcagcacc tgg                                          23

<210> SEQ ID NO 31
<211> LENGTH: 23
<212> TYPE: DNA
<213> ORGANISM: Artificial
<220> FEATURE:
<223> OTHER INFORMATION: polynucleotide

<400> SEQUENCE: 31
ctgatggtcc atgtctgtta ctc                                          23

<210> SEQ ID NO 32
<211> LENGTH: 49
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (7)..(11)
<223> OTHER INFORMATION: wherein n is A, T, C or G

<400> SEQUENCE: 32
cgatgtnnnn nggaatccct tctgcagcac ctgggcgcag gtcacgagg              49

<210> SEQ ID NO 33
<211> LENGTH: 57
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (43)..(46)
<223> OTHER INFORMATION: n is a, c, g, or t
<220> FEATURE:
<221> NAME/KEY: misc_feature
<222> LOCATION: (47)..(51)
<223> OTHER INFORMATION: wherein n is A, T, C or G

<400> SEQUENCE: 33
aattcctcgt gacctgcgcc caggtgctgc agaagggatt ccnnnnnaca tcgcatg     57

<210> SEQ ID NO 34
<211> LENGTH: 49
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (7)..(11)
<223> OTHER INFORMATION: wherein n is A, T, C or G

<400> SEQUENCE: 34
cgatgtnnnn nctgatggtc catgtctgtt actcgcgcag gtcacgagg              49

<210> SEQ ID NO 35
<211> LENGTH: 57
<212> TYPE: DNA
<213> ORGANISM: Artificial
<220> FEATURE:
<223> OTHER INFORMATION: polynucleotide
<220> FEATURE:
<221> NAME/KEY: misc_feature
```

-continued

```
<222> LOCATION: (43)..(46)
<223> OTHER INFORMATION: n is a, c, g, or t
<220> FEATURE:
<221> NAME/KEY: misc_feature
<222> LOCATION: (47)..(51)
<223> OTHER INFORMATION: wherein n is A, T, C or G

<400> SEQUENCE: 35
aattcctcgt gacctgcgcg agtaacagac atggaccatc agnnnnnaca tcgcatg      57

<210> SEQ ID NO 36
<211> LENGTH: 28
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (1)..(5)
<223> OTHER INFORMATION: wherein n is A, C, T or G

<400> SEQUENCE: 36
nnnnnggaat cccttctgca gcacctgg                                      28

<210> SEQ ID NO 37
<211> LENGTH: 28
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (1)..(5)
<223> OTHER INFORMATION: wherein n is A, C, T or G

<400> SEQUENCE: 37
nnnnncctta gggaagacgt cgtggacc                                      28

<210> SEQ ID NO 38
<211> LENGTH: 23
<212> TYPE: RNA
<213> ORGANISM: Artificial
<220> FEATURE:
<223> OTHER INFORMATION: polynucleotide

<400> SEQUENCE: 38
ggaaucccuu cugcagcacc ugg                                           23

<210> SEQ ID NO 39
<211> LENGTH: 24
<212> TYPE: DNA
<213> ORGANISM: Artificial
<220> FEATURE:
<223> OTHER INFORMATION: polynucleotide
<220> FEATURE:
<221> NAME/KEY: misc_feature
<222> LOCATION: (1)..(5)
<223> OTHER INFORMATION: wherein n is A, C, T or G

<400> SEQUENCE: 39
nnnnnggaat cccttctgca gcac                                          24

<210> SEQ ID NO 40
<211> LENGTH: 1592
<212> TYPE: DNA
<213> ORGANISM: Medicago truncatula

<400> SEQUENCE: 40
```

```
actgttaata attttttaaac gtcagcgcac taaaaaaacg aaaagacgga cacgtgaaaa    60
taaaaaacac acactagttt atgacgcaat actattttac ttatgatttg ggtacattag   120
acaaaaccgt gaaagagatg tatcagctat gaaacctgta tacttcaata cagagactta   180
ctcatatcgg atacgtacgc acgaagtatc atattaatta ttttaatttt taataaaatat   240 tttatcggat acttatgtga tactctacat atacacaagg atatttctaa gatactttat   300
agatacgtat cctagaaaaa catgaagagt aaaaagtga dcaatgttg taaaaattca     360 ttataaatgt atatgattca attttagata tgcatcagta taattgattc tcgatgaaac   420
acttaaaatt atatttcttg tggaagaacg tagcgagaga ggtgattcag ttagacaaca   480
ttaaataaaa ttaatgttaa gttcttttaa tgatgtttct ctcaatatca catcatatga   540
aaatgtaata tgattataa gaaaattttt aaaaaattta ttttaataat cacatgtact    600 atttttttaaa aattgtatct tttataataa tacaataata aagagtaatc agtgttaatt   660
tttcttcaaa tataagttttt attataaatc attgttaacg tatcataagt cattaccgta   720
tcgtatctta attttttttt aaaaaccgct aattcacgta cccgtattgt attgtacccg    780
cacctgtatc acaatcgatc ttagttagaa gaattgtctc gaggcggtgc aagacagcat   840
ataatagacg tggactctct tataccaaac gttgtcgtat cacaagggt taggtaacaa    900 gtcacagttt gtccacgtgt cacgttttaa ttggaagagg tgccgttggc gtaatataac   960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatctttc ttttgatccg tcaaatttaa attcaattag ggttttgttc   1200
ttttctttca tctgattgaa atccttctga attgaaccgt ttacttgatt ttactgttta   1260
ttgtatgatt taatcctttg ttttttcaaag acagtcttta gattgtgatt aggggttcat  1320
ataaattttt agatttggat ttttgtattg tatgattcaa aaaatacgtc ctttaattag   1380
attagtacat ggatatttttt tacccgattt attgattgtc agggagaatt tgatgagcaa  1440 gttttttga tgtctgttgt aaattgaatt gattataatt gctgatctgc tgcttccagt   1500
tttcataacc catattcttt taaccttgtt gtacacacaa tgaaaaattg gtgattgatt  1560 catttgttttt tctttgttttt ggattataca gg                              1592
```

<210> SEQ ID NO 41
<211> LENGTH: 2000
<212> TYPE: DNA
<213> ORGANISM: Zea mays

<400> SEQUENCE: 41

```
gtcgtgcccc tctctagaga taaagagcat tgcatgtcta aagtataaaa aattaccaca    60 tattttttg tcacacttat ttgaagtgta gtttatctat ctctatacat atatttaaac   120
ttcactctac aaataatata gtctataata ctaaaataat attagtgttt tagaggatca   180
tataaataaa ctgctagaca tggtctaaag gataattgaa tattttgaca atctacagtt   240
ttatcttttt agtgtgcatg tgatctctct gttttttttg caaatagctt gacctatata   300
atacttcatc cattttatta gtacatccat ttaggattta gggttgatgg tttctataga   360
ctaattttta gtacatccat tttattcttt ttagtctcta aatttttaa aactaaaact    420 ctattttagt tttttattta ataatttaga tataaaatga aataaaataa attgactaca   480
aataaaacaa ataccctttta agaaataaaa aaactaagca aacattttc ttgtttcgag   540
```

```
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
accccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg cttccccttc ctcgcccgcc    840
gtaataaata gacacccct ccacaccctc tttcccaac ctcgtgttcg ttcggagcgc     900
acacacacgc aaccagatct cccccaaatc cagccgtcgg cacctccgct tcaaggtacg    960
ccgctcatcc tccccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag atactgttt    1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct tttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc ttttttttcgc ttggttgtga tgatgtggtc tggttgggcg gtcgttctag   1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taaacaagta tgttttataa    1860
ttattttgat cttgatatac ttggatgatg gcatatgcag cagctatatg tggattttt    1920
agccctgcct tcatacgcta tttatttgct tggtactgtt tcttttgtcc gatgctcacc    1980
ctgttgtttg gtgatacttc                                                2000
```

<210> SEQ ID NO 42
<211> LENGTH: 160
<212> TYPE: PRT
<213> ORGANISM: Unknown
<220> FEATURE:
<223> OTHER INFORMATION: FERNY deaminase

<400> SEQUENCE: 42

```
Phe Glu Arg Asn Tyr Asp Pro Arg Glu Leu Arg Lys Glu Thr Tyr Leu
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
        35                  40                  45

Ile Phe Asn Ala Arg Arg Phe Asn Pro Ser Thr His Cys Ser Ile Thr
    50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Glu Ile Tyr Val Ala Arg
                85                  90                  95
```

```
Leu Tyr Tyr His Glu Asp Glu Arg Asn Arg Gln Gly Leu Arg Asp Leu
            100                 105                 110

Val Asn Ser Gly Val Thr Ile Arg Ile Met Asp Leu Pro Asp Tyr Asn
        115                 120                 125

Tyr Cys Trp Lys Thr Phe Val Ser Asp Gln Gly Gly Asp Glu Asp Tyr
    130                 135                 140

Trp Pro Gly His Phe Ala Pro Trp Ile Lys Gln Tyr Ser Leu Lys Leu
145                 150                 155                 160
```

<210> SEQ ID NO 43
<211> LENGTH: 207
<212> TYPE: PRT
<213> ORGANISM: Artificial
<220> FEATURE:
<223> OTHER INFORMATION: evolved cytidine deaminase

<400> SEQUENCE: 43

```
Thr Asp Ala Glu Tyr Val Arg Ile His Glu Lys Leu Asp Ile Tyr Thr
1               5                   10                  15

Phe Lys Lys Gln Phe Ser Asn Asn Lys Lys Ser Val Ser His Arg Cys
            20                  25                  30

Tyr Val Leu Phe Glu Leu Lys Arg Arg Gly Glu Arg Arg Ala Cys Phe
        35                  40                  45

Trp Gly Tyr Ala Val Asn Lys Pro Gln Ser Gly Thr Glu Arg Gly Ile
    50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Trp Ser Pro Cys
            85                  90                  95

Ala Asp Cys Ala Glu Lys Ile Leu Glu Trp Tyr Asn Gln Glu Leu Arg
            100                 105                 110

Gly Asn Gly His Thr Leu Lys Ile Trp Val Cys Lys Leu Tyr Tyr Glu
        115                 120                 125

Lys Asn Ala Arg Asn Gln Ile Gly Leu Trp Asn Leu Arg Asp Asn Gly
    130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
            165                 170                 175

Glu Lys Thr Leu Lys Arg Ala Glu Lys Arg Arg Ser Glu Leu Ser Ile
        180                 185                 190

Met Phe Gln Val Lys Ile Leu His Thr Thr Lys Ser Pro Ala Val
    195                 200                 205
```

<210> SEQ ID NO 44
<211> LENGTH: 228
<212> TYPE: PRT
<213> ORGANISM: Artificial
<220> FEATURE:
<223> OTHER INFORMATION: evolved cytidine deaminase

<400> SEQUENCE: 44

```
Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45
```

```
Ile Trp Arg His Thr Ser Gln Asn Thr Asn Lys His Val Glu Val Asn
 50                  55                  60

Phe Ile Glu Lys Phe Thr Glu Arg Tyr Phe Cys Pro Asn Thr Arg
 65                  70                  75                  80

Cys Ser Ile Thr Trp Phe Leu Ser Trp Ser Pro Cys Gly Glu Cys Ser
                     85                  90                  95

Arg Ala Ile Thr Glu Phe Leu Ser Arg Tyr Pro Asn Val Thr Leu Phe
                100                 105                 110

Ile Tyr Ile Ala Arg Leu Tyr His Leu Ala Asn Pro Arg Asn Arg Gln
                115                 120                 125

Gly Leu Arg Asp Leu Ile Ser Ser Gly Val Thr Ile Gln Ile Met Thr
130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Ser Gln Leu Thr Ser Phe Thr Ile Ala
                195                 200                 205

Leu Gln Ser Cys His Tyr Gln Arg Leu Pro Pro His Ile Leu Trp Ala
210                 215                 220

Thr Gly Leu Lys
225

<210> SEQ ID NO 45
<211> LENGTH: 162
<212> TYPE: PRT
<213> ORGANISM: Artificial
<220> FEATURE:
<223> OTHER INFORMATION: evolved cytidine deaminase

<400> SEQUENCE: 45

Ser Phe Glu Arg Asn Tyr Asp Pro Arg Glu Leu Arg Lys Glu Thr Tyr
 1                   5                  10                  15

Leu Leu Tyr Glu Ile Lys Trp Gly Lys Ser Gly Lys Leu Trp Arg His
                 20                  25                  30

Trp Cys Gln Asn Asn Arg Thr Gln His Ala Glu Val Tyr Phe Leu Glu
                 35                  40                  45

Asn Ile Phe Asn Ala Arg Arg Phe Asn Pro Ser Thr His Cys Ser Ile
 50                  55                  60

Thr Trp Tyr Leu Ser Trp Ser Pro Cys Ala Glu Cys Ser Gln Lys Ile
 65                  70                  75                  80

Val Asp Phe Leu Lys Glu His Pro Asn Val Asn Leu Glu Ile Tyr Val
                 85                  90                  95

Ala Arg Leu Tyr Tyr Pro Glu Asn Glu Arg Asn Arg Gln Gly Leu Arg
                100                 105                 110

Asp Leu Val Asn Ser Gly Val Thr Ile Arg Ile Met Asp Leu Pro Asp
                115                 120                 125

Tyr Asn Tyr Cys Trp Lys Thr Phe Val Ser Gln Gly Gly Asp Glu
130                 135                 140

Asp Tyr Trp Pro Gly His Phe Ala Pro Trp Ile Lys Gln Tyr Ser Leu
145                 150                 155                 160

Lys Leu
```

```
<210> SEQ ID NO 46
<211> LENGTH: 229
<212> TYPE: PRT
<213> ORGANISM: Rattus norvegicus

<400> SEQUENCE: 46

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 47
<211> LENGTH: 198
<212> TYPE: PRT
<213> ORGANISM: Homo sapiens

<400> SEQUENCE: 47

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95
```

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195

<210> SEQ ID NO 48
<211> LENGTH: 197
<212> TYPE: PRT
<213> ORGANISM: Artificial
<220> FEATURE:
<223> OTHER INFORMATION: cytosine deaminase

<400> SEQUENCE: 48

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Ile Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Cys Thr
        195

<210> SEQ ID NO 49
<211> LENGTH: 3987
<212> TYPE: DNA
<213> ORGANISM: Artificial
<220> FEATURE:
<223> OTHER INFORMATION: polynucleotide

<400> SEQUENCE: 49

```
atggccggga gcaagaagcg ccggataaag caggacacgc agttcgaggg cttcaccaac    60
ctgtaccaag tctccaagac gctccggttc gagcttatcc cgcaagggaa gaccctgaaa   120
cacatccagg aacaaggttt catcgaggag gacaaggccc gcaacgacca ctacaaggag   180
ctcaagccca taatcgatcg gatctacaag acgtacgccg accagtgcct ccaactggtg   240
cagctcgact gggagaacct gagcgccgcc attgacagct accgcaagga aaagacggag   300
gagacgcgca acgcccttat tgaggagcaa gccacctacc gcaacgccat ccacgactac   360
ttcatcgggc gcaccgacaa cctgacggac gcgatcaaca gcgccacgc ggaaatctac    420
aagggccttt tcaaggccga gctcttcaac gggaaggtcc taaaacagct cgggactgtc   480
acgacaaccg agcatgagaa cgccctcctt cgcagcttcg acaagttcac cacatacttc   540
tcgggcttct accggaaccg caagaacgtt ttcagcgccg aggacatctc caccgccatc   600
ccgcacagga tcgtccagga caacttcccc aagttcaagg agaactgcca catcttcacg   660
cgcctgatta cagccgtacc ttcacttcgt gagcacttcg agaacgtcaa aaaggccatc   720
gggatcttcg tctccacgtc catcgaggag gtattctctt tcccgttcta taaccagctc   780
ctgacccaga cgcagatcga cctctacaac cagctactgg gcggcatcag ccggaggcc    840
gggaccgaga aaataaaggg cctcaacgaa gttctcaacc tggccatcca agaacgac    900
gagaccgcgc atatcatcgc atccctgccg catcgcttca ttcctttgtt caagcagata   960
ttgagcgacc ggaacaccct ctcgttcatc ctcgaagaat caagagcga cgaggaggtc   1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aaggcgttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg accggagtt ctccgcgcgc ctcacgggta ttaagctgga gatggagcca   1560
agcttaagct tctacaacaa ggcccgcaac tacgcgacca aaaaccgta tcagtcgag   1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca agccgtcac ggcccacttc cagacgcata ccacgccgat acttctgagc   1920
aacaacttca ttgagccgct agagatcacg aaggagatat acgacctaaa caccccgaa   1980
aaggagccca agaagttcca gacagcctac gctaagaaga caggtgatca aagggatat   2040
aggaggcac tctgcaagtg gatcgacttc acgcgcgact tcctgtcgaa atatacaaag   2100
acgaccagca ttgacctaag ttctctccgc ccatcctccc agtacaagga tctgggcgag  2160
tattatgcgg agctgaaccc attgctgtac cacatcagct ccagaggat cgccgagaag   2220
gagattatgg acgcggtgga gacgggaaa ctataccgtgt tccaaatata taacaaggac   2280
ttcgctaaag ggcaccacgg gaagcccaac ctgcacacac tctactggac gggcttgttt  2340
```

| | |
|---|---|
| tcgccagaaa atttggccaa gacttcgatc aagctcaacg gccaggcgga gttgttttac | 2400 |
| cgtcccaagt ctcgcatgaa gcgcatggcg catcgcctcg agagaaaat gcttaacaag | 2460 |
| aagctcaagg atcagaagac gcccatacct gatacgttgt accaggaatt gtacgactac | 2520 |
| gtgaaccacc gcctatcgca cgacctctca gacgaggccc gcgccctcct cccaaacgtg | 2580 |
| attactaagg aggtttccca tgaaataatc aaggaccgac ggttcaccag cgacaaattt | 2640 |
| tttttccacg tgcctatcac gctcaattac caggcggcca actccccatc gaagttcaac | 2700 |
| cagcgcgtga acgcctacct taaggagcac ccggagaccc caatcatcgg gatcgaccgt | 2760 |
| ggcgagcgga acctgatcta tattacggtg atcgatagca ccgggaagat cctggagcag | 2820 |
| cgctccctga acacaatcca gcagtttgac taccagaaga aactcgacaa ccgggagaag | 2880 |
| gagcgcgtcg cagcccggca agcatggagt gtggtcggca ccataaagga cctgaaacag | 2940 |
| ggttacctaa gtcaagttat ccacgagatc gttgacctga tgatacacta tcaagccgta | 3000 |
| gtcgtgctgg agaacctcaa cttcgggttt aagtccaagc gcaccggcat cgcggagaag | 3060 |
| gcggtgtacc agcagttcga gaagatgctg atcgacaagc tgaactgcct ggtgctcaag | 3120 |
| gactaccctg cggagaaggt cggcggggtc ttgaacccgt accagctaac cgaccagttc | 3180 |
| acgagcttcg ccaaaatggg cacgcagtcc ggattcttgt tttatgtccc ggctccatat | 3240 |
| acaagtaaga tcgacccgct gacagggttt gttgacccat tcgtgtggaa gaccatcaag | 3300 |
| aaccacgaga gcaggaaaca cttcttagag ggcttcgact tcctgcatta cgacgttaag | 3360 |
| acaggcgact tcatcctgca cttcaagatg aaccgcaacc tgtcgttcca gaggggcctg | 3420 |
| cccggcttca tgcccgcctg ggatatcgtc tttgagaaga atgagacgca gttcgacgcg | 3480 |
| aaggggacgc cgttcatcgc tggaaagcgg atcgtgccgg tcatcgagaa ccaccgcttc | 3540 |
| acgggtcgct accgagattt ataccccgcc aacgaactaa ttgcgctgct ggaggagaag | 3600 |
| gggatcgtgt tccgagatgg cagcaacatt ctcccgaagc tgctggagaa cgacgactcg | 3660 |
| cacgctattg acacgatggt cgccctcata cggagcgtgc ttcagatgcg gaacagtaac | 3720 |
| gctgccacgg gcgaggacta cattaactcc cccgtccgcg acctcaacgg ggtctgcttc | 3780 |
| gatagccgct tccagaaccc cggagtggcc tatggatgcg gacgcgaacgg ggcctaccac | 3840 |
| atcgccctca agggccaact cctgctcaac cacttgaagg aaagcaaaga cctcaaattg | 3900 |
| cagaatggca tcagtaacca ggactggctc gcgtacatcc aggaactgag aaacgggtcc | 3960 |
| aagaagcggc gtatcaagca agattga | 3987 |

<210> SEQ ID NO 50
<211> LENGTH: 3987
<212> TYPE: DNA
<213> ORGANISM: Artificial
<220> FEATURE:
<223> OTHER INFORMATION: polynucleotide

<400> SEQUENCE: 50

| | |
|---|---|
| atggcgggaa gcaaaaagcg ccggattaag caagacacgc agttcgaggg cttcacgaac | 60 |
| ctctaccaag tcagcaagac cctccggttc gagctgatac acagggaaa gacgctcaag | 120 |
| cacatccagg aacagggctt catcgaggag gacaaggcgc gcaacgacca ctacaaggag | 180 |
| ttgaaaccga tcatcgaccg catctacaag acgtacgccg accagtgcct ccagctcgtg | 240 |
| cagctcgact gggagaacct ctccgccgcc attgactcgt accggaagga gaagactgag | 300 |
| gagacccgca acgccctgat cgaggagcaa gcaacctacc ggaacgccat ccacgactac | 360 |
| ttcatcggcc gcaccgacaa cctcaccgac gcgatcaaca gcggcacgc ggagatatac | 420 |

```
aaagggctgt tcaaggcgga gctgttcaac ggcaaggtgc tcaagcagct agggacggtg     480
accacgaccg agcacgagaa cgcgctcctc cgcagcttcg acaagttcac cacctacttc     540
agcggcttct accggaaccg caagaatgtg ttcagcgcgg aggacatcag cacggccatc     600
ccgcaccgca tcgtccagga caacttcccg aagttcaagg agaactgcca catcttcacc     660
cgcctgataa ccgccgtccc ctccctgcgg gagcacttcg agaacgtcaa aaaggcaatt     720
gggatcttcg tctcgaccag cattgaggag gtgttcagct tcccttcta caaccagctc      780 ctcacccaga cgcagatcga cctgtacaat cagttgctcg gcgggataag ccgcgaggcg     840
ggaaccgaaa aaatcaaggg gctgaacgaa gtgttgaacc tcgccatcca agaacgac       900 gagaccgcgc acatcatcgc ctccctgccc caccggttca tcccgctgtt caagcagatc     960
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga agtccgcgaa ggagaaggtg    1260
cagcggtccc tcaagcacga ggacatcaac ctccaggaga tcatctcagc ggctgggaaa    1320
gagctgtccg aggcgttcaa gcagaaaacg agcgaaatcc tgtcccacgc gcacgcggcc    1380
ctggatcagc ctctgccgac gaccctcaag aaacaagaag aaaggaaat cctcaagtcg     1440 cagctcgact cgctgctggg cctgtaccat ctcctcgact ggttcgccgt ggacgagagc    1500
aacgaggtgg acccgagtt ctccgcgcgg cttacgggga tcaagctgga gatggagccc     1560
agcctgtcct tctacaacaa ggcgcgcaac tacgccacca agaagcccta cagcgtggag    1620
aagttcaagc tcaacttcca gatgcccact ctcgcacgtg ggtgggacgt caaccgcgaa    1680
aaaaataatg gggcgatcct gttcgtcaag aacggcctgt actacttggg catcatgccg    1740
aaacagaagg gccgctacaa ggccctgagc ttcgaaccga ccgagaaaac gagcgagggg    1800
ttcgacaaga tgtactacga ctacttcccc gacgccgcga agatgattcc aaagtgctcc    1860
acgcagctta aggccgtgac ggcccacttc cagacgcaca cgaccccgat cctcctcagc    1920
aacaacttca tcgagcccct ggagatcacg aaggagatat acgacctgaa caacccggag    1980
aaggagccca gaaattcca ccaccgcctac gccaagaaga caggcgacca aaagggttac    2040
agggaggccc tctgcaagtg gatcgacttc actagggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct ccagcgcat cgcggagaag     2220 gagatcatgg acgcagtgga gacgggcaag ctataccat tcagatata caacaaagac      2280 ttcgctaagg acaccacgg caagcctaac ctgcacaccc tctactggac ggggctcttc     2340
agcccggaga acctcgccaa gacctcgatc aagctcaacg gccaggccga gctgttctac    2400
cggcccaagt cccgcatgaa gcggatggcc caccggctcg gggagaaaat gctcaacaag    2460
aaattgaagg accaaaaaac gccgataccc gacaccctat accaggagct gtacgactat    2520
gtgaaccacc gctgagcca cgacctcagc gacgaggcgc gggccctcct gccgaacgtc     2580
atcacaaagg aggtcagcca cgagatcatc aaggaccggc gcttcacctc cgacaagttt    2640 ttcttcacg tgcccatcac gctcaactac caggccgcca actcgccgtc caagttcaac     2700
cagcgcgtga acgcctacct caaggagcac cccgagaccc cgatcatcgg gattgaccga    2760
```

```
ggggagcgga acctcatcta catcaccgtc atcgacagca ccgggaagat ccttgaacag    2820
cggtcgctca acaccatcca gcagttcgac taccagaaga aactcgacaa ccgggagaag    2880
gagagagtgg cggcccgcca ggcttggtcc gtcgtcggga cgattaagga cttgaaacaa    2940
ggttacctgt cgcaagtgat ccacgagatc gttgacctga tgatccacta ccaagccgtc    3000
gtggtcctgg agaacctcaa cttcggcttc aagagcaaac gaaccggcat cgcggagaag    3060
gccgtgtacc agcagttcga aaaaatgctg atcgacaagc tgaactgcct cgtgctcaag    3120 gactacccg ctgagaaggt cggcggggtg ctgaacccgt accagctcac tgaccagttc    3180
accagcttcg caaagatggg cacccagtcc ggcttcctgt tctacgtgcc tgcgccatac    3240
acctcgaaga tcgacccgct caccgggttc gtggaccct cgtctggaa gaccatcaag    3300 aaccacgaga gccgcaagca cttcctggag ggcttcgact tcctccacta cgacgtcaag    3360 accgggact tcatcctgca cttcaagatg aaccgcaacc tcagtttcca gcgcggcctg    3420
ccggggttca tgcccgcttg ggatatagtc ttcgagaaga atgagacgca gttcgacgcg    3480
aagggcaccc cgttcatcgc cgggaagcgc atcgtgccgg tcatcgagaa ccaccggttc    3540
accgggcgct accgcgacct ataccggcg aacgagttga tcgccctcct ggaggagaag    3600
ggcatcgtgt ccgcgacgg ctccaacatc ctcccgaagc tgctcgaaaa cgacgactcc    3660
cacgccatcg acacgatggt cgcgctgatc cggtcggtgc tccagatgcg gaactccaac    3720
gccgcgacgg gcgaggacta catcaacagt ccggtccgcg atctgaacgg cgtctgcttc    3780
gactcccggt tccagaaccc cgagtggccg atggacgcgg acgcgaacgg cgcataccac    3840
atcgccctaa aagggcaatt gctgctcaac cacctcaagg aatccaaaga cctaaagctc    3900
cagaacggca tctccaacca ggactggctg gcgtacatcc aggaactgcg gaacgggagc    3960
aaaaaacgtc ggatcaagca agattga                                       3987

<210> SEQ ID NO 51
<211> LENGTH: 3987
<212> TYPE: DNA
<213> ORGANISM: Artificial
<220> FEATURE:
<223> OTHER INFORMATION: polynucleotide

<400> SEQUENCE: 51
atggcgggct ccaagaaacg ccggattaag caagatacc agttcgaggg gttcacgaac      60
ctctaccaag tgagcaagac cctccgattc gaactgattc ctcaggggaa gaccctcaag     120
cacatccagg agcaagggtt catcgaggag acaaggcgc ggaacgacca ctacaaggaa     180
ctcaaaccca tcatcgaccg catctacaag acctacgccg atcagtgcct ccagctcgtg     240
cagttggact gggagaacct cagcgcggcc attgactcct accggaagga gaaaacggag     300
gagacgcgca acgcgctcat cgaggaacag gcaacctatc gcaacgccat ccacgactac     360
ttcatcggga ggactgacaa cctcactgac gcgattaaca gcgccacgc ggagatatac     420 aagggactct tcaaagcgga gctgtttaac ggcaaggttc tcaagcaact cggcactgtg     480
accacgaccg agcatgagaa cgccctgctc cgctccttcg acaagttcac cacctacttc     540
tccgggttct accgcaaccg caagaatgtc ttcagcgcgg aggacatcag cacggccatt     600
ccacatcgaa tcgtccaaga taacttcccg aagttcaagg agaactgcca catcttcacc     660
cgactcatta ctgctgtacc gtcgttacgc gaacacttcg agaacgtcaa gaaggcaatt     720
ggaatcttcg tctctacgtc aatagaggag gtgttcagct tcccctttcta caaccagctc     780 cttacgcaga cccagataga cctgtacaat cagctcctcg gtgggatcag ccgggaggcg     840
```

```
gggactgaga agattaaagg gctcaacgag gtcttgaacc tggccatcca aaaaaacgat        900
gagacggcgc acatcatcgc ctcgctgccc caccggttca tcccgctgtt caagcagatc        960
ctcagtgaca ggaacacctt gagctttatc ctagaggagt tcaagagcga cgaggaggtg       1020
atccagagct tctgcaagta caaaaccctg ctgaggaacg agaacgtcct ggagacggcg       1080
gaggcgctgt tcaacgagct gaactctatc gacttaactc acatattcat ctcgcacaag       1140
aagctggaga ctattagctc tgcactctgc gaccactggg cacccctccg caacgcgctc       1200
tacgagcgcc gcatctcgga gctgaccggg aagatcacca atccgcgaa ggaaaaggtc        1260
cagcgttccc tcaaacacga ggatattaac ttacaggaga ttatctcagc ggctgggaag       1320
gagttgtcag aggcgttcaa gcagaaaact tccgagatcc tgagccacgc gcacgcagcg       1380
ctcgaccagc tctgcccac caccctcaaa agcaggaag aaaaagagat cctcaagagc        1440
cagttggact ccctgctggg gctctatcac cttctcgact ggttcgccgt cgatgagtcg       1500
aacgaggtgg accccgagtt ctccgcccgg ctgaccggca tcaagctaga gatggagccg       1560
tccctcagct tctacaataa ggcccgcaac tacgcgacca aaaaccctaa cagcgtggag       1620
aagttcaagc tgaacttcca gatgccgacc ttagcacgcg gttgggacgt aaacagggag       1680
aagaacaatg gagccatcct gttcgtcaag aacgggcttt actacctcgg gataatgccc       1740
aagcagaagg gccgctacaa ggcccttttcc ttcgagccga cggagaaaac ctccgagggg      1800
ttcgacaaga tgtactacga ctacttcccc gacgccgcca agatgatccc gaagtgctca       1860
acgcagctaa aagccgtgac cgcccacttc cagacccaca cgacgccgat cctgctgagc       1920
aacaacttca tcgagcccct tgagatcact aaggagatat acgacctgaa caaccccgag       1980
aaggagccca gaagtttca aaccgcctac gccaaaaaaa ctggcgacca aaagggctac        2040
agggaggcgc tgtgtaagtg gatcgacttc acacgcgact tccttttcgaa gtatacgaag      2100
acaacctcta ttgacctgag cagcctgcgt cctagctccc agtacaaaga tttgggcgag       2160
tactacgcgg agcttaatcc actactctac cacatctcat tccagcgcat cgctgagaag       2220
gaaatcatgg acgcggtgga gacaggcaaa ctgtacctct tccagatata caacaaagac       2280
ttcgctaagg ggcaccacgg gaagcccaac cttcatacgc tctactggac gggcctattc       2340
agccccgaaa atctggccaa gacctccatc aagctgaacg ccaagcgga gctgttctac        2400
agacccaaga gccggatgaa gcggatggcc cacaggctcg gcgagaaaat gcttaacaaa       2460
aagttgaagg accagaaaac ccctatcccc gacaccctct accaggaact gtacgactac       2520
gtgaaccaca ggctctcgca cgacttttcc gacgaggccc gtgccctact cccgaacgtc       2580
attaccaaag aggtttcgca cgagatcatc aaggaccggc ggttcacgag cgacaagttt       2640
ttcttttcacg tccccatcac ccttaactac caggcggcca actccccatc caagttcaac       2700
cagcgtgtga atgcctacct caaggagcac ccagagaccc cgatcattgg gatcgaccgg       2760
ggcgagcgga acctgatcta catcaccgtc atcgactcga cggcaagat tcttgagcag        2820
agatcgttga ataccataca gcagttcgac taccagaaga aactcgacaa ccgcgagaag       2880
gagcgcgtgg cggcccgcca ggcgtggtcc gtcgttggga cgattaagga cttgaaacaa       2940
ggttatctgt cccaagtcat ccacgagatc gttgatctga tgatccacta tcaggcagtg       3000
gtggtgctgg agaatctcaa cttcggcttc aagagtaagc ggacgggaat cgccgagaag       3060
gccgtgtacc agcagttcga gaagatgctg atcgacaagc tcaactgcct tgtgctgaaa       3120
gactacccgg ccgagaaggt cggcggcgtc ctcaacccgt accaacttac cgaccagttc       3180
```

| | |
|---|---|
| acctccttcg ccaagatggg cactcagtcc gggttcttgt tctacgtccc cgcaccttac | 3240 |
| acctctaaga tcgaccctct gactggcttc gtagatccat tcgtgtggaa gaccattaag | 3300 |
| aaccacgaga gccgcaagca cttcctggag ggcttcgact tcctgcacta cgacgtgaag | 3360 |
| accggggact tcatccttca cttcaagatg aaccggaacc tcagcttcca gcggggcctg | 3420 |
| ccggggttca tgcccgcctg ggacatcgtg ttcgagaaga acgagaccca gttcgacgcg | 3480 |
| aagggcacgc ccttcatcgc cgggaagcgt atcgtgccgg tgatcgagaa ccatcgtttc | 3540 |
| acgggtcgct accgtgacct ctacccggcg aacgagctta tcgcactcct ggaggagaag | 3600 |
| ggcatcgtct ccgggacgg ctccaacatc ctcccgaaac tgctggaaaa cgacgactct | 3660 |
| cacgccatcg acacgatggt ggccctcatc cggtccgtgc tccaaatgcg gaacagcaac | 3720 |
| gccgccaccg gtgaggacta catcaacagc ccggtccggg atctgaacgg ggtgtgcttc | 3780 |
| gattcgcggt tccagaatcc tgagtggccg atggacgcg atgcaaacgg ggcgtaccac | 3840 |
| atcgcgctca agggccagtt acttctgaac caccttaagg agtctaaaga tttgaaactc | 3900 |
| cagaacggga tctcgaacca ggactggctg gcctacatcc aagagttgcg gaacggcagc | 3960 |
| aagaagcggc ggattaagca agattag | 3987 |

<210> SEQ ID NO 52
<211> LENGTH: 3790
<212> TYPE: DNA
<213> ORGANISM: Artificial
<220> FEATURE:
<223> OTHER INFORMATION: expression cassette

<400> SEQUENCE: 52

| | |
|---|---|
| ccatgggcag caaactggaa aaatttacga attgttatag cctgtccaag accctgcgtt | 60 |
| tcaaagccat ccccgttggc aaaacccagg agaatattga taataaacgt ctgctggttg | 120 |
| aggatgaaaa aagagcagaa gactataagg gagtcaaaaa actgctggat cggtactacc | 180 |
| tgagctttat aaatgacgtg ctgcatagca ttaaactgaa aaatctgaat aactatatta | 240 |
| gtctgttccg caagaaaacc cgaacagaga aagaaataa agagctggaa aacctggaga | 300 |
| tcaatctgcg taaagagatc gcaaaagctt ttaaaggaaa tgaaggttat aaaagcctgt | 360 |
| tcaaaaaaga cattattgaa accatcctgc cggaatttct ggatgataaa gacgagatag | 420 |
| cgctcgtgaa cagcttcaac gggttcacga ccgccttcac gggcttttc gataacaggg | 480 |
| aaaatatgtt ttcagaggaa gccaaaagca cctcgatagc gttccgttgc attaatgaaa | 540 |
| atttgacaag atatatcagc aacatggata ttttcgagaa agttgatgcg atctttgaca | 600 |
| aacatgaagt gcaggagatt aaggaaaaaa ttctgaacag cgattatgat gttgaggatt | 660 |
| ttttcgaggg ggaattttt aactttgtac tgacacagga aggtatagat gtgtataatg | 720 |
| ctattatcgg cgggttcgtt accgaatccg gcgagaaaat taagggtctg aatgagtaca | 780 |
| tcaatctgta taaccaaaag accaaacaga actgccaaaa attcaaaccg ctgtacaagc | 840 |
| aagtcctgag cgatcgggaa agcttgagct tttacggtga aggttatacc agcgacgagg | 900 |
| aggtactgga ggtctttcgc aatacccctga acaagaacag cgaaattttc agctccatta | 960 |
| aaaagctgga gaaactgttt aagaattttg acgagtacag cagcgcaggt atttttgtga | 1020 |
| agaacggacc tgccataagc accattagca aggatatttt tggagagtgg aatgttatcc | 1080 |
| gtgataaatg gaacgcggaa tatgatgaca tacacctgaa aaagaaggct gtggtaactg | 1140 |
| agaaatatga gacgatcgc cgcaaaagct ttaaaaaaat cggcagcttt agcctggagc | 1200 |
| agctgcagga atatgcggac gccgacctga gcgtggtcga gaaactgaag gaaattatta | 1260 |

```
tccaaaaagt ggatgagatt tacaaggtat atggtagcag cgaaaaactg tttgatgcgg   1320
acttcgttct ggaaaaaagc ctgaaaaaaa atgatgctgt tgttgcgatc atgaaagacc   1380
tgctcgatag cgttaagagc tttgaaaatt acattaaagc attctttggc gagggcaaag   1440
aaacaaacag agacgaaagc ttttatggcg acttcgtcct ggcttatgac atcctgttga   1500
aggtagatca tatatatgat gcaattcgta attacgtaac ccaaaagccg tacagcaaag   1560
ataagttcaa actgtatttc cagaacccgc agtttatggg tggctgggac aaagacaagg   1620
agacagacta tcgcgccact attctgcgtt acggcagcaa gtactatctc gccatcatgg   1680
acaaaaaata tgcaaagtgt ctgcagaaaa tcgataaaga cgacgtgaac ggaaattacg   1740
aaaagattaa ttataagctg ctgccagggc ccaacaagat gttaccgaaa gtattttttt   1800
ccaaaaaatg gatggcatac tataacccga gcgaggatat acagaagatt tacaaaaatg   1860
ggaccttcaa aaaggggat atgttcaatc tgaatgactg ccacaaactg atcgattttt   1920
ttaaagatag catcagccgt tatcctaaat ggtcaaacgc gtatgatttt aatttctccg   1980
aaacggagaa atataaagac attgctggtt tctatcgcga agtcgaagaa cagggttata   2040
aagttagctt tgaatcggcc agcaagaaag aggttgataa actggtggag gagggtaagc   2100
tgtatatgtt tcagatttat aacaaagact ttagcgacaa aagccacggt actcctaatc   2160
tgcatacgat gtactttaaa ctgctgtttg atgagaataa ccacggccaa atccgtctct   2220
ccggtggagc agaactttt atgcggcgtg cgagcctaaa aaggaagaa ctggtggtgc   2280 atcccgccaa cagcccgatt gctaacaaaa atccagataa tcctaagaag accaccacac   2340
tgtcgtacga tgtctataag gataaacgtt tctcggaaga ccagtatgaa ttgcatatac   2400
cgatagcaat taataaatgc ccaaaaaaca ttttcaaaat caacactgaa gttcgtgtgc   2460
tgctgaaaca tgatgataat ccgtatgtga tcggaattga ccgtgggag agaaatctgc   2520 tgtatattgt agtcgttgat ggcaagggca acatcgttga gcagtatagc ctgaatgaaa   2580
taattaataa ttttaacggt atacgtatta aaaccgacta tcatagcctg ctggataaaa   2640
aggagaaaga gcgttttgag gcacgccaaa attggacgag catcgaaaac atcaaggaac   2700
tgaaggcagg atatatcagc caagtagtcc ataaaatctg tgaactggtg gagaagtacg   2760
acgctgtcat tgccctggaa gacctcaata gcggctttaa aaacagccgg gtgaaggtgg   2820
agaaacaggt ataccaaaag tttgaaaaga tgctcattga taagctgaac tatatggttg   2880
ataaaaagag caacccgtgc gccactggcg gtgcactgaa agggtaccaa attaccaata   2940
aatttgaaag ctttaaaagc atgagcacgc agaatgggtt tatttttat ataccagcat   3000 ggctgacgag caagattgac cccagcactg gttttgtcaa tctgctgaaa accaaataca   3060
caagcattgc ggatagcaaa aaatttattt cgagcttcga ccgtattatg tatgttccgg   3120
aggaagatct gtttgaattt gccctggatt ataaaaactt cagccgcacc gatgcagatt   3180
atatcaaaaa atgaagctg tacagttatg gtaatcgtat acgtatcttc cgtaatccga   3240
agaaaaacaa tgtgttcgat tgggaagagg tctgtctgac cagcgcgtat aaagaactgt   3300
tcaacaagta cggaataaat tatcagcaag gtgacattcg cgcactgctg tgtgaacagt   3360
cagataaagc attttatagc agctttatgg cgctgatgag cctgatgctc cagatgcgca   3420
acagcataac cggtcgcaca gatgttgact ttctgatcag ccctgtgaag aatagcgacg   3480
gcatcttcta cgattccagg aactatgaag cacaggaaaa cgctattctg cctaaaaatg   3540
ccgatgccaa cggcgcctat aatattgcac ggaaggttct gtgggcgatt ggacagttca   3600
```

| | |
|---|---|
| agaaagcgga agatgagaag ctggataagg taaaaattgc tattagcaat aaggaatggc | 3660 |
| tggagtacgc acagacatcg gttaaacacg gtagtaaaag gccggcggcc acgaaaaagg | 3720 |
| ccggccaggc aaaaaagaaa aagggagcgg ccgcactcga gcaccaccac caccaccact | 3780 |
| gagcggccgc | 3790 |

<210> SEQ ID NO 53
<211> LENGTH: 8986
<212> TYPE: DNA
<213> ORGANISM: Artificial
<220> FEATURE:
<223> OTHER INFORMATION: vector

<400> SEQUENCE: 53

| | |
|---|---|
| tggcgaatgg gacgcgccct gtagcggcgc attaagcgcg gcgggtgtgg tggttacgcg | 60 |
| cagcgtgacc gctacacttg ccagcgccct agcgcccgct cctttcgctt tcttcccttc | 120 |
| ctttctcgcc acgttcgccg gctttccccg tcaagctcta aatcggggc tccctttagg | 180 |
| gttccgattt agtgctttac ggcacctcga ccccaaaaaa cttgattagg gtgatggttc | 240 |
| acgtagtggg ccatcgccct gatagacggt ttttcgccct ttgacgttgg agtccacgtt | 300 |
| ctttaatagt ggactcttgt tccaaactgg aacaacactc aaccctatct cggtctattc | 360 |
| ttttgattta agggatttt gccgatttc ggcctattgg ttaaaaaatg agctgattta | 420 |
| acaaaaattt aacgcgaatt ttaacaaaat attaacgttt acaatttcag gtggcacttt | 480 |
| tcggggaaat gtgcgcggaa cccctatttg tttattttc taaatacatt caaatatgta | 540 |
| tccgctcatg aattaattct tagaaaaact catcgagcat caaatgaaac tgcaatttat | 600 |
| tcatatcagg attatcaata ccatattttt gaaaaagccg tttctgtaat gaaggagaaa | 660 |
| actcaccgag gcagttccat aggatggcaa gatcctggta tcggtctgcg attccgactc | 720 |
| gtccaacatc aatacaacct attaatttcc cctcgtcaaa aataaggtta tcaagtgaga | 780 |
| aatcaccatg agtgacgact gaatccggtg agaatggcaa aagtttatgc atttctttcc | 840 |
| agacttgttc aacaggccag ccattacgct cgtcatcaaa atcactcgca tcaaccaaac | 900 |
| cgttattcat tcgtgattgc gcctgagcga gacgaaatac gcgatcgctg ttaaaaggac | 960 |
| aattacaaac aggaatcgaa tgcaaccggc gcaggaacac tgccagcgca tcaacaatat | 1020 |
| tttcacctga tcaggatat tcttctaata cctggaatgc tgttttcccg gggatcgcag | 1080 |
| tggtgagtaa ccatgcatca tcaggagtac ggataaaatg cttgatggtc ggaagaggca | 1140 |
| taaattccgt cagccagttt agtctgacca tctcatctgt aacatcattg gcaacgctac | 1200 |
| ctttgccatg tttcagaaac aactctggcg catcgggctt cccatacaat cgatagattg | 1260 |
| tcgcacctga ttgcccgaca ttatcgcgag cccatttata cccatataaa tcagcatcca | 1320 |
| tgttggaatt taatcgcggc ctagagcaag acgtttcccg ttgaatatgg ctcataacac | 1380 |
| cccttgtatt actgtttatg taagcagaca gttttattgt tcatgaccaa aatcccttaa | 1440 |
| cgtgagtttt cgttccactg agcgtcagac cccgtagaaa agatcaaagg atcttcttga | 1500 |
| gatcctttt ttctgcgcgt aatctgctgc ttgcaaacaa aaaaaccacc gctaccagcg | 1560 |
| gtggtttgtt tgccggatca agagctacca actctttttc cgaaggtaac tggcttcagc | 1620 |
| agagcgcaga taccaaatac tgtccttcta gtgtagccgt agttaggcca ccacttcaag | 1680 |
| aactctgtag caccgcctac atacctcgct ctgctaatcc tgttaccagt ggctgctgcc | 1740 |
| agtggcgata agtcgtgtct taccgggttg gactcaagac gatagttacc ggataaggcg | 1800 |
| cagcggtcgg gctgaacggg gggttcgtgc acacagccca gcttggagcg aacgacctac | 1860 |

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccaggtggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
```

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg    4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg cgatataggc gccagcaac cgcacctgtg    4920 gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca aactgaaaaa atttacgaat    5100
tgttatagcc tgtccaagac cctgcgtttc aaagccatcc ccgttggcaa acccaggag    5160 aatattgata ataaacgtct gctggttgag gatgaaaaaa gagcagaaga ctataaggga    5220
gtcaaaaaac tgctggatcg gtactacctg agctttataa atgacgtgct gcatagcatt    5280
aaactgaaaa atctgaataa ctatattagt ctgttccgca agaaacccg aacagagaaa    5340 gaaaataaag agctggaaaa cctggagatc aatctgcgta agagatcgc aaaagctttt    5400 aaaggaaatg aaggttataa aagcctgttc aaaaaagaca ttattgaaac catcctgccg    5460
gaatttctgg atgataaaga cgagatagcg ctcgtgaaca gcttcaacgg gttcacgacc    5520
gccttcacgg gcttttttcga taacagggaa aatatgtttt cagaggaagc caaaagcacc    5580
tcgatagcgt tccgttgcat taatgaaaat ttgacaagat atatcagcaa catggatatt    5640
ttcgagaaag ttgatgcgat cttttgacaaa catgaagtgc aggagattaa ggaaaaaatt    5700
ctgaacagcg attatgatgt tgaggatttt tcgaggggg aattttttaa ctttgtactg    5760
acacaggaag gtatagatgt gtataatgct attatcggcg ggttcgttac cgaatccggc    5820
gagaaaatta agggtctgaa tgagtacatc aatctgtata ccaaaagac caaacagaaa    5880 ctgccaaaat tcaaaccgct gtacaagcaa gtcctgagcg atcgggaaag cttgagcttt    5940
tacggtgaag gttataccag cgacgaggag gtactggagg tctttcgcaa taccctgaac    6000
aagaacagcg aaattttcag ctccattaaa agctgagaga aactgtttaa gaattttgac    6060
gagtacagca gcgcaggtat ttttgtgaag aacggacctg ccataagcac cattagcaag    6120 gatattttg gagagtggaa tgttatccgt gataatggaa acgcggaata tgatgacata    6180
cacctgaaaa agaaggctgt ggtaactgag aaatatgaag acgatcgccg caaaagcttt    6240
aaaaaaatcg gcagctttag cctggagcag ctgcaggaat atgcggacgc cgacctgagc    6300
gtggtcgaga aactgaagga aattattatc caaaaagtgg atgagattta caaggtatat    6360
ggtagcagcg aaaaactgtt tgatgcggac ttcgttctgg aaaaaagcct gaaaaaaat    6420 gatgctgttg ttgcgatcat gaaagacctc tcgatagcg ttaagagctt tgaaaattac    6480
attaaagcat tctttggcga gggcaaagaa acaaacagag acgaaagctt ttatggcgac    6540
ttcgtcctgg cttatgacat cctgttgaag gtagatcata tatatgatgc aattcgtaat    6600
```

```
tacgtaaccc aaaagccgta cagcaaagat aagttcaaac tgtatttcca gaacccgcag   6660
tttatggGtg gctgggacaa agacaaggag acagactatc gcgccactat tctgcgttac   6720
ggcagcaagt actatctcgc catcatggac aaaaaatatg caaagtgtct gcagaaaatc   6780
gataaagacg acgtgaacgg aaattacgaa aagattaatt ataagctgct gccagggccc   6840
aacaagatgt taccgaaagt atttttttcc aaaaaatgga tggcatacta aacccgagc   6900 gaggatatac agaagattta caaaaatggg accttcaaaa aggggatat gttcaatctg   6960 aatgactgcc acaaactgat cgattttttt aaagatagca tcagccgtta tcctaaatgg   7020
tcaaacgcgt atgattttaa tttctccgaa acggagaaat ataaagacat tgctggtttc   7080
tatcgcgaag tcgaagaaca gggttataaa gttagctttg aatcggccag caagaaagag   7140
gttgataaac tggtggagga gggtaagctg tatatgtttc agatttataa caaagacttt   7200
agcgacaaaa gccacggtac tcctaatctg catacgatgt actttaaact gctgtttgat   7260
gagaataacc acgccaaat ccgtctctcc ggtggagcag aacttttat gcggcgtgcg   7320 agcctaaaaa aggaagaact ggtggtgcat cccgccaaca gcccgattgc taacaaaaat   7380
ccagataatc ctaagaagac caccacactg tcgtacgatg tctataagga taaacgtttc   7440
tcggaagacc agtatgaatt gcatataccg atagcaatta ataaatgccc aaaaaacatt   7500
ttcaaaatca acactgaagt tcgtgtgctg ctgaaacatg atgataatcc gtatgtgatc   7560
ggaattgacc gtggggagag aaatctgctg tatattgtag tcgttgatgg caagggcaac   7620
atcgttgagc agtatagcct gaatgaaata attaataatt ttaacggtat acgtattaaa   7680
accgactatc atagcctgct ggataaaaag gagaaagagc gttttgaggc acgccaaaat   7740
tggacgagca tcgaaaacat caaggaactg aaggcaggat atatcagcca agtagtccat   7800
aaaatctgtg aactggtgga aagtacgac gctgtcattg ccctggaaga cctcaatagc   7860
ggctttaaaa acagccgggt gaaggtggag aaacaggtat accaaaagtt tgaaaagatg   7920
ctcattgata agctgaacta tatggttgat aaaaagagca cccgtgcgc cactggcggt   7980 gcactgaaag ggtaccaaat taccaataaa tttgaaagct ttaaaagcat gagcacgcag   8040
aatgggttta ttttttatat accagcatgg ctgacgagca agattgaccc cagcactggt   8100
tttgtcaatc tgctgaaaac caaatacaca agcattgcgg atagcaaaaa atttatttcg   8160
agcttcgacc gtattatgta tgttccggag gaagatctgt ttgaatttgc cctggattat   8220
aaaaacttca gccgcaccga tgcagattat atcaaaaaat ggaagctgta cagttatggt   8280
aatcgtatac gtatcttccg taatccgaag aaaaacaatg tgttcgattg ggaagaggtc   8340
tgtctgacca gcgcgtataa agaactgttc aacaagtacg gaataaatta tcagcaaggt   8400
gacattcgcg cactgctgtg tgaacagtca gataaagcat tttatagcag ctttatggcg   8460
ctgatgagcc tgatgctcca gatgcgcaac agcataaccg tcgcacaga tgttgacttt   8520 ctgatcagcc ctgtgaagaa tagcgacggc atcttctacg attccaggaa ctatgaagca   8580
caggaaaacg ctattctgcc taaaaatgcc gatgccaacg gcgcctataa tattgcacgg   8640
aaggttctgt gggcgattgg acagttcaag aaagcggaag atgagaagct ggataaggta   8700
aaaattgcta ttagcaataa ggaatggctg gagtacgcac agacatcggt taaacacggt   8760
agtaaaaggc cggcggccac gaaaaaggcc ggccaggcaa aaagaaaaa gggagcggcc   8820 gcactcgagc accaccacca ccaccactga gatccggctg ctaacaaagc ccgaaaggaa   8880
gctgagttgg ctgctgccac cgctgagcaa taactagcat aacccctttgg ggcctctaaa   8940
```
cgggtcttga ggggttttttt gctgaaagga ggaactatat ccggat                    8986

<210> SEQ ID NO 54
<211> LENGTH: 23
<212> TYPE: DNA
<213> ORGANISM: Artificial
<220> FEATURE:
<223> OTHER INFORMATION: spacer sequence

<400> SEQUENCE: 54
tcatctgtgc ccctccctcc ctg                                              23

<210> SEQ ID NO 55
<211> LENGTH: 23
<212> TYPE: DNA
<213> ORGANISM: Artificial
<220> FEATURE:
<223> OTHER INFORMATION: spacer sequence

<400> SEQUENCE: 55
gcggatgttc caatcagtac gca                                              23

<210> SEQ ID NO 56
<211> LENGTH: 23
<212> TYPE: DNA
<213> ORGANISM: Artificial
<220> FEATURE:
<223> OTHER INFORMATION: spacer sequence

<400> SEQUENCE: 56
cagcccgctg gccctgtaaa gga                                              23

<210> SEQ ID NO 57
<211> LENGTH: 23
<212> TYPE: DNA
<213> ORGANISM: Artificial
<220> FEATURE:
<223> OTHER INFORMATION: spacer sequence

<400> SEQUENCE: 57
tatgagttac aacgaacacc tca                                              23

<210> SEQ ID NO 58
<211> LENGTH: 23
<212> TYPE: DNA
<213> ORGANISM: Artificial
<220> FEATURE:
<223> OTHER INFORMATION: spacer sequence

<400> SEQUENCE: 58
cacgtctcat atgccccttg gca                                              23

<210> SEQ ID NO 59
<211> LENGTH: 23
<212> TYPE: DNA
<213> ORGANISM: Artificial
<220> FEATURE:
<223> OTHER INFORMATION: spacer sequence

<400> SEQUENCE: 59
gaacatgaaa acttaaatag aac                                              23

<210> SEQ ID NO 60
<211> LENGTH: 23
<212> TYPE: DNA
<213> ORGANISM: Artificial

```
<220> FEATURE:
<223> OTHER INFORMATION: spacer sequence

<400> SEQUENCE: 60
gtcaggttgg ctgctgggct ggc                                            23

<210> SEQ ID NO 61
<211> LENGTH: 23
<212> TYPE: DNA
<213> ORGANISM: Artificial
<220> FEATURE:
<223> OTHER INFORMATION: spacer sequence

<400> SEQUENCE: 61
acagatgggg ctggacaatt ttt                                            23

<210> SEQ ID NO 62
<211> LENGTH: 43
<212> TYPE: RNA
<213> ORGANISM: Artificial
<220> FEATURE:
<223> OTHER INFORMATION: CRISPR RNA

<400> SEQUENCE: 62
aauuucuacu aaguguagau ggaaucccuu cugcagcacc ugg                      43
```

VARIANTS OF CAS12A NUCLEASES AND METHODS OF MAKING AND USE THEREOF

STATEMENT OF PRIORITY

This application claims the benefit, under 35 U.S.C. § 119 (e), of U.S. Provisional Application No. 62/916,392 filed on Oct. 17, 2019, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 1499.7_ST25.txt, 257,771 bytes in size, generated on Oct. 13, 2020 and filed via EFS-Web, is provided in lieu of a paper copy. This Sequence Listing is hereby incorporated herein by reference into the specification for its disclosures.

FIELD OF THE INVENTION

This invention relates to variants of Cas12a CRISPR-Cas nucleases having altered protospacer adjacent motif recognition specificity. The invention further relates to methods of making the CRISPR-CAS nuclease variants and methods of modifying nucleic acids using the variants.

BACKGROUND OF THE INVENTION

Genome editing/modifying is a process that utilizes site-directed nucleases, for example, CRISPR-Cas nucleases, to introduce variation at a targeted genomic location. The most widely utilized nuclease for genome modification, Cas9, can introduce mutations at a genomic region upstream of an NGG motif (e.g., a protospacer adjacent motif (PAM)). Other Cas nucleases have different PAM recognition specificities. When the PAM specificities of these nucleases are particularly stringent, they can reduce the usefulness of the nuclease for genome modification by limiting the number of genomic target sites available for modification by that nuclease.

To address the shortcomings in the art, the present invention provides modified CRISPR-Cas nucleases having improved PAM specificity and methods for designing, identifying and selecting such CRISPR-Cas nucleases.

SUMMARY OF THE INVENTION

One aspect of the invention provides a modified Lachnospiraceae *bacterium* CRISPR (Clustered Regularly Interspaced Short Palindromic Repeats) Cas12a (LbCas12a) polypeptide, wherein the modified LbCas12a polypeptide comprises, consists essentially of, or consists of an amino acid sequence having at least 80% identity to the amino acid sequence of SEQ ID NO:1 (LbCas12a) and a mutation at one or more (e.g., 1, 2, 3, 4, 5, 6, 7, 8, 9, 10, 11, 12, 13 or more) of the following positions of K116, K120, K121, D122, E125, T148, T149, T152, D156, E159, Q529, G532, D535, K538, D541, Y542, L585, K591, M592, K595, V596, S599, K600, K601, Y616, Y646, and/or W649 with reference to the position numbering of SEQ ID NO:1 in any combination, optionally a mutation at one or more of the following positions of K116, K120, K121, D122, E125, T152, D156, E159, G532, D535, K538, D541, and/or K595 with reference to the position numbering of SEQ ID NO:1 in any combination.

A second aspect of the invention provides a Type V Clustered Regularly Interspaced Short Palindromic Repeats (CRISPR)-associated (Cas) (CRISPR-Cas) system comprising: (a) a fusion protein comprising (i) a modified LbCas12a polypeptide of the invention or a nucleic acid encoding the modified LbCas12a polypeptide of the invention, and (ii) a polypeptide of interest or a nucleic acid encoding the polypeptide of interest; and (b) a guide nucleic acid (CRISPR RNA, CRISPR DNA, crRNA, crDNA) comprising a spacer sequence and a repeat sequence, wherein the guide nucleic acid is capable of forming a complex with the modified LbCas12a polypeptide or the fusion protein, and the spacer sequence is capable of hybridizing to a target nucleic acid, thereby guiding the modified LbCas12a polypeptide and the polypeptide of interest to the target nucleic acid, whereby the target nucleic acid is modified or modulated.

A third aspect of the invention provides a method of modifying a target nucleic acid, comprising: contacting the target nucleic acid with: (a)(i) a modified LbCas12a polypeptide of the invention, or a fusion protein comprising a modified LbCas12a polypeptide of the invention, and (ii) a guide nucleic acid (e.g., CRISPR RNA, CRISPR DNA, crRNA, crDNA); (b) a complex comprising the modified LbCas12a polypeptide of the invention and a guide nucleic acid; (c) a composition comprising (i) a modified lbCas12a polypeptide of the invention, or a fusion protein of the invention, and (ii) a guide nucleic acid; and/or (d) a system of the invention, thereby modifying the target nucleic acid.

A fourth aspect of the invention provides a method of modifying a target nucleic acid, comprising contacting a cell or a cell free system comprising the target nucleic acid with: (a)(i) a polynucleotide encoding a modified LbCas12a polypeptide of the invention, or an expression cassette or vector comprising the same, and (ii) a guide nucleic acid, or an expression cassette or vector comprising the same; and/or (b) a nucleic acid construct encoding a (i) complex comprising a modified LbCas12a polypeptide or a fusion protein of the invention, and (ii) a guide nucleic acid, or an expression cassette or vector comprising the same, thereby modifying the target nucleic acid.

A fifth aspect of the invention provides a method of editing a target nucleic acid, comprising: contacting the target nucleic acid with: (a)(i) a fusion protein comprising a modified LbCas12a polypeptide of the invention and (a)(ii) a guide nucleic acid; (b) a complex comprising the fusion protein of the invention, and a guide nucleic acid; (c) a composition comprising the fusion protein of the invention and a guide nucleic acid; and/or, (d) a system of the invention, thereby editing the target nucleic acid.

A sixth aspect of the invention provides a method of editing a target nucleic acid, comprising contacting a cell or a cell free system comprising the target nucleic acid with: (a)(i) a polynucleotide encoding a fusion protein comprising a modified LbCas12a polypeptide of the invention, or an expression cassette or vector comprising the same, and (a)(ii) a guide nucleic acid, or an expression cassette or vector comprising the same; and/or (b) a nucleic acid construct encoding a complex comprising a fusion protein comprising a modified LbCas12a polypeptide of the invention, and a guide nucleic acid, or an expression cassette or vector comprising the same; and/or (c) a system of the invention, thereby editing the target nucleic acid.

A seventh aspect of the invention provides a method of constructing a randomized DNA library comprising double stranded nucleic acid molecules for determining protospacer adjacent motif (PAM) requirements/specificity of a CRISPR-Cas nuclease having a PAM recognition site at the 5' end of the protospacer, the method comprising: preparing two or more double stranded nucleic acid molecules comprising the following steps: (a) synthesizing a non-target oligonucleotide (first) strand and a target oligonucleotide (second) strand for each of the two or more double stranded nucleic acid molecules, wherein the non-target oligonucleotide strand comprises, 5' to 3': (i) a first sequence having about 5 to about 15 nucleotides, (ii) a second sequence having at least four randomized nucleotides, (iii) a protospacer sequence comprising about 16 to about 25 nucleotides, and (iv) a third sequence having about 5 to about 20 nucleotides, wherein the first sequence having about 5 to 15 nucleotides of (i) is immediately adjacent to the 5' end of the second sequence of (ii), the second sequence of (ii) is immediately adjacent to the 5' end of the protospacer sequence of (iii), and the protospacer sequence is immediately adjacent to the 5' end of the third sequence of (iv); and the target oligonucleotide (second) strand complementary to the non-target oligonucleotide strand; and (b) annealing the non-target oligonucleotide strand to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (iii) and the third sequence (iv) of each of the two or more double stranded nucleic acid molecules is identical, thereby constructing the randomized DNA library comprising double stranded nucleic acid molecules.

An eighth aspect of the invention provides a method of constructing a randomized DNA library comprising double stranded nucleic acid molecules for determining protospacer adjacent motif (PAM) requirements/specificity of a CRISPR-Cas nuclease having a PAM recognition site at the 3' end of the protospacer, the method comprising: preparing two or more double stranded nucleic acid molecules comprising the following steps: (a) synthesizing a non-target oligonucleotide (first) strand and a target oligonucleotide (second) strand for each of the two or more double stranded nucleic acid molecules, wherein the non-target oligonucleotide strand comprises, 5' to 3': (i) a first sequence having about 5 to about 20 nucleotides, (ii) a protospacer sequence comprising about 16 to about 25 nucleotides, (iii) a second sequence having at least four randomized nucleotides, and (iv) a third sequence having about 5 to about 15 nucleotides, wherein the first sequence having about 5 to 20 nucleotides of (i) is immediately adjacent to the 5' end of the protospacer sequence of (ii), the second sequence of (iii) is immediately adjacent to the 3' end of the protospacer sequence of (iii), and the third sequence of (iv) is immediately adjacent to the 3' end of the second sequence of (iii); and the target oligonucleotide (second) strand is complementary to the non-target oligonucleotide strand; and (b) annealing the non-target oligonucleotide strand to the complementary target oligonucleotide strand to produce a double stranded nucleic acid molecule, wherein the first sequence (i) comprises a restriction site (at its 5' end) and the third sequence (iv) comprises a restriction site (at its 3' end), wherein the first sequence (i), the protospacer sequence (ii) and the third sequence (iv) of each of the two or more double stranded nucleic acid molecules is identical, thereby constructing the randomized DNA library comprising double stranded nucleic acid molecules.

A ninth aspect of the invention provides a randomized DNA library for determining protospacer adjacent motif (PAM) requirements/specificity of a CRISPR-Cas nuclease having a PAM recognition site on the 5' end of protospacer, the randomized DNA library comprising two or more double stranded nucleic acid molecules each of which comprises: (a) a non-target oligonucleotide (first) strand and a target oligonucleotide (second) strand, wherein the non-target oligonucleotide strand comprises, 5' to 3': (i) a first sequence having about 5 to about 15 nucleotides (e.g., about 5, 6, 7, 8, 9, 10, 11, 12, 13, 14, or 15 nucleotides, and any range or value therein), (ii) a second sequence having at least four randomized nucleotides (e.g., at least 4, 5, 6, 7, 8, 9, 10, or more, and any range or value therein), (iii) a protospacer sequence comprising about 16 to about 25 nucleotides e.g., about 16, 17, 18, 19, 20, 21, 22, 23, 24, or 25 nucleotides, and (iv) a third sequence having about 5 to about 20 nucleotides (e.g., about 5, 6, 7, 8, 9, 10, 11, 12, 13, 14, 15, 16, 17, 18, 19, 20 nucleotides, and any range or value therein), wherein the first sequence having about 5 to 15 nucleotides of (i) is immediately adjacent to the 5' end of the second sequence of (ii), the second sequence of (ii) is immediately adjacent to the 5' end of the protospacer sequence of (iii), and the protospacer sequence is immediately adjacent to the 5' end of the third sequence of (iv); and the target oligonucleotide (second) strand is complementary to the non-target oligonucleotide strand; and (b) the non-target oligonucleotide strand is annealed to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (iii) and the third sequence (iv) of each of the two or more double stranded nucleic acid molecules are identical.

A tenth aspect of the invention provides a randomized DNA library for determining protospacer adjacent motif (PAM) requirements/specificity of a CRISPR-Cas nuclease having a PAM recognition site on the 3' end of protospacer, the randomized DNA library comprising two or more double stranded nucleic acid molecules each of which comprises: (a) a non-target oligonucleotide (first) strand and a target oligonucleotide (second) strand, wherein the non-target oligonucleotide strand comprises, 5' to 3': (i) a first sequence having about 5 to about 20 nucleotides (e.g., about 5, 6, 7, 8, 9, 10, 11, 12, 13, 14, 15, 16, 17, 18, 19, 20 nucleotides, and any range or value therein), (ii) a protospacer sequence comprising about 16 to about 25 nucleotides e.g., about 16, 17, 18, 19, 20, 21, 22, 23, 24, or 25 nucleotides, (iii) a second sequence having at least four randomized nucleotides (e.g., at least 4, 5, 6, 7, 8, 9, 10, or more, and any range or value therein), and (iv) a third sequence having about 5 to about 15 nucleotides (e.g., about 5, 6, 7, 8, 9, 10, 11, 12, 13, 14, 15 nucleotides, and any range or value therein), wherein the first sequence having about 5 to 20 nucleotides of (i) is immediately adjacent to the 5' end of the protospacer sequence of (ii), the second sequence of (iii) is immediately adjacent to the 3' end of the protospacer sequence of (iii), and the third sequence of (iv) is immediately adjacent to the 3' end of the second sequence of (iii); and the target oligonucleotide (second) strand is complementary to the non-target oligonucleotide strand; and (b) the non-target oligonucleotide strand is annealed to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (ii) and the third sequence (iv) of each of the two or more double stranded nucleic acid molecules are identical.

The invention further provides expression cassettes and/or vectors comprising polynucleotides encoding CRISPR-Cas nucleases and/or fusion proteins of the invention and/or cells comprising polynucleotides, polypeptides and/or fusion proteins of the invention and/or kits comprising the same.

These and other aspects of the invention are set forth in more detail in the description of the invention below.

BRIEF DESCRIPTION OF THE SEQUENCES

SEQ ID NOs:1-17, 49, 50 and 51 are exemplary nucleotide sequences encoding Cas12a nucleases.

SEQ ID NOs:18-22 are exemplary adenosine deaminases.

SEQ ID NOs:23-25 and SEQ ID NOs:42-48 are exemplary cytosine deaminases.

SEQ ID NO:26 an exemplary nucleotide sequence encoding a uracil-DNA glycosylase inhibitor (UGI).

SEQ ID NOs: 27-29 provides an example of a protospacer adjacent motif position for a Type V CRISPR-Cas12a nuclease.

SEQ ID NOs:30-39 shows example nucleotide sequences useful for generating a randomized library of this invention for use in, for example, in vitro cleavage assays.

SEQ ID NOs:40-41 are exemplary regulatory sequences encoding a promoter and intron.

SEQ ID NO:52 provides the nucleotide sequence of an example expression cassette.

SEQ ID NO:53 provides the nucleotide sequence of an example vector.

SEQ ID NOs:54-61 provide example spacer sequences.

SEQ ID NO:62 provides an example CRISPR RNA.

BRIEF DESCRIPTION OF THE DRAWINGS

FIG. 3 shows mean accessible cytosines (panels A, B) and adenines (panels C, D) limited by PAMs in corn (panels A, C) and soy (panels B, D). As shown, LbCpf1 cytosines and adenines can access far less cytosines and adenines than Cas9 variants.

FIG. 15 shows that combining mutants K538W and K595Y results in an enzyme LbCas12a-K538W-K595Y with unique PAM recognition sequences. In some cases, shared PAM recognition motifs from K538W (vertical hatched or K595Y (horizontal hatched) are recognized by the combination mutant, but often the combination results in completely novel PAM recognition sequences (thatched).

FIG. 16 shows combining multiple expanded PAM mutations can generate sometimes additive but often unique PAM recognition sequences FIG. 17 compares all non-TTTV PAMs which showed above a 1.67 score from PAN-SCANR (grey boxes) to K595Y (left) and T152R (right). All but one of the PAM-SCALAR positive PAMs above the 1.67 cutoff had PAM depletion scores above the 9.2 cutoff in vitro.

DETAILED DESCRIPTION

Figure 1:
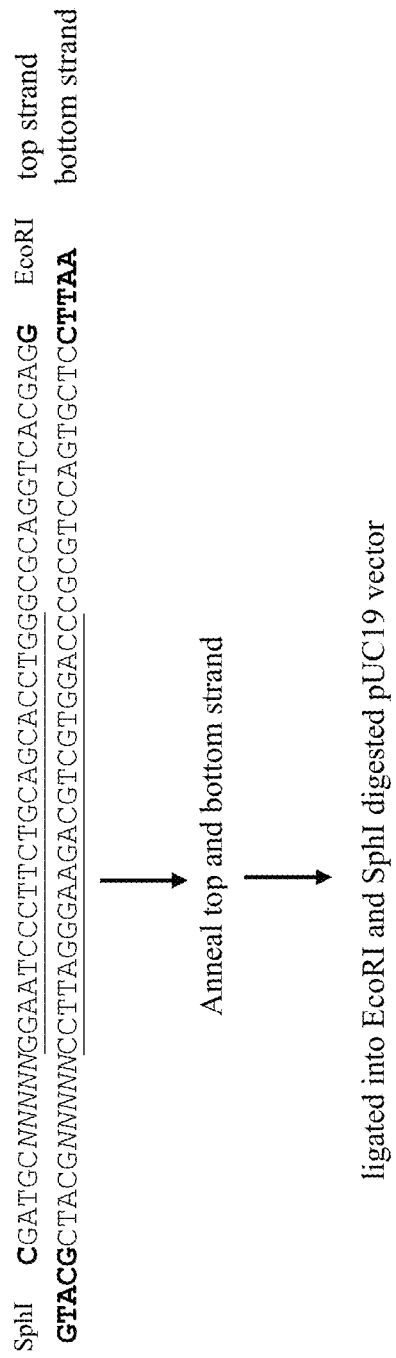
FIG. 1 shows a diagram of an example PAM Library preparation of the invention. In this method, 5' phosphorylated oligonucleotides are annealed and cloned into an EcoRI and SphI digested pUC19 vector. Sca I is used to linearize the vector (AGTACT sequence is not recognized by Lbcpf1). Top strand (SEQ ID NO:32); bottom strand (SEQ ID NO:33).

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild type Cas9 repeat, wild type Cas12a repeat, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

Any nucleotide sequence, polynucleotide and/or recombinant nucleic acid construct of this invention can be codon optimized for expression in any organism of interest. Codon optimization is well known in the art and involves modification of a nucleotide sequence for codon usage bias using species specific codon usage tables. The codon usage tables are generated based on a sequence analysis of the most highly expressed genes for the organism/species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9%, and any range or value therein) to the native nucleotide sequence but which still encodes a polypeptide having the same function as that encoded by the original, native nucleotide sequence. Thus, in some embodiments of the invention, the polynucleotides, nucleic acid constructs, expression cassettes, and/or vectors of the invention (e.g., comprising/encoding a polypeptide, fusion protein, complex of the invention, e.g., a modified CRISPR-Cas nuclease) are codon optimized for expression in a particular species of interest, e.g., a particular plant species, a particular bacterial species, a particular animal species, and the like. In some embodiments, the codon optimized nucleic acid constructs, polynucleotides, expression cassettes, and/or vectors of the invention have about 70% to about 99.9% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the polynucleotides, nucleic acid constructs, expression cassettes, and/or vectors of the invention that have not been codon optimized In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a LbCas12a CRISPR-Cas nuclease domain and a polypeptide of interest (e.g., a nucleic acid-editing domain, a deaminase domain, an adenosine deaminase, a cytosine deaminase). A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or a peptide. In some embodiments, a peptide linker may be about 4 to about 100 or more amino acids in length, for example, about 4, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length. In some embodiments, a peptide linker may be a GS linker. A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:40 or SEQ ID NO:41).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and arabidopsis (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from arabidopsis (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RREs) (Kim et al. *The Plaid Cell* 18:2958-2970 2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen.*

Genet. 207:90-98; Langridge et al. (1983) Cell 34:1015-1022; Reina et al. (1990) Nucleic Acids Res. 18:6425; Reina et al. (1990) Nucleic Acids Res. 18:7449; and Wandelt et al. (1989) Nucleic Acids Res. 17:2354), globulin-1 promoter (Belanger et al. (1991) Genetics 129:863-872), α-tubulin cab promoter (Sullivan et al. (1989) Mol. Gen. Genet. 215:431-440), PEPCase promoter (Hudspeth & Grula (1989) Plant Mol. Biol. 12:579-589), R gene complex-associated promoters (Chandler et al. (1989) Plant Cell 1:1175-1183), and chalcone synthase promoters (Franken et al. (1991) EMBO J. 10:2605-2612).

Useful for seed-specific expression is the pea vicilin promoter (Czako et al. (1992) Mol. Gen. Genet. 235:33-40; as well as the seed-specific promoters disclosed in U.S. Pat. No. 5,625,136. Useful promoters for expression in mature leaves are those that are switched at the onset of senescence, such as the SAG promoter from Arabidopsis (Gan et al. (1995) Science 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof. As a non-limiting example, a nucleic acid construct of the present invention may encode a base editor comprising an optimized CRISPR-Cas nuclease (e.g., SEQ ID NOs:1-11 or 23-25) and a deaminase, wherein the nucleic acid construct further comprises a promoter comprising/associated with an intron. As a further non-limiting example, a nucleic acid construct of the present invention may encode a base editor comprising an optimized CRISPR-Cas nuclease (e.g., SEQ ID NOs:1-11 or 23-25) and a deaminase, wherein the nuclease and/or the deaminase comprises one or more introns and optionally, the nucleic acid construct further comprises a promoter comprising/associated with an intron.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., encoding a modified LbCas12a of the invention), wherein the nucleic acid construct is operably associated with at least a control sequence (e.g., a promoter). Thus, some embodiments of the invention provide expression cassettes designed to express, for example, a nucleic acid construct of the invention (e.g., a nucleic acid construct of the invention encoding a modified LbCas12a of the invention).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. The termination region and/or the enhancer region may be native to the transcriptional initiation region, may be native to a gene encoding, e.g., a LbCas12a nuclease encoded by a nucleic acid construct of the invention, may be native to a host cell, or may be native to another source (e.g., foreign or heterologous to the promoter, to a gene encoding a LbCas12a nuclease encoded by a nucleic acid construct of the invention, to a host cell, or any combination thereof). The enhancer region may be native to a gene encoding a LbCas12a nuclease encoded by a nucleic acid construct of the invention, may be native to a host cell, or may be from another source (e.g., foreign or heterologous to the promoter, to the gene encoding the LbCas12a nuclease encoded by a nucleic acid construct of the invention, to the host cell, or any combination thereof).

An expression cassette of the invention also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art. In some embodiments, the vector may be a high copy number vector (e.g., a high copy number *E. coli* vector; e.g., pUC, pBluescript, pGEM and the like). Thus, for example, a library of the present invention may be constructed using a high copy number vector.

As used herein, "contact", "contacting", "contacted," and grammatical variations thereof, refers to placing the components of a desired reaction together under conditions suitable for carrying out the desired reaction (e.g., transformation, transcriptional control, genome editing, nicking, and/or cleavage). Thus, for example, a target nucleic acid may be contacted with (a) a polynucleotide and/or nucleic acid construct of the invention encoding a modified LbCas12a nuclease of the invention and (b) a guide nucleic acid, under conditions whereby the polynucleotide/nucleic acid construct is expressed and the modified LbCas12a nuclease is produced, wherein the nuclease forms a complex with the guide nucleic acid and the complex hybridizes to the target nucleic acid, thereby modifying the target nucleic acid. In some embodiments, a target nucleic acid may be contacted with (a) a modified LbCas12a nuclease of the invention and/or a fusion protein comprising the same (e.g., the modified LbCas12a nuclease of the invention and a polypeptide of interest (e.g., a deaminase)) and (b) a guide nucleic acid, wherein the modified LbCas12a nuclease forms a complex with the guide nucleic acid and the complex hybridizes to the target nucleic acid, thereby modifying the target nucleic acid. As described herein, the target nucleic acid may be contacted with the polynucleotides/nucleic acid constructs/polypeptides of the invention prior to, concurrently with, or after contact with the guide nucleic acid.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid.

"Introducing," "introduce," "introduced" (and grammatical variations thereof) in the context of a polynucleotide of interest means presenting a nucleotide sequence of interest (e.g., polynucleotide, a nucleic acid construct, and/or a guide nucleic acid) to a host organism or cell of said organism (e.g., host cell; e.g., a plant cell) in such a manner that the nucleotide sequence gains access to the interior of a cell. Thus, for example, a polynucleotide of the invention encoding a modified LbCas12a nuclease as described herein and guide nucleic acid may be introduced into a cell of an organism, thereby transforming the cell with modified LbCas12a nuclease and guide nucleic acid.

The term "transformation" as used herein refers to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a polynucleotide/nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, and/or nucleic acid constructs of the invention and/or expression cassettes and/or vectors comprising the same may be expressed transiently and/or they can be stably incorporated into the genome of the host organism. Thus, in some embodiments, a nucleic acid construct of the invention (e.g., encoding a modified LbCas12a nuclease of the invention, or a fusion protein thereof; e.g., a fusion protein comprising the modified LbCas12a nuclease linked to e.g., a polynucleotide of interest, e.g., a deaminase domain), wherein the nucleic acid construct encoding the modified LbCas12a nuclease is codon optimized for expression in an organism (e.g., a plant, a mammal, a fungus, a *bacterium*, and the like) may be transiently introduced into a cell of the organism along with a guide nucleic acid and as such no DNA maintained in the cell.

A polynucleotide/nucleic acid construct of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In still further embodiments, a polynucleotide/nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence may be incorporated into a plant, for example, as part of a breeding protocol.

The present invention is directed to Cas12a nucleases modified to include non-natural PAM recognition sites/sequences (e.g., a Cas12a nuclease that comprises non-natural PAM recognition specificity in addition to or instead of the natural PAM recognition specificity for that particular Cas12a nuclease). In addition, the present invention is directed to methods for designing, identifying and selecting Cas12a nucleases having desirable characteristics including improved PAM recognition specificity.

As used herein, in reference to a modified Cas12a polypeptide, "altered PAM specificity" means that the PAM specificity of the nuclease is altered from that of the wild type nuclease (e.g., non-native PAM sequences are recognized in addition to and/or instead of the native PAM sequence. For example, a modified Cas12a nuclease would be altered in its PAM specificity if it recognizes a PAM sequence other than and/or in addition to the native Cas12 a PAM sequence of TTTV, wherein V is A, C or G.

The present invention is directed to LbCas12a nucleases having modified PAM recognition specificities. In some embodiments, the present invention provides a modified Lachnospiraceae *bacterium* CRISPR (Clustered Regularly Interspaced Short Palindromic Repeats) Cas12a (LbCas12a) polypeptide, wherein the modified LbCas12a polypeptide comprises an amino acid sequence having at least 80% identity (e.g., about 80, 81, 82, 83, 84, 85, 86, 87, 88, 89, 90, 91, 92, 93, 94, 95, 96, 97, 98, 99, 100% identity; e.g., about 80% to about 100%, about 85% to about 100%, about 90% to about 100% about 95% to about 100%) to the amino acid sequence of SEQ ID NO:1 (LbCas12a) and a mutation at one or more than one (e.g., 2, 3, 4, 5, 6, 7, 8, 9, 10, 11, 12, 13 or more) of the following positions of K116, K120, K121, D122, E125, T148, T149, T152, D156, E159, Q529, G532, D535, K538, D541, Y542, L585, K591, M592, K595, V596, S599, K600, K601, Y616, Y646, and/or W649 with reference to the position numbering of SEQ ID NO:1, optionally a mutation at one or more than one of the following positions of K116, K120, K121, D122, E125, T152, D156, E159, G532, D535, K538, D541, and/or K595 with reference to the position numbering of SEQ ID NO:1. In some embodiments, a mutation of a Cas12a (LbCas12a) polypeptide comprises, consists essentially of, or consists of a mutation at one or more than one of the following positions of K116, K120, K121, D122, E125, T152, D156, E159, G532, D535, K538, D541, and/or K595 with reference to the position numbering of SEQ ID NO:1 in any combination. Thus, a modified LbCas12a polypeptide of this invention may comprise a single mutation at any one of the positions of K116, K120, K121, D122, E125, T148, T149, T152, D156, E159, Q529, G532, D535, K538, D541, Y542, L585, K591, M592, K595, V596, S599, K600, K601, Y616, Y646, and/or W649 with reference to the position numbering of SEQ ID NO:1 or may comprise a combination of mutations any two or more positions of K116, K120, K121, D122, E125, T148, T149, T152, D156, E159, Q529, G532, D535, K538, D541, Y542, L585, K591, M592, K595, V596, S599, K600, K601, Y616, Y646, and/or W649 with reference to the position numbering of SEQ ID NO:1.

In some embodiments, a mutation of a Cas12a (LbCas12a) polypeptide comprises, consists essentially of or consists of one or more than one of the following mutations of K116N, K116R, K120H, K120N, K120Q, K120R, K120T, K121D, K121G, K121H, K121Q, K121R, K121S, K121T, D122H, D122K, D122N, D122R, E125K, E125Q, E125R, E125Y, T148A, T148C, T148H, T148S, T149C, T149F, T149G, T149H, T149N, T149P, T149S, T149V, T152E, T152F, T152H, T152K, T152L, T152Q, T152R, T152W, T152Y, D156E, D156H, D156I, D156K, D156L, D156Q, D156R, D156W, D156Y, E159K, E159Q, E159R, E159Y, Q529A, Q529D, Q529F, Q529G, Q529H, Q529N, Q529P, Q529S, Q529T, Q529W, G532A, G532C, G532D, G532F, G532H, G532K, G532L, G532N, G532Q, G532S, D535A, D535H, D535K, D535N, D535S, D535T, D535V, K538C, K538F, K538G, K538H, K538L, K538M, K538Q, K538R, K538V, K538W, K538Y, D541A, D541E, D541H, D541I, D541N, D541R, D541Y, Y542F, Y542H, Y542K, Y542L, Y542M, Y542N, Y542R, Y542T, Y542V, L585F, L585G, L585H, K591A, K591F, K591G, K591H, K591R, K591S, K591W, K591Y, M592A, M592E, M592Q, K595H, K595L, K595M, K595Q, K595R, K595S, K595W, K595Y, V596H, V596T, S599G, S599H, S599N, K600G, K600H, K600R, K601H, K601Q, K601R, K601T, Y616E, Y616F, Y616H, Y616K, Y616R, Y646E, Y646H, Y646K, Y646N, Y646Q, Y646R, Y646W, W649H, W649K, W649R, W649S and/or W649Y with reference to the position numbering of SEQ ID NO:1. As would be understood, any single Cas12a polypeptide having two or more mutations would comprise only a single mutation at any given position. Thus, for example, a polypeptide may have mutation at position D535 of any one of D535A, D535H, D535K, D535N, D535S, D535T, or D535V, but the same polypeptide may further comprise a mutation at one or more than one of any of the other positions as described herein. In some embodiments, a mutation of a Cas12a (LbCas12a) polypeptide comprises, consists essentially of or consists of one or more than one mutation of K116N, K116R, K120H, K120N, K120Q, K120R, K120T, K121D, K121G, K121H, K121Q, K121R, K121S, K121T, D122H, D122K, D122N, D122R, E125K, E125Q, E125R, E125Y, T152E, T152F, T152H, T152K, T152L, T152Q, T152R, T152W, T152Y, D156E, D156H, D156I, D156K, D156L, D156Q, D156R, D156W, D156Y, E159K, E159Q, E159R, E159Y, G532A, G532C, G532D, G532F, G532H, G532K, G532L, G532N, G532Q, G532S, D535A, D535H, D535K, D535N, D535S, D535T, D535V, K538C, K538F, K538G, K538H, K538L, K538M, K538Q, K538R, K538V, K538W, K538Y, D541A, D541E, D541H, D541I, D541N, D541R, D541Y, K595H, K595L, K595M, K595Q, K595R, K595S, K595W, and/or K595Y with reference to the residue position numbering of SEQ ID NO:1 in any combination. In some embodiments, a mutation of a Cas12a (LbCas12a) polypeptide comprises, consists essentially of or consists of one or more than one mutation of K116R, K116N, K120Y, K121S, K121R, D122H, D122N, E125K, T152R, T152K, T152Y, T152Q, T152E, T152F, D156R, D156W, D156Q, D156H, D156I, D156V, D156L, D156E, E159K, E159R, G532N, G532S, G532H, G532K, G532R, G532L, D535N, D535H, D535T, D535, SD535A, D535W, K538R K538V, K538Q, K538W, K538Y, K538F, K538H, K538L, K538M, K538C, K538G, K538A, D541E, K595R, K595Q, K595Y, K595W, K595H, K595S, and/or K595M with reference to the position numbering of SEQ ID NO:1. As would be understood, any single Cas12a polypeptide having two or more mutations would comprise a single mutation at any given position. Thus, for example, a polypeptide may have a mutation at position D535 of any one of D535A, D535H, D535K, D535N, D535S, D535T, or D535V, and may further comprise a mutation at one or more than one at any other position as described herein.

In some embodiments, the mutation does not comprise, consist essentially of or consist of a mutation of D156R, G532R, K538R, K538V, Y542R or K595R with reference to position numbering of SEQ ID NO:1. In some embodiments, the mutation of the Cas12a (LbCas12a) polypeptide does not comprise, consist essentially of or consist of the combination of mutations of G532R and K595R, of G532R, K538V and Y542R, or of D156R, G532R and K532R with reference to position numbering of SEQ ID NO:1.

In some embodiments, the modified LbCas12a polypeptide may comprise one or more amino acid mutations of SEQ ID NO:1 as set forth in Table 2 (in Example 2).

In some embodiments, the modified LbCas12a polypeptide may comprise an altered protospacer adjacent motif (PAM) specificity as compared to wild type LbCas12a (e.g., SEQ ID NO:1). A modified LbCas12a polypeptide of the present invention may comprise an altered PAM specificity, wherein the altered PAM specificity includes, but is not limited to, NNNG, NNNT, NNNA, NNNC, NNG, NNT, NNC, NNA, NG, NT, NC, NA, NN, NNN, NNNN, wherein each N of each sequence is independently selected from any of T, C, G, or A. In some embodiments, the altered PAM specificity may include, but is not limited to, TTTA, TTTC, TTTG, TTTT, TTCA, TTCC, TTCG, TTCT, ATTC, CTTA, CTTC, CTTG, GTTC, TATA, TATC, CTCC, TCCG, TACA, TCCG, TACA, TCCG, TCCC, TCCA, and/or TATG. In some embodiments, the altered PAM specificity may be NNNN, wherein each N of each sequence is independently selected from any of T, C, G, or A.

In addition to having an altered PAM recognition specificity a modified LbCas12a nuclease may further comprise a mutation in the nuclease active site (e.g., RuvC domain) (e.g., deadLbCas12a, dLbCas12a). Such modifications may result in the LbCas12a polypeptide having reduced nuclease activity (e.g., nickase activity) or no nuclease activity.

In some embodiments, a Type V Clustered Regularly Interspaced Short Palindromic Repeats (CRISPR)-associated (Cas) (CRISPR-Cas) system is provided, the system comprising: (a) a fusion protein comprising (i) a modified LbCas12a nuclease of the invention or a nucleic acid encoding the modified LbCas12a nuclease of the invention, and (ii) a polypeptide of interest or a nucleic acid encoding the polypeptide of interest; and (b) a guide nucleic acid (CRISPR RNA, CRISPR DNA, crRNA, crDNA) comprising a spacer sequence and a repeat sequence, wherein the guide nucleic acid is capable of forming a complex with the modified LbCas12a nuclease or the fusion protein and the spacer sequence is capable of hybridizing to a target nucleic acid, thereby guiding modified LbCas12a nuclease and the polypeptide of interest to the target nucleic acid, whereby the system is capable of modifying (e.g., cleaving or editing) or modulating (e.g., modulating transcription) the target nucleic acid. In some embodiments, the system comprises a polypeptide of interest linked to the C-terminus and/or the N-terminus of the modified LbCas12a nuclease (e.g., a fusion protein), optionally via a peptide linker.

Additionally, provided herein are fusion proteins that comprise a modified Cas12a nuclease of the invention. In some embodiments, the fusion protein may comprise a polypeptide of interest linked to the C-terminus and/or to the N-terminus of the modified LbCas12a. In some embodiments, the present invention provides a fusion protein comprising a modified LbCas12a and an optional intervening linker linking the polypeptide of interest.

Any linker known in the art or later identified that does not interfere with the activity of the fusion protein may be used. A linker that does not "interfere" with the activity of a fusion protein is a linker that does not reduce or eliminate the activity of the polypeptides of the fusion protein (e.g., the nuclease and/or the polypeptide of interest); that is, the nuclease activity, nucleic acid binding activity, editing activity, and/or any other activity of the nuclease or peptide of interest is maintained in a fusion protein in which the nuclease and the polypeptide of interest are tethered to one another via the linker. In some embodiments, a peptide linker may be linked (e.g., at its N-terminus) to the C-terminus of a modified LbCas12a, optionally wherein the fusion protein may further comprise a polypeptide of interest linked to the C-terminus of the linker. In some embodiments, a peptide linker may be linked (e.g., at its C-terminus) to the N-terminus of a modified LbCas12a, optionally wherein the fusion protein may further comprise a polypeptide of interest linked to the N-terminus of the linker. In some embodiments, a modified LbCas12a of the invention may be linked at both its C-terminus and N-terminus to a linker and/or a polypeptide of interest (directly or via a linker).

In some embodiments, a linker useful with the invention may be an amino acid or a peptide. In some embodiments, a peptide linker useful with this invention may be about 4 to about 100 or more amino acids in length, for example, about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 4 to about 40, about 4 to about 50, about 4 to about 60, about 4 to about 40, about 5 to about 50, about 5 to about 60, about 9 to about 40, about 9 to about 50, about 9 to about 60, about 10 to about 40, about 10 to about 50, about 10 to about 60, or about 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length). In some embodiments, a peptide linker may be a GS linker.

A polypeptide of interest useful with this invention can include, but is not limited to, a polypeptide or protein domain having deaminase (deamination) activity, nickase activity, recombinase activity, transposase activity, methylase activity, glycosylase (DNA glycosylase) activity, glycosylase inhibitor activity (e.g., uracil-DNA glycosylase inhibitor (UGI)). demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

In some embodiments, a polypeptide of interest may comprise at least one polypeptide or protein domain having deaminase activity. In some embodiments, the at least one polypeptide or protein domain may be an adenine deaminase domain. An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally-occurring adenine deaminase. Thus, in some embodiments, an adenosine deaminase useful with the invention may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a *bacterium*, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in an organism.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:18. In some embodiments, a mutated/evolved *E. coli* TadA* comprises the amino acid sequence of SEQ ID NOs:19-22. In some embodiments, a polynucleotide encoding a TadA/TadA* may be codon optimized for expression in an organism.

A cytosine deaminase (or cytidine deaminase) useful with this invention may be any known or later identified cytosine deaminase from any organism (see, e.g., U.S. Pat. No. 10,167,457, which is incorporated by reference herein for its disclosure of cytosine deaminases). In some embodiments, the at least one polypeptide or protein domain may be a cytosine deaminase polypeptide or domain. In some embodiments, a cytosine deaminase polypeptide/domain may be an apolipoprotein B mRNA editing catalytic polypeptide-like (APOBEC) domain. In some embodiments, a polypeptide of interest may comprise at least one polypeptide or protein domain having glycosylase inhibitor activity. In some embodiments, the polypeptide of interest may be a uracil-DNA glycosylase inhibitor (UGI) polypeptide/domain. In some embodiments, a nucleic acid construct encoding a modified LbCas12a nuclease of this invention and a cytosine deaminase domain (e.g., encoding a fusion protein comprising a modified LbCas12a nuclease and a cytosine deaminase domain) may further encode a uracil-DNA glycosylase inhibitor (UGI), wherein the UGI is codon optimized for expression in an organism. In some embodiments, the invention provides a fusion protein comprising a modified LbCas12a nuclease, a cytosine deaminase domain, and a UGI and/or one or more polynucleotides encoding the same, optionally wherein the one or more polynucleotides may be codon optimized for expression in an organism.

A cytosine deaminase catalyzes the hydrolytic deamination of cytidine or deoxycytidine to uridine or deoxyuridine, respectively. In some embodiments, a deaminase or deaminase domain may be a cytidine deaminase domain, catalyzing the hydrolytic deamination of cytosine to uracil. In some embodiments, a cytosine deaminase may be a variant of a naturally-occurring cytosine deaminase, including but not limited to a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase). In some embodiments, a polynucleotide encoding a cytosine deaminase polypeptide/domain may be codon optimized for expression in an organism.

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same. In some embodiments, the cytosine deaminase may be an APOBEC1 deaminase having the amino acid sequence of SEQ ID NO:23, SEQ ID NO:44 or SEQ ID NO:46. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25 or SEQ ID NO:43. In some embodiments, the cytosine deaminase may be a FERNY deaminase, optionally a FERNY having the amino acid sequence of SEQ ID NO:42 or SEQ ID NO:45. In some embodiments, the cytosine deaminase may be a human activation induced deaminase (hAID) having the amino acid sequence of SEQ ID NO:47 or SEQ ID NO:48. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NOs: 42-48 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25 or SEQ ID NOs:42-48). In some embodiments, a polynucleotide encoding a cytosine deaminase may be codon optimized for expression in an organism and the codon optimized polypeptide may be about 70% to 99.5% identical to the reference polynucleotide.

A "uracil glycosylase inhibitor" (UGI) useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:26 or a polypeptide having about 70% to about 99.5% identity to the amino acid sequence of SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:26). For example, in some embodiments, a UGI domain may comprise a fragment of the amino acid sequence of SEQ ID NO:26 that is 100% identical to a portion of consecutive nucleotides (e.g., about 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:26. In some embodiments, a UGI domain may be a variant of a known UGI (e.g., SEQ ID NO:26) having 70% to about 99.5% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGA may be codon optimized for expression in an organism and the codon optimized polypeptide may be about 70% to about 99.5% identical to the reference polynucleotide.

In some embodiments, a modified LbCas12a nuclease may comprise a mutation in its nuclease active site (e.g., RuvC). A modified LbCas12a nuclease having a mutation in its nuclease active site(s) and no longer comprising nuclease activity are commonly referred to as "dead," e.g., dLbCas12a. In some embodiments, a modified LbCas12a domain or polypeptide having a mutation in its nuclease active site(s) may have impaired activity or reduced activity (e.g., nickase activity) as compared to the same LbCas12a nuclease without the mutation.

The modified LbCas12a nucleases of the invention may be used in combination with a guide RNA (gRNA, CRISPR array, CRISPR RNA, crRNA), designed to function with the modified LbCas12a nuclease, to modify a target nucleic acid. A guide nucleic acid useful with this invention comprises at least a spacer sequence and a repeat sequence. The guide nucleic acid is capable of forming a complex with the LbCas12a nuclease domain encoded and expressed by a polynucleotide/nucleic acid construct of the invention encoding a modified LbCas12a nuclease and the spacer sequence is capable of hybridizing to a target nucleic acid, thereby guiding the nucleic acid construct (e.g., the modified LbCas12a nuclease (and/or a polypeptide of interest)) to the target nucleic acid, wherein the target nucleic acid may be modified (e.g., cleaved or edited) or modulated (e.g., modulating transcription) by the modified LbCas12a nuclease (and/or an encoded deaminase domain and/or polypeptide of interest). As an example, a nucleic acid construct encoding an LbCas12a domain linked to a cytosine deaminase domain (e.g., a fusion protein) may be used in combination with an LbCas12a guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding an LbCas12a domain linked to an adenine deaminase domain (e.g., a fusion protein) may be used in combination with an LbCas12a guide nucleic acid to modify a target nucleic acid, wherein the adenine deaminase domain of the fusion protein deaminates an adenosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target nucleic acid (e.g., protospacer), and at least one repeat sequence (e.g., a repeat of a Type V Cas12a CRISPR-Cas system, or a fragment or portion thereof), wherein the repeat sequence may be linked to the 5' end and/or the 3' end of the spacer sequence. The design of a gRNA of this invention may be based on a Type V Cas12a system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one "repeat sequence-spacer" sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type Cas12a locus (e.g., a LbCas12a locu.) or a repeat sequence of a synthetic crRNA that is functional with the LbCas12a nuclease encoded by the nucleic acid constructs of the invention. A repeat sequence useful with this invention can be any known or later identified repeat sequence of a Cas12a locus or it can be a synthetic repeat designed to function in a Cas12a Type V CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from a wild-type V CRISPR-Cas locus (e.g., a wild type Cas12a locus). A repeat sequence from a wild-type Cas12a locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide RNA, crRNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100, or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more consecutive nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, and any range or value therein)) to a target nucleic acid. Thus, in some embodiments, the spacer sequence can have one, two, three, four, or five mismatches as compared to the target nucleic acid, which mismatches can be contiguous or non-contiguous. In some embodiments, the spacer sequence can have about 70% complementarity to a target nucleic acid. In other embodiments, the spacer nucleotide sequence can have about 80% complementarity to a target nucleic acid. In still other embodiments, the spacer nucleotide sequence can have about 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., about 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that may be at least about 15 nucleotides to about 30 nucleotides in length. In some embodiments, the spacer may be about 20, 21, 22, 23, 24, or 25 nucleotides in length. In some embodiments, the spacer may be 23 nucleotides in length.

In some embodiments, the 5' region of a spacer sequence of a guide RNA may be identical to a target nucleic acid, while the 3' region of the spacer may be substantially complementary to the target nucleic acid (e.g., Type V CRISPR-Cas), or the 3' region of a spacer sequence of a guide RNA may be identical to a target nucleic acid, while the 5' region of the spacer may be substantially complementary to the target nucleic acid (e.g., Type II CRISPR-Cas), and therefore, the overall complementarity of the spacer sequence to the target nucleic acid may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence, may be 100% complementary to the target nucleic acid, while the remaining nucleotides in the 3' region of the spacer sequence may be substantially complementary (e.g., at least about 70% complementary) to the target nucleic acid. In some embodiments, the first 1 to 8 nucleotides (e.g., the first 1, 2, 3, 4, 5, 6, 7, 8, nucleotides, and any range therein) of a 5' end of the spacer sequence may be 100% complementary to the target nucleic acid, while the remaining nucleotides in the 3' region of the spacer sequence may be substantially complementary (e.g., at least about 50% complementary (e.g., about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target nucleic acid.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refer to a region of an organism's genome that is fully complementary (100% complementary) or substantially complementary (e.g., at least 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, and any range or value therein)) to a spacer sequence in a guide RNA of this invention. In some embodiments, a target region useful for a Type V CRISPR-Cas system (e.g., LbCas12a) is located immediately 3' to a PAM sequence in the genome of the organism (e.g., a plant genome, an animal genome, a bacterial genome). In some embodiments, a target region may be selected from any at least 15 consecutive nucleotides (e.g., 15, 16, 17, 18, 19, 20, 21, 22, 23, 24, 25, 26, 27, 28, 29, 30 or more nucleotides, and any range or value therein; e.g., about 19 to about 25 nucleotides, about 20 to about 24 nucleotides in length, and the like) located immediately adjacent to a PAM sequence.

A "protospacer sequence" refers to the target nucleic acid and specifically to the portion of the target nucleic acid (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas Cas12a systems, the protospacer sequence is flanked (immediately adjacent to) a protospacer adjacent motif (PAM). The PAM is located at the 5' end on the non-target strand and at the 3' end of the target strand (see below, as an example).

In some embodiments, the present invention provides a composition comprising (a) a modified LbCas12a polypeptide of the invention or a fusion protein of the invention and (b) a guide nucleic acid.

In some embodiments, the present invention provides expression cassettes and/or vectors comprising the polynucleotides/nucleic acid constructs of the invention. In some embodiments, expression cassettes and/or vectors comprising the polynucleotides/nucleic acid constructs of the invention and/or one or more guide nucleic acids may be provided. In some embodiments, a nucleic acid construct encoding a modified CRISPR-Cas nuclease and/or a fusion protein comprising a modified CRISPR-Cas nuclease of the invention may be comprised in the same or a separate expression cassette or vector from that comprising the guide nucleic acid. When the nucleic acid construct is comprised in a separate expression cassette or vector from that comprising the guide nucleic acid, a target nucleic acid may be contacted with (e.g., provided with) the expression cassette or vector comprising the nucleic acid construct of the invention prior to, concurrently with, or after the expression cassette comprising the guide nucleic acid is provided (e.g., contacted with the target nucleic acid).

In some embodiments, the present invention provides expression cassettes and/or vectors encoding compositions and/or complexes of the invention or comprising systems of the invention.

In some embodiments, the polynucleotides, nucleic acid constructs, expression cassettes and/or vectors of the invention that are optimized for expression in an organism may be about 70% to about 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, and any value or range therein) to the polynucleotides, nucleic acid constructs, expression cassettes and/or vectors encoding the same modified CRISPR-Cas nuclease or fusion protein of the invention but which has not been codon optimized for expression in an organism. An organ-

```
5'-NNNNNNNNNNNNNNNNNNNNN-3'  RNA Spacer (SEQ ID NO: 27)
   |||||||||||||||||||||
3'AAANNNNNNNNNNNNNNNNNNNNN-5'  Target strand (SEQ ID NO: 28)
   ||||
5'TTTNNNNNNNNNNNNNNNNNNNNN-3'  Non-target strand (SEQ ID NO: 29)
```

Canonical Cas12a PAMs are T rich. In some embodiments, a canonical Cas12a PAM sequence may be 5'-TTN, 5'-TTTN, or 5'-TTTV.

The polypeptides, fusion proteins and/or systems of the invention may be encoded by polynucleotides or nucleic acid constructs. In some embodiments, a polynucleotide/ nucleic acid construct encoding the polypeptides, fusion proteins and/or systems of the invention may be operably associated with regulatory elements (e.g., promotors, terminators and the like) for expression in an organism of interest and/or a cell of an organism of interest as described herein. In some embodiments, a polynucleotide/nucleic acid construct encoding a polypeptide, fusion protein and/or system of the invention may be codon optimized for expression in an organism.

In some embodiments, the present invention provides a complex comprising (a) a modified LbCas12a polypeptide of the invention or a fusion protein of the invention and (b) a guide nucleic acid (e.g., CRISPR RNA, CRISPR DNA, crRNA, crDNA).

ism for which a polynucleotide or nucleic acid construct may be optimized may include but is not limited to, an animal, a plant, a fungus, an archaeon, or a *bacterium*. In some embodiments, a polynucleotide or nucleic acid construct of the invention is codon optimized for expression in a plant.

In some embodiments, the invention provides cells comprising one or more polynucleotides, guide nucleic acids, nucleic acid constructs, systems, expression cassettes and/or vectors of the invention.

The nucleic acid constructs of the invention (e.g., encoding a modified CRISPR-Cas nuclease of the invention and/or a fusion protein comprising a modified CRISPR-Cas nuclease of the invention) and expression cassettes/vectors comprising the same may be used for modifying target nucleic acids and/or their expression in vivo (e.g., in an organism or the cell of an organism; e.g., a plant) and in vitro (e.g., in a cell or a cell free system).

The present invention further provides methods for altering the PAM specificity of a Cas12a polypeptide. In some embodiments, a method for altering PAM specificity is provided that comprises introducing a mutation into the Cas12a polypeptide wherein the mutation is at amino acid residue K116, K120, K121, D122, E125, T148, T149, T152, D156, E159, Q529, D535, K538, D541, Y542, L585, K591, M592, K595, V596, S599, K600, K601, Y616, Y646, W649 with reference to the position numbering of SEQ ID NO:1. In some embodiments, the mutation that is introduced into the Cas12a polypeptide is K116R, K116N, K120R, K120H, K120N, K120T, K120Y, K120Q, K121S, K121T, K121H, K121R, K121G, K121D, K121Q, D122R, D122K, D122H, D122E, D122N, E125R, E125K, E125Q, E125Y, T148H, T148S, T148A, T148C, T149A, T149C, T149S, T149G, T149H, T149P, T149F, T149N, T149D, T149V, T152R, T152K, T152W, T152Y, T152H, T152Q, T152E, T152L, T152F, D156R, D156K, D156Y, D156W, D156Q, D156H, D156I, D156V, D156L, D156E, E159K, E159R, E159H, E159Y, E159Q, Q529N, Q529T, Q529H, Q529A, Q529F, Q529G, Q529G, Q529S, Q529P, Q529W, Q529D, G532D, G532N, G532S, G532H, G532F, G532K, G532R, G532Q, G532A, G532L, G532C, D535N, D535H, D535V, D535T, D535, S D535A, D535W, D535K, K538R K538V, K538Q, K538W, K538Y, K538F, K538H, K538L, K538M, K538C, K538G, K538A, K538P, D541N, D541H, D541R, D541K, D541Y, D541I, D541A, D541S, D541E, Y542R, Y542K, Y542H, Y542Q, Y542F, Y542L, Y542M, Y542P, Y542V, Y542N, Y542T, L585G, L585H, L585F, K591W, K591F, K591Y, K591H, K591R, K591S, K591A, K591G, K591P, M592R, M592K, M592Q, M592E, M592A, K595R, K595Q, K595Y, K595L, K595W, K595H, K595E, K595S, K595D, K595M, V596T, V596H, V596G, V596A, S599G, S599H, S599N, S599D, K600R, K600H, K600G, K601R, K601H, K601Q, K601T, Y616K, Y616R, Y616E, Y616F, Y616H, Y646R, Y646E, Y646K, Y646H, Y646Q, Y646W, Y646N, W649H, W649K, W649Y, W649R, W649E, W649S, W649V, and/or W649T with reference to the position numbering of SEQ ID NO:1. In some embodiments, the mutation that is introduced into the Cas12a polypeptide is at amino acid residue position K116, K120, K121, D122, E125, T152, D156, E159, G532, D535, K538, D541, and/or K595 with reference to position numbering of SEQ ID NO:1, optionally wherein the mutation is K116R, K116N, K120Y, K121S, K121R, D122H, D122N, E125K, T152R, T152K, T152Y, T152Q, T152E, T152F, D156R, D156W, D156Q, D156H, D156I, D156V, D156L, D156E, E159K, E159R, G532N, G532S, G532H, G532K, G532R, G532L, D535N, D535H, D535T, D535, S D535A, D535W, K538R K538V, K538Q, K538W, K538Y, K538F, K538H, K538L, K538M, K538C, K538G, K538A, D541E, K595R, K595Q, K595Y, K595W, K595H, K595S, and/or K595M with reference to position numbering of SEQ ID NO:1. The mutation that is introduced may be a single mutation or it may be a combination of two or more mutations. As would be understood, any single Cas12a polypeptide having two or more mutations would comprise only a single mutation at any given position. In some embodiments, the Cas12a polypeptide that is altered in PAM specificity by the methods of this invention is a LbCas12a polypeptide (Lachnospiraceae *bacterium*).

Modified Cas12a polypeptides or nucleases (e.g., LbCas12a nucleases) of the invention may be used for modifying a target nucleic acid in a cell or a cell free system (e.g., altering the target nucleic acid, altering the genome of the cell/organism). Accordingly, in some embodiments, a method of modifying a target nucleic acid is provided, the method comprising: contacting the target nucleic acid with: (a)(i) a modified LbCas12a polypeptide of the invention, or a fusion protein of the invention (e.g., a modified LbCas12a polypeptide of the invention and a polypeptide of interest (e.g., a deaminase)), and (ii) a guide nucleic acid; (b) a complex of the invention comprising (i) a modified LbCas12a polypeptide or a fusion protein of the invention, and (ii) a guide nucleic acid; (c) a composition comprising (i) a modified LbCas12a polypeptide of the invention, or a fusion protein of the invention, and (ii) a guide nucleic acid; and/or (d) a system of the invention, thereby modifying the target nucleic acid. In some embodiments, a method of modifying/altering the genome of a cell or organism is provided, the method comprising: contacting a target nucleic acid in the genome of the cell/organism with: (a)(i) a modified LbCas12a polypeptide of the invention, or a fusion protein of the invention (e.g., a modified LbCas12a polypeptide of the invention and a polypeptide of interest (e.g., a deaminase)), and (ii) a guide nucleic acid; (b) a complex of the invention comprising (i) a modified LbCas12a polypeptide or a fusion protein of the invention, and (ii) a guide nucleic acid; (c) a composition comprising (i) a modified CRISPR-Cas nuclease (e.g., a modified LbCas12a polypeptide) of the invention, or a fusion protein of the invention, and (ii) a guide nucleic acid; and/or (d) a system of the invention, thereby modifying/altering the genome of a cell or organism. In some embodiments, the cell or organism is a plant cell or a plant.

In some embodiments, a method of modifying a target nucleic acid is provided, the method comprising: contacting a cell or a cell free system comprising the target nucleic acid with: (a)(i) a polynucleotide of the invention (e.g., encoding a modified LbCas12a polypeptide of the invention, or encoding fusion protein comprising a modified LbCas12a polypeptide of the invention and a polypeptide of interest (e.g., a deaminase)), or an expression cassette or vector comprising the same, and (ii) a guide nucleic acid, or an expression cassette and/or vector comprising the same; and/or (b) a nucleic acid construct encoding a complex of the invention comprising a modified LbCas12a polypeptide of the invention, or fusion protein comprising a modified LbCas12a polypeptide of the invention and a polypeptide of interest (e.g., a deaminase), or an expression cassette and/or vector comprising the same, wherein the contacting is carried out under conditions whereby the polynucleotide and/or nucleic acid construct is/are expressed and the modified LbCas12a polypeptide and/or fusion protein is/are produced, which forms a complex with the guide nucleic acid, thereby modifying the target nucleic acid. In some embodiments, a method of modifying/altering the genome of a cell and/or organism is provided, the method comprising: contacting a cell and/or cell in an organism comprising the target nucleic acid with: (a)(i) a polynucleotide of the invention (e.g., encoding a modified LbCas12a polypeptide of the invention, or encoding fusion protein comprising a modified LbCas12a polypeptide of the invention and a polypeptide of interest (e.g., a deaminase)), or an expression cassette or vector comprising the same, and (ii) a guide nucleic acid, or an expression cassette and/or vector comprising the same; and/or (b) a nucleic acid construct encoding a complex of the invention comprising a modified LbCas12a polypeptide of the invention, or fusion protein comprising a modified LbCas12a polypeptide of the invention and a polypeptide of interest (e.g., a deaminase), or an expression cassette and/or vector comprising the same, wherein the contacting is under conditions whereby the polynucleotide and/or nucleic acid construct is/are expressed and the modified LbCas12a polypeptide and/or fusion protein is/are produced, which form(s) a complex with the guide nucleic acid, thereby modifying the target nucleic acid.

In some embodiments, the present invention provides a method of editing a target nucleic acid, the method comprising: contacting the target nucleic acid with: (a)(i) a fusion protein of the present invention (comprising a modified LbCas12a polypeptide of the invention and a polypeptide of interest (e.g., a deaminase), and (a)(ii) a guide nucleic acid; (b) a complex comprising a fusion protein of the present invention, and a guide nucleic acid; (c) a composition comprising the fusion protein of the present invention and a guide nucleic acid; and/or (d) a system of the invention, thereby editing the target nucleic acid.

In some embodiments, the present invention provides a method of editing a target nucleic acid, the method comprising: contacting a cell or a cell free system comprising the target nucleic acid with: (a)(i) a polynucleotide encoding a fusion protein of the invention (e.g., a modified LbCas12a polypeptide of the invention and a polypeptide of interest (e.g. a deaminase)) or an expression cassette and/or vector comprising the same, and (a)(ii) a guide nucleic acid, or an expression cassette and/or vector comprising the same; (b) a nucleic acid construct encoding a complex comprising a fusion protein of the present invention, and a guide nucleic acid, or an expression cassette and/or vector comprising the same; and/or (c) a system of the present invention wherein the contacting is carried out under conditions whereby the polynucleotide and/or nucleic acid construct is/are expressed and the modified CRISPR-Cas nuclease and/or fusion protein is/are produced, which form(s) a complex with the guide nucleic acid, thereby editing the target nucleic acid.

The CRISPR-Cas nucleases having modified PAM recognition specificities may be utilized in many ways including, but not limited to, creating indels (NHEJ), in homology directed repair, as a genome recognition element without a nuclease function (dead Cpf1), as a genome recognition element with a partially functional nuclease (nickase Cpf1), in fusion proteins for catalytic editing of genomic DNA (DNA base editors), in fusions proteins for catalytic editing of RNA (RNA base editors), for targeting of other macromolecules to specific genomic regions; for targeting of small chemicals to specific genomic regions, for labeling of specific genomic regions and/or for CRISPR-directed genomic recombination strategies.

When provided on different nucleic acid constructs, expression vectors, and/or vectors, a nucleic acid construct of the invention may be contacted with a target nucleic acid prior to, concurrently with or after contacting the target nucleic acid with a guide nucleic acid.

The modified CRISPR-Cas nucleases of the invention and polypeptides and nucleic acid constructs encoding the same may be used for modifying a target nucleic acid in any organism, including but not limited to, an animal, a plant, a fungus, an archaeon, or a *bacterium*. An animal can include, but is not limited to, a mammal, an insect, a fish, a bird, and the like. Exemplary mammals for which this invention may be useful include, but are not limited to, primates (human and non-human (e.g., a chimpanzee, baboon, monkey, gorilla, etc.)), cats, dogs, mice, rats, ferrets, gerbils, hamsters, cows, pigs, horses, goats, donkeys, or sheep.

A target nucleic acid of any plant or plant part may be modified and/or edited (e.g., mutated, e.g., base edited, cleaved, nicked, and the like) using the nucleic acid constructs of the invention. Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, *miscanthus, arundo*, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (e.g., sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (e.g., wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (e.g., field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil seed plant (e.g., rape, canola, mustard, poppy, olive, sunflower, coconut, castor oil plant, cocoa bean, groundnut, oil palm, soybean, Camelina, and the like), duckweed, *Arabidopsis*, a fiber plant (cotton, flax, hemp, jute), *Cannabis* (e.g., *Cannabis sativa, Cannabis* indica, and *Cannabis ruderalis*), lauraceae (e.g., cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit to carry out methods of this invention. A kit of this invention can comprise reagents, buffers, and/or apparatus for mixing, measuring, sorting, labeling, etc, as well as instructions and the like as would be appropriate for modifying a target nucleic acid.

In some embodiments, the invention provides a kit comprising one or more polynucleotides and/or nucleic acid constructs of the invention, and/or expression cassettes and/or vectors comprising the same, with optional instructions for the use thereof. In some embodiments, a kit may further comprise a polypeptide of interest and/or polynucleotide encoding the same and expression cassette and/or vector comprising the same. In some embodiments, a guide nucleic acid may be provided on the same expression cassette and/or vector as a nucleic acid construct of the invention. In some embodiments, a guide nucleic acid may be provided on a separate expression cassette or vector from that comprising the nucleic acid construct of the invention.

Accordingly, in some embodiments, kits are provided comprising a nucleic acid construct comprising (a) a polynucleotide encoding a modified CRISPR-Cas nuclease as provided herein and (b) a promoter that drives expression of the polynucleotide of (a). In some embodiments, the kit may further comprise a nucleic acid construct encoding a guide nucleic acid, wherein the construct comprises a cloning site for cloning into the backbone of the guide nucleic acid a nucleic acid sequence that is identical or complementary to a target nucleic acid sequence.

In some embodiments, the kit may comprise a nucleic acid construct comprising/encoding one or more nuclear localization signals, wherein the nuclear localization signals are fused to the CRISPR-Cas nuclease. In some embodiments, kits are provided comprising a nucleic acid construct of the invention encoding a modified CRISPR-Cas nuclease of the invention or, and/or an expression cassette and/or vector comprising the same, wherein the nucleic acid constructs, expression cassettes and/or vectors may further encode one or more selectable markers useful for identifying transformants (e.g., a nucleic acid encoding an antibiotic resistance gene, herbicide resistance gene, and the like). In some embodiments, the nucleic acid construct may be an mRNA that encodes one or more introns within the encoded CRISPR-Cas nuclease. In some embodiments, a kit may comprise promoters and promoters with introns for use in expression of the polypeptides and nucleic acid constructs of the invention.

Methods for Modifying PAM Specificities of CRISPR-Cas Nucleases and Related Compositions CRISPR-Cas systems are directed towards target nucleic acids using two major criteria: homology of the guide RNA to the targeted DNA sequence, and presence of a protospacer adjacent motif (PAM) of a particular sequence. Different CRISPR-Cas nucleases have different PAM sequence requirements, such as NGG for SpCas9 or TTTV (where V is any non-thymidine nucleotide) for LbCas12a (Cpf1). Screening new CRISPR nucleases or mutants thereof for their PAM requirements can be complicated and unpredictable because so many iterations are possible. In vitro assays, particularly PAM Determination Assays (PAMDA), may be used to screen PAM specificity for any particular CRISPR nuclease or mutant thereof. These assays rely on a randomized portion of DNA that is adjacent to a defined/known protospacer sequence. Guide RNAs can be designed to target the known protospacer sequence and if the randomized PAM region contains the appropriate DNA sequence (e.g., recognized by the CRISPR nuclease or mutants thereof), then the CRISPR nuclease can bind and cut the target.

The PAM recognition sites for CRISPR-Cas nucleases may be assessed using PAM site-depletion assays (e.g., PAM depletion assays) or PAM Determination Assays (PAMDA) (Kleinstiver et al. *Nat Biotechnol* 37: 276-282 (2019)). For PAM depletion assays, a library of plasmids bearing randomized nucleotides (base pairs) adjacent to a protospacer is tested for cleavage by a CRISPR nuclease in a bacterium (e.g., *E. coli*). The plasmids may comprise, for example, polynucleotides conferring antibiotic resistance that are adjacent to randomized PAM sequences. Those sequences which are not cut upon exposure to a CRISPR-Cas nuclease enable a cell to survive in the presence of an antibiotic due to the presence of the antibiotic resistance gene, whereas plasmids bearing targetable PAMs are cleaved and depleted from the library due to cell death. Sequencing of the surviving (uncleaved) population of plasmids enables the calculation of a post-selection PAM depletion value, which is compared to a library that has not been exposed to the CRISPR-Cas nuclease. Those sequences which are depleted from the pool of sequences in the experimental library contain the PAM sequence(s) recognized by the CRISPR-Cas nuclease.

Another method that may be used to identify PAM sequences is a PAM Determination Assay (PAMDA) (Kleinstiver et al. *Nat Biotechnol* 37: 276-282 (2019)). In this case, cleavage is performed outside of living cells. In PAMDA, a single DNA strand is synthesized with a randomized portion of nucleotides next to a defined protospacer sequence. An oligonucleotide is annealed to the 3'-end of the synthesized DNA strand and extended using an exonuclease minus (-exo) Klenow fragment, polymerizing over the defined and random sequences. This generates a duplex library that is then cut with restriction endonucleases and cloned into bacteria in order to amplify the total DNA. The plasmids are extracted and linearized with another restriction endonuclease to make a linear template. The template is contacted with a CRISPR-Cas nuclease-guide RNA complex. Only those sequences containing a PAM that is recognized by the CRISPR-Cas nuclease will be cleaved. Both the experimental library and the control library (not exposed to the CRISPR-Cas nuclease) are then amplified via PCR. Only the sequences that are not cleaved by the CRISPR-Cas nuclease will be amplified. The PCR amplified sequences from the control library and the experimental library (treated with CRISPR-Cas nuclease) are sequenced and compared. The PAM sequences that are present in the control (not exposed to CRISPR-Cas nuclease) library but not in the experimental library are the PAM sequences that are recognized by the CRISPR-Cas nuclease (thereby, allowing the protospacer to be cleaved).

For the assessment of nuclease requirements in vitro, a randomized PAM library is prepared. Steps described for this method involve preparation of an unbiased randomized DNA library containing all PAM sequences to be evaluated, cloning into a plasmid, introduction of the library into bacteria to increase the total amount of starting DNA, extraction of the plasmids, linearization of the plasmids with a restriction enzyme to remove supercoiling, exposing the linearized molecules to the CRIPSR-Cas nuclease, amplifying the fragments (e.g., PCR), and finally sequencing analysis (e.g., next generation sequencing, NGS). The initial steps of generating an unbiased library and restriction digests require at least two restriction enzymes, Klenow extension, and cleaning of the products before ligating into a vector. Using two to three restriction enzymes typically eliminates some PAM sequences from the library, which introduces bias into the library. In addition, subsequent Klenow extension and cleanup steps can also eliminate PAM sequences, thereby introducing further bias into the library. In order to avoid the loss of PAM sequences and to generate a more complete and unbiased library, the present invention provides a new method for generating randomized PAM libraries using overlapping solid-state synthesized oligonucleotides (e.g., annealed oligonucleotides) with overhangs (see, e.g., FIG. 1b) instead of restriction endonucleases and Klenow extension. The randomized PAM libraries produced using the methods of the invention can then be used to test the PAM specificities of CRISPR-Cas nucleases with more accuracy than was previously available with libraries produced via prior art methods.

Accordingly, in some embodiments, the present invention provides a method of constructing a randomized DNA library comprising double stranded nucleic acid molecules for determining protospacer adjacent motif (PAM) requirements/specificity of a CRISPR-Cas nuclease having a PAM recognition site at the 5' end of the protospacer, the method comprising: preparing two or more double stranded nucleic acid molecules comprising the following steps: (a) synthesizing a non-target oligonucleotide (first) strand and a target oligonucleotide (second) strand for each of the two or more double stranded nucleic acid molecules, wherein the non-target oligonucleotide strand comprises, 5' to 3': (i) a first sequence having about 5 to about 15 nucleotides (e.g., about 5, 6, 7, 8, 9, 10, 11, 12, 13, 14, or 15 nucleotides, and any range therein), (ii) (ii) a second sequence having at least four randomized nucleotides (e.g., at least 4, 5, 6, 7, 8, 9, 10, or more, and any range therein), (ii) a protospacer sequence comprising about 16 to about 25 nucleotides (e.g., about 16, 17, 18, 19, 20, 21, 22, 23, 24, or 25 nucleotides, and any range therein), and (iv) a third sequence having about 5 to about 20 nucleotides (e.g., about 5, 6, 7, 8, 9, 10, 11, 12, 13, 14, 15, 16, 17, 18, 19, 20 nucleotides, and any range therein), wherein the first sequence having about 5 to 15 nucleotides of (i) is immediately adjacent to the 5' end of the second sequence of (ii), the second sequence of (ii) is immediately adjacent to the 5' end of the protospacer sequence of (iii), and the protospacer sequence is immediately adjacent to the 5' end of the third sequence of (iv); and the target oligonucleotide (second) strand is complementary to the non-target oligonucleotide strand; and (b) annealing the non-target oligonucleotide strand to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (iii) and the third sequence (iv) of each of the two or more double stranded nucleic acid molecules is identical, thereby constructing the randomized DNA library comprising double stranded nucleic acid molecules. In some embodiments, the target strand and/or the non-target strand may be 5' phosphorylated.

In some embodiments, the present invention provides a method of constructing a randomized DNA library comprising double stranded nucleic acid molecules for determining protospacer adjacent motif (PAM) requirements/specificity of a CRISPR-Cas nuclease having a PAM recognition site at the 3' end of the protospacer, the method comprising: preparing two or more double stranded nucleic acid molecules comprising the following steps: (a) synthesizing a non-target oligonucleotide (first) strand and a target oligonucleotide (second) strand for each of the two or more double stranded nucleic acid molecules, wherein the non-target oligonucleotide strand comprises, 5' to 3': (i) a first sequence having about 5 to about 20 nucleotides (e.g., about 5, 6, 7, 8, 9, 10, 11, 12, 13, 14, 15, 16, 17, 18, 19, 20 nucleotides, and any range therein), (ii) a protospacer sequence comprising about 16 to about 25 nucleotides (e.g., about 16, 17, 18, 19, 20, 21, 22, 23, 24, or 25 nucleotides, and any range therein), (iii) a second sequence having at least four randomized nucleotides (e.g., at least 4, 5, 6, 7, 8, 9, 10, or more, and any range therein), and (iv) a third sequence having about 5 to about 15 nucleotides (e.g., about 5, 6, 7, 8, 9, 10, 11, 12, 13, 14, 15 nucleotides, and any range therein), wherein the first sequence having about 5 to 20 nucleotides of (i) is immediately adjacent to the 5' end of the protospacer sequence of (ii), the second sequence of (iii) is immediately adjacent to the 3' end of the protospacer sequence of (iii), and the third sequence of (iv) is immediately adjacent to the 3' end of the second sequence of (iii); and the target oligonucleotide (second) strand is complementary to the non-target oligonucleotide strand; and (b) annealing the non-target oligonucleotide strand to the complementary target oligonucleotide strand to produce a double stranded nucleic acid molecule, wherein the first sequence (i) comprises a restriction site (at its 5' end) and the third sequence (iv) comprises a restriction site (at its 3' end), wherein the first sequence (i), the protospacer sequence (ii) and the third sequence (iv) of each of the two or more double stranded nucleic acid molecules is identical, thereby constructing the randomized DNA library comprising double stranded nucleic acid molecules. In some embodiments, the target strand and/or the non-target strand may be 5' phosphorylated.

In some embodiments, the double stranded nucleic acid molecules may be ligated into a vector to produce a vector comprising the randomized DNA library. In some embodiments, the vector may be a high copy number vector. In some embodiments, the randomized DNA library may be amplified by, for example, introducing the vector comprising the randomized DNA library into one or more bacterial cells and culturing the one or more bacterial cells. In some embodiments, the vector comprising the randomized DNA library may be isolated from the one or more bacterial cells after culturing. The isolated vector may then be linearized (e.g., by contacting the vector with one or more restriction enzymes; e.g., ScaI or PfoI) for use in, for example, the analysis of the PAM recognition specificity of a CRISPR-Cas nuclease. In some embodiments, Pfo1 may be used to linearize the isolated vector.

In some embodiments, a randomized DNA library may be provided for determining protospacer adjacent motif (PAM) requirements/specificity of a CRISPR-Cas nuclease having a PAM recognition site on the 5' end of protospacer, the randomized DNA library comprising two or more double stranded nucleic acid molecules each of which comprises: (a) a non-target oligonucleotide (first) strand and a target oligonucleotide (second) strand, wherein the non-target oligonucleotide strand comprises, 5' to 3': (i) a first sequence having about 5 to about 15 nucleotides (e.g., about 5, 6, 7, 8, 9, 10, 11, 12, 13, 14, or 15 nucleotides, and any range therein), (ii) a second sequence having at least four randomized nucleotides (e.g., at least 4, 5, 6, 7, 8, 9, 10, or more, and any range therein), (iii) a protospacer sequence comprising about 16 to about 25 nucleotides (.g., about 16, 17, 18, 19, 20, 21, 22, 23, 24, or 25 nucleotides, and any range therein), and (iv) a third sequence having about 5 to about 20 nucleotides (e.g., about 5, 6, 7, 8, 9, 10, 11, 12, 13, 14, 15, 16, 17, 18, 19, 20 nucleotides, and any range therein), wherein the first sequence having about 5 to 15 nucleotides of (i) is immediately adjacent to the 5' end of the second sequence of (ii), the second sequence of (ii) is immediately adjacent to the 5' end of the protospacer sequence of (iii), and the protospacer sequence is immediately adjacent to the 5' end of the third sequence of (iv); and the target oligonucleotide (second) strand is complementary to the non-target oligonucleotide strand; and (b) the non-target oligonucleotide strand is annealed to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (iii) and the third sequence (iv) of each of the two or more double stranded nucleic acid molecules are identical. In some embodiments, the target strand and/or the non-target strand may be 5' phosphorylated.

In some embodiments, a randomized DNA library may be provided for determining protospacer adjacent motif (PAM) requirements/specificity of a CRISPR-Cas nuclease having a PAM recognition site on the 3' end of protospacer, the randomized DNA library comprising two or more double stranded nucleic acid molecules each of which comprises: (a) a non-target oligonucleotide (first) strand and a target oligonucleotide (second) strand, wherein the non-target oligonucleotide strand comprises, 5' to 3': (i) a first sequence having about 5 to about 20 nucleotides (e.g., about 5, 6, 7, 8, 9, 10, 11, 12, 13, 14, 15, 16, 17, 18, 19, 20 nucleotides, and any range therein), (ii) a protospacer sequence comprising about 16 to about 25 nucleotides (e.g., about 16, 17, 18, 19, 20, 21, 22, 23, 24, or 25 nucleotides, and any range therein), (iii) a second sequence having at least four randomized nucleotides (e.g., at least 4, 5, 6, 7, 8, 9, 10, or more, and any range therein), and (iv) a third sequence having about 5 to about 15 nucleotides (e.g., about 5, 6, 7, 8, 9, 10, 11, 12, 13, 14, 15 nucleotides, and any range therein), wherein the first sequence having about 5 to 20 nucleotides of (i) is immediately adjacent to the 5' end of the protospacer sequence of (ii), the second sequence of (iii) is immediately adjacent to the 3' end of the protospacer sequence of (iii), and the third sequence of (iv) is immediately adjacent to the 3' end of the second sequence of (iii); and the target oligonucleotide (second) strand is complementary to the non-target oligonucleotide strand; and (b) the non-target oligonucleotide strand is annealed to the complementary target oligonucleotide strand to produce a double stranded nucleic acid molecule, wherein the first sequence comprises a restriction site (at its 5' end) and the third sequence comprises a restriction site (at its 3' end), wherein the first sequence (i), the protospacer sequence (ii) and the third sequence (iv) of each of the two or more double stranded nucleic acid molecules are identical. In some embodiments, the target strand and/or the non-target strand may be 5' phosphorylated.

In some embodiments, the present invention provides a method of determining protospacer adjacent motif (PAM) specificity of a CRISPR-Cas nuclease, the method comprising: contacting the CRISPR-Cas nuclease with a randomized DNA library of the present invention; and sequencing the double stranded nucleic acid molecules of the randomized DNA library before (e.g., the control) and after contact with the CRISPR-Cas nuclease, wherein double stranded nucleic acid molecules present in the randomized DNA library prior to contact with the CRISPR-Cas nuclease but absent in the randomized DNA library after contact with the CRISPR-Cas nuclease identifies the PAM recognition sequence of the CRISPR-Cas nuclease, thereby determining the PAM specificity of the CRISPR-Cas nuclease.

In some embodiments, a method of determining protospacer adjacent motif (PAM) specificity of a CRISPR-Cas nuclease, comprises: contacting the CRISPR-Cas nuclease with a randomized DNA library of the present invention; sequencing the double stranded nucleic acid molecules of the randomized DNA library before (e.g., the control) and after contact with the CRISPR-Cas nuclease, and identifying the PAM recognition sequence of the nuclease, wherein identifying comprises comparing the double stranded nucleic acid molecules present in the library before contact with the CRISPR-Cas nuclease to the double stranded nucleic acid molecules present in the library after contact with the CRISPR-Cas nuclease and wherein the double stranded nucleic acid molecules present in the randomized DNA library before contact with the CRISPR-Cas nuclease but absent from the randomized DNA library after contact with the CRISPR-Cas nuclease identifies the PAM specificity of the CRISPR-Cas nuclease.

The results of sequencing of the randomized library prior to contact can serve as a control to the results of sequencing after contact. In some embodiments, determining the PAM specificity of a CRISPR-Cas nuclease may comprise performing nucleic acid sequencing. In some embodiments, the sequence may comprise next generation sequencing (NGS).

Any CRISPR-Cas nuclease may be used with the methods of this invention for modifying PAM recognition specificity. Accordingly, a CRISPR-Cas nuclease that may be modified to have a different PAM specificity as compared to wild type can include, but is not limited, to a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 polypeptide or domain.

Cas12a is a Type V Clustered Regularly Interspaced Short Palindromic Repeats (CRISPR)-Cas nuclease originally identified in *Prevotella* spp. and *Francisella* spp. Cas12a (previously referred to as Cpf1) differs in several respects from the more well-known Type II CRISPR Cas9 nuclease. For example, Cas9 recognizes a G-rich protospacer adjacent motif (PAM) that is 3' to its guide RNA (gRNA, sgRNA) binding site (protospacer, target nucleic acid, target DNA) (3'-NGG), while Cas12a recognizes a T-rich PAM that is located 5' to the binding site (protospacer, target nucleic acid, target DNA) (5'-TTN, 5'-TTTN). In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a polypeptide or CRISPR Cas12a domain useful with this invention may be any known or later identified Cas12a nuclease (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired/reduced activity as compared to the same Cas12a polypeptide without the same mutation (e.g., nickase activity).

In some embodiments, a Cas12a domain can include, but is not limited to, the amino acid sequence of any one of SEQ ID NOs:1-17 (e.g., SEQ ID NOs:1, 2, 3, 4, 5, 6, 7, 8, 9, 10, 11, 12, 13, 14, 15, 16 and/or 17) or a polynucleotide encoding the same. In some embodiments, a fusion protein of the invention may comprise a Cas12a domain from Lachnospiraceae bacterium ND2006 Cas12a (LbCas12a) (e.g., SEQ ID NO:1).

A CRISPR Cas9 polypeptide or CRISPR Cas9 domain useful with this invention may be any known or later identified Cas9 nuclease. In some embodiments, a Cas9 polypeptide useful with this invention comprises at least 70% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to an amino acid sequence of any known Cas9. CRISPR-Cas9 systems are well known in the art and include, but are not limited to, Cas9 polypeptides from *Legionella pneumophila* str. Paris, *Streptococcus thermophilus* CNRZ1066, *Streptococcus pyogenes* MI, or *Neisseria lactamica* 020-06, and the like.

Other nucleases that may be useful with this invention for identifying novel PAM recognition sequence include but are not limited to, C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Randomized Library

An example is provided of the method of this invention for the efficient and cost-effective generation of libraries for in vitro cleavage assays (PAM Determination Assays (PAMDA)). Two libraries were generated for protospacers 1 and 2 (see Table 1). Oligonucleotides with a randomized 5 nucleotide sequence at the 5r-end were synthesized and verified (Integrated DNA Technologies) so that each protospacer sequence occupies an equal molar ratio (Table 1). The oligonucleotides for protospacer 1 (PM0518, PM0519) and for protospacer 2 (PM0520, PM0521) were annealed by placing the mixture in a thermal cycler at 95° C. for 5 mins with a cool down for 0.1° C./sec to 25° C./room temperature.

TABLE 1

| Protospacer name | Oligo number | Sequence |
| --- | --- | --- |
| PAMDA library 1 | Protospacer 1 | GGAATCCCTTCTGCAGCACCTGG (SEQ ID NO: 30) |
| PAMDA library 2 | Protospacer 2 | CTGATGGTCCATGTCTGTTACTC (SEQ ID NO: 31) |
| Protospacer 1 top strand | PM0518 | /5Phos/CGATGTNNNNNGGAATCCCTTCTGCAGCACCTGGGCG CAGGTCACGAGG (SEQ ID NO: 32) |
| Protospacer 1 bottom strand | PM0519 | /5Phos/AATTCCTCGTGACCTGCGCCCAGGTGCTGCAGAAGGG ATTCCNNNNNACATCGCATG (SEQ ID NO: 33) |
| Protospacer 2 top strand | PM0520 | /5Phos/CGATGTNNNNNCTGATGGTCCATGTCTGTTACTCGCG CAGGTCACGAGG (SEQ ID NO: 34) |
| Protospacer 2 bottom strand | PM0521 | /5Phos/AATTCCTCGTGACCTGCGCGAGTAACAGACATGGACC ATCAGNNNNNACATCGCATG (SEQ ID NO: 35) |

The annealed double stranded fragments were ligated directly to a SphI and EcoRI digested pUC19 vector. The ligated protospacer constructs were used to transform XL1-blue Electro competent *E. coli* cells (Agilent) and recovered in 1 ml SOC media at 37° C. for 1 hr. Carbenicillin plates were used to check for the presence of the ligated products in the *E. coli* cells. The transformed *E. coli* cells were grown in LB broth supplemented (200 ml) with carbenicillin (50 mg/mL) for 16 hrs. The plasmids comprising the protospacer constructs were purified using Zymo midiprep kit. The plasmids/vectors were subjected to deep sequencing analysis to calculate the frequency of A/T/G/C at each PAM position using an Illumina Miseq.

This method can be used to generate libraries for PAM determination using any protospacer oligonucleotide(s) of choice wherein the annealed oligonucleotides may comprise any appropriate restriction site selected so as to retain the full complement of PAM sequences in the library.

Example 2

Figure 2:
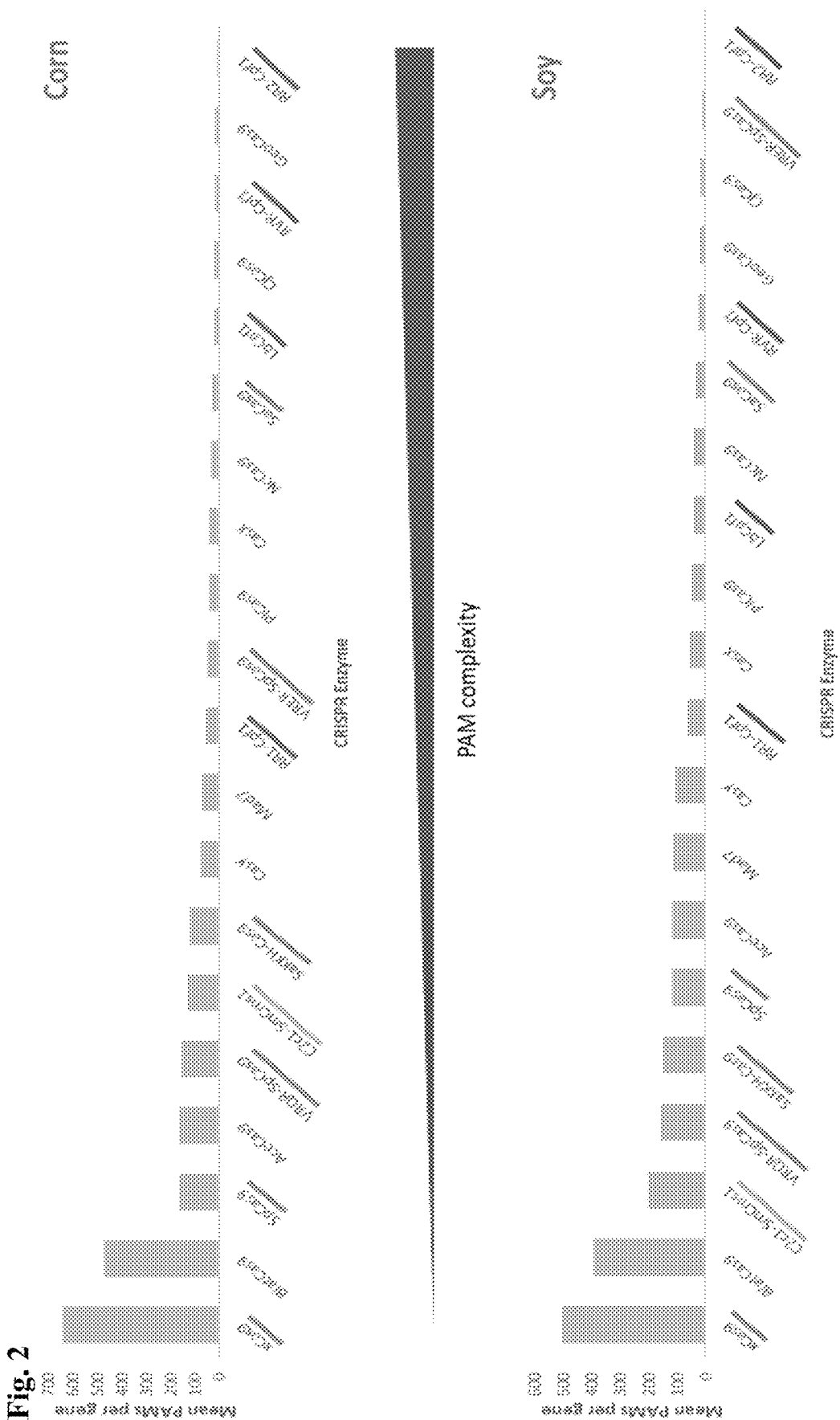
FIG. 2 shows mean protospacer adjacent motifs (PAMs) per gene for corn (top panel) and soy (bottom panel) within coding sequences. LbCpf1 genes can access far less gene sequences than Cas9 variants.

Lachnospiraceae bacterium ND2006 Cpf1 (LbCpf1) requires a highly specific protospacer adjacent motif (PAM). The 'TTTV' sequence occurs only about 1 in 85 bases in comparison to random nucleotides. This is contrast to the relative promiscuity of NGG for SpCas9 which occurs about 1 in 16 bases in random DNA, TTN for AaC2c1 which occurs about 1 in 16 bases in random DNA, and xCas9/Cas9-NG whose NG PAM requirements occur about 1 in 4 bases. Cpf1 PAMs are far less abundant in corn and soy genes than Cas9 PAMs (FIG. 2). Additionally, adenines and cytosines (the current targets for base editors) are far less accessible to LbCpf1 based on its strict PAM requirement (FIG. 3).

Such stringency as that shown in FIG. 3 for the CRISPR-Cas nucleases greatly reduces the potential targets and generation of new traits. The present invention is directed to generation of CRISPR-Cas nucleases, in particular, LbCpf1 (Cas12a) nucleases having an improved ratio of accessible PAM sequences (e.g., nucleases that has a PAM recognition site that occurs at a ratio of about 1:4 or better). Such engineered Cas12a PAM mutants may be used as nucleases (for NHEJ or HDR applications) or inactivated versions can be used as genomic recognition element in genome editing tools.

PAMDA Assay

Figure 4:
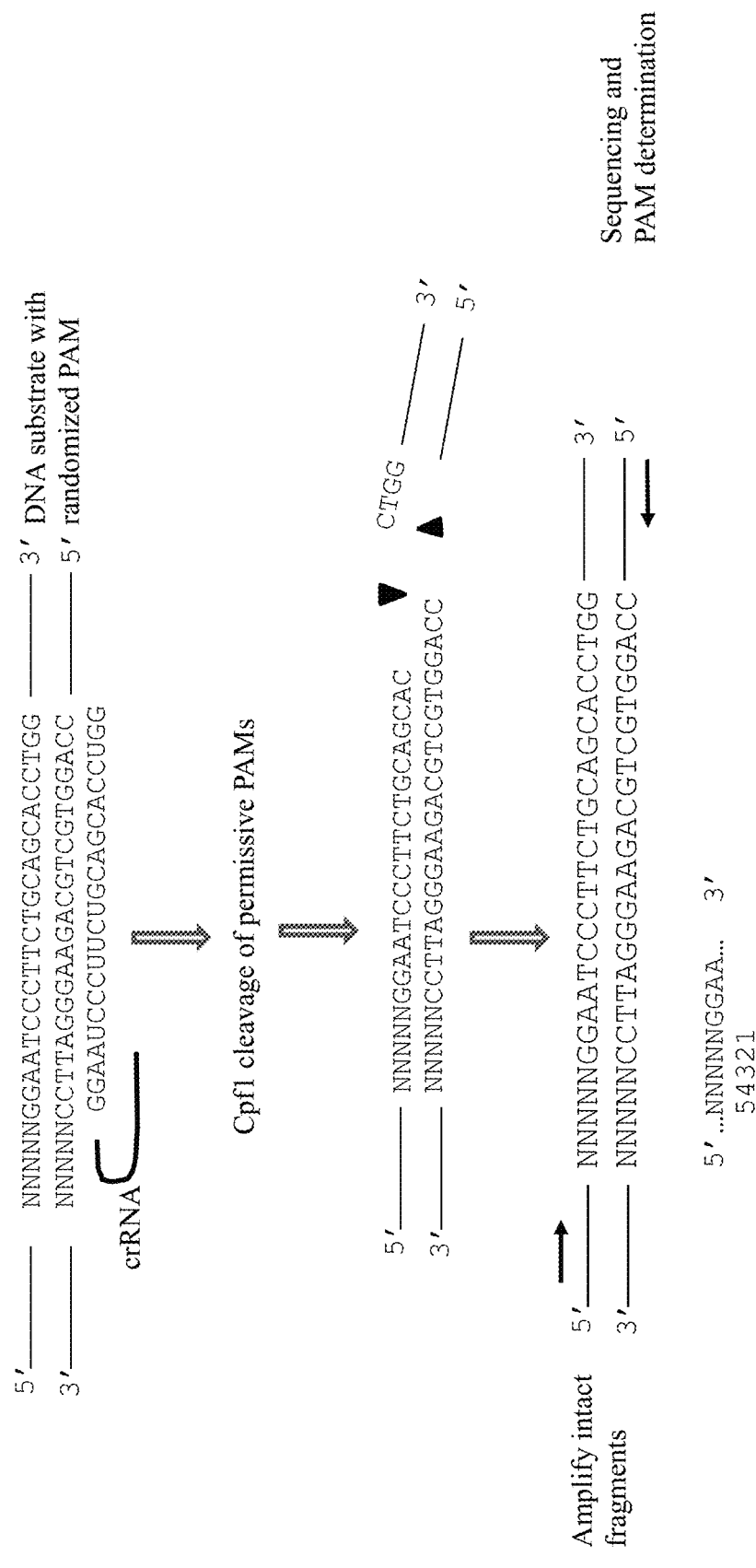
FIG. 4 provides a diagram showing a simplified PAM Determination Assay of Gao et al. (*Nat Biotechnol* 35(8): 789-792 (2017)). Amplified fragments represent sequences that were not cut by the CRISPR-Cas nuclease, whereas fragments that are not amplified were cut by the CRISPR-Cas nuclease. Sequencing and comparison to an enzyme-free control identifies the nucleic acid sequences that were not amplified (i.e., that are present in the control population but not in the edited population) and thus, identifies the sequences that are recognized and cut by the nuclease. Top panel: top sequence (SEQ ID NO:36), middle sequence (SEQ ID NO:37), bottom sequence (SEQ ID NO:38); middle panel: top sequence (SEQ ID NO:39), bottom sequence (SEQ ID NO:37); bottom panel: top sequence (SEQ ID NO:36), bottom sequence (SEQ ID NO: 37).

PAM Determination Assays (PAMDAs) are useful for testing PAM requirements for CRISPR enzymes with unknown PAM recognition. These are in vitro assays which take advantage of the ability of CRISPR-Cas nucleases to cleave target sequences only after successful PAM binding. Briefly, a library of DNA substrates with randomized PAM sequences are incubated with the CRISPR nuclease and then DNA is amplified via PCR. Only intact fragments (e.g., those not recognized by the nuclease) are amplified. Cleaved fragments (those that are recognized by the nuclease) are not amplified. The DNA from both the library that is exposed to the nuclease and a control library (not exposed to the nuclease) are sequenced. The two sets of sequencing results are compared to determine which sequences were cleaved, and thus, not present in the sequencing assemblies post exposure to the nuclease (see, as an example, FIG. 4). A modified PAMDA that uses multiple time points was used to determine PAM binding and subsequent cleavage.

LbCpf1 Mutagenesis

One hundred and eighty six (186) point mutations (Table 2) were designed and individually tested in a PAMDA assay as described herein. Successful engineering may change the PAM recognition sequence generating novel PAM recognizing LbCpf1s or may relax PAM stringency resulting in a more promiscuous LbCpf1.

TABLE 2

Residues for substitution in SEQ ID NO: 1

| | | | | | | |
|---|---|---|---|---|---|---|
| K116R | K120R | K121S | D122R | E125R | T148H | T149A |
| K116N | K120H | K121T | D122K | E125K | T148S | T149C |
| | K120N | K121H | D122H | E125Q | T148A | T149S |
| | K120T | K121R | D122E | E125Y | T148C | T149G |
| | K120Y | K121G | D122N | | | T149H |
| | K120Q | K121D | | | | T149P |
| | | K121Q | | | | T149F |
| | | | | | | T149N |
| | | | | | | T149D |
| | | | | | | T149V |
| T152R | D156R | E159K | Q529N | G532D | D535N | K538R |
| T152K | D156K | E159R | Q529T | G532N | D535H | K538V |
| T152W | D156Y | E159H | Q529H | G532S | D535V | K538Q |
| T152Y | D156W | E159Y | Q529A | G532H | D535T | K538W |
| T152H | D156Q | E159Q | Q529F | G532F | D535S | K538Y |
| T152Q | D156H | | Q529G | G532K | D535A | K538F |
| T152E | D156I | | Q529S | G532R | D535W | K538H |
| T152L | D156V | | Q529P | G532Q | D535K | K538L |
| T152F | D156L | | Q529W | G532A | | K538M |
| | D156E | | Q529D | G532L | | K538C |
| | | | | G532C | | K538G |
| | | | | | | K538A |
| | | | | | | K538P |
| D541N | Y542R | L585G | K591W | M592R | K595R | V596T |
| D541H | Y542K | L585H | K591F | M592K | K595Q | V596H |
| D541R | Y542H | L585F | K591Y | M592Q | K595Y | V596G |
| D541K | Y542Q | | K591R | M592E | K595L | V596A |
| D541Y | Y542F | | K591R | M592A | K595W | |
| D541I | Y542L | | K591S | | K595H | |
| D541A | Y542M | | K591A | | K595E | |
| D541S | Y542P | | K591G | | K595S | |
| D541E | Y542V | | K591P | | K595D | |
| | Y542N | | | | K595M | |
| | Y542T | | | | | |
| S599G | K600R | K601R | Y616K | Y646Y | W649H | |
| S599H | K600H | K601H | Y616R | Y646E | W649K | |
| S599N | K600G | K601Q | Y616E | Y646K | W649R | |
| S599D | | K601T | Y616F | Y646H | W649Y | |
| | | | Y616H | Y646Q | W649E | |
| | | | | Y646W | W649S | |
| | | | | Y646N | W649V | |
| | | | | | W649T | |

In addition to the individual mutations, combinations of mutations which alter the PAM recognition are combined and evaluated via PAMDA to provide a second generation of LbCpf1 mutations.

Example 3

Three methods were used to test the 186 mutations:

(1) An in vitro method, known as a PAMDA assay (Kleinstiver et al. Nat Biotechnol 37:276-282 (2019)), which uses purified protein and a plasmid library to test each point mutation across the library. A depletion of a library member was scored using next generation sequencing (NGS). Depletions were calculated either to the library itself (to determine absolute activity against a particular PAM) or against cleavage by wild-type LbCas12a (to determine if the mutation imparted new PAM recognition as compared to wild-type).

(2) A bacterial method, known as PAM-SCALAR (Leenay et al. Mol Cell 62:137-147 (2016)), which uses a library in Escherichia coli to test binding of Cas12a mutations to the 256 possible PAM NNNN variants. It does not test cleavage, just binding. Since the mutations made were nowhere near the catalytic region, binding is expected to reflect cleavage as well (verified later in the 293T assay). The advantage to PAM-SCALAR is the ability to rapidly test not only point mutations, but combinations of amino acid point mutations in a quick and accurate way. This assay can be more stringent than in vitro cleavage assays.

(3) An INDEL assay in human HEK293T cells. This assay is provides valuable eukaryotic INDEL data. In order to get insertions and deletions in eukaryotes, a number of criteria have to be met: the CRISPR enzyme needs to be expressed and stable in the cell, the crRNA needs to be expressed and correctly processed, the protein:RNA complex needs to form, the complex needs to be stable, the complex needs to translocate in sufficient quantities into the nucleus, the target DNA needs to be accessible, the DNA has to be well-targeted by the particular guide-RNA design, and double-stranded breaks need to occur at a rate high enough to yield the occasional DNA repair mistake via an insertion or deletion (INDEL). This makes eukaryotic assays the most stringent assays in this study. A few dozen PAMs were tested for each of the 3 point mutants described below, rather than all 256 due to the experiment being low-throughput. Three different targets were chosen for each PAM-mutant combination to try to avoid false-negatives since often a particular guide is ineffective due to target accessibility.

1. Determining PAM Binding and Cleavage In Vitro

Building a PAM Plasmid-Based Library

A DNA library consisting of 5 random nucleotides directly 5' to a 23 nucleotide spacer sequence was prepared. LbCas12.a is known to have a 4 nucleotide Protospacer Adjacent Motif (PAM), however we chose to use 5 random nucleotides rather than 4 to allow for replication within the experiment. The spacer sequence used was 5'-GGAATCCCTTCTGCAGCACCTGG (SEQ ID NO:30). The library contained the sequence 5'-NNNNNG-GAATCCCTTCTGCAGCACCTGG (SEQ ID NO:36). Having 5 random nucleotides yield 1024 possible PAMs assayed in this library.

We used a novel way to generate this library. Rather than using a single randomized pool of PAM-spacer fusions and using a polymerase to generate the complimentary strand as has been previously described (Kleinstiver et al. *Nat Biotechnol* 37:276-282 (2019)), we chose a more direct method. Two 5'-phosphorylated sequences were synthesized:

```
                                          (SEQ ID NO: 32)
5'phos/CGATGTNNNNNGGAATCCCTTCTGCAGCACCTGGGCGCAGGTC ACGAGG
and (SEQ ID NO: 35)
AATTCCTCGTGACCTGCGCCCAGGTGCTGCAGAAGGGATTCCNNNNNACA TCGCATG/5'phos.
```

When heated and annealed, complimentary sequences between the two NNNNN sequences anneal and the resulting ends have overhangs corresponding to overhangs generated by SphI and EcoRI restriction endonucleases. The two oligonucleotides were annealed at an equal molar ratio in a thermal cycler at 95° C. for 5 min, and cooled for 0.1° C./sec to 25° C./room temperature.

The annealed double stranded fragments were ligated directly to SphI and EcoRI digested pUC19 vector. The ligated spacer constructs were used to transform XL1-blue Electro competent *E. coli* cells (Agilent) and recovered in 1 mi Super Optimal broth with glucose (SOC) media at 37° degree for 1 hr. A proportion of aliquot was plated on carbenicillin plates to check for the presence of the ligated products. The remaining transformed cells were grown in 200 ml Luria broth (LB) supplemented with 50 mg/mL carbenicillin for 16 hrs. The spacer plasmids were purified using plasmid midiprep kit (Zymo Research).

Verification of PAM Library

The spacer vectors were subjected to deep sequencing analysis to calculate the frequency of A/T/G/C at each position of PAM using an Illumina MiSeq according to manufacturer's protocols. Briefly, 10 ng of DNA was used as template for PCR. Phasing gene specific forward and reverse PCR primers were designed to amplify across the target site. Amplicon libraries were generated using a two-step PCR method, where primary PCR with 5' tails allow a secondary PCR to add Illumina i5 and i7 adapter sequences and barcodes for sorting multiplexed samples. PCR amplifications were performed using the following parameters: 98° C. for 30 s; 25 cycles for PCR1 and 8 cycles for PCR2 (98° C. 10 s, 55° C. 20 s, 72° C. 30 s); 72° C. for 5 min; hold at 12° C. The PCR reactions were performed with Q5 High-Fidelity DNA Polymerase (New England BioLabs, Beverly, MA, United States). The secondary PCR amplicon samples were individually purified using AMPure XP beads according to manufacturer's instruction (Beckman Coulter, Brea, CA, United States); all purified samples were quantified using a plate reader, pooled with an equal molar ratio, and run on AATI fragment analyzer (Agilent Technologies, Palo Alto, CA, United States). The pooled amplicon libraries were sequenced on an Illumina MiSeq (2×250 paired end) using a MiSeq Reagent kit v2 (Illumina, San Diego, CA, United States).

Figure 5:
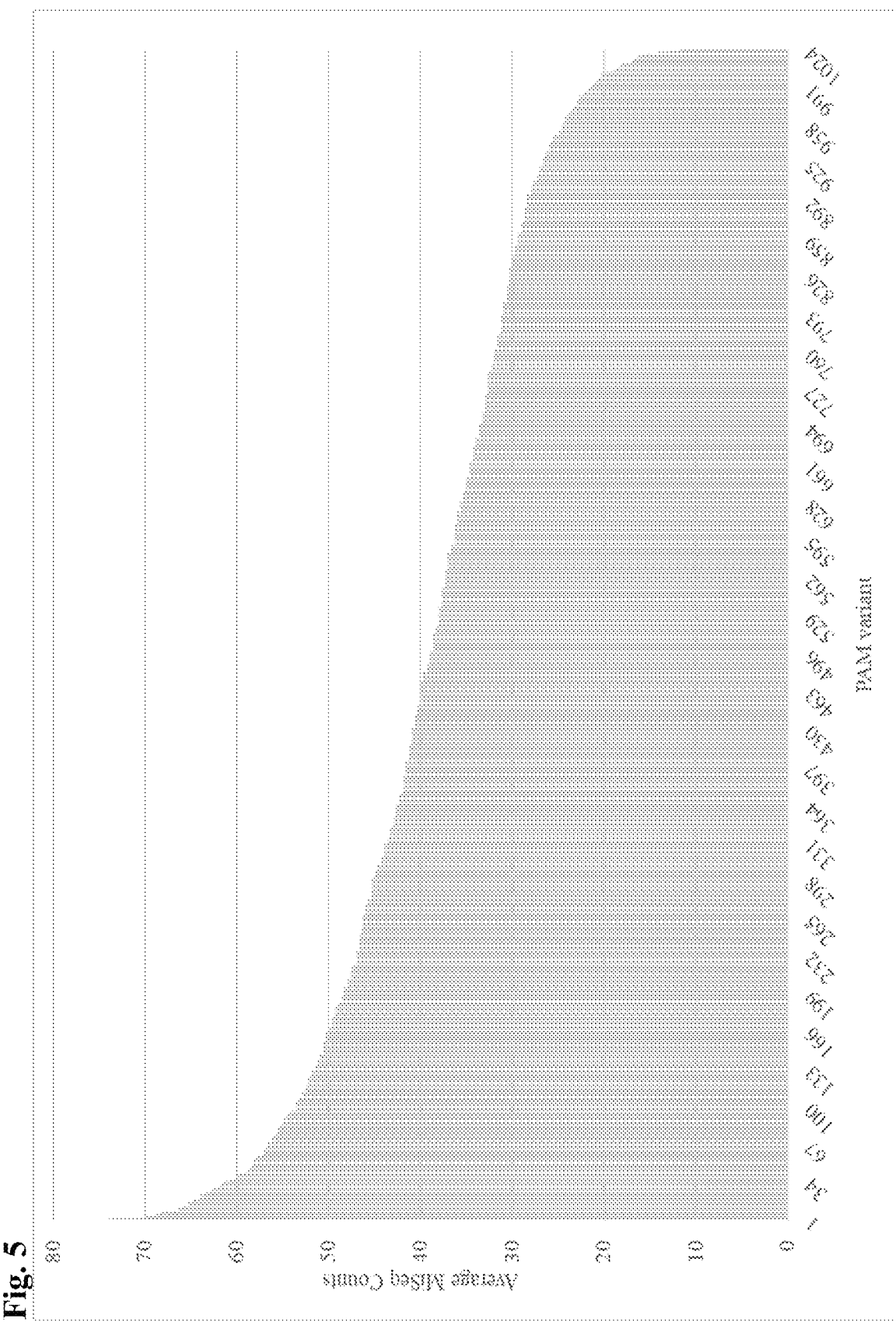
FIG. 5. Average of 3 Illumina MiSeq NGS reads of the PAMDA library plotted highest to lowest number of counts. The 1024 library members, containing NNNNN, follow a normal distribution with an average of 39 reads.

Three separate reads were generated for the library and averaged. The resulting 1024 library members had an average read count of 39 reads and a standard deviation of 11.9 reads. The maximum number of average reads for any PAM sequence was 74 and the minimum was 12. PAM counts followed a normal distribution (FIG. 5)

Cloning LbCas12a Mutations

A DNA cassette composed of an LbCas12a sequence, followed by a nucleoplasmin NLS and a 6× histidine tag was synthesized (GeneWiz) (SEQ ID NO:52) and cloned into a pET28a vector between NcoI and XhoI, generating pWISE450 (SEQ ID NO:53). An additional glycine was added to the sequence between Met-1 and Ser-2 to facilitate cloning. Numbering throughout this document excludes this extra glycine. Then, 186 different amino acid point mutations (Table 2) were made using a similar strategy yielding 186 different plasmid vectors.

Expression and Purification of LbCas12a Mutations

Glycerol stocks of each mutant in BL21 Star (DE3) cells (ThermoFisher Scientific) were used to inoculate one mL of media with 50 µg/mL of kanamycin in a 24-well block. Cultures were sealed with AirPore tape sheets (Qiagen) and grown overnight at 37° C. with shaking. The next morning four mL of ZYP autoinduction media with kanamycin were inoculated with 100 µL of overnight culture and incubated at 37° C. with shaking until OD 600 nm range of 0.2-0.5. The temperature was reduced to 18° C. and cultures were grown overnight for protein expression. Cells were harvested by centrifugation and pellets were stored at −80° C.

The following buffers were used for cell lysis and purification. A lysis buffer comprising non-ionic detergents, lysing agents, reducing agents, protease inhibitors, buffers, and salts. This solution was able to lyse bacteria, reduce viscosity, and allow for downstream purification of enzymes free from interfering nucleases. Buffer A composed of 20 mM Hepes-KOH pH 7.5, 0.5 M NaCl, 10% glycerol, 2 mM TCEP and 10 mM Imidazole pH 7.5. Buffer B was the same as buffer A but also included Imidazole at 20 mM. Buffer C contained 20 mM Hepes-KOH pH 7.5, 150 mM NaCl, 10% glycerol, 0.5 mM TCEP, and 200 mM Imidazole pH 7.5.

Purification was performed using a multi-well format. Two stainless steel ⁵⁄₃₂" BBs were added to all wells containing cell pellets. Pellets were resuspended in 0.5 mL cold lysis buffer and incubated at room temperature for 30 minutes with orbital mixing. The crude lysates, 0.5 mL, were added to pre-equilibrated His MultiTrap™ plates (Cytiva LifeSciences). The plates were incubated for five minutes at room temperature to allow for protein binding. The remaining steps were performed per manufacturer's instructions. Briefly, plates were washed two times with 0.5 mL buffer A followed by one wash with 0.5 mL buffer B before eluting in 0.2 mL of buffer C. Protein concentrations were determined using Pierce™ Coomassie Plus (Bradford) Assay Reagent. The protein eluates were stored at 4° C.

Test Cleavage of PAM Library by wtLbCas12a

A pre-test was performed to assess three aspects of the experiment: ensure the experiment was free from non-specific nucleases, ensure that there was depletion at NTTTV PAMs from the library upon addition of crRNA guides, and to see the extent of depletion at 15 minutes for a spiked sample of CTTTA.

Reaction conditions for the test depletions were: 27 μL total volume of containing nuclease-free water, 3 μL NEB buffer 2.1 (New England Biolabs), 3 μL stock of the crRNA at 300 nM (5'-AAUUUCUACUAAGUGUAGAUG-GAAUCCCUUCUGCAGCACCUGG-3' (SEQ ID NO:62), Synthego Corporation), and 1 μL of the purified wtLbCas12a at 1 μM stock were incubated at room temperature for 10 minutes. 3 μL of a 10 ng/μL stock was added to start the reaction. The library was either added as-is or 1 μL of the CTTTA-containing plasmid was added first at 0.75 ng/μL. Total volumes were all 30 μL. The reaction was incubated at 37° C. for 15 minutes.

Table 3 provides the results of the experiment. The library counts for TTTV sequences were between 219 and 515 counts (column 2), adding the wildtype protein which was purified as described in the absence of a crRNA did not result in depletion of the library members (column 3), addition of a crRNA and the protein resulted in depletion of all the NTTTV containing PAMs (column 4), spiking the library with CTTTA resulted in approximately 35 times as many CTTTA NGS counts (column 5), addition of wtLbCas12a and the crRNA resulted in a depletion of all library members, including CTTTA decreasing from 10,776 to 193 counts. Also shown are NACGA PAM-containing library members which show no depletion under the conditions tested, as is expected since ACGA is not a PAM recognized by LbCas12a. Thus, as shown in Table 3, NTTTV PAM library members are efficiently cleaved and depleted by wtLbCas12a, whereas PAMs not recognized by wtLbCas12a (NACGA) are not.

TABLE 3

PAM library cleavage and depletion.

| PAM | Library member NGS count | Library + wtLbCas12a NO crRNA | Library + wtLbCas12a + crRNA (15 min) | Library spiked with CTTTA (15 min) | Library spiked with CTTTA + wtLbCas12a + crRNA |
|---|---|---|---|---|---|
| (substrate) | | | | | |
| ATTTG | 314 | 336 | 13 | 294 | 30 |
| CTTTC | 219 | 245 | 13 | 225 | 15 |
| ATTTC | 317 | 392 | 22 | 294 | 22 |
| ATTTA | 515 | 490 | 37 | 396 | 37 |
| TTTTC | 359 | 382 | 33 | 286 | 28 |
| TTTTA | 489 | 666 | 46 | 446 | 32 |
| GTTTG | 330 | 438 | 34 | 297 | 30 |
| GTTTA | 395 | 492 | 41 | 378 | 31 |
| CTTTG | 299 | 333 | 35 | 263 | 28 |
| TTTTG | 348 | 430 | 41 | 343 | 24 |
| CTTTA | 293 | 379 | 35 | 10776 | 193 |
| GTTTC | 299 | 349 | 39 | 269 | 14 |
| (non-substrate) | | | | | |
| AACGA | 215 | 271 | 237 | 197 | 211 |
| GACGA | 273 | 282 | 274 | 251 | 282 |
| CACGA | 264 | 294 | 253 | 194 | 235 |
| TACGA | 302 | 268 | 255 | 225 | 243 |

The results in Table 3 show that (1) effective and nuclease-free purification of wtLbCAs12a was achieved, (2) the library can be depleted under conditions tested for members containing a PAM-substrate, (3) the depletion results upon the addition of a spacer-targeting crRNA, and (4) the enzyme-crRNA complex is in vast-excess of the individual library members since large amounts of CTTTA substrate does not alter the depletion of the substrates.

Cleavage of PAM Library by LbCas12a Mutants

Identical reaction conditions were tested for each of the 186 PAM mutations as were shown in the test example of wtLbCas12a. Three time points were chosen for each mutation: 75, 435, and 900 seconds at 37° C. Multiple library-only controls were included. The products were subjected to Illumina HiSeq analysis (Genewiz). The data are reported in Table 4.

Absolute Depletion Scores Processing

We observed little difference in depletion between the four possibilities for any 5 nucleotide PAM. In other words: ANNNN, CNNNN, GNNNN, and TNNNN for any 4 nucleotide sequence had similar PAM depletions. This was in-line with what we observed in the wildtype LbCAs12a experiment which showed NTTTV sequences were all depleted at a similar amount regardless if the N was A, C, G, or T (Table 3). Secondly, we observed the three time points of 75, 435, and 900 seconds all had similar depletions. This indicated that the reaction was nearly complete after just 75 seconds at 37° C. We, therefore, were able to average all four 4nt PAMs from the 5nt library and average all three time points, effectively resulting in 12 data points for each PAM. We then took that average and divided it by the median library values for each PAM. This gave us a depletion score for each 4 nucleotide PAM against all 186 mutants. A depletion of 10 indicates 90% of the 4 parental plasmid library members with that 4 nt PAM were depleted, while a score of 20 indicates 95% depletion.

The depletion score for wildtype LbCas12a was 9.2 for TTTV sequences, so any mutant which cleaved a PAM at or better than this 9.2 score was considered efficacious using wild type as a benchmark. For example, Table 4 shows the mutant LbCas12a-K595Y depleting in vitro 45 different PAM 4mers from the library at or better than wtLbCas12a cleaves TTTV-containing sequences. This analysis was used to score each of the 186 mutations to determine in vitro PAM recognition and cleavage by each of the mutants. The data containing recognition sequences are shown in Table 4, which shows LbCas12a-K595Y PAMDA depletion scores at or better than wtLbCas12a scores against TTTV-containing sequences of 9.2.

TABLE 4

PAM depletion data

| Mutant | 4mer | Depletion |
|---|---|---|
| D122H | TCCC | 18.76 |
| D122H | ATTC | 17.15 |
| D122H | GTTC | 16.7 |
| D122H | TCCG | 15.92 |
| D122H | TTCA | 14.95 |
| D122H | TCGC | 14.8 |
| D122H | TTCT | 14.68 |
| D122H | CCCC | 14.61 |
| D122H | CTTG | 14.37 |
| D122H | GTTG | 14.14 |
| D122H | ATTA | 13.66 |
| D122H | TCTA | 12.99 |
| D122H | CCTG | 12.96 |
| D122H | GTTA | 12.87 |
| D122H | CCTA | 12.77 |
| D122H | TTCG | 12.68 |
| D122H | CCTC | 12.5 |
| D122H | ATTG | 12.43 |
| D122H | TTGA | 12.14 |
| D122H | TTAC | 11.87 |
| D122H | GCGC | 11.86 |
| D122H | CTTA | 11.78 |
| D122H | CTCA | 11.77 |
| D122H | TCTC | 11.75 |
| D122H | TCCA | 11.74 |
| D122H | CCGC | 11.64 |
| D122H | TCGG | 11.3 |
| D122H | CCCG | 11.05 |
| D122H | CTTC | 11.01 |
| D122H | TCAC | 10.9 |
| D122H | TTTT | 10.85 |
| D122H | TTTC | 10.27 |
| D122H | TTTA | 10.18 |
| D122H | ACTC | 10.17 |
| D122H | GCTC | 10.01 |
| D122H | TTGC | 9.8 |
| D122H | TTCC | 9.8 |
| D122H | TTGG | 9.66 |
| D122H | CCCA | 9.34 |
| D122K | TCCC | 13.07 |
| D122K | TCCG | 13.02 |
| D122K | TCTA | 12.97 |
| D122K | GTTA | 11.7 |
| D122K | TCTC | 11.54 |
| D122K | CCCC | 11.24 |
| D122K | TCTG | 10.77 |
| D122K | GTTC | 10.77 |
| D122K | TTAC | 10.53 |
| D122K | ATTC | 10.5 |
| D122K | CCGC | 10.33 |
| D122K | TTCT | 10.1 |
| D122K | CTCC | 10.09 |
| D122K | GTTG | 10.04 |
| D122K | ATTG | 10.02 |
| D122K | TCGC | 9.84 |
| D122K | TCGG | 9.84 |
| D122K | ATTA | 9.76 |
| D122K | TTCA | 9.46 |
| D122K | CTTG | 9.44 |
| D122K | CTTC | 9.39 |
| D122K | CCTA | 9.34 |
| D122K | TTTT | 9.23 |
| D122K | TCCA | 9.11 |
| D122K | TCAC | 8.97 |
| D122K | GCTA | 8.88 |
| D122K | TTCC | 8.77 |
| D122K | GCGC | 8.76 |
| D122K | CCTC | 8.6 |
| D122K | TTGC | 8.56 |
| D122K | TTCG | 8.43 |
| D122K | TTTC | 8.41 |
| D122N | TCCC | 11.48 |
| D122N | TTTT | 11 |
| D122N | TCTA | 10.38 |
| D122N | GTTG | 10.31 |
| D122N | ATTC | 10.27 |
| D122N | CCCC | 10.22 |
| D122N | TTCA | 10.16 |
| D122N | TCCG | 10.02 |
| D122N | TTCT | 9.86 |
| D122N | CTTG | 9.79 |
| D122N | TCGC | 9.72 |
| D122N | TCTG | 9.66 |
| D122N | ATTA | 9.62 |
| D122N | CTTA | 9.61 |
| D122N | CTTC | 9.49 |
| D122N | TCCA | 9.46 |
| D122N | TTCC | 9.44 |
| D122N | TTGC | 9.39 |
| D122N | TTAC | 9.36 |
| D122N | GTTC | 9.22 |
| D122N | CCTA | 9.18 |
| D122N | CCTC | 9.16 |
| D122N | GTTA | 9.14 |
| D122N | TTCG | 9.04 |
| D122N | TCTC | 9.01 |
| D122N | TTGG | 8.97 |
| D122N | ATTG | 8.7 |
| D122R | TCCC | 10.09 |
| D122R | GTTC | 9.87 |
| D122R | CCCC | 9.85 |
| D122R | ATTG | 9.82 |
| D122R | TTGC | 9.8 |
| D122R | GTTA | 9.53 |
| D122R | TTAC | 8.94 |
| D122R | TTCG | 8.87 |
| D122R | CTTA | 8.8 |
| D122R | GCGC | 8.73 |
| D122R | TTCT | 8.6 |
| D122R | CCGC | 8.6 |
| D122R | CCTC | 8.53 |
| D122R | ATTA | 8.25 |
| D122R | TCAC | 8.17 |
| D122R | TTTT | 8.09 |
| D122R | GTTG | 7.81 |
| D122R | TTCG | 14.53 |
| D156E | TTTT | 14.35 |
| D156E | CTTA | 13.86 |
| D156E | TTGC | 13.64 |
| D156E | ATTC | 13.58 |
| D156E | TTCT | 13.51 |
| D156E | TTCA | 13.24 |
| D156E | TCTG | 13.06 |

TABLE 4-continued

PAM depletion data

| Mutant | 4mer | Depletion |
|---|---|---|
| D156E | TCCC | 13.05 |
| D156E | CTTG | 13 |
| D156E | TTCC | 12.52 |
| D156E | ATTG | 12.43 |
| D156E | TCTA | 12.35 |
| D156E | TTAC | 12.06 |
| D156E | TCTC | 11.97 |
| D156E | GTTG | 11.9 |
| D156E | ATTA | 11.88 |
| D156E | CCCG | 11.88 |
| D156E | CTTC | 11.51 |
| D156E | TTTC | 11.46 |
| D156E | CCTG | 11.34 |
| D156E | CCTA | 11.19 |
| D156E | GTTA | 11.16 |
| D156E | GTTC | 10.73 |
| D156E | TTTG | 10.61 |
| D156E | TTTA | 10.25 |
| D156E | CCCC | 10.16 |
| D156E | CCTC | 9.91 |
| D156E | CTCC | 9.83 |
| D156E | CTCA | 9.57 |
| D156E | TTGG | 8.81 |
| D156E | GCTC | 8.57 |
| D156H | CCTG | 13.3 |
| D156H | TCTG | 12.9 |
| D156H | TTCC | 12.22 |
| D156H | TTAC | 12.08 |
| D156H | ATTC | 12.04 |
| D156H | CCTC | 11.12 |
| D156H | CCCA | 10.92 |
| D156H | TCGC | 10.89 |
| D156H | TTGC | 10.87 |
| D156H | GCTA | 10.68 |
| D156H | GTTG | 10.6 |
| D156H | CCCG | 10.37 |
| D156H | CCTA | 10.3 |
| D156H | GTTA | 10.27 |
| D156H | GCTC | 10.15 |
| D156H | CTCC | 10.03 |
| D156H | GCGC | 10 |
| D156H | ATTA | 10 |
| D156H | TCCG | 9.99 |
| D156H | TCAC | 9.98 |
| D156H | TCTA | 9.95 |
| D156H | TCTC | 9.74 |
| D156H | TTCT | 9.69 |
| D156H | GTTC | 9.51 |
| D156H | CCGC | 9.45 |
| D156H | TTCA | 9.4 |
| D156H | CCCC | 9.28 |
| D156H | TCGA | 9.14 |
| D156H | TTTT | 9.13 |
| D156H | GCCC | 9.1 |
| D156H | TCCA | 9.05 |
| D156H | ACTC | 8.98 |
| D156H | TTCG | 8.89 |
| D156H | ATTG | 8.88 |
| D156H | ACTA | 8.4 |
| D156H | CTCG | 8.13 |
| D156I | CCGC | 10.23 |
| D156I | TCAG | 9.16 |
| D156I | TCGA | 8.68 |
| D156I | ACCC | 8.52 |
| D156I | GCGC | 8.42 |
| D156I | ATTC | 8.37 |
| D156I | TCCC | 8.33 |
| D156I | ACTC | 8.31 |
| D156I | GCCC | 8.05 |
| D156I | GTTG | 7.84 |
| D156K | TTCC | 12.11 |
| D156K | TTCT | 12.02 |
| D156K | ATTA | 11.58 |
| D156K | CCTG | 11.51 |
| D156K | CCTA | 11.41 |
| D156K | TCCC | 11.39 |
| D156K | TCCG | 11.32 |
| D156K | GTTC | 11.24 |
| D156K | TTGA | 11.23 |
| D156K | ATTC | 11.16 |
| D156K | ATTG | 10.87 |
| D156K | GCTC | 10.8 |
| D156K | GTTA | 10.77 |
| D156K | TTGC | 10.71 |
| D156K | CTTC | 10.65 |
| D156K | TTCA | 10.57 |
| D156K | TCTG | 10.41 |
| D156K | CCCC | 10.25 |
| D156K | TCGC | 10.15 |
| D156K | CTCC | 10 |
| D156K | TCTA | 9.99 |
| D156K | TTCG | 9.98 |
| D156K | TTAC | 9.83 |
| D156K | CCTC | 9.73 |
| D156K | TCCA | 9.65 |
| D156K | TTTT | 9.64 |
| D156K | ACTA | 9.56 |
| D156K | GTTG | 9.44 |
| D156K | TCTC | 9.37 |
| D156K | CCCG | 9.21 |
| D156K | TCAC | 9.18 |
| D156K | TTTC | 9.13 |
| D156K | CTTG | 9.05 |
| D156K | CTCA | 9 |
| D156K | TTTG | 8.92 |
| D156K | GCTG | 8.91 |
| D156K | TTGG | 8.53 |
| D156K | ACTC | 8.42 |
| D156L | GTTG | 15.01 |
| D156L | ATTC | 14.48 |
| D156L | CTTC | 14.39 |
| D156L | TCCC | 14.28 |
| D156L | ATTA | 13.69 |
| D156L | TCCG | 13.57 |
| D156L | CCCG | 13.52 |
| D156L | TTAC | 13.32 |
| D156L | CCTG | 13.25 |
| D156L | TCGC | 13.04 |
| D156L | TTCT | 12.9 |
| D156L | CCTC | 12.55 |
| D156L | ATTG | 12.52 |
| D156L | CCCCC | 12.48 |
| D156L | TTGC | 12.37 |
| D156L | GTTC | 12.31 |
| D156L | ACTA | 12.29 |
| D156L | TCTC | 11.89 |
| D156L | TCTA | 11.73 |
| D156L | CCTA | 11.49 |
| D156L | TTTT | 11.47 |
| D156L | CTTA | 11.36 |
| D156L | CTTG | 11.36 |
| D156L | TTCG | 11.36 |
| D156L | TCTG | 11.07 |
| D156L | GTTA | 11.02 |
| D156L | CCCA | 10.93 |
| D156L | GCTA | 10.87 |
| D156L | TTTG | 10.8 |
| D156L | TTCC | 10.73 |
| D156L | TCCA | 10.63 |
| D156L | CTCC | 10.14 |
| D156L | TTCA | 10.07 |
| D156L | TTTC | 9.96 |
| D156L | CTCA | 9.82 |
| D156L | TCAC | 9.8 |
| D156L | TTTA | 9.69 |
| D156L | ACTG | 9.67 |
| D156L | GCGC | 9.08 |
| D156L | CCGC | 8.68 |
| D156L | GCTC | 8.48 |
| D156L | TCAG | 8.46 |
| D156L | CTCG | 8.35 |
| D156Q | GTTC | 15.61 |

TABLE 4-continued

PAM depletion data

| Mutant | 4mer | Depletion |
|---|---|---|
| D156Q | TCCC | 15.02 |
| D156Q | ATTC | 14.2 |
| D156Q | TCCA | 14.13 |
| D156Q | TCTA | 13.69 |
| D156Q | CCTA | 13.4 |
| D156Q | CCTG | 13.17 |
| D156Q | ATTG | 12.94 |
| D156Q | TCTG | 12.76 |
| D156Q | TCTC | 12.71 |
| D156Q | CTCC | 12.58 |
| D156Q | CCCC | 12.54 |
| D156Q | CTTG | 12.5 |
| D156Q | GTTG | 12.46 |
| D156Q | CCTC | 11.6 |
| D156Q | CTCA | 11.56 |
| D156Q | TTTT | 11.44 |
| D156Q | CCCG | 11.41 |
| D156Q | ACTG | 11.38 |
| D156Q | ATTA | 11.35 |
| D156Q | GTTA | 11.2 |
| D156Q | CTTA | 11.06 |
| D156Q | TTCA | 10.96 |
| D156Q | CTTA | 10.86 |
| D156Q | TTCG | 10.7 |
| D156Q | TTGC | 10.65 |
| D156Q | TTAC | 10.6 |
| D156Q | ACTA | 10.58 |
| D156Q | TCGC | 10.58 |
| D156Q | TTCT | 10.47 |
| D156Q | TTGA | 10.35 |
| D156Q | TCCG | 10.31 |
| D156Q | GCTA | 10.26 |
| D156Q | GCTG | 10.21 |
| D156Q | TTTG | 10.17 |
| D156Q | GCTC | 10.12 |
| D156Q | TTTC | 10.01 |
| D156Q | TCAC | 9.87 |
| D156Q | CCCA | 9.86 |
| D156Q | CTCG | 9.78 |
| D156Q | GCGC | 9.58 |
| D156Q | TTCC | 9.43 |
| D156Q | TTTA | 9.38 |
| D156Q | CTTT | 9.36 |
| D156Q | TTAG | 9.1 |
| D156R | CCTG | 11.46 |
| D156R | GCTA | 11.19 |
| D156R | TTCT | 11.15 |
| D156R | CCGC | 11.01 |
| D156R | CCTC | 10.98 |
| D156R | TCCA | 10.93 |
| D156R | CCCC | 10.57 |
| D156R | TCTG | 10.53 |
| D156R | TTGC | 10.34 |
| D156R | CTTC | 9.92 |
| D156R | TCGC | 9.46 |
| D156R | ACTA | 9.41 |
| D156R | GTTG | 9.21 |
| D156R | TCTA | 9.19 |
| D156R | TTTT | 9.1 |
| D156R | TCCC | 8.96 |
| D156R | CTCA | 8.63 |
| D156W | ACTA | 13.47 |
| D156W | CCTG | 12.62 |
| D156W | CCCA | 11.99 |
| D156W | GTTG | 11.77 |
| D156W | TCTG | 11.72 |
| D156W | CCTA | 11.4 |
| D156W | CCCG | 11.4 |
| D156W | GCTA | 11.28 |
| D156W | TCGC | 11.27 |
| D156W | CCTC | 11.21 |
| D156W | CCCC | 11.16 |
| D156W | TTGC | 10.91 |
| D156W | TCCG | 10.66 |
| D156W | ATTG | 10.65 |
| D156W | GTTC | 10.5 |
| D156W | TCCA | 10.43 |
| D156W | TCTC | 10.34 |
| D156W | TCTA | 10.25 |
| D156W | TTCC | 10.18 |
| D156W | TTCT | 10.1 |
| D156W | GTTA | 10.08 |
| D156W | TTCG | 9.92 |
| D156W | TTTT | 9.65 |
| D156W | CTCA | 9.63 |
| D156W | CTTC | 9.54 |
| D156W | TCCCC | 9.49 |
| D156W | ATTA | 9.47 |
| D156W | CTTG | 9.45 |
| D156Y | TCTG | 12.9 |
| D156Y | ATTC | 12.41 |
| D156Y | TCTA | 12.32 |
| D156Y | TCCC | 11.75 |
| D156Y | TCTC | 11.68 |
| D156Y | ATTG | 10.93 |
| D156Y | CTTA | 10.52 |
| D156Y | TTCC | 10.34 |
| D156Y | GTTG | 10.31 |
| D156Y | CTTC | 10.17 |
| D156Y | TTCT | 10.02 |
| D156Y | TTGC | 9.75 |
| D156Y | TTTA | 9.64 |
| D156Y | TTCG | 9.59 |
| D535A | TTCC | 17.75 |
| D535A | TTCA | 16.69 |
| D535A | CTTG | 16.57 |
| D535A | CTTA | 15.51 |
| D535A | TCTC | 15.39 |
| D535A | TCGC | 15.38 |
| D535A | TCTA | 15.02 |
| D535A | TTGC | 14.6 |
| D535A | TCCC | 14.6 |
| D535A | TTTA | 14.59 |
| D535A | TTAC | 14.56 |
| D535A | TTTT | 13.92 |
| D535A | TTCG | 13.69 |
| D535A | TTTC | 12.57 |
| D535A | CTTC | 12.57 |
| D535A | TCTG | 12.5 |
| D535A | TCCG | 12.08 |
| D535A | TTTG | 11.96 |
| D535A | ATTA | 11.71 |
| D535A | TTAG | 11.43 |
| D535A | CCCC | 11.28 |
| D535A | ATTG | 11.06 |
| D535A | TTGA | 10.6 |
| D535A | TTCT | 10.56 |
| D535A | GCGC | 10.49 |
| D535A | ATTC | 10.41 |
| D535A | TCCA | 10.31 |
| D535A | GTTG | 10.15 |
| D535A | TCAC | 9.7 |
| D535A | GTTC | 8.85 |
| D535A | CCCG | 8.33 |
| D535A | TCAG | 8.01 |
| D535H | TCAC | 12.82 |
| D535H | TTCA | 11.72 |
| D535H | TCCG | 11.42 |
| D535H | TTCG | 11.3 |
| D535H | TCTA | 11.27 |
| D535H | TCTC | 10.82 |
| D535H | CCCC | 10.68 |
| D535H | TTCT | 10.51 |
| D535H | TTTT | 10.43 |
| D535H | TCAG | 10.24 |
| D535H | ATTA | 10.22 |
| D535H | ATTG | 10.1 |
| D535H | TTAC | 10.04 |
| D535H | TCCC | 10.02 |
| D535H | TTCC | 9.97 |
| D535H | CTTC | 9.97 |
| D535H | TCGC | 9.95 |

TABLE 4-continued

PAM depletion data

| Mutant | 4mer | Depletion |
|---|---|---|
| D535H | TTGC | 9.74 |
| D535H | TTTG | 9.52 |
| D535H | CCTA | 9.5 |
| D535H | CTTA | 9.28 |
| D535H | CCAG | 9.27 |
| D535H | TCTG | 9.24 |
| D535H | TTTA | 9.15 |
| D535H | TTGG | 8.73 |
| D535H | CCAC | 8.4 |
| D535H | GCAC | 8.08 |
| D535K | TTTA | 14.65 |
| D535K | TTTC | 13.64 |
| D535K | TTTG | 13.58 |
| D535K | TTGC | 11.64 |
| D535K | TTAC | 10.49 |
| D535N | TTGC | 10.94 |
| D535N | TTAG | 10.83 |
| D535N | TTCC | 10.61 |
| D535N | TTTC | 10.54 |
| D535N | TTTT | 10.52 |
| D535N | TCGC | 10.51 |
| D535N | TTAC | 10.39 |
| D535N | TTTA | 10.34 |
| D535N | TCAC | 10.22 |
| D535N | TTTG | 10.01 |
| D535N | TTAA | 9.04 |
| D535N | TCAG | 8.94 |
| D535N | TCCC | 8.46 |
| D535N | TTGG | 7.82 |
| D535S | TTCG | 12.34 |
| D535S | TCTG | 12.09 |
| D535S | CTTG | 12.07 |
| D535S | CTTA | 11.85 |
| D535S | TCTC | 11.41 |
| D535S | TTTA | 10.73 |
| D535S | TCCC | 10.7 |
| D535S | TTAC | 10.6 |
| D535S | TTAG | 10.49 |
| D535S | TTCC | 10.47 |
| D535S | TCAG | 10.46 |
| D535S | TCTA | 10.4 |
| D535S | TTCA | 10.36 |
| D535S | TCGC | 10.31 |
| D535S | ATTA | 10.14 |
| D535S | TTGA | 10.13 |
| D535S | TTTT | 10.1 |
| D535S | TCAC | 10.07 |
| D535S | TTTC | 9.76 |
| D535S | CCCC | 9.75 |
| D535S | TTGC | 9.72 |
| D535S | CCGC | 9.66 |
| D535S | ATTG | 9.64 |
| D535S | GTTG | 9.6 |
| D535S | TTCT | 9.51 |
| D535S | TTTG | 9.4 |
| D535S | CCTG | 9.34 |
| D535S | CCCG | 9.18 |
| D535S | TCCA | 9.11 |
| D535S | TTGG | 9.02 |
| D535S | TTAA | 8.98 |
| D535T | CTTA | 14.25 |
| D535T | TTCG | 13.61 |
| D535T | TTTT | 13.51 |
| D535T | TCCC | 12.73 |
| D535T | TCTA | 12.41 |
| D535T | CTTG | 12.36 |
| D535T | TCTG | 11.75 |
| D535T | TTGC | 11.65 |
| D535T | TCCG | 11.65 |
| D535T | TCTC | 11.38 |
| D535T | TCGC | 11.38 |
| D535T | TTAC | 11.38 |
| D535T | TTTA | 11.34 |
| D535T | TTTG | 11.25 |
| D535T | CTTC | 11.2 |
| D535T | TTGG | 10.8 |
| D535T | TTCT | 10.42 |
| D535T | TCAC | 10.06 |
| D535T | TCAG | 9.75 |
| D535T | TTTC | 9.07 |
| D535T | GTTA | 8.61 |
| D535T | CTCC | 8.06 |
| D535V | TTTG | 15.43 |
| D535V | TTTA | 13.9 |
| D535V | TTTC | 12.89 |
| D535V | TTGC | 9.81 |
| D535V | TTTT | 9.77 |
| D541A | ATTG | 9.99 |
| D541E | CTTC | 15.41 |
| D541E | TTTG | 14.24 |
| D541E | TTTT | 14.15 |
| D541E | CTTA | 13.23 |
| D541E | TTTC | 12.78 |
| D541E | CTTG | 11.68 |
| D541E | TTCA | 11.56 |
| D541E | TTCC | 11.02 |
| D541E | TTTA | 10.69 |
| D541E | CCGC | 10.13 |
| D541E | TCTA | 9.86 |
| D541E | TCTC | 9.77 |
| D541E | TCCG | 9.75 |
| D541E | TCCC | 9.37 |
| D541E | TTGC | 9.33 |
| D541E | TTCG | 9.03 |
| D541E | CCCC | 8.91 |
| D541E | TTAC | 8.69 |
| D541E | CCTG | 8.3 |
| D541E | ATTG | 8.18 |
| D541E | CCTA | 7.96 |
| D541E | GTTA | 7.84 |
| D541H | TTCG | 8.67 |
| D541H | CTTC | 8.58 |
| D541I | TTTC | 11.44 |
| D541I | TTTG | 10 |
| D541I | CTTA | 9.11 |
| D541I | TTTT | 8.7 |
| D541N | TCCC | 8.36 |
| D541R | TTTG | 8.99 |
| D541Y | CTTA | 10.32 |
| D541Y | TTTC | 9.36 |
| D541Y | CTTC | 8 |
| E125K | TTGC | 10.22 |
| E125K | TCTC | 9.44 |
| E125K | ATTG | 9.32 |
| E125K | TTAC | 9.11 |
| E125K | CCCC | 8.94 |
| E125K | TTCG | 8.93 |
| E125K | CTTC | 8.83 |
| E125K | TCCC | 8.81 |
| E125K | TTCT | 8.62 |
| E125K | TTTA | 8.56 |
| E125K | TTTT | 8.43 |
| E125K | TTGA | 8.25 |
| E125K | TCGA | 8.15 |
| E125K | ATTC | 8.04 |
| E125Q | TTCA | 12.74 |
| E125Q | CTTC | 12.55 |
| E125Q | CTTA | 12.14 |
| E125Q | TCCC | 11.7 |
| E125Q | TTCG | 11.66 |
| E125Q | TCTA | 11.06 |
| E125Q | TTGC | 10.88 |
| E125Q | ATTC | 10.84 |
| E125Q | ATTA | 10.53 |
| E125Q | TTTG | 10.51 |
| E125Q | TTTT | 10.08 |
| E125Q | CCCC | 10.04 |
| E125Q | TCTC | 10.03 |
| E125Q | CCCG | 9.96 |
| E125Q | TCCA | 9.94 |
| E125Q | TTGG | 9.92 |
| E125Q | TTCC | 9.88 |

TABLE 4-continued

PAM depletion data

| Mutant | 4mer | Depletion |
|---|---|---|
| E125Q | TCCG | 9.84 |
| E125Q | TTCT | 9.61 |
| E125Q | CTTG | 9.55 |
| E125Q | ATTG | 9.45 |
| E125Q | GTTG | 9.29 |
| E125Q | TCTG | 9.17 |
| E125Q | TTTA | 9.1 |
| E125Q | TTAC | 8.56 |
| E125Q | TCGC | 8.55 |
| E125Q | TCAC | 8.5 |
| E125Q | CCTG | 8.42 |
| E125Q | CTCG | 8.25 |
| E125R | CCCG | 11.21 |
| E125R | TCCC | 8.35 |
| E125R | TCCA | 8.03 |
| E125Y | TTCG | 11.77 |
| E125Y | TTGC | 10.69 |
| E125Y | CTTC | 9.94 |
| E125Y | CCCC | 9.82 |
| E125Y | TTTT | 9.39 |
| E159K | TTCT | 12.66 |
| E159K | CCCC | 12.33 |
| E159K | ATTG | 11.53 |
| E159K | CTTG | 11.38 |
| E159K | CTTA | 11.24 |
| E159K | TCTC | 11.21 |
| E159K | ATTC | 11.05 |
| E159K | TCCC | 11.04 |
| E159K | TTCG | 10.86 |
| E159K | TTCA | 10.67 |
| E159K | TCTA | 10.64 |
| E159K | TTGC | 10.56 |
| E159K | CTTC | 10.36 |
| E159K | TCTG | 10.17 |
| E159K | TTAC | 10.12 |
| E159K | TTCC | 9.92 |
| E159K | TCGC | 9.78 |
| E159K | GTTA | 9.69 |
| E159K | TCCG | 9.67 |
| E159K | CCTG | 9.31 |
| E159K | GTTG | 9.04 |
| E159K | GCCC | 8.85 |
| E159K | CCTC | 8.85 |
| E159K | GCGC | 8.65 |
| E159K | ACTC | 8.23 |
| E159K | TTTT | 11.37 |
| E159K | TTCG | 10.89 |
| E159K | CTTA | 10.51 |
| E159K | TTGC | 10.5 |
| E159K | TTTC | 10.15 |
| E159K | TTCC | 9.95 |
| E159K | CTTG | 9.91 |
| E159K | TTCA | 9.8 |
| E159K | TTTA | 9.44 |
| E159K | TTTG | 9.27 |
| E159R | GTTC | 14.77 |
| E159R | GTTG | 13.13 |
| E159R | TCCG | 12.2 |
| E159R | TTGC | 11.82 |
| E159R | TTGC | 11.71 |
| E159R | CCTC | 11.67 |
| E159R | ATTG | 11.35 |
| E159R | CCCC | 11.09 |
| E159R | TTAC | 11.05 |
| E159R | CTTC | 10.88 |
| E159R | TCTG | 10.85 |
| E159R | ATTC | 10.72 |
| E159R | TTCT | 10.71 |
| E159R | TCTC | 10.63 |
| E159R | GTTA | 10.62 |
| E159R | TTCA | 10.59 |
| E159R | CTTG | 10.51 |
| E159R | TCGC | 10.29 |
| E159R | TCTA | 10.16 |
| E159R | ATTA | 10.06 |
| E159R | ACCC | 9.76 |
| E159R | TTTG | 9.55 |
| E159R | CCTA | 9.52 |
| E159R | CTTA | 9.47 |
| E159R | GCGC | 9.32 |
| E159R | ACTC | 8.95 |
| E159R | CCGC | 8.91 |
| E159Y | TTTT | 11.72 |
| E159Y | CTTC | 11.71 |
| E159Y | TTTA | 11.42 |
| E159Y | CTTA | 10.79 |
| E159Y | TTTG | 10.39 |
| E159Y | TTGC | 10.37 |
| E159Y | TTCC | 9.94 |
| E159Y | CTTG | 9.51 |
| E159Y | TCCC | 9.43 |
| G532A | TTTT | 13.95 |
| G532A | CTTG | 12.83 |
| G532A | ATTC | 12.56 |
| G532A | CTTC | 11.75 |
| G532A | TCTC | 11.56 |
| G532A | TTCC | 11.55 |
| G532A | TTCG | 11.5 |
| G532A | TCTA | 11.01 |
| G532A | TTCA | 10.91 |
| G532A | CCCC | 10.36 |
| G532A | CTTA | 10.35 |
| G532A | TTGC | 10.19 |
| G532A | GTTG | 10.18 |
| G532A | TCCC | 10.1 |
| G532A | TCTG | 9.94 |
| G532A | ATTG | 9.6 |
| G532A | TTTA | 9.47 |
| G532A | GTTA | 9.4 |
| G532C | TTTT | 15.09 |
| G532C | TTCC | 12.43 |
| G532C | TTTC | 12.3 |
| G532C | TTGC | 11.56 |
| G532C | CTTA | 11.27 |
| G532C | TTAC | 11.02 |
| G532C | TTTG | 10.94 |
| G532C | TTCA | 10.93 |
| G532C | CTTG | 10.62 |
| G532C | TTTA | 10.31 |
| G532C | TCCC | 10.29 |
| G532C | TCTA | 10.26 |
| G532C | TCTG | 10.19 |
| G532C | GTTA | 9.93 |
| G532C | TCTC | 9.91 |
| G532C | CTTC | 9.78 |
| G532C | GTTG | 8.88 |
| G532D | CTTG | 21.38 |
| G532D | CTTA | 15.81 |
| G532D | TTCC | 15.28 |
| G532D | TTTT | 14.57 |
| G532D | CTTC | 13.93 |
| G532D | TTTC | 13.65 |
| G532D | TTTG | 13.59 |
| G532D | TTCG | 13.54 |
| G532D | TTCT | 13.13 |
| G532D | TTCA | 12.84 |
| G532D | CCCC | 12.66 |
| G532D | TTTA | 12.54 |
| G532D | TTGC | 12.49 |
| G532D | GTTG | 11.87 |
| G532D | TCCG | 11.41 |
| G532D | ATTG | 11.27 |
| G532D | ATTA | 11 |
| G532D | TCCC | 10.91 |
| G532D | ATTC | 10.56 |
| G532D | TCTA | 10.36 |
| G532D | CTCC | 9.98 |
| G532D | TTAC | 9.81 |
| G532D | TCGC | 9.2 |
| G532F | CTTA | 13.56 |
| G532F | ATTG | 11.28 |
| G532F | CTTC | 11.1 |

TABLE 4-continued

PAM depletion data

| Mutant | 4mer | Depletion |
|---|---|---|
| G532F | TTCA | 10.82 |
| G532F | TTGC | 10.74 |
| G532F | TTTT | 10.6 |
| G532F | TCTA | 10.52 |
| G532F | TTAC | 10.48 |
| G532F | TTTA | 10.31 |
| G532F | TTTG | 10.25 |
| G532F | ATTA | 10.2 |
| G532F | GTTA | 9.82 |
| G532F | TTTC | 9.64 |
| G532F | ATTC | 9.47 |
| G532F | TCCC | 9.44 |
| G532F | CTTG | 9.28 |
| G532F | TCTC | 9.23 |
| G532F | TCCG | 8.95 |
| G532F | TCTG | 8.91 |
| G532F | CCCC | 8.33 |
| G532F | GTTG | 8.17 |
| G532F | CCTA | 8.08 |
| G532H | TTCA | 16.2 |
| G532H | CTTC | 15.09 |
| G532H | GTTG | 14.43 |
| G532H | TTTT | 13.93 |
| G532H | TTCG | 13.87 |
| G532H | CTTG | 13.72 |
| G532H | TCTG | 13.22 |
| G532H | GTTC | 12.71 |
| G532H | TTGG | 12.66 |
| G532H | CTTA | 12.54 |
| G532H | TTGC | 12.31 |
| G532H | TCTA | 12.2 |
| G532H | TTCT | 12.15 |
| G532H | ATTC | 11.94 |
| G532H | CCCC | 11.91 |
| G532H | TTTC | 11.89 |
| G532H | TCCG | 11.71 |
| G532H | TTTA | 11.67 |
| G532H | TCCC | 11.6 |
| G532H | TTTC | 11.23 |
| G532H | CTCA | 11.23 |
| G532H | ATTA | 11.16 |
| G532H | TCCA | 11.11 |
| G532H | ATTG | 11.02 |
| G532H | TTAC | 10.74 |
| G532H | TCTC | 10.55 |
| G532H | TCGC | 10.42 |
| G532H | CCTA | 10.3 |
| G532H | CTCC | 9.99 |
| G532H | GTTA | 9.77 |
| G532H | CCCA | 9.61 |
| G532H | CCTG | 9.15 |
| G532H | CCTC | 9.03 |
| G532H | CCCG | 8.84 |
| G532H | TCAC | 7.76 |
| G532K | CTCA | 13.19 |
| G532K | GCCC | 12.17 |
| G532K | CTTA | 11.31 |
| G532K | CTTC | 11.17 |
| G532K | TTGC | 10.91 |
| G532K | CTTG | 10.78 |
| G532K | ATTA | 10.64 |
| G532K | GCCG | 10.53 |
| G532K | TTAC | 10.41 |
| G532K | TTTT | 9.96 |
| G532K | TCCA | 9.94 |
| G532K | ACCG | 9.8 |
| G532K | CCCC | 9.69 |
| G532L | CTTC | 15.2 |
| G532L | TTTT | 14.33 |
| G532L | TTTA | 12.17 |
| G532L | CTTG | 12.04 |
| G532L | CTTA | 11.73 |
| G532L | TTGC | 11.67 |
| G532L | TTCA | 11.66 |
| G532L | TTAC | 11.57 |
| G532L | TTTG | 11.5 |

TABLE 4-continued

PAM depletion data

| Mutant | 4mer | Depletion |
|---|---|---|
| G532L | ATTA | 11.36 |
| G532L | TTTC | 11.15 |
| G532L | TTCC | 10.89 |
| G532L | ATTG | 10.02 |
| G532L | GTTG | 9.71 |
| G532L | TCTA | 9.46 |
| G532L | CCTA | 9.29 |
| G532L | ATTC | 8.98 |
| G532L | TCCC | 8.77 |
| G532L | TTGA | 8.33 |
| G532N | CTTG | 15.59 |
| G532N | TCCC | 15.09 |
| G532N | TTCG | 14.11 |
| G532N | ATTG | 13.73 |
| G532N | CTTC | 12.97 |
| G532N | TTGC | 12.7 |
| G532N | TTAC | 12.61 |
| G532N | TTCT | 12.13 |
| G532N | ATTA | 12.03 |
| G532N | TCTA | 12.02 |
| G532N | TTCC | 12 |
| G532N | TTTT | 11.95 |
| G532N | TCTC | 11.91 |
| G532N | ATTC | 11.98 |
| G532N | CTTA | 11.8 |
| G532N | TTTC | 11.52 |
| G532N | TTCA | 11.33 |
| G532N | TCTG | 11.3 |
| G532N | TTTA | 11.23 |
| G532N | TTTG | 11.18 |
| G532N | TCCG | 11.17 |
| G532N | GTTG | 11.14 |
| G532N | GTTA | 10.53 |
| G532N | CCCG | 10.51 |
| G532N | GTTC | 9.62 |
| G532N | CTCC | 9.48 |
| G532N | CCCC | 9.46 |
| G532N | TCCA | 9.45 |
| G532N | CCTA | 9.35 |
| G532N | CCTG | 9.28 |
| G532Q | TTTG | 16.46 |
| G532Q | TTGC | 14.95 |
| G532Q | TTCA | 14.64 |
| G532Q | CTTC | 13 |
| G532Q | TTTT | 12.79 |
| G532Q | ATTA | 12.41 |
| G532Q | TTCC | 12.4 |
| G532Q | TTAC | 11.52 |
| G532Q | TTCT | 11.34 |
| G532Q | CTTG | 11.2 |
| G532Q | TCTA | 11.19 |
| G532Q | TTTA | 10.72 |
| G532Q | CTTA | 10.58 |
| G532Q | ATTG | 10.43 |
| G532Q | TTTC | 10.32 |
| G532Q | TTCG | 10.23 |
| G532Q | TCCC | 10.05 |
| G532Q | GTTG | 9.8 |
| G532Q | CCCC | 9.74 |
| G532Q | TCTC | 9.47 |
| G532S | TTAC | 13.85 |
| G532S | TTTT | 13.71 |
| G532S | GTTA | 13.01 |
| G532S | TCTC | 12.51 |
| G532S | TTCA | 12.5 |
| G532S | CTTA | 12.33 |
| G532S | TCCC | 12.3 |
| G532S | ATTG | 12.3 |
| G532S | CTTC | 12.28 |
| G532S | ATTC | 12.08 |
| G532S | TTCC | 11.95 |
| G532S | TCTA | 11.79 |
| G532S | TCTG | 11.78 |
| G532S | TCCG | 11.58 |
| G532S | ATTA | 11.51 |
| G532S | TTTC | 11.49 |

TABLE 4-continued

PAM depletion data

| Mutant | 4mer | Depletion |
|---|---|---|
| G532S | CTTG | 11.43 |
| G532S | GTTC | 11.1 |
| G532S | TTCG | 11.03 |
| G532S | GTTG | 10.72 |
| G532S | TTTG | 10.63 |
| G532S | TTTA | 10.56 |
| G532S | TTCT | 10.36 |
| G532S | TTGC | 10.15 |
| G532S | TCGC | 9.46 |
| G532S | TTAG | 9.38 |
| G532S | CCCC | 9.11 |
| K116N | CTCC | 8.12 |
| K116N | CTTA | 12.52 |
| K116N | CTTC | 11.57 |
| K116N | TCCC | 10.05 |
| K116N | TTAC | 10.99 |
| K116N | TCTA | 10.97 |
| K116N | TCTC | 10.9 |
| K116N | TCCA | 10.84 |
| K116N | TCTG | 10.77 |
| K116N | TCCG | 10.73 |
| K116N | TTCG | 10.7 |
| K116N | TTCA | 10.66 |
| K116N | ATTA | 10.47 |
| K116N | TTTT | 10.21 |
| K116N | TTGC | 10.17 |
| K116N | TTTC | 9.92 |
| K116N | CTTG | 9.87 |
| K116N | TTCC | 9.85 |
| K116N | TTCT | 9.64 |
| K116N | CCTA | 9.42 |
| K116N | GTTA | 9.31 |
| K116N | CCTG | 9.21 |
| K116N | CCCC | 9.13 |
| K116N | TCGC | 9.04 |
| K116N | GTTC | 8.91 |
| K116N | CTCA | 8.61 |
| K116N | CCGC | 8.39 |
| K116N | TTGA | 7.69 |
| K116R | TCCG | 13.47 |
| K116R | ATTC | 13.02 |
| K116R | TTAC | 12.37 |
| K116R | GTTC | 11.83 |
| K116R | CCTA | 11.44 |
| K116R | TTCT | 11.35 |
| K116R | ATTG | 11.11 |
| K116R | TCTA | 11.03 |
| K116R | CCCC | 11.03 |
| K116R | CTCC | 10.97 |
| K116R | TCTC | 10.84 |
| K116R | TCGC | 10.29 |
| K116R | GTTG | 10.27 |
| K116R | GCTC | 10.2 |
| K116R | CTTA | 10.15 |
| K116R | TTGC | 10.12 |
| K116R | CCTG | 10.04 |
| K116R | ATTA | 10.02 |
| K116R | TTTT | 9.98 |
| K116R | CCTC | 9.78 |
| K116R | TCCC | 9.72 |
| K116R | GTTA | 9.65 |
| K116R | CCCG | 9.62 |
| K116R | ACTA | 9.61 |
| K116R | TTCG | 9.54 |
| K116R | TCCA | 9.36 |
| K116R | GCGC | 9.27 |
| K116R | TTCC | 9.22 |
| K116R | TTCA | 9.14 |
| K116R | GCTA | 9.14 |
| K116R | CCCA | 8.96 |
| K116R | CTTC | 9.95 |
| K116R | TCTG | 8.93 |
| K116R | TTGG | 8.82 |
| K116R | CCGC | 8.81 |
| K116R | GCTG | 8.67 |
| K116R | ACGC | 8.32 |
| K116R | ACTC | 8.29 |
| K116R | CTCA | 8.06 |
| K120H | TCTC | 10.27 |
| K120H | TTCG | 10.07 |
| K120H | TTTT | 9.97 |
| K120H | CTTG | 9.77 |
| K120H | CTTA | 9.69 |
| K120H | TTCC | 9.3 |
| K120H | TTCA | 9.02 |
| K120H | TTTG | 8.5 |
| K120H | TCGC | 8.43 |
| K120H | TTTC | 8.26 |
| K120H | TTTA | 8.02 |
| K120H | TTGC | 7.89 |
| K120H | TCCC | 7.56 |
| K120H | CCCC | 7.55 |
| K120N | TTTA | 12.31 |
| K120N | TTTT | 11.86 |
| K120N | CCCC | 11.41 |
| K120N | TCTC | 11.4 |
| K120N | TTCC | 11.21 |
| K120N | TCCC | 11.18 |
| K120N | CTTA | 10.93 |
| K120N | TTTC | 10.91 |
| K120N | TTGC | 10.55 |
| K120N | TCTG | 10.41 |
| K120N | ATTA | 10.4 |
| K120N | CTTC | 10.32 |
| K120N | ATTC | 10.31 |
| K120N | TTTG | 9.99 |
| K120N | TTCA | 9.95 |
| K120N | TCTA | 9.86 |
| K120N | CCCG | 9.64 |
| K120N | CTTG | 9.6 |
| K120N | TCCG | 9.49 |
| K120N | TTCG | 9.48 |
| K120N | TTCT | 9.32 |
| K120N | GCGC | 9.07 |
| K120N | CCTA | 8.43 |
| K120N | CTCC | 8.18 |
| K120Q | TTTC | 12.01 |
| K120Q | TTCC | 11.56 |
| K120Q | TTCA | 11.1 |
| K120Q | CTTG | 10.57 |
| K120Q | TTGC | 10.37 |
| K120Q | TTTG | 10.25 |
| K120Q | TTCG | 10.25 |
| K120Q | TTTT | 9.91 |
| K120Q | CTTC | 9.83 |
| K120Q | TTTA | 9.72 |
| K120Q | ATTG | 9.25 |
| K120Q | TTAC | 9.25 |
| K120Q | TCTA | 9.18 |
| K120Q | GTTC | 9.03 |
| K120Q | CTTA | 8.96 |
| K120Q | ATTC | 8.71 |
| K120R | TTCA | 10.74 |
| K120R | CTTA | 9.7 |
| K120T | TTTT | 7.73 |
| K120T | TTCG | 7.73 |
| K120T | TTGA | 7.34 |
| K121D | TTTA | 12.69 |
| K121D | TTTG | 11.07 |
| K121D | TTTC | 10.18 |
| K121G | TTTT | 16.86 |
| K121G | TTCA | 15.35 |
| K121G | TTCC | 15.22 |
| K121G | CTTG | 14.67 |
| K121G | TTGC | 14.52 |
| K121G | CTTA | 14.02 |
| K121G | TTTC | 13.96 |
| K121G | TTTA | 13.42 |
| K121G | CTTC | 13.37 |
| K121G | TTCG | 13.33 |
| K121G | TTTG | 12.87 |
| K121G | TTCT | 12.72 |

TABLE 4-continued

PAM depletion data

| Mutant | 4mer | Depletion |
|---|---|---|
| K121G | ATTG | 12.35 |
| K121G | ATTC | 11.96 |
| K121G | ATTA | 11.89 |
| K121G | TTAC | 11.65 |
| K121G | TCCC | 11.12 |
| K121G | TCTA | 10.53 |
| K121G | TCGC | 9.78 |
| K121G | GTTA | 9.62 |
| K121G | GTTG | 9.32 |
| K121G | TCTC | 9.08 |
| K121G | CCCC | 8.06 |
| K121G | GTTC | 7.89 |
| K121H | TTCA | 10.11 |
| K121H | TTGC | 9.93 |
| K121H | TCTA | 9.6 |
| K121H | TTCC | 9.53 |
| K121H | CTTG | 9.11 |
| K121H | TTTT | 8.99 |
| K121H | TTCG | 8.82 |
| K121H | TTTC | 8.53 |
| K121H | TTTA | 8.28 |
| K121H | CTTC | 7.95 |
| K121H | TCCG | 7.77 |
| K121H | CCTG | 7.66 |
| K121H | TCTC | 7.51 |
| K121Q | TTTA | 8.76 |
| K121Q | TTTG | 8.76 |
| K121Q | TTTT | 8.28 |
| K121Q | TTCT | 7.93 |
| K121Q | TTCC | 7.89 |
| K121R | TTCT | 14.44 |
| K121R | CTTC | 13.38 |
| K121R | TTCA | 13.05 |
| K121R | TTTT | 13.03 |
| K121R | CCTG | 12.96 |
| K121R | ATTG | 12.3 |
| K121R | TTAC | 12.28 |
| K121R | CCCC | 12.28 |
| K121R | TCGC | 12.01 |
| K121R | ATTA | 12 |
| K121R | TCCG | 11.99 |
| K121R | TCTA | 11.97 |
| K121R | TTCG | 11.79 |
| K121R | TCTC | 11.72 |
| K121R | TTGC | 11.55 |
| K121R | CCGC | 11.31 |
| K121R | GTTA | 11.23 |
| K121R | GTTG | 11.05 |
| K121R | TTTG | 10.86 |
| K121R | ATTC | 10.84 |
| K121R | CTTA | 10.83 |
| K121R | CCTA | 10.71 |
| K121R | CCTC | 10.52 |
| K121R | TTCC | 10.4 |
| K121R | CCCG | 10.37 |
| K121R | CTCC | 10.21 |
| K121R | TCCA | 10.18 |
| K121R | TTTA | 10.07 |
| K121R | TCCC | 9.9 |
| K121R | CTTG | 9.72 |
| K121R | GCGC | 9.67 |
| K121R | TCAC | 9.59 |
| K121R | CCCA | 9.45 |
| K121R | GTTC | 9.23 |
| K121R | CTCA | 9.04 |
| K121R | TTTC | 8.93 |
| K121R | TCTG | 8.87 |
| K121S | TTGC | 11.77 |
| K121S | CCTG | 11.74 |
| K121S | TCCA | 11.66 |
| K121S | TTTT | 10.88 |
| K121S | TTCA | 10.85 |
| K121S | CCTC | 10.72 |
| K121S | TCTC | 10.62 |
| K121S | CTTA | 10.33 |
| K121S | TTCT | 10.1 |
| K121S | TCTA | 10.06 |
| K121S | CCCC | 10.02 |
| K121S | TTCC | 9.9 |
| K121S | CTTG | 9.88 |
| K121S | TCCC | 9.81 |
| K121S | TTCG | 9.71 |
| K121S | CTCC | 9.65 |
| K121S | TCCG | 9.59 |
| K121S | CTTC | 9.59 |
| K121S | ATTC | 9.53 |
| K121S | TCTG | 9.47 |
| K121S | TTAC | 9.46 |
| K121S | TTTA | 9.31 |
| K121S | GCGC | 9.26 |
| K121S | GTTC | 9.25 |
| K121S | ATTA | 9.2 |
| K121S | CCGC | 9.14 |
| K121S | ACTA | 8.94 |
| K121S | GCCC | 8.9 |
| K121S | TTTC | 8.89 |
| K121S | CTTT | 8.79 |
| K121S | TTGA | 8.76 |
| K121S | TCGC | 8.63 |
| K121S | CCCG | 8.61 |
| K121S | GTTA | 8.5 |
| K121S | GTTG | 8.35 |
| K121S | ACTG | 7.89 |
| K121S | CTCG | 7.8 |
| K121S | GCTA | 7.57 |
| K121T | TTTC | 13.85 |
| K121T | TTTT | 13.26 |
| K121T | TTTA | 13.02 |
| K121T | TTTG | 12.09 |
| K121T | CTTA | 11.65 |
| K121T | CTTC | 10.99 |
| K121T | CTTG | 10.52 |
| K121T | TTCA | 10.44 |
| K121T | TTCC | 10.36 |
| K121T | TTGC | 9.85 |
| K538C | CTTC | 9.67 |
| K538F | TTTA | 17.03 |
| K538F | TTTC | 15.83 |
| K538F | CTTG | 11.01 |
| K538F | CTTC | 10.62 |
| K538F | CTTA | 9.14 |
| K538G | TTTC | 11.42 |
| K538G | TTTA | 10.22 |
| K538G | TTTG | 9.79 |
| K538G | CTTC | 9.18 |
| K538H | TTTG | 11.31 |
| K538H | CTTC | 10.74 |
| K538L | TTTC | 10.95 |
| K538L | TTTA | 10 |
| K538L | CTTA | 9.31 |
| K538M | TTTG | 13.69 |
| K538M | TTTA | 13.09 |
| K538M | TTTC | 11.36 |
| K538M | CTTC | 10 |
| K538M | CTTA | 9.97 |
| K538Q | CTTC | 13.23 |
| K538Q | TTTC | 12.93 |
| K538Q | TTTA | 12.91 |
| K538Q | CTTA | 11.77 |
| K538Q | TTTG | 11.17 |
| K538Q | CTTG | 11.03 |
| K538R | TTTG | 12.33 |
| K538R | TTTC | 12.28 |
| K538R | TTTA | 12.26 |
| K538R | CTTA | 11.95 |
| K538R | TTTT | 9.32 |
| K538R | CTTG | 9.16 |
| K538V | CTTC | 18.4 |
| K538V | CTTG | 18.05 |
| K538V | TTTA | 17.53 |
| K538V | TTTG | 17.49 |
| K538V | TTTC | 15.98 |

TABLE 4-continued

PAM depletion data

| Mutant | 4mer | Depletion |
|---|---|---|
| K538V | CTTA | 14.13 |
| K538W | TTTC | 11.69 |
| K538W | TTTG | 11.18 |
| K538W | TTTA | 11.03 |
| K538W | TATA | 10.38 |
| K538W | CTTC | 10 |
| K538W | TATC | 9.66 |
| K538W | CTTA | 9.26 |
| K538Y | CTTG | 9.14 |
| K538Y | CTTA | 8.3 |
| K538Y | CTTC | 8.08 |
| K591A | TTTG | 8.62 |
| K591F | TTTA | 13.44 |
| K591F | TTTG | 12.35 |
| K591F | TTTC | 11.17 |
| K591F | TTTT | 10.9 |
| K591G | TTTA | 11.71 |
| K591G | TTTC | 11.25 |
| K591G | TTTT | 10.92 |
| K591G | TTTG | 10.78 |
| K591H | TTTC | 16.42 |
| K591H | TTTA | 14.07 |
| K591H | TTTG | 14.02 |
| K591H | TTTT | 12.41 |
| K591R | TTTG | 10.31 |
| K591R | TTCC | 9.81 |
| K591R | TTTC | 9.07 |
| K591R | CTTG | 8.61 |
| K591S | TTTT | 11.24 |
| K591S | TTCC | 9.81 |
| K591S | TTTA | 9.37 |
| K591S | TTTC | 9.23 |
| K591S | CTTG | 8.98 |
| K591S | TTTG | 8.89 |
| K591S | TTCG | 8.04 |
| K591W | TTTA | 13.93 |
| K591W | TTTC | 11.17 |
| K591W | TTTG | 11.14 |
| K591Y | TTTC | 12.29 |
| K591Y | TTTA | 11.4 |
| K591Y | TTTG | 10.79 |
| K595H | TTGC | 12.45 |
| K595H | TTTT | 11.42 |
| K595H | TTTG | 10.91 |
| K595H | TTCA | 10.39 |
| K595H | TTTC | 10.21 |
| K595H | TTCG | 9.36 |
| K595L | TTTA | 16.84 |
| K595L | TTCC | 15.92 |
| K595L | TTTG | 14.92 |
| K595L | CCTG | 13.79 |
| K595L | TTCG | 13.45 |
| K595L | TTTC | 13.12 |
| K595L | TCTA | 12.6 |
| K595L | TCTC | 12.15 |
| K595L | TCCA | 12.14 |
| K595L | TCTG | 11.7 |
| K595L | ACTC | 11.46 |
| K595L | TCCG | 11.37 |
| K595L | CCTC | 10.6 |
| K595L | TTCA | 10.5 |
| K595L | TCCC | 10.24 |
| K595L | ACTG | 9.69 |
| K595M | TTGC | 13.18 |
| K595M | TTTA | 12.88 |
| K595M | CCTG | 12.36 |
| K595M | TTTG | 12.07 |
| K595M | TCCC | 11.4 |
| K595M | TTTT | 11.26 |
| K595M | CCTC | 10.96 |
| K595M | TCTG | 10.95 |
| K595M | TTTC | 10.84 |
| K595M | TTCA | 10.81 |
| K595M | ACTG | 10.74 |
| K595M | TCTA | 10.34 |
| K595M | TCTT | 10.1 |
| K595M | TCCG | 9.83 |
| K595M | ACGC | 9.6 |
| K595M | TTCC | 9.51 |
| K595M | CCCC | 9.4 |
| K595M | TCGG | 9.21 |
| K595M | GCTG | 9.12 |
| K595M | CTTC | 8.62 |
| K595M | CTTA | 8.14 |
| K595Q | TCCG | 15.13 |
| K595Q | TTCC | 14.56 |
| K595Q | TTCA | 13.57 |
| K595Q | TCTG | 13.57 |
| K595Q | TCTC | 12.93 |
| K595Q | TTTG | 12.45 |
| K595Q | TTTA | 12.22 |
| K595Q | TCTA | 12.06 |
| K595Q | TTCG | 11.85 |
| K595Q | TTTC | 11.69 |
| K595Q | TCCC | 10.62 |
| K595Q | ACCC | 10.09 |
| K595Q | CCCC | 9.21 |
| K595R | TCTT | 8.5 |
| K595R | TCCC | 8 |
| K595S | TCCC | 14.55 |
| K595S | TTGC | 14.34 |
| K595S | TCGC | 14.23 |
| K595S | TTTA | 13.22 |
| K595S | TCTC | 12.48 |
| K595S | TCTA | 12.47 |
| K595S | TCCG | 12.3 |
| K595S | CCGC | 12.29 |
| K595S | ACGC | 11.62 |
| K595S | TTCC | 11.53 |
| K595S | TTTC | 10.96 |
| K595S | TCGG | 10.45 |
| K595S | CCCC | 10.13 |
| K595S | TTCA | 9.48 |
| K595S | TTCG | 8.92 |
| K595W | CCCC | 11.92 |
| K595W | TCGA | 11.62 |
| K595W | ACGG | 11.48 |
| K595W | ACCC | 11.35 |
| K595W | CCTG | 11.35 |
| K595W | TCTC | 11.28 |
| K595W | TTTT | 10.53 |
| K595W | GCCG | 10.42 |
| K595W | TTTA | 10.21 |
| K595W | ACTA | 10.18 |
| K595W | ACGA | 9.87 |
| K595W | GCGC | 9.81 |
| K595W | ATGC | 9.77 |
| K595W | TCGT | 9.71 |
| K595W | ATTG | 9.63 |
| K595W | TCCT | 9.25 |
| K595W | CCGG | 9.19 |
| K595W | TTGT | 9.08 |
| K595W | TCGG | 9.03 |
| K595W | TTCT | 8.95 |
| K595W | ACTG | 8.88 |
| K595Y | ACCC | 18.7 |
| K595Y | TCCC | 18.62 |
| K595Y | ACCG | 18.58 |
| K595Y | CCCG | 18.42 |
| K595Y | TTCG | 17.75 |
| K595Y | GCGC | 17.47 |
| K595Y | TCCA | 16.89 |
| K595Y | CCGC | 16.66 |
| K595Y | CCGG | 16.59 |
| K595Y | GCGG | 16.46 |
| K595Y | TCCG | 16.23 |
| K595Y | CCCC | 16.05 |
| K595Y | TTTC | 15.82 |
| K595Y | TCGA | 14.88 |
| K595Y | TCGG | 14.74 |
| K595Y | TTTA | 14.31 |
| K595Y | CCGA | 14.29 |

TABLE 4-continued

PAM depletion data

| Mutant | 4mer | Depletion |
|---|---|---|
| K595Y | TTTG | 14.12 |
| K595Y | CTGC | 14.03 |
| K595Y | TCGT | 14.01 |
| K595Y | ACGA | 13.83 |
| K595Y | ACGG | 13.62 |
| K595Y | ACGG | 13.55 |
| K595Y | TCTG | 13.36 |
| K595Y | TCTC | 13.31 |
| K595Y | TCGC | 13.26 |
| K595Y | GCCG | 13.19 |
| K595Y | GCCC | 13.15 |
| K595Y | TTGA | 12.32 |
| K595Y | TTCT | 12.28 |
| K595Y | TTCA | 12.22 |
| K595Y | TTGT | 12.12 |
| K595Y | TTGG | 12.01 |
| K595Y | TCTA | 11.81 |
| K595Y | GCGA | 11.57 |
| K595Y | CCCA | 11.52 |
| K595Y | CTCG | 11.51 |
| K595Y | TTGC | 11.46 |
| K595Y | TTCC | 11.3 |
| K595Y | ACCA | 11.3 |
| K595Y | ACTG | 11.29 |
| K595Y | CCTG | 10.54 |
| K595Y | CTCC | 10.3 |
| K595Y | ACTC | 9.54 |
| K595Y | ATGC | 9.28 |
| K600G | ATTG | 14.1 |
| K600G | TTTT | 13.53 |
| K600G | TCTC | 13.48 |
| K600G | CTTG | 13.02 |
| K600G | TTTA | 12.84 |
| K600G | CTTC | 12.82 |
| K600G | TCTG | 12.69 |
| K600G | ATTA | 12.52 |
| K600G | TCTA | 12.41 |
| K600G | TTCA | 12.15 |
| K600G | TTTC | 12.11 |
| K600G | CTTA | 12.01 |
| K600G | TTCG | 11.67 |
| K600G | TTCC | 11.66 |
| K600G | TTTG | 11.58 |
| K600G | TTAC | 11.52 |
| K600G | TCCC | 11.4 |
| K600G | CCTG | 11.38 |
| K600G | CCCC | 10 |
| K600G | GTTA | 9.75 |
| K600G | GTTG | 9.72 |
| K600G | TCCG | 9.69 |
| K600G | TTCT | 9.48 |
| K600G | CCTA | 9.4 |
| K600G | TCCA | 9.38 |
| K600H | CTTC | 16.65 |
| K600H | TTTG | 14.45 |
| K600H | TTCC | 14.11 |
| K600H | TTTT | 13.78 |
| K600H | TTCA | 13.27 |
| K600H | CTTA | 12.42 |
| K600H | TCTA | 12.26 |
| K600H | TCTC | 12.2 |
| K600H | TCCC | 12.16 |
| K600H | ATTG | 12.02 |
| K600H | ATTA | 11.77 |
| K600H | CTTG | 11.23 |
| K600H | TTCG | 11.13 |
| K600H | TTTC | 10.82 |
| K600H | TTAC | 10.54 |
| K600H | GTTC | 9.1 |
| K600H | GTTG | 8.65 |
| K600H | CCGC | 8.41 |
| K600R | ATTC | 13.41 |
| K600R | TTGC | 12.52 |
| K600R | TTCT | 11.83 |
| K600R | TTCC | 11.61 |
| K600R | TTCA | 11.08 |
| K600R | TTTT | 11.07 |
| K600R | CCCC | 11.05 |
| K600R | TCGC | 11.02 |
| K600R | TCTA | 10.96 |
| K600R | GTTC | 10.91 |
| K600R | TCCA | 10.84 |
| K600R | TCCC | 10.63 |
| K600R | CCTC | 10.42 |
| K600R | TTCG | 10.1 |
| K600R | CTCA | 8.96 |
| K601H | CCTG | 14.33 |
| K601H | CTTG | 12.41 |
| K601H | TCTA | 12.13 |
| K601H | TCTC | 11.97 |
| K601H | ATTC | 11.89 |
| K601H | TCCG | 11.84 |
| K601H | TTTG | 11.78 |
| K601H | CCCG | 11.7 |
| K601H | TTTT | 11.35 |
| K601H | CCTA | 11.15 |
| K601H | TTGC | 10.89 |
| K601H | CTTC | 10.79 |
| K601H | TTTC | 10.65 |
| K601H | CTTA | 10.45 |
| K601H | CCCC | 10.42 |
| K601H | TTCG | 10.39 |
| K601H | ATTG | 10.26 |
| K601H | TTTA | 10.21 |
| K601H | ATTA | 10.2 |
| K601H | TTCA | 10.12 |
| K601H | TCTG | 10.09 |
| K601H | CCTC | 9.82 |
| K601H | TCGC | 9.4 |
| K601H | GCTC | 8.68 |
| K601Q | CTTA | 13.97 |
| K601Q | TTTG | 11.17 |
| K601Q | TTTC | 10.17 |
| K601Q | CTTG | 9.73 |
| K601Q | TTTT | 9.44 |
| K601R | TCTA | 12.21 |
| K601R | TTGC | 12.09 |
| K601R | ATTC | 11.08 |
| K601R | TTTT | 10.98 |
| K601R | TTCC | 10.95 |
| K601R | TCTG | 10.8 |
| K601R | TTCA | 10.77 |
| K601R | CCTA | 10.4 |
| K601R | ATTG | 10.33 |
| K601R | CTTG | 10.31 |
| K601R | CTTC | 10.11 |
| K601R | TCTC | 9.85 |
| K601R | TCCG | 9.65 |
| K601R | ATTA | 9.5 |
| K601R | TCCA | 8.91 |
| K601R | CCTG | 8.54 |
| K601R | TTTC | 8.41 |
| K601T | CTTA | 12.42 |
| K601T | TTTG | 11.55 |
| K601T | TTCC | 11.36 |
| K601T | TTCG | 11.26 |
| K601T | TTTT | 11.13 |
| K601T | CTTC | 11.06 |
| K601T | TTTA | 10.99 |
| K601T | TTCA | 10.85 |
| K601T | TTTG | 10.2 |
| K601T | TCCC | 10.17 |
| K601T | TCCG | 9.65 |
| K601T | CCTG | 9.53 |
| K601T | TCTC | 9.29 |
| K601T | CCCC | 8.18 |
| L585F | TTTG | 13.66 |
| L585F | TTTT | 11.79 |
| L585F | TTTA | 11.72 |
| L585F | TTTC | 10.51 |
| L585G | TTCC | 13.33 |
| L585G | TTAC | 11.98 |

TABLE 4-continued

PAM depletion data

| Mutant | 4mer | Depletion |
|---|---|---|
| L585G | CTTG | 11.26 |
| L585G | TTTT | 11.21 |
| L585G | TCCC | 11.09 |
| L585G | TTCA | 10.97 |
| L585G | CTTC | 10.32 |
| L585G | TTTA | 9.92 |
| L585G | TCTC | 9.8 |
| L585G | TTGC | 9.57 |
| L585G | CTTA | 9.48 |
| L585G | TCAC | 9.48 |
| L585G | TTTG | 9.02 |
| L585G | TTTC | 8.8 |
| L585H | TTCC | 9.49 |
| L585H | TTTT | 8.29 |
| L585H | TCTC | 8.06 |
| M592A | TTTG | 15.81 |
| M592A | TTTA | 11.41 |
| M592A | TTTC | 10.98 |
| M592A | CTTA | 10.8 |
| M592A | TTCA | 10.53 |
| M592A | TCTA | 10.38 |
| M592A | TTTT | 9.48 |
| M592E | TTTA | 12.63 |
| M592E | TTTG | 11.85 |
| M592E | TTTC | 11.64 |
| M592Q | TTCA | 12.54 |
| M592Q | TTTA | 10.68 |
| M592Q | TCCG | 10.66 |
| M592Q | CTTG | 10.19 |
| M592Q | TTCG | 9.93 |
| M592Q | CTTA | 9.45 |
| M592Q | CCCG | 9.41 |
| M592Q | TCTG | 9.39 |
| M592Q | TTTG | 9.37 |
| M592Q | CCCA | 9.22 |
| M592Q | TCCC | 9.17 |
| M592Q | TTCC | 9.16 |
| M592Q | CCCC | 8.93 |
| M592Q | TTTC | 8.89 |
| M592Q | CTCA | 8.41 |
| Q529A | TCTG | 13.89 |
| Q529A | CCCC | 13.38 |
| Q529A | TTCC | 12.5 |
| Q529A | ATTC | 12.31 |
| Q529A | TCCA | 12.26 |
| Q529A | TCTC | 12.21 |
| Q529A | TTGC | 11.88 |
| Q529A | CCCG | 11.81 |
| Q529A | TTTT | 11.69 |
| Q529A | TTCG | 11.43 |
| Q529A | TCTA | 11.31 |
| Q529A | CTTC | 11.2 |
| Q529A | ATTG | 10.94 |
| Q529A | CCTA | 10.85 |
| Q529A | ATTA | 10.79 |
| Q529A | TTTA | 10.73 |
| Q529A | CTTA | 10.63 |
| Q529A | CCTG | 10.54 |
| Q529A | CTTG | 10.47 |
| Q529A | TCCG | 10.4 |
| Q529A | CCTC | 10.38 |
| Q529A | TCCC | 10.18 |
| Q529A | TTCA | 10.16 |
| Q529A | TTCT | 9.89 |
| Q529A | CCGC | 9.68 |
| Q529A | TTTG | 9.62 |
| Q529A | TTTC | 9.51 |
| Q529A | GTTA | 9.4 |
| Q529D | TTTC | 13.64 |
| Q529D | TTTT | 13.03 |
| Q529D | TTTG | 12.45 |
| Q529D | TTCC | 12.36 |
| Q529D | CTTC | 12.27 |
| Q529D | TTTA | 12.24 |
| Q529D | TTGC | 10.98 |
| Q529D | CTTG | 10.85 |
| Q529D | CTTA | 10.81 |
| Q529D | TTCA | 10.36 |
| Q529D | TCCC | 8.52 |
| Q529F | CTTA | 14.01 |
| Q529F | CTTG | 13.75 |
| Q529F | TTTG | 12.84 |
| Q529F | TTTA | 11.62 |
| Q529F | TTTC | 10.91 |
| Q529G | CTTC | 13.9 |
| Q529G | TTCA | 11.91 |
| Q529G | TCTA | 11.71 |
| Q529G | CCCC | 11.18 |
| Q529G | TTTA | 10.86 |
| Q529G | TCTG | 10.79 |
| Q529G | TTTC | 10.63 |
| Q529G | CTTA | 10.61 |
| Q529G | TTTG | 10.19 |
| Q529G | CTTG | 9.88 |
| Q529G | CCTA | 9.67 |
| Q529G | TCCC | 9.5 |
| Q529G | TTCG | 9.15 |
| Q529G | TCTC | 9.11 |
| Q529G | ATTC | 8.98 |
| Q529G | CCTG | 8.96 |
| Q529G | ATTA | 8.33 |
| Q529G | TCGC | 8.2 |
| Q529G | TCCG | 8.11 |
| Q529H | TTTC | 11.09 |
| Q529H | CTTG | 10.43 |
| Q529H | TTTA | 10.39 |
| Q529H | TTCC | 10.29 |
| Q529H | TTCG | 10.26 |
| Q529H | CTTC | 9.59 |
| Q529H | ATTG | 9.52 |
| Q529H | TTTG | 9.12 |
| Q529H | TTCA | 9.07 |
| Q529H | ATTA | 8.47 |
| Q529N | TCGC | 13.73 |
| Q529N | TCTC | 13.48 |
| Q529N | TCCG | 12.62 |
| Q529N | TTTT | 12.48 |
| Q529N | TCTG | 12.38 |
| Q529N | TTGC | 12.3 |
| Q529N | TTCC | 12.2 |
| Q529N | TCCA | 11.98 |
| Q529N | TCCC | 11.38 |
| Q529N | TCTA | 11.04 |
| Q529N | TTCA | 10.89 |
| Q529N | TTCG | 10.81 |
| Q529N | ATTC | 10.79 |
| Q529N | CCCC | 10.6 |
| Q529N | TTTA | 10.57 |
| Q529N | CTTG | 10.24 |
| Q529N | CTTA | 10.18 |
| Q529N | TTCT | 9.91 |
| Q529N | CTTC | 9.87 |
| Q529N | ATTA | 9.85 |
| Q529N | TTTC | 9.83 |
| Q529N | CCTA | 9.49 |
| Q529N | GTTA | 9.32 |
| Q529N | GTTC | 9.18 |
| Q529N | TCTT | 8.71 |
| Q529N | TCAC | 8.3 |
| Q529N | CCCG | 8.23 |
| Q529P | TTTA | 14.13 |
| Q529P | TTTG | 12.06 |
| Q529P | TTTC | 10.87 |
| Q529S | TTCA | 11.88 |
| Q529S | CTTA | 11.14 |
| Q529S | TTTG | 11.09 |
| Q529S | TTTA | 11.06 |
| Q529S | TCTA | 10.17 |
| Q529S | TTTC | 10.1 |
| Q529S | CCCC | 10.1 |
| Q529S | TTTT | 10.03 |
| Q529S | TTCC | 10.02 |

TABLE 4-continued

PAM depletion data

| Mutant | 4mer | Depletion |
|---|---|---|
| Q529S | CTTG | 9.9 |
| Q529S | TCCC | 9.77 |
| Q529S | TCTG | 9.68 |
| Q529S | ATTA | 8.81 |
| Q529T | CTTG | 15.39 |
| Q529T | TTCA | 14.62 |
| Q529T | TCTG | 13.74 |
| Q529T | TCTC | 13.63 |
| Q529T | TCTA | 13.2 |
| Q529T | TTCC | 13.17 |
| Q529T | TTTT | 12.6 |
| Q529T | TCCG | 12.44 |
| Q529T | TCCA | 12.34 |
| Q529T | ATTA | 12.15 |
| Q529T | CTTC | 12.13 |
| Q529T | TTCG | 11.89 |
| Q529T | TCCC | 11.35 |
| Q529T | TTGC | 11.17 |
| Q529T | CCTA | 11.07 |
| Q529T | GTTG | 10.96 |
| Q529T | ATTG | 10.9 |
| Q529T | TTTC | 10.88 |
| Q529T | TTTA | 10.73 |
| Q529T | TTTG | 10.51 |
| Q529T | ATTC | 10.41 |
| Q529T | CTTA | 10.37 |
| Q529T | CCTC | 10.12 |
| Q529T | TCGC | 10.06 |
| Q529T | GTTA | 9.83 |
| Q529T | CCCC | 9.78 |
| Q529T | GTTC | 9.72 |
| Q529T | CCTG | 9.3 |
| Q529T | TTCT | 8.86 |
| Q529T | TTAC | 7.99 |
| Q529W | TTTG | 15.75 |
| Q529W | CTTA | 14.5 |
| Q529W | TTTA | 12.69 |
| Q529W | TTTC | 11.31 |
| Q529W | CTTC | 9.28 |
| S599G | CTTG | 12.09 |
| S599G | TTTT | 11.66 |
| S599G | TTTA | 10.2 |
| S599G | TTCC | 9.87 |
| S599G | CCCC | 9.47 |
| S599G | TTCA | 9.36 |
| S599H | TTTA | 10.82 |
| S599H | TTTG | 9.61 |
| S599N | CTTA | 13.93 |
| S599N | TTTG | 13.04 |
| S599N | TTTA | 11.64 |
| S599N | TTTC | 11.3 |
| S599N | CTTC | 11.15 |
| S599N | CTTG | 10.54 |
| S599N | TTCA | 8.73 |
| T148A | TTTC | 13.06 |
| T148A | TTTA | 11.98 |
| T148A | TTTT | 11.53 |
| T148A | TTGC | 11.48 |
| T148A | TTTG | 11.33 |
| T148A | TTCC | 10.97 |
| T148A | CTTG | 9.83 |
| T148A | TTCA | 9.26 |
| T148C | TTCA | 15.44 |
| T148C | TTTG | 15.17 |
| T148C | TTTC | 15.09 |
| T148C | CTTG | 14.75 |
| T148C | CTTA | 13.98 |
| T148C | CTTC | 13.67 |
| T148C | TTTT | 13.43 |
| T148C | TTTA | 13.16 |
| T148C | TTCC | 12.16 |
| T148C | TTGC | 11.1 |
| T148C | TCTA | 10.77 |
| T148C | GTTG | 10.01 |
| T148C | TCTC | 9.93 |
| T148H | TTTC | 14.35 |
| T148H | TTTG | 13.68 |
| T148H | TTTA | 13.64 |
| T148S | TTTT | 13.35 |
| T148S | CTTA | 12.93 |
| T148S | TTTA | 12.48 |
| T148S | TTCG | 12.31 |
| T148S | TTCA | 11.85 |
| T148S | TTGC | 11.56 |
| T148S | TTTG | 11.55 |
| T148S | TTCC | 11.39 |
| T148S | TTTC | 11.01 |
| T148S | CTTC | 11.01 |
| T148S | CTTG | 10.8 |
| T148S | ATTA | 9.58 |
| T148S | TCTA | 8.54 |
| T148S | ATTG | 8.31 |
| T149C | TTTC | 11.35 |
| T149C | TTTA | 11.08 |
| T149C | TTTG | 10.49 |
| T149C | CTTA | 10.35 |
| T149C | TTTT | 9.98 |
| T149F | TTTC | 13.56 |
| T149F | TTTG | 13.11 |
| T149F | TTTA | 11.72 |
| T149G | TTTG | 12.06 |
| T149G | TTTA | 10.59 |
| T149G | CTTG | 10.14 |
| T149G | TCCC | 10.11 |
| T149G | GTTG | 10.08 |
| T149G | TTTC | 9.96 |
| T149G | TTCA | 9.78 |
| T149G | TTTT | 9.77 |
| T149G | CCCC | 9.29 |
| T149G | ATTG | 9.26 |
| T149G | TTCC | 9.2 |
| T149G | CTTC | 8.83 |
| T149G | TCTA | 8.83 |
| T149G | ATTC | 8.6 |
| T149G | TCCG | 8.58 |
| T149G | CCCG | 8.57 |
| T149G | TCTC | 8.45 |
| T149H | TTTA | 15.77 |
| T149H | TTTC | 11.31 |
| T149N | TTTA | 13.97 |
| T149N | TTTC | 13.27 |
| T149N | TTTG | 10.86 |
| T149P | TTTC | 10.27 |
| T149P | TTTA | 10.14 |
| T149P | TTTG | 9.22 |
| T149S | TTCC | 14.11 |
| T149S | CTTC | 14.01 |
| T149S | ATTG | 13.88 |
| T149S | TCTG | 13.24 |
| T149S | TTCA | 12.74 |
| T149S | ATTC | 12.36 |
| T149S | CTTA | 12.32 |
| T149S | TTTT | 12.24 |
| T149S | CTTG | 11.87 |
| T149S | CCTG | 11.55 |
| T149S | ATTA | 11.51 |
| T149S | TCTC | 11.38 |
| T149S | TTCG | 11.34 |
| T149S | TCTA | 11.17 |
| T149S | GTTA | 10.66 |
| T149S | GTTC | 10.45 |
| T149S | GTTG | 10.44 |
| T149S | TCGC | 10.43 |
| T149S | CCCC | 10.4 |
| T149S | TCCG | 10.35 |
| T149S | TTGC | 10.2 |
| T149S | TCCA | 9.82 |
| T149S | CCTA | 9.7 |
| T149S | TTTC | 9.68 |
| T149S | TCCC | 9.33 |
| T149S | TTCT | 9.18 |
| T149S | TTTA | 9.08 |

TABLE 4-continued

PAM depletion data

| Mutant | 4mer | Depletion |
|---|---|---|
| T149S | CCGC | 8.88 |
| T149S | CCCG | 8.63 |
| T149S | CCTC | 8.45 |
| T149V | TTCA | 13.47 |
| T149V | TTTA | 13.34 |
| T149V | TTCC | 12.51 |
| T149V | TTTG | 12.3 |
| T149V | TTTT | 11.86 |
| T149V | TTCG | 11.21 |
| T149V | TTTC | 10.58 |
| T149V | TCCC | 9.41 |
| T149V | CTTG | 8.81 |
| T149V | TCTC | 8.75 |
| T152E | CCTC | 18.07 |
| T152E | CTTC | 16.54 |
| T152E | TTGC | 15.59 |
| T152E | TTCA | 14.71 |
| T152E | TCTG | 14.5 |
| T152E | TCCC | 14.43 |
| T152E | TCGC | 14.25 |
| T152E | TCTC | 14.21 |
| T152E | GTTC | 14.11 |
| T152E | TTTC | 14.1 |
| T152E | TTTT | 14.1 |
| T152E | ATTC | 13.83 |
| T152E | CTTG | 13.72 |
| T152E | TTTA | 13.71 |
| T152E | TCCG | 13.52 |
| T152E | CCCC | 12.98 |
| T152E | TTCC | 12.87 |
| T152E | TTCG | 12.63 |
| T152E | ACTC | 12.45 |
| T152E | CCGC | 12.05 |
| T152E | GCGC | 12.01 |
| T152E | CTTA | 11.75 |
| T152E | TTTG | 11.67 |
| T152E | TTCT | 11.58 |
| T152E | TCAC | 10.76 |
| T152E | CCAC | 10.72 |
| T152E | GTTG | 10.4 |
| T152F | TTCC | 16.18 |
| T152F | CTTC | 15.86 |
| T152F | CTTA | 15.51 |
| T152F | TTTC | 14.6 |
| T152F | TTGC | 14.54 |
| T152F | TTCA | 14.36 |
| T152F | TTTT | 13.43 |
| T152F | TTTG | 13.17 |
| T152F | CTTG | 12.61 |
| T152F | ATTA | 12.5 |
| T152F | TCTC | 11.97 |
| T152F | TTCG | 11.93 |
| T152F | TCCC | 11.76 |
| T152F | TTTA | 11.14 |
| T152F | TCGC | 10.44 |
| T152F | CCCC | 9.98 |
| T152H | TCCC | 12.04 |
| T152H | TTGC | 11.41 |
| T152H | CCCC | 11.3 |
| T152H | TTTT | 11.27 |
| T152H | CTTA | 11.1 |
| T152H | TTCC | 11.06 |
| T152H | TCTC | 10.51 |
| T152H | CTTG | 10.27 |
| T152H | TTTC | 10.23 |
| T152H | TTTA | 10.06 |
| T152H | TCGC | 10.02 |
| T152H | ATTC | 10.01 |
| T152H | TTTG | 9.94 |
| T152H | TCTG | 9.88 |
| T152H | CCTC | 9.85 |
| T152H | CTTC | 9.81 |
| T152H | TCCG | 9.76 |
| T152H | TTCA | 9.71 |
| T152H | ATTA | 9.64 |
| T152H | TCTA | 9.63 |
| T152H | TTCT | 9.34 |
| T152H | TCCA | 9.05 |
| T152H | TTAC | 8.95 |
| T152H | ATTG | 8.74 |
| T152H | TTCG | 8.46 |
| T152K | CTTG | 14.08 |
| T152K | CCGC | 13.88 |
| T152K | CCTA | 13.58 |
| T152K | ATTA | 13.28 |
| T152K | ACTC | 13.28 |
| T152K | TCCC | 13.26 |
| T152K | GTTG | 13.22 |
| T152K | GCTC | 13.21 |
| T152K | CCCC | 12.99 |
| T152K | TTCT | 12.84 |
| T152K | TCAC | 12.63 |
| T152K | GCTA | 12.51 |
| T152K | CCTG | 12.5 |
| T152K | CTTA | 12.46 |
| T152K | GTTC | 12.46 |
| T152K | ATTG | 12.29 |
| T152K | ATTC | 12.24 |
| T152K | TCTC | 12.23 |
| T152K | TCTG | 12.2 |
| T152K | CTTC | 12.12 |
| T152K | TTCA | 11.99 |
| T152K | TTCG | 11.88 |
| T152K | CCTC | 11.81 |
| T152K | CCAC | 11.76 |
| T152K | ACTG | 11.5 |
| T152K | TCTA | 11.44 |
| T152K | GCGC | 11.41 |
| T152K | TCGC | 11.15 |
| T152K | TCCA | 11.08 |
| T152K | GTTA | 10.94 |
| T152K | TTAC | 10.94 |
| T152K | CTCC | 10.78 |
| T152K | TTTA | 10.44 |
| T152K | TCGA | 10.16 |
| T152K | ACTA | 10.14 |
| T152K | TTCC | 10.09 |
| T152K | GCCC | 9.97 |
| T152K | TTTT | 9.85 |
| T152K | ACGC | 9.71 |
| T152K | TTGC | 9.68 |
| T152K | GCTG | 9.59 |
| T152K | TCCG | 9.4 |
| T152K | TTGA | 9.39 |
| T152K | CCCG | 9.34 |
| T152K | ACCC | 9.3 |
| T152K | TTTG | 9.21 |
| T152K | CTTT | 8.75 |
| T152L | CTTA | 15.37 |
| T152L | ATTC | 14.54 |
| T152L | TCGC | 13.95 |
| T152L | TCTA | 13.76 |
| T152L | CTTG | 13.75 |
| T152L | CTTC | 13.54 |
| T152L | TCTC | 13.15 |
| T152L | CCCC | 12.44 |
| T152L | TTGC | 12.23 |
| T152L | TTCC | 12.04 |
| T152L | TTCG | 11.39 |
| T152L | ATTG | 10.85 |
| T152L | TTTT | 10.5 |
| T152L | CCTA | 10.43 |
| T152L | TTAC | 10.32 |
| T152L | GTTG | 9.55 |
| T152L | CCTC | 9.38 |
| T152L | TCTG | 9.22 |
| T152L | TTTA | 8.96 |
| T152L | CCTG | 8.96 |
| T152Q | TCGC | 11.48 |
| T152Q | CCTG | 11.36 |
| T152Q | CCTA | 11.27 |
| T152Q | CCCA | 10.85 |

TABLE 4-continued

PAM depletion data

| Mutant | 4mer | Depletion |
|---|---|---|
| T152Q | TCAC | 9.99 |
| T152Q | CCGC | 9.9 |
| T152Q | ATTC | 9.85 |
| T152Q | TCTG | 9.82 |
| T152Q | CTTC | 9.78 |
| T152Q | TTGC | 9.7 |
| T152Q | TCTC | 9.7 |
| T152Q | GTTG | 9.64 |
| T152Q | TTGA | 9.56 |
| T152Q | TCTA | 9.37 |
| T152Q | ATTG | 9.12 |
| T152Q | TTAG | 9.09 |
| T152Q | TTCT | 9.04 |
| T152Q | ATTA | 8.96 |
| T152Q | TTGG | 8.65 |
| T152Q | TCCA | 8.57 |
| T152Q | TTTG | 8.56 |
| T152Q | ACTC | 8.52 |
| T152Q | GCCC | 8.37 |
| T152Q | TTTT | 8.32 |
| T152Q | CTTA | 7.83 |
| T152Q | TTCC | 7.74 |
| T152Q | TTCG | 7.35 |
| T152R | CTTC | 16.05 |
| T152R | CCTG | 14.82 |
| T152R | CCTC | 13.67 |
| T152R | GCCC | 12.97 |
| T152R | CCCC | 12.95 |
| T152R | GTTG | 12.67 |
| T152R | GCCG | 12.64 |
| T152R | ACTC | 12.49 |
| T152R | CCGC | 12.38 |
| T152R | CCGG | 12.22 |
| T152R | TCGA | 12.16 |
| T152R | CTGC | 11.86 |
| T152R | CCCG | 11.78 |
| T152R | TCGG | 11.59 |
| T152R | ATTA | 11.55 |
| T152R | CCCA | 11.27 |
| T152R | TCAG | 11.2 |
| T152R | TTCA | 11.03 |
| T152R | CTTA | 10.87 |
| T152R | CCTA | 10.82 |
| T152R | ATTG | 10.8 |
| T152R | TTCG | 10.71 |
| T152R | TCCG | 10.7 |
| T152R | ACGA | 10.69 |
| T152R | TCCA | 10.66 |
| T152R | ATTC | 10.62 |
| T152R | TCGT | 10.58 |
| T152R | GCAC | 10.54 |
| T152R | TTAC | 10.46 |
| T152R | TCTA | 10.44 |
| T152R | ACCC | 10.44 |
| T152R | GCTA | 10.41 |
| T152R | TTTT | 10.4 |
| T152R | GCCA | 10.38 |
| T152R | GTTA | 10.31 |
| T152R | ACTG | 10.25 |
| T152R | GCTG | 10.24 |
| T152R | GCGA | 10.23 |
| T152R | ACTA | 10.21 |
| T152R | TTGT | 10.12 |
| T152R | TTCT | 10.07 |
| T152R | GCTC | 10.05 |
| T152R | ACCG | 10.01 |
| T152R | CCGA | 9.99 |
| T152R | TCGC | 9.92 |
| T152R | GTTC | 9.85 |
| T152R | CTCG | 9.82 |
| T152R | GCGG | 9.74 |
| T152R | TTAG | 9.7 |
| T152R | TCCC | 9.66 |
| T152R | TCTC | 9.58 |
| T152R | ACCA | 9.58 |
| T152R | CTTG | 9.53 |
| T152R | TTGG | 9.53 |
| T152R | CTCA | 9.17 |
| T152R | TTGC | 9.03 |
| T152R | ACGG | 8.22 |
| T152W | TTGC | 16.19 |
| T152W | TTCA | 14.29 |
| T152W | TTCG | 13.39 |
| T152W | TTCC | 13.36 |
| T152W | TTTT | 13.32 |
| T152W | TCTA | 12.94 |
| T152W | TTTG | 12.53 |
| T152W | CTTC | 12.39 |
| T152W | CTTG | 12.21 |
| T152W | ATTA | 12.11 |
| T152W | TCCG | 12.04 |
| T152W | CCTG | 11.72 |
| T152W | CTTA | 11.67 |
| T152W | TTTC | 11.21 |
| T152W | TTTA | 11.1 |
| T152W | ATTG | 11.02 |
| T152W | CCTA | 10.57 |
| T152W | TCTC | 10.48 |
| T152W | TTAC | 10.29 |
| T152W | ATTC | 9.95 |
| T152W | GTTA | 9.86 |
| T152W | GTTC | 9.45 |
| T152Y | TCCA | 16.58 |
| T152Y | TCTG | 15.9 |
| T152Y | TCTC | 18.89 |
| T152Y | CCTC | 14.57 |
| T152Y | TCTA | 15.43 |
| T152Y | TTAC | 15.31 |
| T152Y | CCTG | 15.3 |
| T152Y | CTTG | 15.16 |
| T152Y | ACTG | 14.71 |
| T152Y | GCTA | 14.52 |
| T152Y | ATTA | 14.36 |
| T152Y | ACTC | 14.29 |
| T152Y | ATTG | 14.24 |
| T152Y | TTCG | 14.05 |
| T152Y | CCGC | 13.93 |
| T152Y | GCCC | 13.92 |
| T152Y | TCCG | 13.65 |
| T152Y | CTTC | 13.65 |
| T152Y | GCTC | 13.61 |
| T152Y | GTTG | 13.55 |
| T152Y | TCAC | 13.42 |
| T152Y | ATTC | 13.38 |
| T152Y | CTTA | 13.2 |
| T152Y | TTGC | 13.03 |
| T152Y | TCGC | 12.87 |
| T152Y | GTTA | 12.47 |
| T152Y | TCCC | 12.23 |
| T152Y | ACTA | 12.07 |
| T152Y | CCTA | 12.04 |
| T152Y | GCTG | 11.97 |
| T152Y | ACGC | 11.96 |
| T152Y | TTCA | 11.9 |
| T152Y | TTCC | 11.9 |
| T152Y | GTTC | 11.89 |
| T152Y | TCGG | 11.8 |
| T152Y | TTCT | 11.68 |
| T152Y | CCCC | 11.49 |
| T152Y | CCAC | 11.49 |
| T152Y | GCGC | 11.42 |
| T152Y | CCCA | 11.39 |
| T152Y | GCAC | 11.15 |
| T152Y | TTGA | 10.7 |
| T152Y | CTCC | 10.58 |
| T152Y | CCCG | 10.42 |
| T152Y | CTTT | 10.32 |
| T152Y | TTTT | 10.31 |
| T152Y | ACCC | 10.09 |
| T152Y | TTGG | 9.8 |
| T152Y | TTTC | 9.37 |
| T152Y | ACAC | 8.65 |

TABLE 4-continued

PAM depletion data

| Mutant | 4mer | Depletion |
|---|---|---|
| V596H | TTTG | 11.75 |
| V596H | TTTC | 11.08 |
| V596T | CTTA | 20.31 |
| V596T | TTTG | 16.49 |
| V596T | TTCA | 15.21 |
| V596T | CTTG | 14.59 |
| V596T | TTTA | 14.55 |
| V596T | CTTC | 14.43 |
| V596T | TCTA | 13.11 |
| V596T | TTCC | 13 |
| V596T | TTGC | 12.93 |
| V596T | TCCC | 12.65 |
| V596T | TTTT | 12.27 |
| V596T | TCTC | 12.27 |
| V596T | TCTG | 12.07 |
| V596T | CCCC | 12.03 |
| V596T | TTTC | 12.02 |
| V596T | TTCG | 10.87 |
| V596T | CCCG | 9.96 |
| V596T | TCCG | 9.6 |
| V596T | GTTC | 9.3 |
| V596T | GCGC | 9.17 |
| W649H | TTTC | 11.36 |
| W649H | TTTA | 11.18 |
| W649H | TTTG | 10.47 |
| W649K | TTTA | 13.34 |
| W649R | TTTA | 8.84 |
| W649S | TTTA | 9.77 |
| W649Y | TTTC | 11.78 |
| W649Y | TTTG | 11.48 |
| W649Y | TTTA | 11.05 |
| Y542F | TTTA | 11.24 |
| Y542F | TTTC | 10.25 |
| Y542F | TTTG | 9.9 |
| Y542H | CTTA | 11.46 |
| Y542H | TTTT | 11.44 |
| Y542H | CTTA | 10.96 |
| Y542H | TTTC | 10.6 |
| Y542H | TCCC | 10.37 |
| Y542H | GTTA | 10.23 |
| Y542H | TTCG | 10.16 |
| Y542H | TTCA | 10.06 |
| Y542H | TTTG | 10.04 |
| Y542H | CCAC | 8.42 |
| Y542H | GCTC | 8.27 |
| Y542K | TTTA | 10.62 |
| Y542K | TTTG | 9.4 |
| Y542K | TTCA | 8.45 |
| Y542L | CTTA | 12.93 |
| Y542L | TTTA | 10.46 |
| Y542L | TTTC | 10.2 |
| Y542L | TTTG | 10.04 |
| Y542M | TTTG | 11.54 |
| Y542M | TTTA | 11.15 |
| Y542M | TTTC | 10.32 |
| Y542M | CTTG | 10.17 |
| Y542M | CTTA | 10.05 |
| Y542M | CTTC | 8.67 |
| Y542N | TTGC | 11.39 |
| Y542N | TTTA | 11.38 |
| Y542N | TTTG | 11.27 |
| Y542N | TTCC | 11.06 |
| Y542N | TTTT | 10.31 |
| Y542N | GTTC | 10.16 |
| Y542N | CCCC | 9.87 |
| Y542N | ATTA | 9.39 |
| Y542N | TCCC | 9.37 |
| Y542N | TTTC | 9.21 |
| Y542R | TTTT | 10.21 |
| Y542R | CTTG | 8.75 |
| Y542R | TTCA | 8.73 |
| Y542R | TCCC | 8.68 |
| Y542R | GTTA | 7.7 |
| Y542T | TTTA | 11.46 |
| Y542T | TTTC | 9.68 |
| Y542T | TTTG | 9.59 |
| Y542V | TTTG | 12.03 |
| Y542V | TTTA | 10.76 |
| Y616E | TTTG | 12.92 |
| Y616E | TTTA | 12.58 |
| Y616E | TTTC | 12.02 |
| Y616F | TTTT | 12.56 |
| Y616F | TTTA | 12.36 |
| Y616F | CTTA | 12.33 |
| Y616F | CTTG | 11.97 |
| Y616F | TTTG | 11.74 |
| Y616F | TTCA | 11.5 |
| Y616F | ATTG | 11.46 |
| Y616F | CTTC | 11.34 |
| Y616F | TTCC | 11.06 |
| Y616F | TCTA | 10.99 |
| Y616F | ATTA | 10.97 |
| Y616F | TTTC | 10.79 |
| Y616F | TTCT | 10.63 |
| Y616F | GTTG | 10.46 |
| Y616F | TTGC | 9.95 |
| Y616F | TTCG | 9.74 |
| Y616F | TCTG | 9.65 |
| Y616F | ATTC | 9.45 |
| Y616F | TTAC | 8.77 |
| Y616H | CTTA | 12.23 |
| Y616H | CTTG | 11.73 |
| Y616H | TTTC | 11.26 |
| Y616H | CTTC | 11.18 |
| Y616H | TTTT | 11.11 |
| Y616H | TTTA | 11 |
| Y616H | TTTG | 11 |
| Y616H | TTCA | 10.45 |
| Y616H | TTCC | 10.28 |
| Y616H | TTGC | 10.16 |
| Y616K | TTTG | 9.23 |
| Y616K | TTCC | 8.66 |
| Y616R | TTTG | 10.22 |
| Y616R | TTCC | 9.77 |
| Y646E | TTTA | 13.43 |
| Y646E | CTTA | 12.79 |
| Y646E | TTTT | 11.99 |
| Y646E | TTTG | 11.63 |
| Y646E | TTTC | 11.28 |
| Y646E | CTTC | 11.26 |
| Y646E | CTTG | 10.71 |
| Y646E | TTCC | 9.96 |
| Y646H | TTGC | 13.8 |
| Y646H | GTTC | 12.39 |
| Y646H | GTTA | 12.24 |
| Y646H | TCTA | 11.57 |
| Y646H | TCTC | 11.45 |
| Y646H | ATTA | 10.92 |
| Y646H | TTCT | 10.69 |
| Y646H | TCTG | 10.57 |
| Y646H | TCCC | 10.3 |
| Y646H | CTTC | 10.25 |
| Y646H | ATTG | 10.23 |
| Y646H | CTTG | 10.13 |
| Y646H | TTCC | 9.81 |
| Y646H | CCTG | 9.69 |
| Y646H | ATTC | 9.61 |
| Y646H | GTTG | 9.13 |
| Y646K | TTTT | 10.71 |
| Y646K | CTTA | 9.82 |
| Y646K | TTTC | 9.2 |
| Y646N | TTCA | 10.45 |
| Y646N | ATTA | 10.38 |
| Y646N | TTTA | 8.91 |
| Y646N | TCTA | 8.61 |
| Y646Q | ATTA | 11.69 |
| Y646Q | ATTG | 11.67 |
| Y646Q | TCTA | 11.39 |
| Y646Q | TTCC | 11.24 |
| Y646Q | CTTC | 10.99 |
| Y646Q | TTTT | 10.98 |
| Y646Q | TTCA | 10.58 |

TABLE 4-continued

PAM depletion data

| Mutant | 4mer | Depletion |
|---|---|---|
| Y646Q | CTTA | 9.82 |
| Y646Q | TCTC | 9.52 |
| Y646Q | TTTG | 9.27 |
| Y646R | TTTC | 10.17 |
| Y646R | TCTA | 9.17 |
| Y646R | TTTA | 8.09 |
| Y646W | TTTT | 10.69 |
| Y646W | TTTC | 9.78 |
| Y646W | CTTG | 9.6 |

We observed 36 unique PAM sequences cleaved in vitro using two LbCas12a controls. This is in line with the observation that in vitro wtLbCas12a can recognize and cleave more sequences than just TTTV. TTCN, CTTN, TCTN, and others have been shown to be recognized and cleaved by LbCas12a in vitro, where AsCas12a was shown only to cleave TTTN (Zetsche et al. Cell 163:759-771 (2015)).

Some of the mutants increased the total number of PAM sequences recognition and cleavage in vitro (Table 5) as compared to wtLbCas12a. This does not speak to the absolute PAM recognition sequences, but to the overall promiscuity imparted by individual mutations. Some individual point mutants were more promiscuous than wildtype. For example, T152R recognized 57 different PAMs and K959Y recognized 45.

TABLE 5

Some of the more promiscuous LbCas12a mutants as judged by the number of PAMs (nPAM) the recognized and cleaved in vitro.

| Mutant | nPAM |
|---|---|
| T152R | 57 |
| T152Y | 50 |
| T152K | 47 |
| D156Q | 45 |
| K595Y | 45 |
| D156L | 43 |
| D122H | 39 |
| K116R | 39 |
| D156K | 38 |
| K121S | 38 |
| K121R | 37 |
| wildtype | 36 |

Comparing Depletions to Wildtype LbCas12a

In vitro wtLbCas12a can recognize and cleave more sequences than just TTTV (Zetsche et al. Cell 163:759-771 (2015)). TTCN, CTTN, TCTN, and others have been shown to be recognized and cleaved by LbCas12a in vitro, where AsCas12a was shown only to cleave TTTN (Zetsche et al. Cell 163:759-771 (2015)). The goal of this study was to expand LbCas12a's PAM recognition beyond its wildtype capabilities. To this end, we employed a different analysis than library depletion scores alone. Those scores are important for determining absolute PAM recognition and cleavage in vitro, but do not readily highlight the changes to the PAM recognition by the enzyme due to the introduced point mutations.

First, the 5 nucleotide depletion results were collapsed into 4 nucleotide PAMS, as before. Each time point was maintained individually. Each mutant-time point NGS total counts were normalized to 100 counts per PAM to account for loading differences on the NGS chip. Then the global medians for each 4 nt PAMs were compared to each mutant-time point. This provided a depletion as compared to wildtype, rather than a depletion as compared to the total library. The results highlight which mutations changed the PAM recognition profiles. We took a conservative approach and chose a depletion score of 4 or over as an indication of new PAM recognition by a mutant. A depletion score of 4 indicated four times as much of that particular PAM-containing library member was cleaved as compared to the median for wildtype. For example if 100 NGS counts were remaining for a PAM with GCGC for wildtype and 25 counts remained for a particular mutant-time point, then a score of 4 was calculated.

A summary of each of the 186 mutations is shown below in Table 6. Mutations provided in bold lettering indicates that the mutation recognized and cleaved more than 3 new PAM sequences as compared to wildtype with a score above 4. Mutations provided in italics indicates the mutant acquired between 1 and 3 or new PAM sequences as compared to wildtype with a score above 4. Mutations in regular font (not bolded or italicized) indicates the point mutation did not cleave new PAM sequences as compared to wildtype with a score above 4. Certain amino acids, such as T149 did not acquire new PAM recognitions despite being near the PAM-recognition domain of the protein and testing 10 new amino acids. Other amino acids, such as D156, appeared to be a hot-spot for engineering new PAM recognition motifs. Aspartate 156 when changed to 10 differing amino acids had with 7 mutations recognizing multiple new PAMs, 1 showing a few new PAMs, and two not acquiring new PAMs as compared to wtLbCAs12a. In general, any locations which showed a difference in PAM recognition and cleavage as compared to wildtype could be combined into double, triple, or multiple mutations to further alter PAM recognition. In total 130/186 point mutations did not acquire new PAMs over wtLbCas12a (regular font/not bold or italicized) above a score of 4, 40/186 acquired many new PAMs (bold font), and 16/186 acquired 1-3 new PAMs (italicized font). An overall 30% success rating (56/186) indicates an efficacious method was used to design novel PAM recognition motifs by making point mutations to LbCas12a.

TABLE 6

Summary table for the 186 LbCas12a point mutations (reference sequence SEQ ID NO: 1).

| | | | | | | | | | | | | |
|---|---|---|---|---|---|---|---|---|---|---|---|---|
| K116R | K120R | K121S | D122R | E125R | T148H | T149A | T152R | D156R | E159K | Q529N | G532D | D535N |
| K116N | K120H | K121T | D122K | E125K | T148S | T149C | T152K | D156K | E159R | Q529T | G532N | D535H |
| | K120N | K121H | D122H | E125Q | T148A | T149S | T152W | D156Y | E159H | Q529H | G532S | D535V |
| | K120T | K121R | D122E | E125Y | T148C | T149G | T152Y | D156W | E159Y | Q529A | G532H | D535T |
| | K120Y | K121G | D122N | | | T149H | T152H | D156Q | E159Q | Q529F | G532F | D535S |
| | K120Q | K121D | | | | T149P | T152Q | D156H | | Q529G | G532K | D535A |
| | | K121Q | | | | T149F | T152E | D156I | | Q529S | G532R | D535W |
| | | | | | | T149N | T152L | D156V | | Q529P | G532Q | D535K |

TABLE 6-continued

Summary table for the 186 LbCas12a point mutations (reference sequence SEQ ID NO: 1).

| | | | | | | T149D<br>T149V | T152F | D156L<br>D156E | | Q529W<br>Q529D | G532A<br>G532L<br>G532C | | |
|---|---|---|---|---|---|---|---|---|---|---|---|---|---|
| K538R | D541N | Y542R | L585G | K591W | M592R | K595R | V596T | S599G | K600R | K601R | Y616K | Y646R | W649H |
| K538V | D541H | Y542K | L585H | K591F | M592K | K595Q | V596H | S599H | K600H | K601H | Y616R | Y646E | W649K |
| K538Q | D541R | Y542H | L585F | K591Y | M592Q | K595Y | V596G | S599N | K600G | K601Q | Y616E | Y646K | W649R |
| K538W | D541K | Y542Q | | K591H | M592E | K595L | V596A | S599D | | K601T | Y616F | Y646H | W649Y |
| K538Y | D541Y | Y542F | | K591R | M592A | K595W | | | | | Y616H | Y646Q | W649E |
| K538F | D541I | Y542L | | K591S | | K595H | | | | | | Y646W | W649S |
| K538H | D541A | Y542M | | K591A | | K595E | | | | | | Y646N | W649V |
| K538L | D541S | Y542P | | K591G | | K595S | | | | | | | W649T |
| K538M | D541E | Y542V | | K591P | | K595D | | | | | | | |
| K538C | | Y542N | | | | K595M | | | | | | | |
| K538G | | Y542T | | | | | | | | | | | |
| K538A | | | | | | | | | | | | | |
| K538P | | | | | | | | | | | | | |

Many of the point mutations imparted novel PAM recognition to LbCas12a, allowing it to cleave DNA preceded by these sequences in vitro. Some mutations caused an increase in overall promiscuity, while others designed and tested were not shown to change wtLbCas12a recognition and cleavage. Overall 130/186 point mutations did not acquire new PAMs over wtLbCas12a (Table 6, regular font/not italicized or bold) above a score of 4, 40/186 acquired many new PAMs (Table 6, bold font), and 16/186 acquired 1-3 new PAMs (Table 6, italicized font). An overall 30% success rating (56/186) indicates an efficacious method was used to design novel PAM recognition motifs by making point mutations to LbCas12a.

2. Determining Binding of Point Mutations and Combinations in Prokaryotes

Combinations of individual mutations can alter the PAM recognition even more than single mutations. However, such experiments rapidly scale to large numbers of combinations to test. Taking just the 40 mutations which caused LbCas12a to recognize 3 or more new PAMs and making a library of double mutants a total of $40^2$ or 1,600 enzymes could be tested. Making a triple-mutant library would result in $40^3$ or 64,000 enzymes to purify and assay in replicates, which is not practical. We, therefore, adapted a bacterial method, known as PAM-SCANR (Leenay et al. Mol Cell 62, 137-147 (2016)) to assess combinatorial mutations. We used a library in Escherichia coli to test binding of Cas12a mutations to the 256 possible PAM NNNN variants. This assay does not test cleavage, rather it tests binding in vivo. Since the mutations made were nowhere near the catalytic region, binding is expected to reflect cleavage as well (this was verified later in the 293T assay). The advantage to PAM-SCANR is the ability to rapidly test not only point mutations, but combinations of amino acid point mutations in a quick and accurate way. It also tends to be more stringent than in vitro cleavage assays.

Reporter Plasmid

Plasmid pWISE1963 was used as the base vector for generating reporters with each of the 256 PAMS. The plasmid contains Spectinomycin resistance, ColE1 origin of replication, LacI, and eGFP under control of the lac promoter. 256 gene blocks containing the fragment between the NotI and SmaI restriction site (from just 5' of the lacI promoter into the lacI gene) were synthesized by Twist Bioscience. Each fragment contained a different 4-mer PAM directly 5' of the lacI promoter. Each gene block was cloned into the pWISE1963 via restriction and ligation. Clones were selected for each variant and the identity of the PAM was verified by Sanger sequencing.

CRISPR-Cas Plasmid

Plasmid pWISE2031 was used as the base vector for generating all CRISPR-Cas plasmids. The plasmid contains Chloramphenicol resistance, a CloDF13 origin of replication, dLbCas12a driven by promoter BbaJ23108, and the LbCas12a with a crRNA targeting the lacI promoter driven by the BbaJ23119 promoter. The negative control plasmid, pWISE1961 contains the same components as pWISE2031 with the exception that a non-targeting crRNA was used. Each point and combinatorial mutant (pWISE2984-pWISE3007) was constructed via site-directed mutagenesis of pWISE2031 at Genewiz.

Cell Line

An E. coli cell line containing a chromosomal deletion of the lacI gene, JW0336, was obtained from Dharmacon Horizon Discovery. Electrocompetent cells were prepared according to the protocol described (Sambrook, J., and Russell, D. W. (2006). Transformation of E. coli by Electroporation. Cold Spring Harb Protoc 2006, pdb.prot3933). E. coli JW0336 was used in all library transformation and cell sorting experiments.

Preparation of Reporter Library 10 ng of each reporter plasmid described in the section above was pooled into a single tube to generate a library for transformation and amplification. $1/20^{th}$ of the pooled plasmid library (approximately 0.5 ng of each reporter) was transformed into supercompetent XL1-Blue according to manufacturer's instructions. After 1-hour of recovery at 37° C. with shaking at 225 rpm the entire transformation was transferred to 1-L of LB Spectinomycin and grown overnight at 37° C. with shaking at 225 rpm. The following day plasmid DNA was extracted from the overnight culture using a ZymoPURE plasmid gigaprep kit according to manufacturer's instructions. The DNA was quantified by nanodrop and used in all subsequent library transformations.

Library Transformations and Cell Sorting 100 ng of reporter plasmid library and 100 ng of Crispr/Cas plasmid were co-transformed into 40 uL of JW0336 by electroporation. Transformations were recovered at 37° C. with shaking at 225 rpm for 1-hour. At the end of recovery, 10 uL of transformation was removed, mixed with 90 uL LB and plated onto LB agar plates with chloramphenicol and spectinomycin to determine transformation efficiency. The remaining amount of recovery (990 uL) was transferred to an overnight culture containing 29 mL of LB with Spectinomycin and Chloramphenicol. The cultures were grown overnight at 37° C. with shaking at 225 rpm. The following morning colonies were counted on the transformation plates to determine transformation efficiency; all transformations except for 2 of them showed >2,000 transformants, equating to 10× or greater coverage of the reporter library. The two samples that did not show 10× or greater coverage were repeated. Glycerol stocks of the overnight cultures were then prepared and stored at −80 C, and 6-mL of each culture was miniprepped using a Qiagen miniprep kit, according to manufacturer's instructions. These minipreps were labeled "pre-sort" and stored at 4° C.

One optical density (OD) of each overnight library culture was spun down in a tabletop microcentrifuge at 8,000 rpm, 4° C. for 5 minutes. The supernatant was pipetted off, and 1 mL of filter sterilized 1×PBS buffer was added to each tube. The pellets were carefully re-suspended by pipetting. The wash with 1×PBS was repeated 2 more times, and after the final re-suspension the cells (about $10^8$ cells per mL in 1×PBS) were placed on ice. Each sample was sorted on a Beckman-Coulter MoFlo XDP cell sorter. A negative control (WT-dLbCas12a+non-targeting crRNA+reporter library) and positive control (WT-dLbCas12a+targeting crRNA+reporter library) were used to set gating parameters for cell sorting. Samples were sorted on single-cell purity mode, with voltage 425, ssc voltage 535, fsc voltage (gain) of 4.0. The typical rate of sorting was about 4000 events/second. Each sample had a minimum of $1.0 \times 10^6$ events; cell sorting was performed until 50,000 GFP-positive events were collected or the sample was depleted. In cases where the sample was depleted, a minimum of 200 GFP positive events were collected. GFP-positive events were collected into tubes containing 2-mL of LB with Spectinomycin and Chloramphenicol. Post-sort, the samples were diluted to 6-mL with additional LB with Spectinomycin and Chloramphenicol, and then grown overnight at 37° C. with shaking at 225 rpm.

Figure 6:
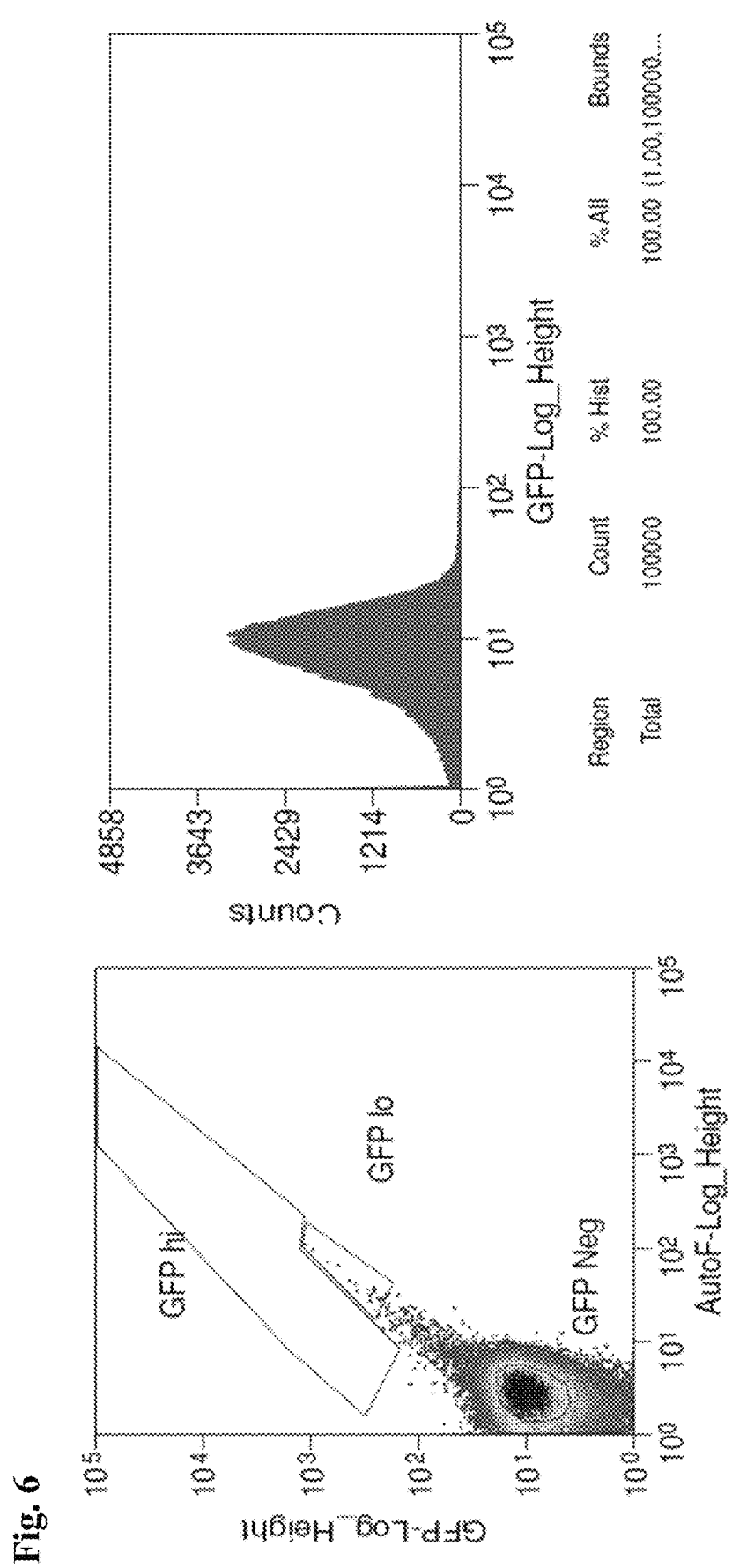
FIG. 6. Cell sorting results of a negative control containing wtLbCas12a and a crRNA which did not target the plasmid spacers.
Figure 7:
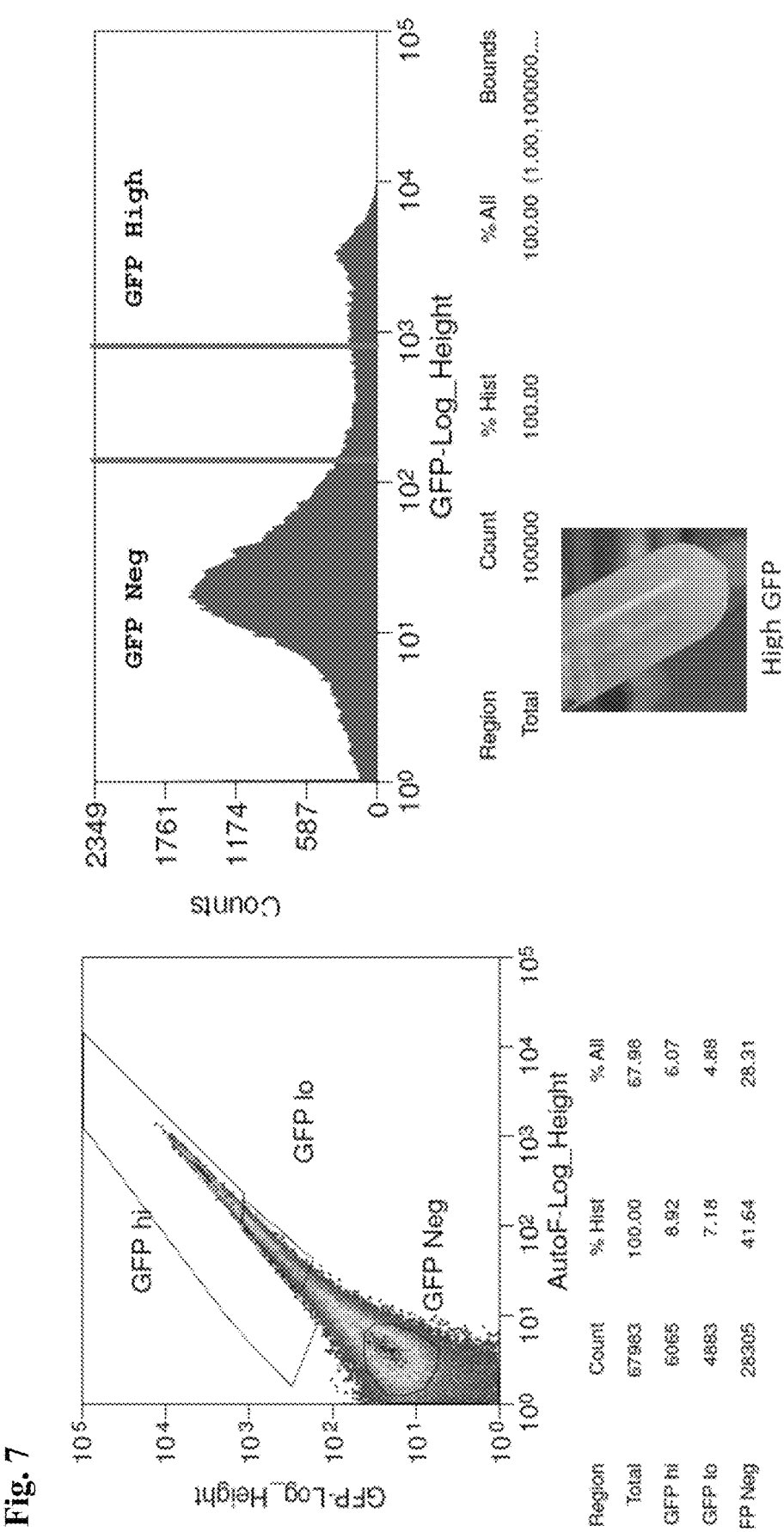
FIG. 7. Cell sorting results of wtLbCas12a and a crRNA targeting the plasmid spacers.
Figure 8:
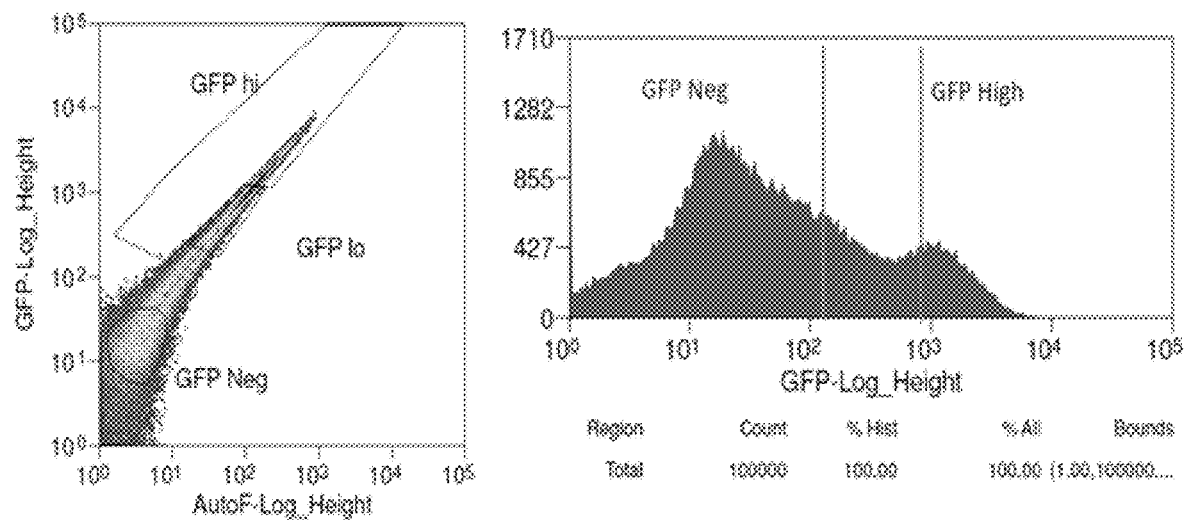
FIG. 8. Cell sorting results of LbCas12a-K595Y and a crRNA targeting the plasmid spacers.
Figure 9:
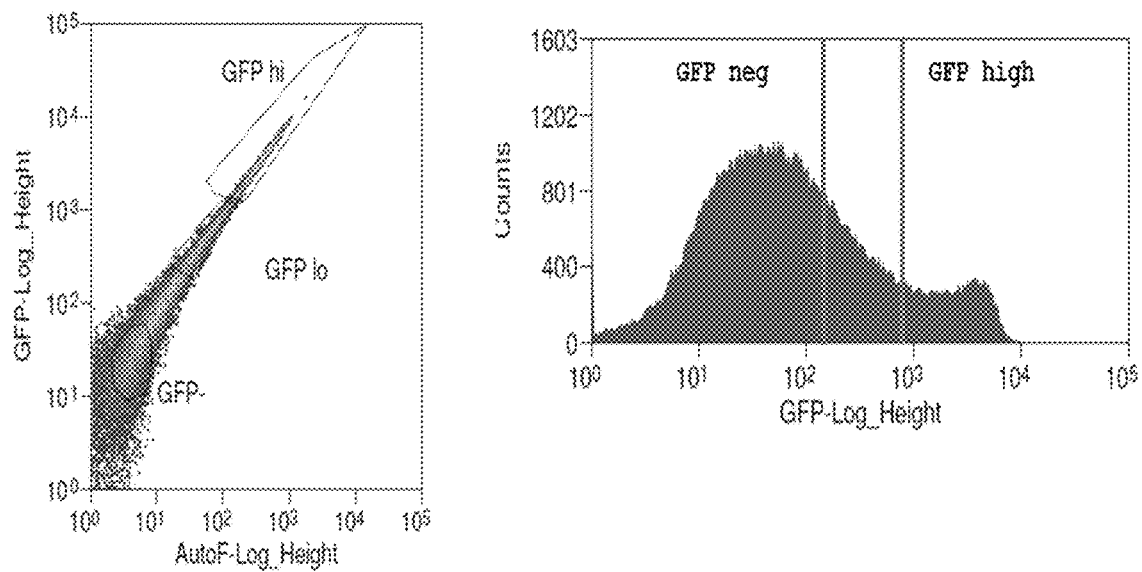
FIG. 9. Cell sorting results of LbCas12a-G532R-K595R double mutation control and a crRNA targeting the plasmid spacers.
Figure 10:
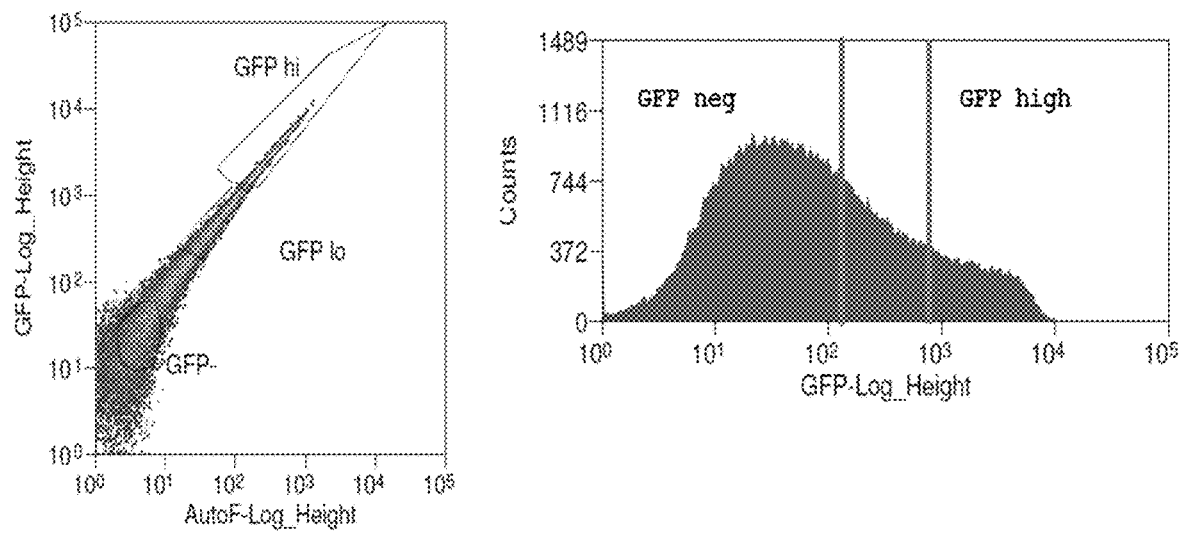
FIG. 10. Cell sorting results of LbCas12a-T152R-K595Ydouble mutation, a combination of two of the point mutations in this study, with a crRNA targeting the plasmid spacers.
Figure 11:
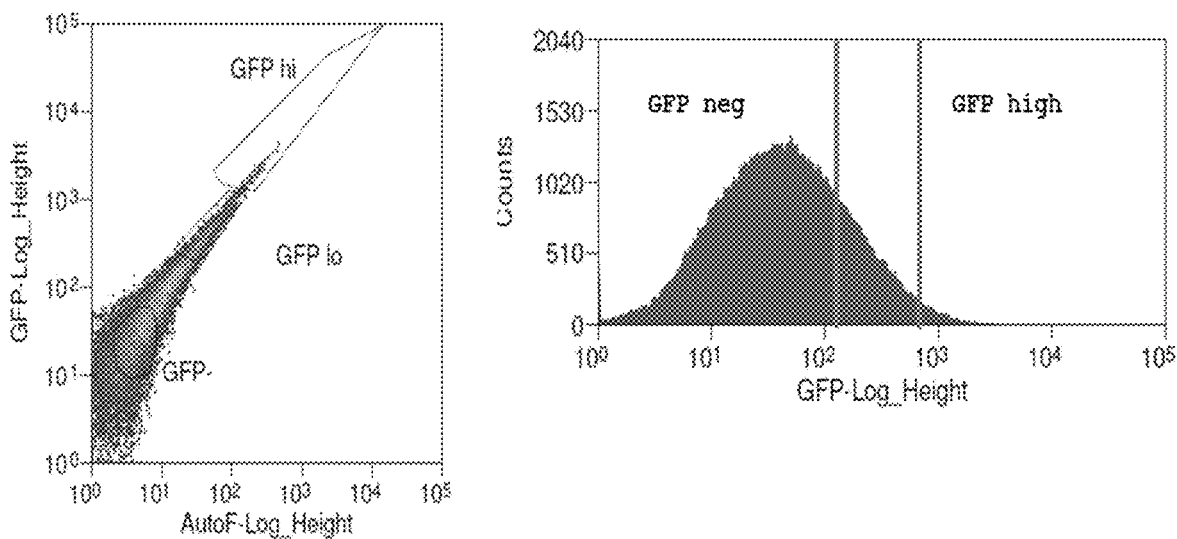
FIG. 11. Cell sorting results of LbCas12a-T152R-K538W-K595Ytriple mutation, a combination of three of the point mutations with a crRNA targeting the plasmid spacers.

Example sorts are provided in FIGS. 6-11. FIG. 6 shows the cell sorting results of a negative control containing wtLbCas12a and a crRNA, which did not target the plasmid spacers. Sorted cells from the GFP high samples show no cells in the sorted fraction (left panel) and a single population of GFP signal, indicated by a single peak (right panel). FIG. 7 shows cell sorting results of wtLbCas12a and a crRNA targeting the plasmid spacers. Sorted cells from the GFP high samples show cells in the sorted fraction (left panel, GFP hi) and a two populations of GFP signal, indicated by two predominant peaks (right panel, GFP neg and GFP High). Also shown is the GFP high sorted cells fluorescing (lower right panel). FIG. 8 shows cell sorting results of LbCas12a-K595Y and a crRNA targeting the plasmid spacers. Sorted cells from the GFP high samples show cells in the sorted fraction (left panel, GFP hi) and a population indicated by two predominant peaks (right panel, GFP neg and GFP high). FIG. 9 shows the cell sorting results of LbCas12a-G532R-K595R double mutation control (Gao et al. Nat Biotechnol 35, nbt.3900 (2017)) and a crRNA targeting the plasmid spacers. Sorted cells from the GFP high samples show cells in the sorted fraction (left panel, GFP hi) and a population indicated by two predominant peaks (right panel). FIG. 10 shows cell sorting results of LbCas12a-T152R-K595Ydouble mutation, a combination of two of the point mutations used with a crRNA targeting the plasmid spacers. Sorted cells from the GFP high samples show cells in the sorted fraction (left panel, GFP hi) and a population indicated by two predominant peaks (right panel). FIG. 11 shows cell sorting results of LbCas12a-T152R-K538W-K595Ytriple mutation, a combination of three of the point mutations used with a crRNA targeting the plasmid spacers. Sorted cells from the GFP high samples show cells in the sorted fraction (left, GFP hi) and a population indicated (right, green lines).

Next Generation Sequencing

The following morning after sorting glycerol stocks of each overnight culture were prepared and stored at −80 C. The remaining amount of each 6-mL culture was miniprepped with a Qiagen miniprep kit according to manufacturer's instructions. These minipreps were labeled "post-sort" and were stored at 4° C. Pre-sort and post-sort minipreps were quantified by nanodrop, diluted 10-fold and handed off for sequencing on an Illumina Mi-Seq.

The spacer vectors were subjected to deep sequencing analysis to calculate the frequency of A/T/G/C at each position of PAM using an Illumina MiSeq according to manufacturer's protocols. Briefly, 10 ng of DNA was used as template for PCR. Phasing gene specific forward and reverse PCR primers were designed to amplify across the target site. Amplicon libraries were generated using a two-step PCR method, where primary PCR with 5' tails allow a secondary PCR to add Illumina i5 and i7 adapter sequences and barcodes for sorting multiplexed samples. PCR amplifications were performed using the following parameters: 98° C. for 30 s; 25 cycles for PCR1 and 8 cycles for PCR2 (98° C. 10 s, 55° C. 20 s, 72° C. 30 s); 72° C. for 5 min; hold at 12° C. The PCR reactions were performed with Q5 High-Fidelity DNA Polymerase (New England BioLabs, Beverly, MA, United States). The secondary PCR amplicon samples were individually purified using AMPure XP beads according to manufacturer's instruction (Beckman Coulter, Brea, CA, United States); all purified samples were quantified using a plate reader, pooled with an equal molar ratio, and run on AATI fragment analyzer (Agilent Technologies, Palo Alto, CA, United States). The pooled amplicon libraries were sequenced on an Illumina MiSeq (2×250 paired end) using a MiSeq Reagent kit v2 (Illumina, San Diego, CA, United States).

Sequencing Results of the Highly Fluorescent Sorted Cells

Figure 12:
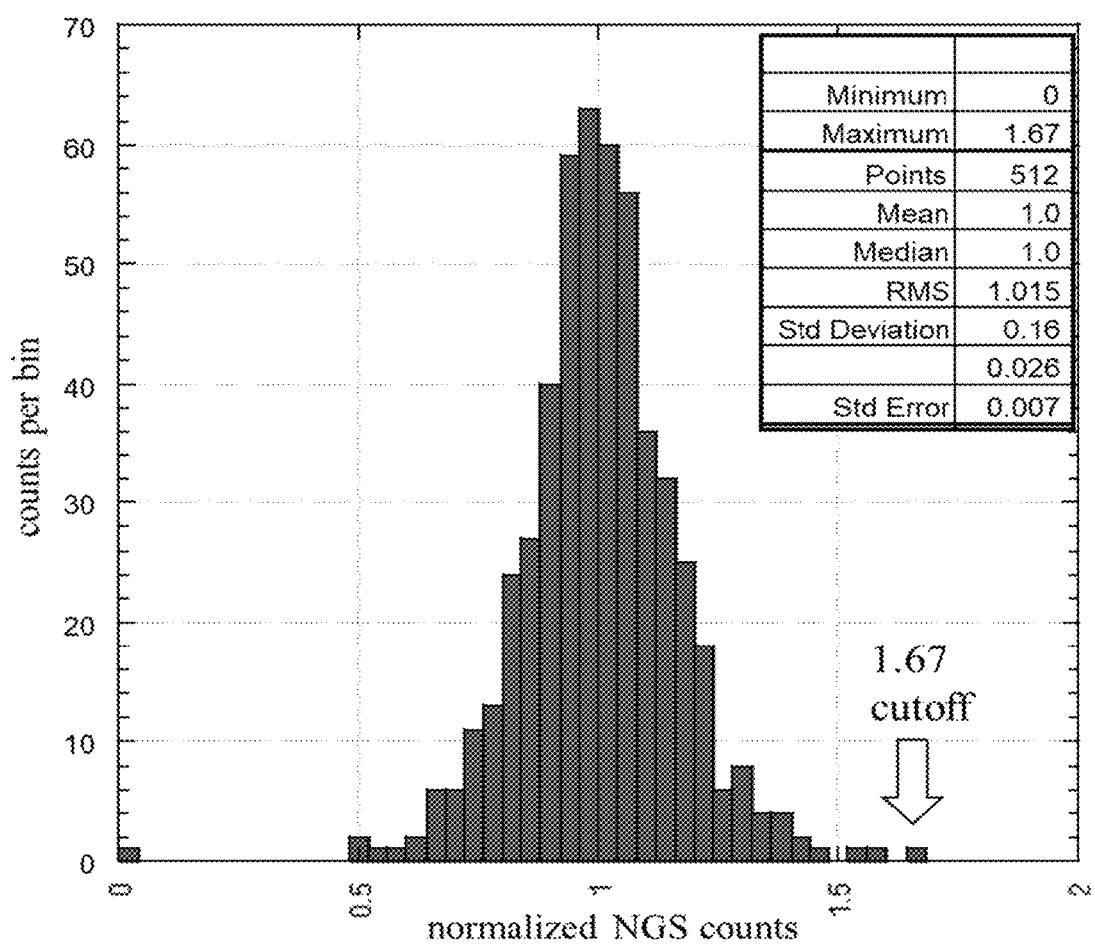
FIG. 12. Total normalized NGS counts for two separate no crRNA controls and wildtype dLbCas12a and the reporter library.

Two negative control samples were run containing wtdLbCas12a and a non-targeting crRNA in the presence of the 256-member reporter library. After normalization to 1.0, the value for each member of the library was plotted as a histogram (FIG. 12). FIG. 12 shows the total normalized NGS counts for two separate no crRNA controls and wild-type dLbCas12a and the reporter library. Two separate samples were analyzed and combined (total 512 points representing 256 PAMs×2). We chose the conservative 1.67 value, the highest count, as the cutoff for these experiments, above which we scored as PAM binding. The standard deviation was 0.16. Rather than choosing some multiplier of the standard deviation as a cutoff, we chose the absolute largest value found in either of the two negative controls, 1.67. This gave a highly stringent cutoff over 10 times the standard deviation of the data. In fact, only 3 PAM sequences were found above 1.5.

Figure 13:
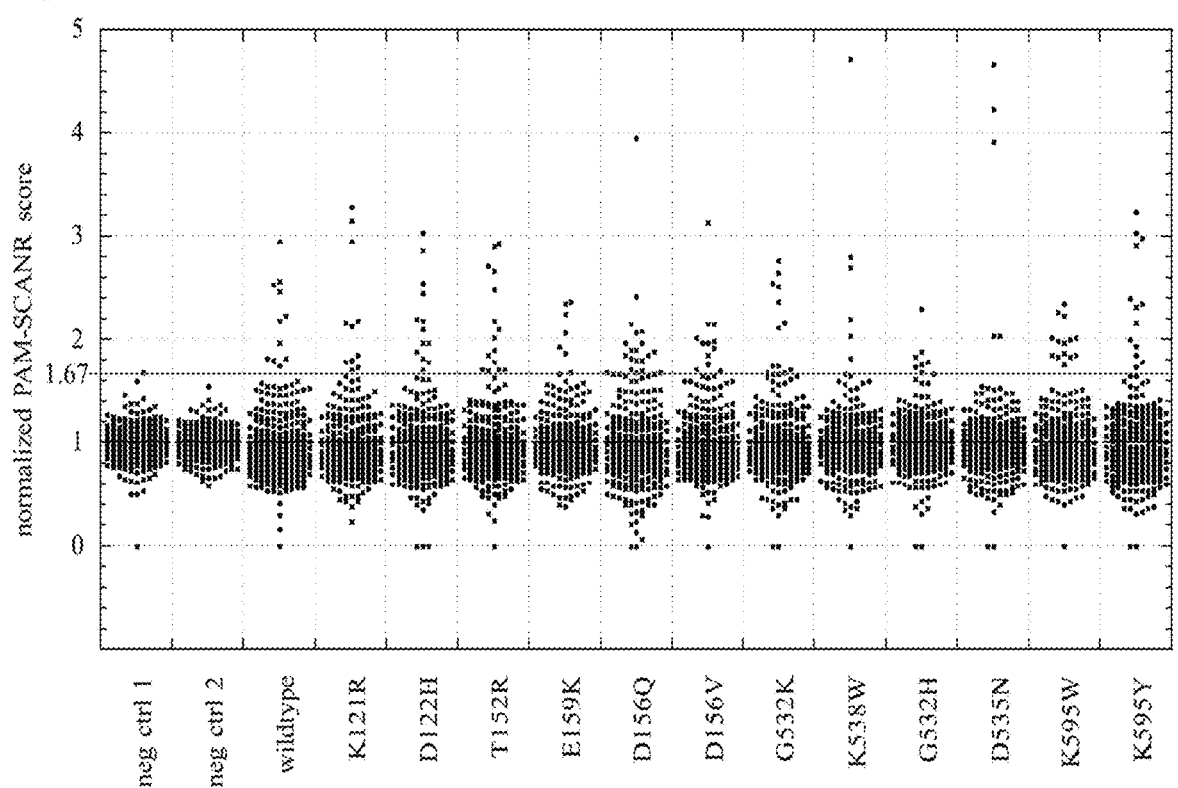
FIG. 13. Single point mutation normalized PAM-SCALAR scores for each of the 256 four nucleotide PAMs. The line through the graph shows the highest observed score for either of the two negative controls, 1.67.

The pre-sorted pools were all sequenced prior to sorting. The average reads per PAM was from about 250 to 500 NGS reads, depending on the sample. The highly fluorescent post-sorted pools were sequenced and had similar read counts per PAM at about 250-500 reads per PAM. Both samples were then normalized to control for small loading differences in each NGS experiment. The two values were then subtracted and normalized to 1.0. Many PAM sequences were bound by the point mutation library above the 1.67 cutoff (FIG. 13, Table 7).

TABLE 7

The ability of point mutations to bind PAMs above the 1.67 threshold, sorted by normalized score. TTTV sequences for wildtype are in bold.

| Wildtype PAM | wildtype score | T152R PAM | T152R Score | K538W PAM | K538W Score | K595Y PAM | K595Y Score | D122H PAM | D122H Score |
|---|---|---|---|---|---|---|---|---|---|
| TTTC | 2.96 | TTTG | 2.94 | TTTA | 4.71 | TCGC | 3.23 | TTTC | 3.03 |
| CTTG | 2.56 | TTTA | 2.9 | CTTA | 2.80 | TCCC | 3.03 | TTTG | 2.87 |
| TTTA | 2.54 | CTTA | 2.72 | AGCT | 2.70 | TTGC | 2.98 | TTTA | 2.56 |
| TTTG | 2.47 | TTTC | 2.66 | AATG | 2.19 | GCGC | 2.93 | TTTT | 2.46 |
| CCGC | 2.23 | GTTA | 2.48 | CTTC | 2.03 | ACGC | 2.40 | CTTA | 2.20 |
| CTTA | 2.19 | CTTG | 2.19 | TTTC | 1.82 | TCCA | 2.35 | TTTC | 2.19 |
| CTTC | 1.97 | GTTG | 2.1 | | | TTCC | 2.32 | CTTG | 2.10 |
| GTTC | 1.82 | CTTC | 2.02 | | | TCCG | 2.17 | GTTA | 1.97 |
| TTCC | 1.82 | AGAG | 1.91 | | | TTCG | 2.01 | ATTG | 1.96 |
| GTTG | 1.80 | ATTG | 1.85 | | | TCGG | 1.93 | CTTC | 1.89 |
| GTTA | 1.75 | TCCA | 1.79 | | | CCGC | 1.84 | TCTG | 1.82 |
| | | GCCA | 1.72 | | | CCCA | 1.79 | CCCA | 1.79 |
| | | TCTA | 1.72 | | | ACCC | 1.74 | GTTG | 1.72 |
| | | TTTT | 1.72 | | | | | | |
| | | GTTC | 1.71 | | | | | | |

| D156V PAM | D156V Score | D156Q PAM | D156Q Score | D535N PAM | D535N Score | E159K PAM | E159K Score | G532H PAM | G532H Score |
|---|---|---|---|---|---|---|---|---|---|
| AATG | 3.13 | TGTG | 3.96 | TTTG | 4.66 | TTTG | 2.37 | AATG | 2.30 |
| GTTG | 2.16 | CCTC | 2.42 | TTTC | 4.23 | TTTC | 2.36 | CCTA | 1.89 |
| TTTT | 2.15 | CCCA | 2.14 | TTTA | 3.91 | TTTA | 2.25 | GTTG | 1.83 |
| TTTA | 2.02 | GTTG | 2.09 | TTTT | 2.04 | CTTA | 2.07 | GTTA | 1.79 |
| CTTA | 1.99 | GTTC | 2.07 | CACG | 2.03 | CTTG | 1.94 | TTTA | 1.77 |
| GTTA | 1.98 | CTTC | 1.97 | | | CTTC | 1.86 | TCTA | 1.73 |
| ATTA | 1.97 | ATTC | 1.96 | | | CCCA | 1.68 | CTTA | 1.68 |
| CTTG | 1.93 | TTCC | 1.90 | | | GTTA | 1.67 | | |
| GTTC | 1.85 | TTGC | 1.90 | | | | | | |
| CTTC | 1.77 | TTCA | 1.88 | | | | | | |
| TCTC | 1.71 | ACTC | 1.86 | | | | | | |
| TTCA | 1.70 | ACAC | 1.85 | | | | | | |
| | | CTTG | 1.82 | | | | | | |
| | | AGCT | 1.80 | | | | | | |
| | | AATG | 1.80 | | | | | | |
| | | AAGC | 1.72 | | | | | | |
| | | GTAC | 1.70 | | | | | | |
| | | TCGC | 1.69 | | | | | | |
| | | CCTG | 1.69 | | | | | | |
| | | GTTA | 1.69 | | | | | | |
| | | TCCC | 1.67 | | | | | | |

| G532K PAM | G532K Score | K121R PAM | K121R Score | K595W PAM | K595W Score | K538W PAM | K538W Score | D535N PAM | D535N Score |
|---|---|---|---|---|---|---|---|---|---|
| TTTA | 2.76 | TTTG | 3.28 | TTTG | 2.35 | TTTA | 11.18 | GCGG | 18.70 |
| TTTC | 2.66 | TTTA | 3.15 | TTCC | 2.27 | CTTA | 9.57 | TTTG | 16.34 |
| TTTG | 2.56 | TTTC | 2.95 | TTTA | 2.23 | TTTC | 8.45 | TTTA | 13.15 |
| CCGC | 2.51 | CTTG | 2.18 | GCGC | 2.03 | TTTG | 7.27 | TTTC | 3.87 |
| TTCC | 2.37 | CTTA | 2.17 | TTCG | 2.02 | CTTC | 6.70 | TTGG | 3.83 |
| TTCA | 2.16 | TTTT | 2.14 | TTTC | 2.01 | CTTG | 6.33 | TTAC | 2.94 |
| TCCC | 2.13 | CTTC | 1.85 | TTCA | 1.99 | TATC | 5.35 | TCAC | 2.78 |
| TCCA | 1.76 | GTTG | 1.80 | ACCG | 1.97 | TATA | 4.90 | TTGC | 2.38 |
| GTTA | 1.75 | GTTA | 1.78 | TCCG | 1.87 | TATG | 4.39 | TTCC | 1.87 |
| ATTG | 1.72 | TTGG | 1.74 | TCGC | 1.85 | AATG | 2.75 | CCAC | 1.87 |
| CCCC | 1.69 | TTCC | 1.71 | TCCC | 1.84 | CCGC | 2.19 | TCGC | 1.84 |
| CTTA | 1.68 | | | AACG | 1.84 | AATC | 2.13 | CTTG | 1.67 |
| | | | | TTGC | 1.83 | GTTA | 1.89 | TTTT | 1.67 |
| | | | | TCCA | 1.76 | AATA | 1.68 | | |

We combined the three point mutations T152R, K538W, and K595Y in various combinations to make double and triple dLbCas12a mutants (T152R+K538W, K538W+K595Y, and T152R+K538W+K595Y). This was compared to a previously described control, which was developed in AsCas12a known as 'RR' whose LbCas12a mutations correspond to G532R+K595R control (Gao et al. *Nat Biotechnol* 35(8):789-792 (2017)). 'RR' have been described as being able to cause INDELs in TYCV+CCCC sequences in AsCas12a and subsequently LbCas12a.

Figure 14:
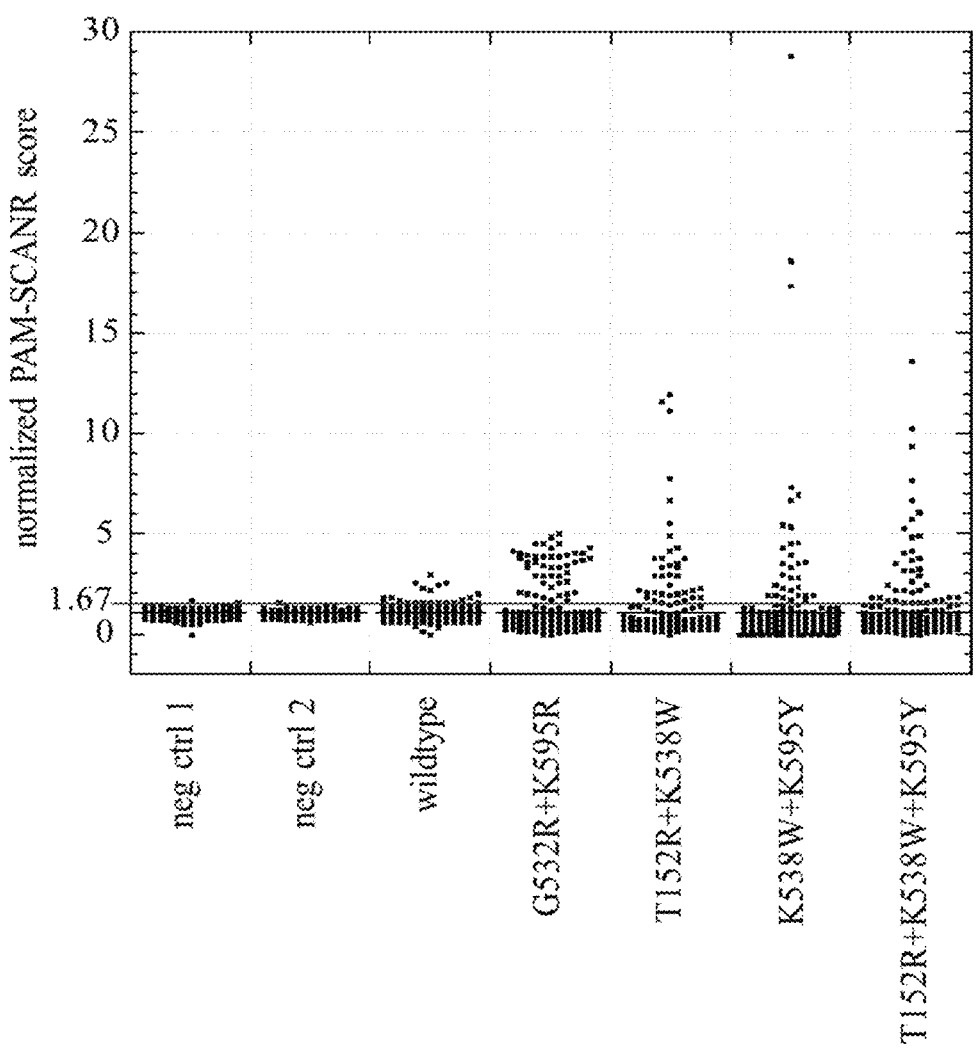
FIG. 14. Combinatorial mutations normalized PAM-SCALAR scores for each of the 256 four nucleotide PAMs.

The same methodology was applied to score the combinatorial mutations. Pre and post-sorted pools were sequenced each having an average of about 250-500 MiSeq NGS reads per PAM library member. The pre and post-sort pools were normalized and subtracted, the difference being normalized to 1.0. Many PAM sequences were bound by the combinations above the 1.67 cutoff (FIG. 14, Table 8).

TABLE 8

Ability of combinatorial mutations to bind PAMs above the 1.67 threshold, sorted by normalized score. TTTV sequences for wildtype are in bold. TYCV + CCCC sequences for the G532R + K595R control are underlined.

| wildtype PAM | wildtype score | G532R + K595R PAM | G532R + K595R Score | T152R + K538W PAM | T152R + K538W Score | K538W + K595Y PAM | K538W + K595Y Score | T152R + K538W + K595Y PAM | T152R + K538W + K595Y Score |
|---|---|---|---|---|---|---|---|---|---|
| TTTC | 2.96 | TTTT | 5.07 | TTTC | 11.96 | TTTC | 11.96 | AGCC | 13.65 |
| CTTG | 2.56 | TTCG | 4.81 | TTTA | 11.62 | TTTA | 11.62 | TGGC | 10.28 |
| TTTA | 2.54 | <u>ACCC</u> | 4.52 | TTTG | 11.19 | TTTG | 11.19 | TACC | 9.35 |
| TTTG | 2.47 | TCCG | 4.51 | GTTG | 7.75 | GTTG | 7.75 | TGCC | 7.68 |
| CCGC | 2.23 | <u>TTCA</u> | 4.46 | GTTA | 6.68 | GTTA | 6.68 | CTGC | 6.69 |
| CTTA | 2.19 | <u>TTTA</u> | 4.30 | CTTG | 5.53 | CTTG | 5.53 | GGGC | 6.09 |
| CTTC | 1.97 | TTTG | 4.28 | CTTA | 4.93 | CTTA | 4.93 | GGCC | 5.71 |
| GTTC | 1.82 | GCCG | 4.15 | GTTC | 4.34 | GTTC | 4.34 | AGGC | 5.26 |
| TTCC | 1.82 | TTCT | 4.07 | TTCC | 4.11 | TTCC | 4.11 | TAGC | 4.96 |
| GTTG | 1.80 | CTCC | 4.03 | TCCC | 3.82 | TCCC | 3.82 | CGGC | 4.89 |
| GTTA | 1.75 | GCCA | 4.01 | TTCA | 3.78 | TTCA | 3.78 | ACCC | 4.15 |
|  |  | CCCG | 4.00 | ATTG | 3.78 | ATTG | 3.78 | GACC | 4.08 |
|  |  | TCCA | 3.92 | TCCG | 3.48 | TCCG | 3.48 | AAGC | 3.81 |
|  |  | <u>ACTA</u> | 3.90 | TTGG | 3.43 | TTGG | 3.43 | AGCA | 3.69 |
|  |  | GTCC | 3.87 | GCCC | 3.32 | GCCC | 3.32 | GCGC | 3.49 |
|  |  | <u>CCCC</u> | 3.87 | CTTC | 3.30 | CTTC | 3.30 | TACA | 3.26 |
|  |  | <u>TTTC</u> | 3.84 | CCCC | 2.95 | CCCC | 2.95 | TCCC | 3.17 |
|  |  | CCCA | 3.78 | TCTA | 2.88 | TCTA | 2.88 | CCCA | 3.15 |
|  |  | TCTA | 3.75 | GCCA | 2.86 | GCCA | 2.86 | TGCA | 2.87 |
|  |  | TCCT | 3.68 | TCCA | 2.86 | TCCA | 2.86 | GCCC | 2.66 |
|  |  | GCTA | 3.63 | ATTA | 2.44 | ATTA | 2.44 | CCCC | 2.49 |
|  |  | GCCC | 3.59 | CTCC | 2.29 | CTCC | 2.29 | TTGC | 2.42 |
|  |  | GTTA | 3.58 | CCCG | 2.19 | CCCG | 2.19 | ACGC | 2.21 |
|  |  | ACCA | 3.43 | ACCC | 2.16 | ACCC | 2.16 | GGCA | 2.21 |
|  |  | TCCC | 3.38 | TTCG | 2.13 | TTCG | 2.13 | ACCA | 2.18 |
|  |  | <u>TTCC</u> | 3.36 | GTCC | 2.13 | GTCC | 2.13 | AACC | 2.09 |
|  |  | <u>ACCG</u> | 3.36 | CCCA | 2.06 | CCCA | 2.06 | GACA | 1.83 |
|  |  | TCTG | 3.31 | GCCG | 1.99 | GCCG | 1.99 | CAGC | 1.81 |
|  |  | TCTT | 3.05 | GCTA | 1.97 | GCTA | 1.97 | ACCG | 1.80 |
|  |  | CTTA | 2.92 | TCTG | 1.96 | TCTG | 1.96 | GGGG | 1.80 |
|  |  | TCTC | 2.89 | TCTC | 1.84 | TCTC | 1.84 | TACG | 1.72 |
|  |  | CCCT | 2.89 | TTTT | 1.81 | TTTT | 1.81 | TTCC | 1.69 |
|  |  | CTCA | 2.86 | ATTC | 1.79 | ATTC | 1.79 |  |  |
|  |  | GTCA | 2.63 | GTCA | 1.67 |  |  |  |  |
|  |  | GTCG | 2.54 |  |  |  |  |  |  |
|  |  | CCTA | 2.54 |  |  |  |  |  |  |
|  |  | ATCC | 2.34 |  |  |  |  |  |  |
|  |  | GTTC | 2.11 |  |  |  |  |  |  |
|  |  | TTAC | 2.10 |  |  |  |  |  |  |
|  |  | CTCG | 2.03 |  |  |  |  |  |  |
|  |  | ATTA | 2.01 |  |  |  |  |  |  |
|  |  | GCTC | 1.94 |  |  |  |  |  |  |
|  |  | GCCT | 1.89 |  |  |  |  |  |  |
|  |  | CCTC | 1.82 |  |  |  |  |  |  |
|  |  | GCTT | 1.71 |  |  |  |  |  |  |

Overall Analysis of PAM-SCALAR Data

Wildtype LbCas12a showed strong TTTV binding the LbCas12a-G532R-K595R control showed strong TYCV and CCCC binding. This mutation, called 'RR' was developed in AsCas12a and shown to bind TYCV and CCCC (Gao et al. *Nat Biotechnol* 35(8):789-792 (2017)). However, in vitro wtLbCas12a can recognize and cleave TTCN, CTTN, TCTN, and others, where AsCas12a was shown only to cleave TTTN (Zetsche et al., *Cell* 163:759-771 (2015)). We deduced that the 'RR' mutation placed in the LbCas12a context would be more promiscuous than when it is placed in the AsCas12a context and this was what was observed for this control, with LbCas12a-RR recognizing 45 sequences. Both the wildtype and LbCas12a-RR results demonstrate the validity of the selection and sorting parameters The mutations tested clearly indicated that novel PAMs are recognized in vivo by individual point mutations identified in vitro. For example, K595Y bound 13 PAMs above the 1.67 threshold, 11 of which were not recognized by wtLbCas12a, and none of which contained the TTTV sequence known to be bound by Cas12a. Similarly, T152R recognized 15 distinct PAMs, however in this case it retained the TTTV of wildtype. Overall out of the 12 point mutations tested, each had novel PAM binding sequences outside of the canonical TTTV motif and distinct from dLbCas12a controls.

Effects of Combinations

We found that combining multiple point mutations did not lead to a linear addition of the PAM sequences of the point mutations (FIG. 15). For example, combining LbCas12a point mutants K538W and K595Y result in an enzyme LbCas12a-K538W-K595Y which in some cases shares PAM recognition motifs with K538W (vertical hatched) or K595Y (horizontal hatched), but more often results in completely novel PAM recognition sequences (thatched). Using the same example, K538W recognizes AGCT, however K538W+K595Y does not. K595Y recognizes ACGC, however K538W+K595Y does not. CCCC is neither recognized by K538W nor K595Y, yet the double mutant binds it with high affinity.

Overall, the combination of mutations results in a more than linear expansion of PAM recognition. For example K538W recognizes 6 PAM sequences, K595Y recognizes 13, but together they recognize 32 sequences (FIG. 15). A simple additive effect would result in 19 PAMs for the double mutant, rather than the 32 we observe. Furthermore, only 11 of the 32 sequences recognized by the double mutant are recognized by either of the two single mutations. A similar pattern is observed when combining three mutations (FIG. 16). The combination of T152R, K538W, and K595Y result in a triple mutation with different PAM recognitions than any of the three individual mutations alone. For example: GGCA, GGCC, GGGC, and GGGG only are recognized when all three mutations are made on LbCas12a. None of these PAMs are bound by any of the single or double mutations, but only when T152R, K538W, and K595Y are all mutated together.

Comparing Point Mutations PAM Recognition in PAM-SCALAR Versus In Vitro PAMDA

Figures 17, 18:
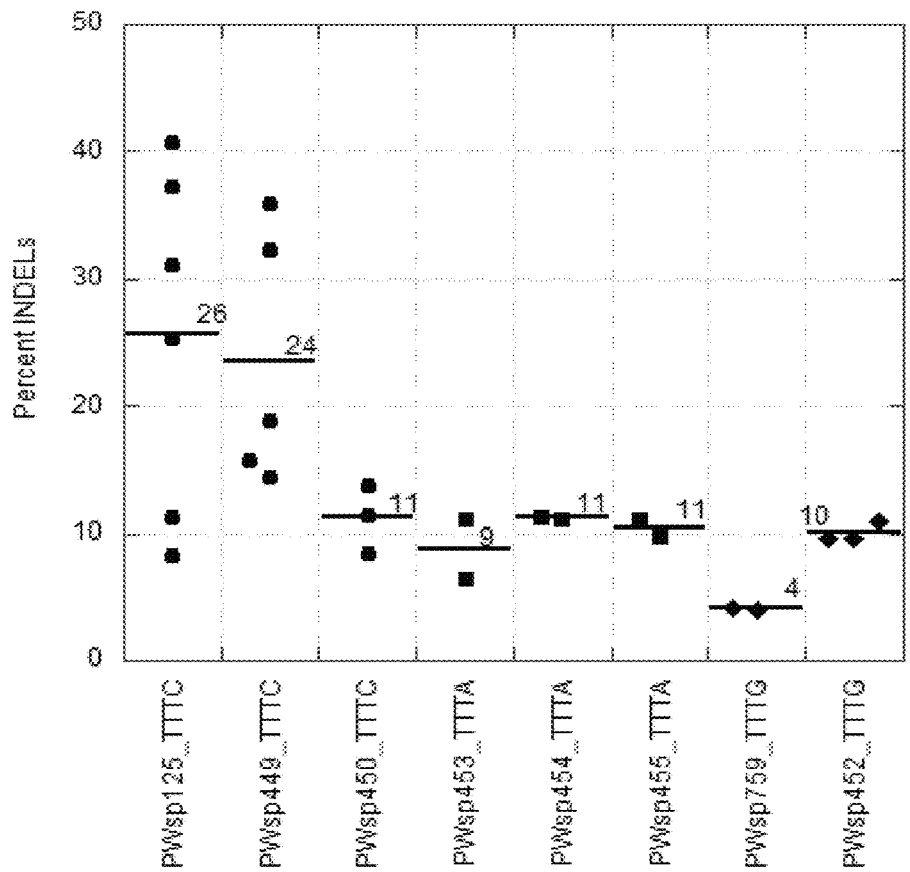
FIG. 18 shows percentage indel formed in HEK293T cells for each TTTV-containing spacer. Individual indel percentages are shown as circles, squares, or triangles for TTTC, TTTA, and TTTG, respectively. An average line and the value rounded to the nearest whole number is also shown for each spacer.

Taken as a whole for the 12 point mutations tested, PAM-SCALAR hits above 1.67 were well represented in the in vitro PAMDA depletion assay. K595Y and T152R examples are shown (FIG. 17). FIG. 17 compares all non-TTTV PAMs which showed above a 1.67 score from PAN-SCALAR (grey boxes) to K595Y (left panel) and T152R (right panel). All but one of the PAM-SCALAR positive PAMs above the 1.67 cutoff had PAM depletion scores above the 9.2 cutoff in vitro. However, the PAM-SCALAR method and analysis were more stringent than in vitro assays and analyses. For example, 13 different PAMs were sorted, sequences, and normalized to have values above 1.67 in PAM-SCALAR. That is contrasted to the PAMDA assay which identified 45 sequences as readily cleaved in vitro. This is likely a function of relative concentrations inside of cells versus in test tubes, but it could also be a function of setting too stringent of a cutoff for PAM-SCALAR or too permissive of a cutoff for PAMDA assays.

There is correlation between the datasets indicating our engineering of residues far from the catalytic site is affecting PAM recognition and binding and not catalysis. If mutations at these residues had affected nuclease activity along with PAM binding then there would be many hits in the PAM-SCANR assay (which measures binding but not cleavage) which did not show cleavage in the PAMDA assay. We do not see that pattern. We observe mutations which affected a change in binding (PAM-SCALAR) also resulted were cleaved in vitro (PAMDA).

3. Determining Binding, Cleavage, and INDEL Formation in Eukaryotes

We chose three mutations T152R, K538W, and K595Y to test their ability to cause insertions or deletions (INDELs) in eukaryotic HEK293T cells. This assay gives valuable eukaryotic INDEL data. In order to get insertions and deletions in eukaryotes a number of criteria all have to be met: the CRISPR enzyme needs to be expressed and stable in the cell, the crRNA needs to be expressed and correctly processed, the protein:RNA complex needs to form, the complex needs to be stable, the complex needs to translocate in sufficient quantities into the nucleus, the target DNA needs to be accessible, the DNA has to be well-targeted by the particular guide-RNA design, and double-stranded breaks need to occur at a rate high enough to yield the occasional DNA repair mistake via an insertion or deletion (INDEL). This makes eukaryotic assays the most stringent assays in this study. A few dozen PAMs were tested for each of the 3 point mutants described below, rather than all 256 due to the experiment being low-throughput. Three different targets were chosen for each PAM-mutant combination to try to avoid false-negatives since often a particular guide is ineffective due to target accessibility.

HEK293T Cell Testing

Eukaryotic HEK293T (ATCC CRL-3216) cells were cultured in Dulbecco's Modified Eagle's Medium plus Gluta-Max (ThermoFisher) supplemented with 10% (v/v) FBS (FBS), at 37° C. with 5% CO2. Wildtype and mutant LbCas12 were synthesized using solid-state synthesis and subsequently cloned into plasmids behind a CMV promoter. CRISPR RNAs (crRNAs) were cloned behind a human U6 promoter (Table 9). HEK293T cells were seeded on 48-well collagen-coated BioCoat plates (Corning). Cells were transfected at about 70% confluency. 750 ng of protein plasmid and 250 ng of crRNA expression plasmids were transfected using 1.5 µl of Lipofectamine 3000 (ThermoFisher Scientific) per well according to the manufacturer's protocol. Genomic DNA from transfected cells were obtained after 3 days and indels were detected and quantified using high-throughput Illumina amplicon sequencing.

The spacer vectors were subjected to deep sequencing analysis to calculate the frequency of A/T/G/C at each position of PAM using an Illumina MiSeq according to manufacturer's protocols. Briefly, 10 ng of DNA was used as template for PCR. Phasing gene specific forward and reverse PCR primers were designed to amplify across the target site. Amplicon libraries were generated using a two-step PCR method, where primary PCR with 5' tails allow a secondary PCR to add Illumina i5 and i7 adapter sequences and barcodes for sorting multiplexed samples. PCR amplifications were performed using the following parameters: 98° C. for 30 s; 25 cycles for PCR1 and 8 cycles for PCR2 (98° C. 10 s, 55° C. 20 s, 72° C. 30 s); 72° C. for 5 min; hold at 12° C. The PCR reactions were performed with Q5 High-Fidelity DNA Polymerase (New England BioLabs, Beverly, MA, United States). The secondary PCR amplicon samples were individually purified using AMPure XP beads according to manufacturer's instruction (Beckman Coulter, Brea, CA, United States); all purified samples were quantified using a plate reader, pooled with an equal molar ratio, and run on AATI fragment analyzer (Agilent Technologies, Palo Alto, CA, United States). The pooled amplicon libraries were sequenced on an Illumina MiSeq (2×250 paired end) using a MiSeq Reagent kit v2 (Illumina, San Diego, CA, United States).

Wildtype Control

Wildtype LbCas12a (wtLbCas12a) recognizes TTTV (TTTA, TTTC, and TTTG). We used crRNA spacers (Table 9) to test the wildtype protein against TTTV containing 23 nucleotide spacer targets (FIG. 18).

TABLE 9

Spacers and targets

| Spacer name | HEK target | PAM | spacer sequence | SEQ ID NO |
|---|---|---|---|---|
| PWsp125 | EMX1 | TTTC | TCATCTGTGCCCCTCCCTCCCTG | 54 |
| PWsp449 | FANCF1 | TTTC | GCGGATGTTCCAATCAGTACGCA | 55 |
| PWsp450 | HEK2 | TTTC | CAGCCCGCTGGCCCTGTAAAGGA | 56 |
| PWsp453 | RNF2 | TTTA | TATGAGTTACAACGAACACCTCA | 57 |
| PWsp454 | RNF2 | TTTA | CACGTCTCATATGCCCCTTGGCA | 58 |
| PWsp455 | RNF2 | TTTA | GAACATGAAAACTTAAATAGAAC | 59 |

TABLE 9-continued

Spacers and targets

| Spacer name | HEK target | PAM | spacer sequence | SEQ ID NO |
|---|---|---|---|---|
| PWsp759 | DNMT1 | TTTG | GTCAGGTTGGCTGCTGGGCTGGC | 60 |
| PWsp452 | HEK2 | TTTG | ACAGATGGGGCTGGACAATTTTT | 61 |

Choice of Proteins and Targets

There were many point mutations which showed increased PAM accessibility in the PAMDA in vitro assay. Testing all of the efficacious PAM mutants against endogenous 293T cell targets is effectively impossible given our many point mutations and 256 possible 4 nucleotide (nt) PAMS due to the complexity, cost, and time of the experiment. We, therefore, chose three point mutations to test against a subset of PAMs. The three point mutations tested were T152R, K538W, and K595Y.

Genomic targets in 293T cells were chosen based on their PAM sequences. Genomic targets for the three point mutations were chosen at random using no particular rules other than having the appropriate 4 nt PAM and selecting 23 nucleotides downstream from that PAM. Three different spacers were chosen to assay each PAM. This is to account for the observation that activities of CRISPR enzymes is target-specific and often cannot be predicted.

Figure 19:
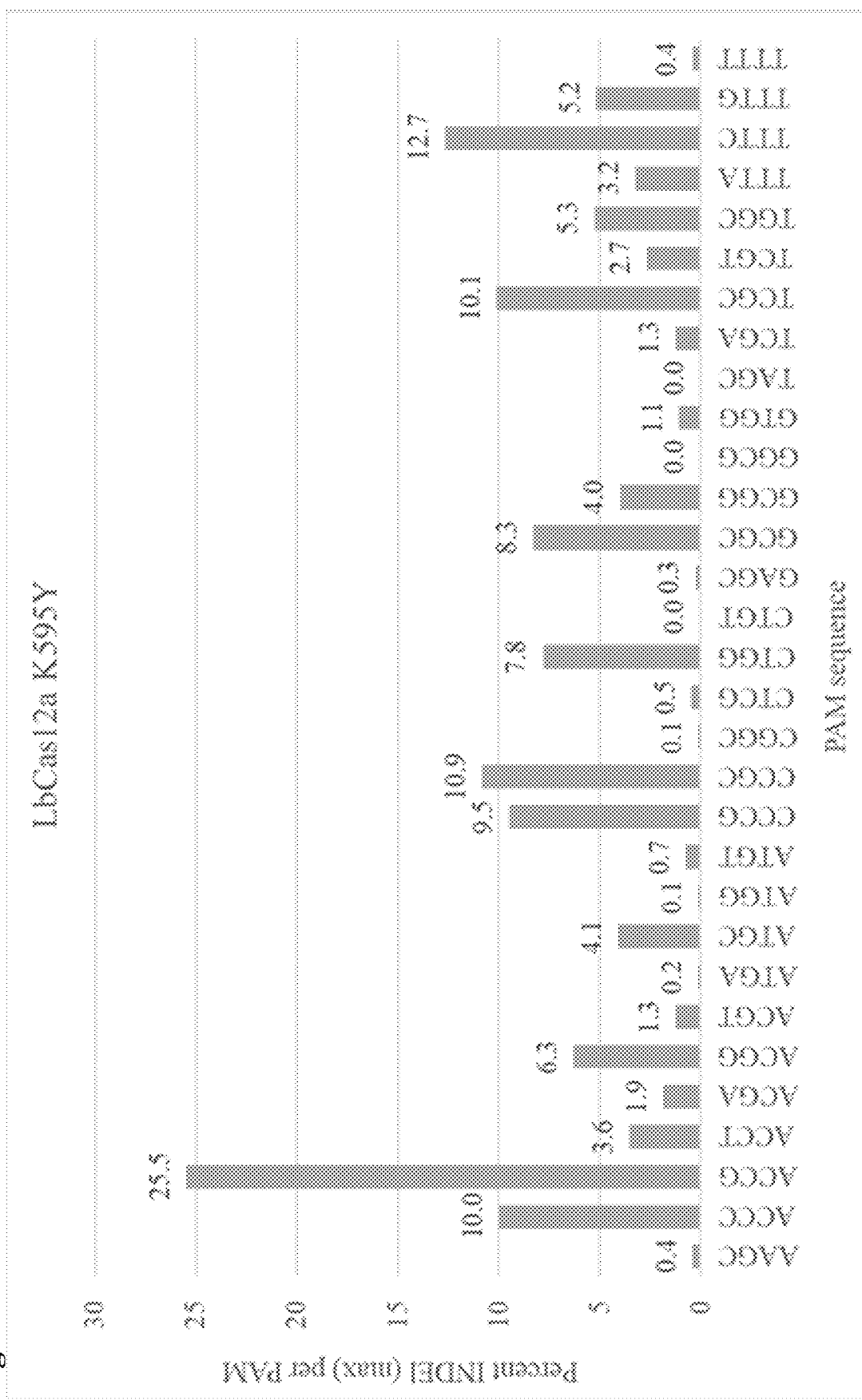
FIG. 19 shows LbCas12a_K595Y HEK293T maximum observed INDEL percentages per PAM tested. Values above 0.1% are outside of the noise of sequencing and represent authentic INDELs.
Figure 20:
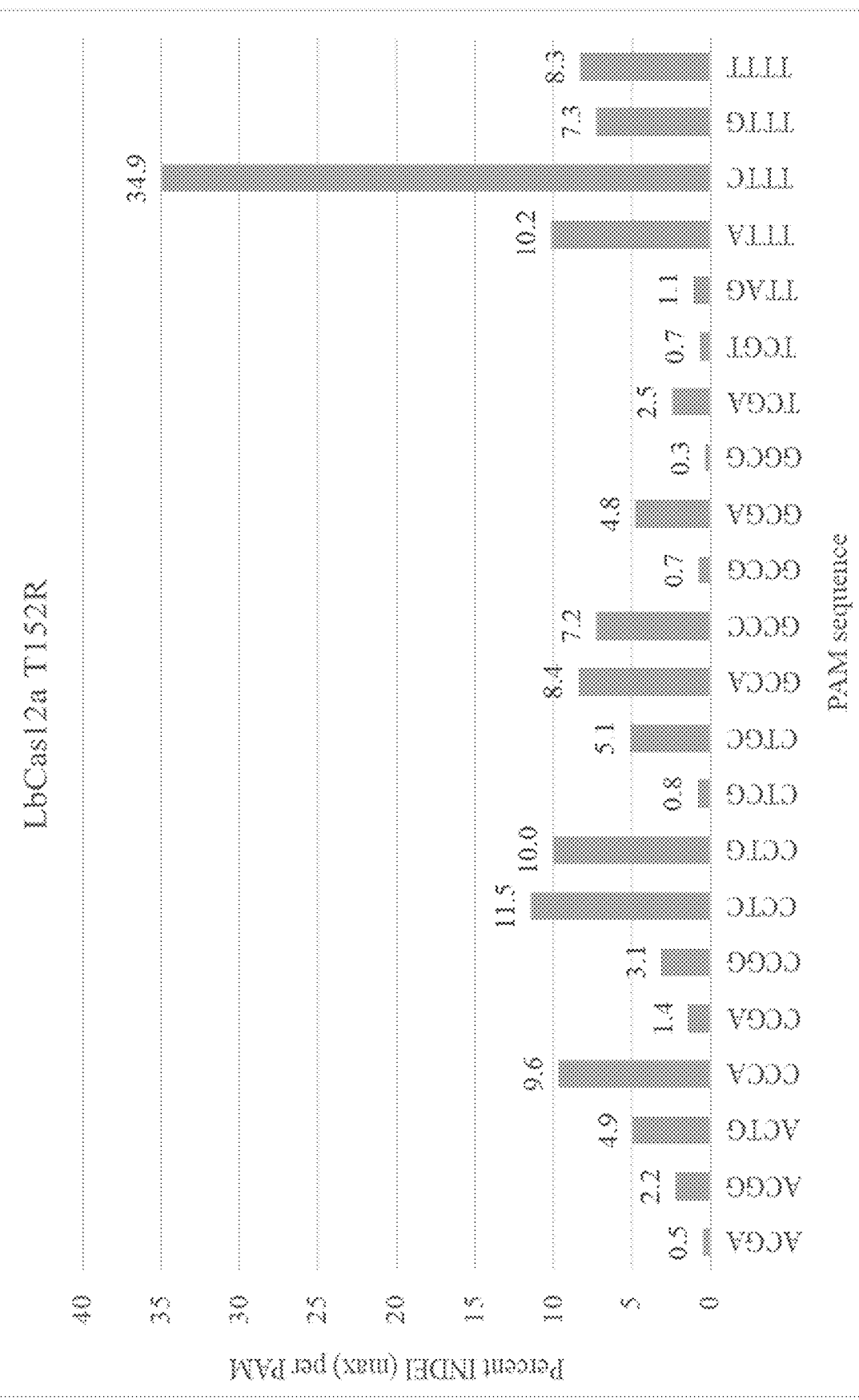
FIG. 20 shows LbCas12a_T152R HEK293T maximum observed INDEL percentages per PAM tested. Values above 0.1% are outside of the noise of sequencing and represent authentic INDELs.
Figure 21:
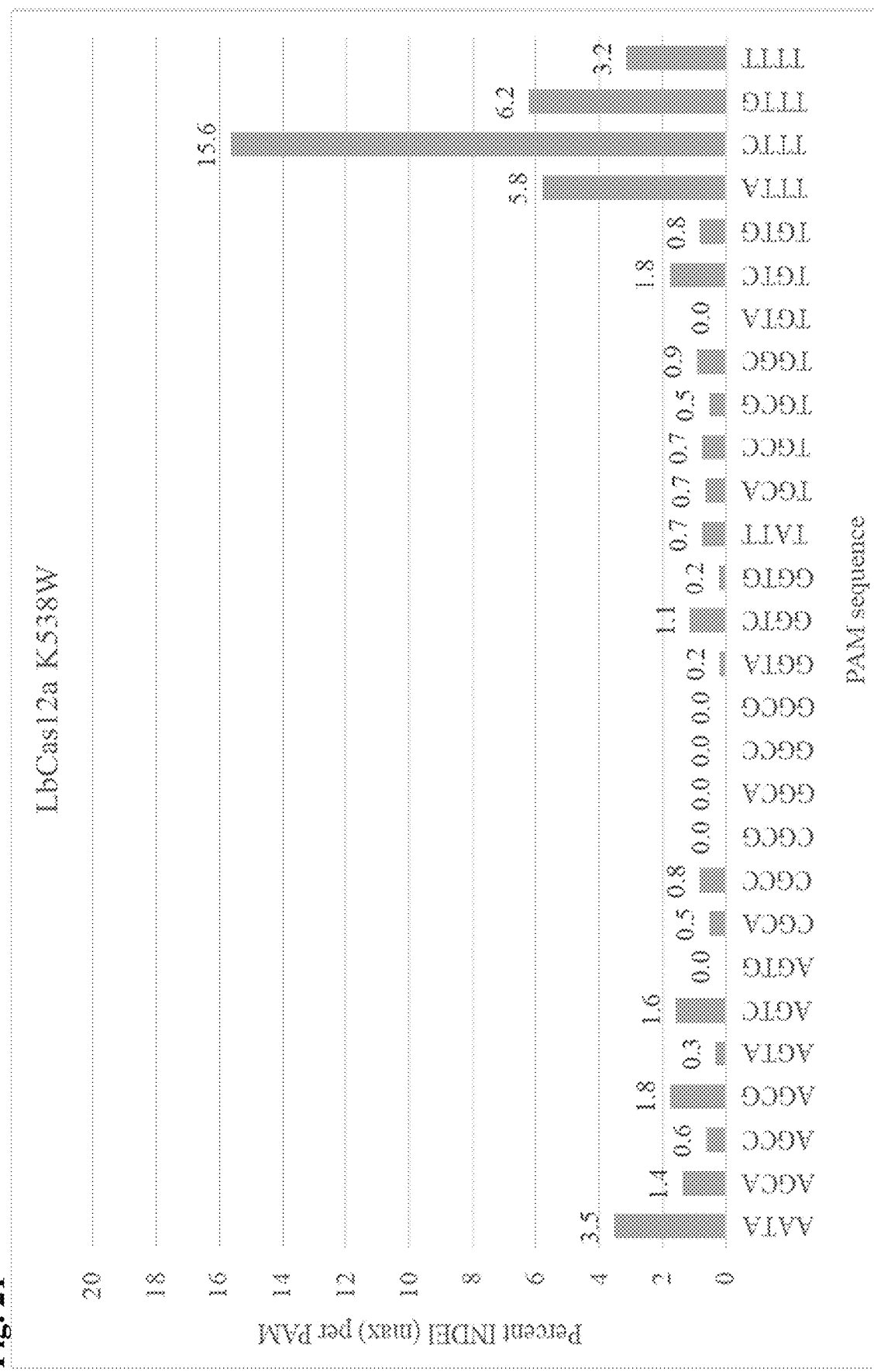
FIG. 21 shows LbCas12a_K538W HEK293T maximum observed INDEL percentages per PAM tested. Values above 0.1% are outside of the noise of sequencing and represent authentic INDELs.

On average, we have observed that about half of 23 nucleotide wtLbCas12a spacers tested are ineffective despite having correct PAM TTTV sequences. With only three data points for each PAM and the observation that about 50% of targets will not produce INDELs, it is more informative to assess PAM recognition by visualizing maximum INDEL percentage per PAM rather than an average for randomly designed spacers (FIGS. 19-21). If a larger number of spacers for each PAM were assayed, then statistical tests may be used to assess their average editing efficiency.

Our overall transfection and assay conditions result in wildtype LbCAs12a causing INDELs in HEK293T cells at approximately 11-26% for TTTC, and 10% for TTTA, and 4-10% for TTTG (FIG. 18). These are pre-defined HEK293T targets sites and guides from the literature and, thus, are expected to be more effective than any randomly chosen guide. Despite a random design for the crRNA guides for the mutant, many new Cas12a PAM recognition sites caused INDELs at rates similar to wildtype at TTTV sequences (FIGS. 19-21). Any INDELs above 0.1% are above the noise of the sequencing assay which were read at 10,000 NGS read-depth.

K595Y was able to cause INDELs at ACCG at 25.5%, CCGC at 10.9%, TCGC at 10.1%, CCCG at 9.5%, GCGC at 8.3%, CTGG at 7.8%, ACGG at 6.3%, CCCG at 6.0%, TGGC at 5.3%, and others (FIG. 19). These numbers are all within the range of the TTTV controls for wtLbCas12a despite being randomly designed. One major hallmark of Cas12a proteins is that they recognize T-rich PAMs (Zetsche et al. Cell 163:759-771 (2015)). This limits their utility in genome editing technologies. K595Y clearly prefers C and G-rich PAMs, which will expand Cas2a utility to targets previously predominantly targets of Cas9 CRISPR enzymes which utilize G-rich PAMs (Jinek et al. Science 337, 816-821 (2012)). Only 31 of the total 256 possible four nucleotide PAMs were tested in 293T cells (or 12%) for K595Y. There are likely many other PAMs which could be recognized by K595Y and cause INDELs in eukaryotic cells.

T152R was able to cause INDELs at CCTC at 11.5%, CCTG at 10.0%, CCCA at 9.6%, GCCA at 8.4%, GCCC at 7.2%, CTGC at 5.1%, and others (FIG. 20). Interestingly, T152R retained the TTTV recognition of wtLbCas12a by causing INDELs at TTTC at 34.9%, TTTA at 10.2%, and TTTG at 6.2%. It also picked up a TTTT recognition, causing INDELs at 8.3%. Only 22 of the total 256 possible four nucleotide PAMs were tested in 293T cells (or 9%) for T152R. There are likely many other PAMs which could be recognized by T152R and cause INDELs in eukaryotic cells.

As shown in FIG. 21, 22 out of the 28 PAM targets did have activity above the background of 0.1%, indicating 79% of the PAMs tested were recognized and cleaved by this enzyme, although at times lower than may be desired for some applications. Six PAMs tested did not have any editing above background for the three targets chosen. The three TTTV targets all still had good activity with 15.6%, 6.2%, and 5.8% for TTTC, TTTG, and TTTA, respectively. Other PAM sequences with over 1% INDEL formation included ATTA (3.5%), TTTT (3.2%), TGTC (1.8%), AGCG (1.8%), AGTC (1.6%), AGCA (1.4%), and GGTC (1.1%). This point mutation was used in combination with T152R and/or K595Y in the PAM-SCALAR experiments to generate a wide variety of PAM recognition, however, on its own it bound relatively few PAMs using that assay. It may be an excellent choice to use in future double mutations rather than alone to generate INDELs in HEK293T cells. Similar to the other two point mutations, only 28 out of the possible 256 four nucleotide PAMs were tested (11%) and it is possible that this mutant may recognize PAMs or targets not tested here.

Correlation Between HEK293T INDELs and PAM-SCANR Binding

Figure 22A:
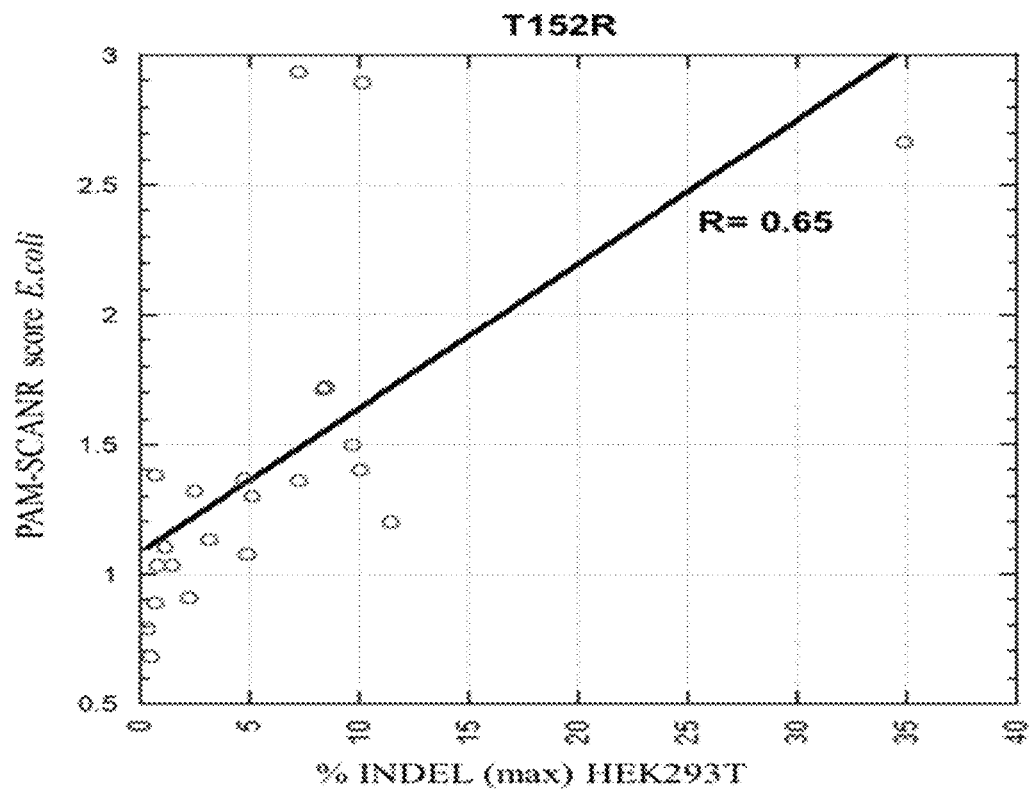
FIGS. 22A-22B. Linear correlation between % INDEL (max) and the normalized bacterial PAM-SCALAR score for LbCas12a-T152R (FIG. 22A) and LbCas12a-K595Y (FIG. 22B).
Figure 22B:
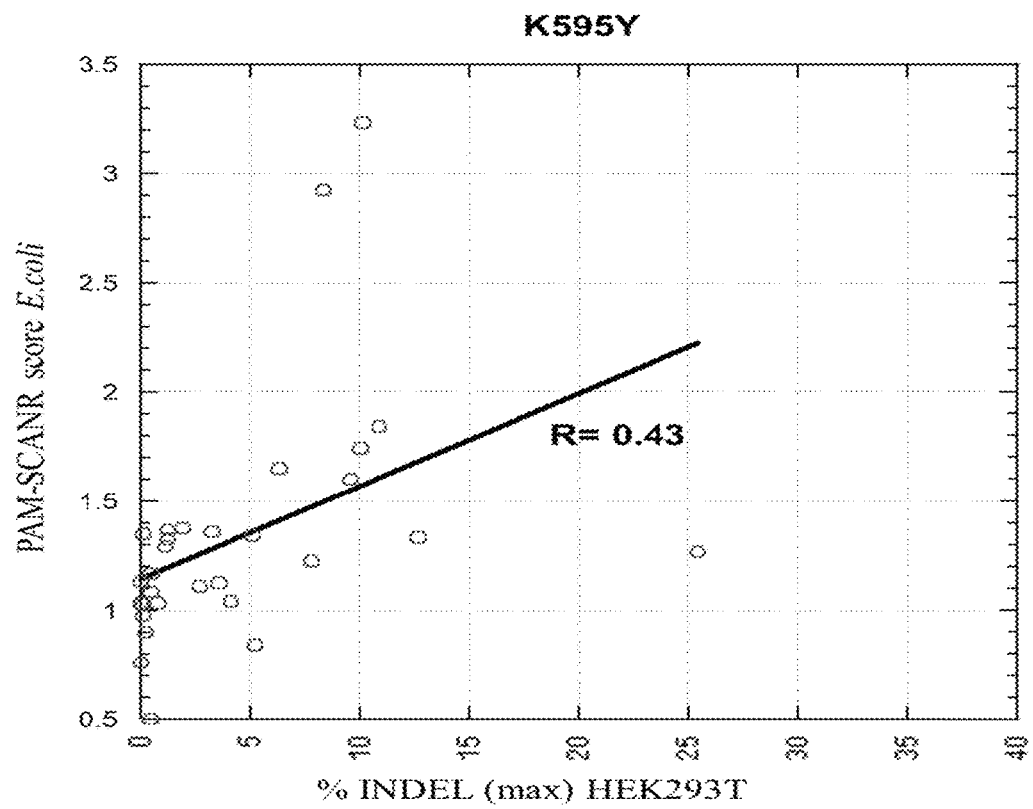

A correlation was observed between the maximal INDEL percentages observed and PAM-SCALAR scores for T152R and K595Y (FIGS. 22A-22B). FIGS. 22A-22B shows the linear correlation between % INDEL (max) and the normalized bacterial PAM-SCANR score for LbCas12a-T152R (FIG. 22A) and LbCas12a-K595Y (FIG. 22B).

Notably, any point mutation with a PAM-SCALAR score over 1.5 tested generated INDELs in 293T cells at rates greater than 5%. This suggests that any of the mutations tested in the PAM-SCANR experiment with a normalized score greater than 1.5 (rather than our stringent 1.67 cutoff) is likely to be able to generate INDELs at rates useful for most eukaryotic applications.

The foregoing is illustrative of the present invention, and is not to be construed as limiting thereof. The invention is defined by the following claims, with equivalents of the claims to be included therein.

That which is claimed is:

1. A modified Lachnospiraceae bacterium CRISPR (Clustered Regularly Interspaced Short Palindromic Repeats) Cas12a (LbCas12a) polypeptide, wherein the modified LbCas12a polypeptide comprises an amino acid sequence having at least 95% identity to the amino acid sequence of SEQ ID NO:1 (LbCas12a) and a mutation of K595Y with reference to position numbering of SEQ ID NO:1, wherein the modified LbCas12a polypeptide exhibits a reduced PAM stringency and increased recognition of new protospacer adjacent motifs (PAMs) as compared to wild type LbCas12a, SEQ ID NO:1.

2. The modified LbCas12a polypeptide of claim 1, wherein the modified LbCas12a polypeptide comprises a further mutation located at one or more of the following positions of K116, K120, K121, D122, E125, T148, T149, T152, D156, E159, Q529, D535, G532, K538, D541, Y542, L585, K591, M592, V596, S599, K600, K601, Y616, Y646, and/or W649 Y616K, Y616R, Y616E, Y616F, Y616H, Y646R with reference to position numbering of SEQ ID NO:1.

3. The modified LbCas12a polypeptide of claim 1, further comprising a mutation in the RuvC domain.

4. A fusion protein comprising the modified LbCas12a polypeptide of claim 1, and a polypeptide of interest.

5. The fusion protein of claim 4, wherein the polypeptide of interest comprises at least one polypeptide or protein domain having deaminase (deamination) activity, nickase activity, recombinase activity, transposase activity, methylase activity, glycosylase (DNA glycosylase) activity, glycosylase inhibitor activity (e.g., uracil-DNA glycosylase inhibitor (UGI)), demethylase activity, transcription activation activity, transcription repression activity, transcription release factor activity, histone modification activity, nuclease activity, single-strand RNA cleavage activity, double-strand RNA cleavage activity, restriction endonuclease activity, nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

6. The fusion protein of claim 4, wherein the polypeptide of interest comprises at least one polypeptide or protein domain having deaminase activity.

7. The fusion protein of claim 6, wherein the at least one polypeptide or protein domain having deaminase activity is a cytosine deaminase domain or an adenine deaminase domain.

8. The fusion protein of claim 4, wherein the at least one polypeptide has glycosylase inhibitor activity, optionally wherein the at least one polypeptide is a uracil-DNA glycosylase inhibitor (UGI).

9. A polynucleotide encoding the modified LbCas12a polypeptide of claim 1.

10. The polynucleotide of claim 9, wherein the polynucleotide encoding the modified LbCas12a polypeptide is operatively associated with a promoter, optionally wherein the promoter is a promoter region comprising an intron.

11. The polynucleotide of claim 9, wherein the polynucleotide is codon optimized for expression in an organism.

12. An expression cassette or vector comprising the polynucleotide claim 9.

13. A cell comprising the polynucleotide of claim 9.

14. A Type V Clustered Regularly Interspaced Short Palindromic Repeats (CRISPR)-associated (Cas) (CRISPR-Cas) system comprising:
 a guide nucleic acid comprising a spacer sequence and a repeat sequence, and
 (a) a fusion protein comprising the modified LbCas12a polypeptide of claim 1 and a polypeptide of interest, or
 (b) a nucleic acid encoding the modified LbCas12a polypeptide of claim 1 and a nucleic acid encoding a polypeptide of interest, wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, whereby the target nucleic acid is modified or modulated.

15. A method of modifying a target nucleic acid, comprising:
contacting the target nucleic acid with:
(a)(i) the modified LbCas12a polypeptide of claim 1, and (ii) a guide nucleic acid;
(b) a composition comprising (i) the modified LbCas12a polypeptide of claim 1, and (ii) a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 1 and a polypeptide of interest, or
(ii) a nucleic acid encoding the modified LbCas12a polypeptide of claim 1 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, whereby the target nucleic acid is modified or modulated.

16. A method of modifying a target nucleic acid, comprising contacting a cell or a cell free system comprising the target nucleic acid with
(i) a polynucleotide encoding the modified LbCas12a polypeptide of claim 1, or an expression cassette or vector comprising the same, and (ii) a guide nucleic acid, or an expression cassette or vector comprising the same, thereby modifying the target nucleic acid.

17. A method of editing a target nucleic acid, comprising:
contacting the target nucleic acid with:
(a)(i) a fusion protein comprising the modified LbCas12a polypeptide of claim 1 and a polypeptide of interest, and (a)(ii) a guide nucleic acid;
(b) a complex or a composition comprising a fusion protein comprising the modified LbCas12a polypeptide of claim 1 and a polypeptide of interest, and a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 1 and a polypeptide of interest, or
(ii) a nucleic acid encoding the modified LbCas12a polypeptide of claim 1 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

18. A method of editing a target nucleic acid, comprising contacting a cell or a cell free system comprising the target nucleic acid with:
(a)(i) a polynucleotide encoding a fusion protein comprising the modified LbCas12a polypeptide of claim 1 and a polypeptide of interest, or an expression cassette or vector comprising the same, and (a)(ii) a guide nucleic acid, or an expression cassette or vector comprising the same; and/or
(b) a nucleic acid construct encoding a complex comprising a fusion protein comprising the modified LbCas12a polypeptide of claim 1 and a polypeptide of interest, and a guide nucleic acid, or an expression cassette or vector comprising the same; and/or
(c) a Type V CRISPR-Cas system comprising:
a guide nucleic acid comprising a spacer sequence and a repeat sequence, and
(i) a fusion protein comprising the modified LbCas12a polypeptide of claim 1 and a polypeptide of interest, or
(ii) a nucleic acid encoding the modified LbCas12a polypeptide of claim 1 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

19. The modified LbCas12a polypeptide of claim 1, wherein the modified LbCas12a polypeptide further comprises the mutation of K116R, K116N, K120R, K120H, K120N, K120T, K120Y, K120Q, K121S, K121T, K121H, K121R, K121G, K121D, K121Q, D122R, D122K, D122H, D122E, D122N, E125R, E125K, E125Q, E125Y, T148H, T148S, T148A, T148C, T149A, T149C, T149S, T149G, T149H, T149P, T149F, T149N, T149D, T149V, T152R, T152K, T152W, T152Y, T152H, T152Q, T152E, T152L, T152F, D156R, D156K, D156Y, D156W, D156Q, D156H, D156I, D156V, D156L, D156E, E159K, E159R, E159H, E159Y, E159Q, Q529N, Q529T, Q529H, Q529A, Q529F, Q529G, Q529G, Q529S, Q529P, Q529W, Q529D, D535N, D535H, D535V, D535T, D535, S D535A, D535W, D535K, K538R K538V, K538Q, K538W, K538Y, K538F, K538H, K538L, K538M, K538C, K538G, K538A, K538P, G532D, G532N, G532S, G532H, G532F, G532K, G532R, G532Q, G532A, G532L, G532C, D541N, D541H, D541R, D541K, D541Y, D541I, D541A, D541S, D541E, Y542R, Y542K, Y542H, Y542Q, Y542F, Y542L, Y542M, Y542P, Y542V, Y542N, Y542T, L585G, L585H, L585F, K591A, K591F, K591G, K591H, K591R, K591S, K591W, K591Y, M592A, M592E, M592Q, V596H, V596T, S599G, S599H, S599N, K600G, K600H, K600R, K601H, K601Q, K601R, K601T, Y616E, Y616F, Y616H, Y616K, Y616R, Y646E, Y646H, Y646K, Y646N, Y646Q, Y646R, Y646W, W649H, W649K, W649R, W649S and/or W649Y with reference to position numbering of SEQ ID NO:1.

20. A method of modifying a target nucleic acid, comprising: contacting the target nucleic acid with:
(a)(i) the modified LbCas12a polypeptide of claim 19, and (ii) a guide nucleic acid;
(b) a composition comprising (i) the modified LbCas12a polypeptide of claim 19, and (ii) a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 19 and a polypeptide of interest, or
(ii) a nucleic acid encoding the modified LbCas12a polypeptide of claim 19 and a nucleic acid encoding a polypeptide of interest, wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, whereby the target nucleic acid is modified or modulated.

21. A method of modifying a target nucleic acid, comprising contacting a cell or a cell free system comprising the target nucleic acid with
(i) a polynucleotide encoding the modified LbCas12a polypeptide of claim 19, or an expression cassette or vector comprising the same, and (ii) a guide nucleic acid, or an expression cassette or vector comprising the same, thereby modifying the target nucleic acid.

22. A method of editing a target nucleic acid, comprising: contacting the target nucleic acid with:
(a)(i) a fusion protein comprising the modified LbCas12a polypeptide of claim 19 and a polypeptide of interest, and (a)(ii) a guide nucleic acid;
(b) a complex or a composition comprising a fusion protein comprising the modified LbCas12a polypeptide of claim 19 and a polypeptide of interest, and a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 19 and a polypeptide of interest, or
(ii) a nucleic acid encoding the modified LbCas12a polypeptide of claim 19 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

23. A method of editing a target nucleic acid, comprising contacting a cell or a cell free system comprising the target nucleic acid with:
(a)(i) a polynucleotide encoding a fusion protein comprising the modified LbCas12a polypeptide of claim 19 and a polypeptide of interest, or an expression cassette or vector comprising the same, and (a)(ii) a guide nucleic acid, or an expression cassette or vector comprising the same; and/or
(b) a nucleic acid construct encoding a complex comprising a fusion protein comprising the modified LbCas12a polypeptide of claim 19 and a polypeptide of interest, and a guide nucleic acid, or an expression cassette or vector comprising the same; and/or
(c) a Type V CRISPR-Cas system comprising:
a guide nucleic acid comprising a spacer sequence and a repeat sequence, and (i) a fusion protein comprising the modified LbCas12a polypeptide of claim 19 and a polypeptide of interest, or (ii) a nucleic acid encoding the modified LbCas12a polypeptide of claim 19 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

24. The modified LbCas12a polypeptide of claim 1, wherein the modified LbCas12a polypeptide comprises an amino acid sequence having at least 95% identity to the amino acid sequence of SEQ ID NO:1 (LbCas12a) and a mutation at K116, E125, T152, D156, G532, K538, Y542, and/or L585 with reference to position numbering of SEQ ID NO:1.

25. The modified LbCas12a polypeptide of claim 24, further comprising a mutation at the position of K538 with reference to position numbering of SEQ ID NO:1.

26. A method of modifying a target nucleic acid, comprising: contacting the target nucleic acid with:
(a)(i) the modified LbCas12a polypeptide of claim 24, and (ii) a guide nucleic acid;
(b) a composition comprising (i) the modified LbCas12a polypeptide of claim 24, and (ii) a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 24 and a polypeptide of interest, or
(ii) a nucleic acid encoding the modified LbCas12a polypeptide of claim 24 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, whereby the target nucleic acid is modified or modulated.

27. A method of modifying a target nucleic acid, comprising contacting a cell or a cell free system comprising the target nucleic acid with
(i) a polynucleotide encoding the modified LbCas12a polypeptide of claim 24, or an expression cassette or vector comprising the same, and (ii) a guide nucleic acid, or an expression cassette or vector comprising the same, thereby modifying the target nucleic acid.

28. A method of editing a target nucleic acid, comprising: contacting the target nucleic acid with:
(a)(i) a fusion protein comprising the modified LbCas12a polypeptide of claim 24 and a polypeptide of interest, and (a)(ii) a guide nucleic acid;
(b) a complex or a composition comprising a fusion protein comprising the modified LbCas12a polypeptide of claim 24 and a polypeptide of interest, and a guide nucleic acid; and/or
(c) a Type V CRISPR-Cas system comprising:
a guide nucleic acid comprising a spacer sequence and a repeat sequence, and
(i) a fusion protein comprising the modified LbCas12a polypeptide of claim 24 and a polypeptide of interest, or
(ii) a nucleic acid encoding the modified LbCas12a polypeptide of claim 24 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

29. A method of editing a target nucleic acid, comprising contacting a cell or a cell free system comprising the target nucleic acid with:
(a)(i) a polynucleotide encoding a fusion protein comprising the modified LbCas12a polypeptide of claim 24 and a polypeptide of interest, or an expression cassette or vector comprising the same, and (a)(ii) a guide nucleic acid, or an expression cassette or vector comprising the same; and/or
(b) a nucleic acid construct encoding a complex comprising a fusion protein comprising the modified LbCas12a polypeptide of claim 24 and a polypeptide of interest, and a guide nucleic acid, or an expression cassette or vector comprising the same; and/or
(c) a Type V CRISPR-Cas system comprising:
a guide nucleic acid comprising a spacer sequence and a repeat sequence, and
(i) a fusion protein comprising the modified LbCas12a polypeptide of claim 24 and a polypeptide of interest, or
(ii) a nucleic acid encoding the modified LbCas12a polypeptide of claim 24 and a nucleic acid encoding a polypeptide of interest,
wherein the guide nucleic acid is capable of forming a complex with the modified LbCas12a polypeptide or the fusion protein and the spacer sequence is capable of hybridizing to a target nucleic acid, thereby guiding the modified LbCas12a polypeptide and the polypeptide of interest to the target nucleic acid, thereby editing the target nucleic acid.

* * * * *

UNITED STATES PATENT AND TRADEMARK OFFICE
CERTIFICATE OF CORRECTION

| | |
|---|---|
| PATENT NO. | : 11,866,745 B2 |
| APPLICATION NO. | : 17/071095 |
| DATED | : January 9, 2024 |
| INVENTOR(S) | : Joseph Matthew Watts |

It is certified that error appears in the above-identified patent and that said Letters Patent is hereby corrected as shown below:

In the Specification

Column 2, Line 30: Please correct "lbCas12a" to read --LbCas12a--

Column 6, Lines 32-33: Please correct "PAM-SCALAR" to read --PAM-SCANR--

Column 6, Lines 36-37: Please correct "PAM-SCALAR" to read --PAM-SCANR--

Column 6, Line 50: Please correct "PAN-SCANAR" to read --PAM-SCANR--

Column 6, Lines 51-52: Please correct "PAM-SCALAR" to read --PAM-SCANR--

Column 7, Line 6: Please correct "PAM-SCALAR" to read --PAM-SCANR--

Column 16, Line 39: Please correct "*Plaid*" to read --*Plant*--

Column 22, Line 8: Please correct "5599," to read --S599,--

Column 22, Line 24: Please correct "5599," to read --S599,--

Column 23, Line 23: Please correct "D535, SD535A," to read --D535S, D535A,--

Column 33, Line 6: Please correct "5599," to read --S599,--

Column 33, Line 21: Please correct "D535, S D535A," to read --D535S, D535A,--

Column 33, Line 22: Please correct "D535, S D535A," to read --D535S, D535A,--

Column 38, Line 35: Please correct "3′-end" to read --3′end--

Signed and Sealed this
Twenty-ninth Day of October, 2024

Katherine Kelly Vidal
*Director of the United States Patent and Trademark Office*

CERTIFICATE OF CORRECTION (continued)
U.S. Pat. No. 11,866,745 B2

Column 39, Line 34: Please correct "(ii) (ii)" to read --(ii)--

Column 39, Line 36: Please correct "(ii)" to read --(iii)--

Column 42, Line 39: Please correct "Cash," to read --Cas6,--

Column 44, Line 27: Please correct "5r-end" to read --5′-end--

Column 46, Line 56: Please correct "PAM-SCALAR" to read --PAM-SCANR--

Column 46, Line 62: Please correct "PAM-SCALAR" to read --PAM-SCANR--

Column 47, Line 61: Please correct "mi" to read --ml--

Column 54, Line 42, TABLE 4- continued: Please correct "CCCCC" to read --CCCC--

Column 56, Line 14, TABLE 4- continued: Please correct "TCCCC" to read --TCCC--

Column 83, Line 61: Please correct "Lad," to read --Lacl--

Column 89, Line 47: Please correct "PAM-SCALAR" to read --PAM-SCANR--

Column 91, Lines 18-19: Please correct "PAM-SCALAR" to read --PAM-SCANR--

Column 91, Line 21: Please correct "PAM-SCALAR" to read --PAM-SCANR--

Column 91, Lines 24-25: Please correct "PAN-SCALAR" to read --PAM-SCANR--

Column 91, Line 28: Please correct "PAM-SCALAR" to read --PAM-SCANR--

Column 91, Line 32: Please correct "PAM-SCALAR" to read --PAM-SCANR--

Column 91, Line 36: Please correct "PAM-SCALAR" to read --PAM-SCANR--

Column 91, Line 46: Please correct "(PAM-SCALAR)" to read --(PAM-SCANR)--

Column 94, Line 32: Please correct "PAM-SCALAR" to read --PAM-SCANR--

Column 94, Line 43: Please correct "PAM-SCALAR" to read --PAM-SCANR--

Column 94, Line 48: Please correct "PAM-SCALAR" to read --PAM-SCANR--

In the Claims

Column 255, Lines 48-49, Claim 2: Please correct "following positions of K116, K120, K121, D122, E125, T148, T149, T152, D156, E159, Q529, D535, G532, K538, D541, Y542, L585, K591,

CERTIFICATE OF CORRECTION (continued)
U.S. Pat. No. 11,866,745 B2

M592, K595, V596, S599, K600, K601, Y616, Y646, and/or W649 Y616K, Y616R, Y616E, Y616F, Y616H, Y646R with reference to position numbering of SEQ ID NO:1." to read --following positions of K116, K120, K121, D122, E125, T148, T149, T152, D156, E159, Q529, D535, G532, K538, D541, Y542, L585, K591, M592, K595, V596, S599, K600, K601, Y616, Y646, and/or W649 with reference to position numbering of SEQ ID NO:1.--

Column 256, Line 54, Claim 13: Please correct "polynucleotide claim 9." to read --polynucleotide of claim 9.--

Column 258, Line 36, Claim 19: Please correct "Q529G, Q529G," to read --Q529G,--

Column 258, Line 37, Claim 19: Please correct "D535, S D535A," to read --D535S, D535A,--